US008173861B2

(12) United States Patent
Madsen et al.

(10) Patent No.: US 8,173,861 B2
(45) Date of Patent: May 8, 2012

(54) TRANSGENIC PIG MODEL FOR A HEREDITARY NEURODEGENERATIVE AUTOSOMAL DOMINANT DISEASE

(75) Inventors: Lone Bruhn Madsen, Hadsten (DK); Christian Bendixen, Ulstrup (DK); Knud Larsen, Aarhus N (DK); Connie Jakobsen Juhl, Viborg (DK); Bo Thomsen, Aarhus V (DK)

(73) Assignee: Aarhus Universitet, Aarhus C (DK)

( * ) Notice: Subject to any disclaimer, the term of this patent is extended or adjusted under 35 U.S.C. 154(b) by 0 days.

(21) Appl. No.: 12/298,974

(22) PCT Filed: Apr. 30, 2007

(86) PCT No.: PCT/DK2007/000204
§ 371 (c)(1),
(2), (4) Date: Mar. 26, 2009

(87) PCT Pub. No.: WO2007/124751
PCT Pub. Date: Nov. 8, 2007

(65) Prior Publication Data

US 2009/0304595 A1 Dec. 10, 2009

Related U.S. Application Data

(60) Provisional application No. 60/796,196, filed on May 1, 2006.

(51) Int. Cl.
*C12N 15/00* (2006.01)
*A01K 67/027* (2006.01)
*G01N 33/00* (2006.01)

(52) U.S. Cl. .................... 800/17; 800/3; 800/9; 800/12; 800/25; 435/455

(58) Field of Classification Search ........................ None
See application file for complete search history.

(56) References Cited

U.S. PATENT DOCUMENTS

| | | | |
|---|---|---|---|
| 6,265,632 | B1 | 7/2001 | Yayon et al. |
| 6,485,911 | B1 | 11/2002 | St. George-Hyslop et al. |

FOREIGN PATENT DOCUMENTS

| | | |
|---|---|---|
| EP | 1116790 | 7/2001 |
| JP | 2000-316420 | 11/2000 |
| WO | WO 96/40896 | 12/1996 |
| WO | WO 99/31969 | 7/1999 |
| WO | WO 02/16417 | 2/2002 |
| WO | WO 2004/004451 | 1/2004 |
| WO | WO 2004/064768 | 8/2004 |

OTHER PUBLICATIONS

Lavitrano et al. Efficient Production by Sperm-Mediated Gene Transfer of human decay acclerating factor (hDAF) transgenic pigs for xenotransplantation. PNAS (USA), 2002, vol. 99, pp. 14230-14235.*

Lavitrano et al. Efficienct Production by Sperm-Mediated Gene Transger of Human Decay Accelerating Factor (hDAF) Transgenic Pigs for Xenotransplantation. PNAS, 2002, vol. 99, pp. 14230-14235.*

Gispert et al. Transgenic mice expressing mutant A53T human alpha-synuclein show neuronal dysfunction in the absence of aggregate formation Molec. Cell. Neurosci., 2003, vol. 24, pp. 419-429.*

Petters et al. Genetically Engineered Large Animal Model for Studying Cone Photoreceptor Survival and Degeneration in Retinitis Pirgmentosa. Nature Biotechnology, 1997, vol. 15, pp. 965-970.*

Tammen et al. Transgenic mice expressing mutant A53T human alpha-synuclein show neuronal dysfunction in the absence of aggregate formation. American Genetic Association, 1999, vol. 90, pp. 472-476.*

Kulvaniemi H et al. (1997), Mutations in Fibrillar Collagens (Types I, II, III and XI), Fibril-Associated Collagen (Type IX), and Network-Forming Collagen (Type X) Cause a Spectrum of Diseases of Bone, Cartilage and Blood Vessels, Hum Mutat, 9: p. 300-315.

Kusafuka K. et al. (2001), Ossification of tracheal cartilage in aged humans a historical and immunohistochemical analysis. J Bone Miner Metab 19; p. 168-174.

La Spada A.P. et al. (1992), Meiotic stability and genotype-phenotype correlation of the trinucleotide repeat in X-linked spinal and bulbar muscular atrophy, Nat Genet 2(4), p. 301-304.

Lachman R.S. et al. (1988), Metaphyseal chondrodyspiasia, Schmid type Clinical and radiographic delineation with a review of the literature, Pediatr Radiol 18, p. 93-102.

Lavedan C.N. et al, (1997), Trinucleotide repeats (CGG)22TGG(CGG)43TGG(CGG)21 from the fragile X game remain stable in Transgenic mice, Hum Genet 100(3-4), p. 407-414.

Lavitrano et al. Sperm-mediated gene transper—(XP002453316)—Abstract.

Lee M.K. et al (1996), Expression of presenillin 1 and 2 (PS1 and Ps2) in human and murine tissues, J. Neurosci 16, p. 7613-7625.

Libby R.T. et al. (2003), Genomic context drives SCA7 CAG repeat instability, while expressed SCA7 cDNAs are intergenerationally and somatically stable in trangenic mice. Hum Mol. Genet 12(1), p. 41-50.

Limprasert P. et al (1996), Analysis of CAG repeat of the Machado-Joseph gene in human, chimpanzee and monkey populations: a variant nucleotide is associated with the number of CAG repeats, Hum Mol Genet 6(2), p. 207-213.

Limpresert P. et al. (1997), Comparative studies of the CAG repeats in the spinocerebellar ataxia type 1 (SCA1) gene, Am J Med Genet 74(6), p. 488-493.

Felbecker et al. (2010), Four familial ALS pedigrees discordant for two SOD1 mutations: are all SOD1 mutations pathogenic?, J. Neurol Neurosurg Psychiatry 2010, vol. 81, p. 572-577.

(Continued)

*Primary Examiner* — Deborah Crouch
(74) *Attorney, Agent, or Firm* — Weingarten, Schurgin, Gagnebin & Lebovici LLP

(57) ABSTRACT

The present invention discloses a non-human animal model for a hereditary autosomal dominant disease. The non-human animal model expresses at least one phenotype associated with the disease and is obtained by a genetic determinant. The invention also relates to sperm cells and embryos comprising the genetic determinant for an autosomal dominant disease. Furthermore, methods for producing the non-human animal model, sperm cell, and embryos are disclosed.

22 Claims, 39 Drawing Sheets

OTHER PUBLICATIONS

Alba, M.M. et al. (2004) Comparative analysis of amino acid repeats in rodents and humans, Genome Res. 14(4): p. 549-54.
Aldudo J et al. (1998), Missense mutation E318G of the presenilin-1 gene appears to be a nonpathogenic polymarphism, Ann Neurol, 44: p. 985-986.
Andres, A.M. et al. (2002), Dynamics of CAG repeat loci revealed by the analysis of their variability, Hum Mutat. 21(1): p. 61-70.
Andres, A.M. et al. (2004), Comparative genetics of functional trinucleotide tandem repeats in humans and apes, J Mol Evol, 59(3): p. 329-39.
Appet et al. (1994), Evidence for autoimmunity in amyotrophic lateral sclerosis, Journal of the Neurological Sciences 124(Suppl):14-19.
Bauer et al. (1999), Somatic gene therapy in animal models of Parkinson's disease, J Neural Transm (Suppl.)55 131-147.
Beauchamp C. et al. (1971), Superoxide dismutase: improved assays and an assay applicable to acrylamide gels, Anal Biochem, 44: p. 275-267.
Beish, Jerry (2000), ALS diagnostic criteria of El Escorial Revisited: do they meet the needs clinicians as well as researchers? Amyotroph Lateral Scier Other Motor Neuron Disord, 1 Suppl 1: S57-S60.
Bowman, A.B. et al. (2007), Duplication of AtxnII suppresses SCA1 neutropathology by decreasing incorporation of polyglutamine-expanded ataxin-1 into native complexes, Nat Genet, 39(3): p. 373-379.
Brinkmanri, B. et al. (1998), Mutation rate in human microsatellites: influence of the structure and length of the tandem repeat. Am J Hum Genet, 62(6): p. 1408-15.
Brook, J.D. et al. (1992), Molecular basis of myotonic dystrophy: expansion of a trinucleotide (CTG) repeat at the 3' end of a transcript encoding a protein kinase family member, Cell, 69(2): p. 385.
Chiba et al. (2006), Colivelin protongs survival of an ALB model mouse, Biochemical and Biophysical Research Communications 343:793-768.
Cho, D.H. et al. (2005), Antisense transcription and heterochromatin at the DM1 CTG repeats are constrained by CTCF, Mol Cell, 20(3), p. 483-9.
Choudhry, S. et al. (2001), CAG repeat instability at SCA2 locus: anchoring CAA interruptions and linked single nucletids polymorphisms, Hum Mol Genet, 10(21): p. 2437-46.
Cleary, J.D. et al. (2001), Evidence of cis-acting factors in replication-mediated trinucleotide repeat instability in primate cells, Nat Genet, 31(1): p. 37-46.
Colacicco AM et al. (2002), F175S change and a novel polymorphism in presenilin-1 gene in late-onset familial Alzheimer's disease, Eur Neurol, 47: p. 209-213.
Czech et al. (1998), Characterization of Human Presenilin 1 Transgenic Rats: Increased Sensitivity to Apoptosis in Primary Neuronal Cultures, Neuroscience vol. 87(2):325-336.
David, G. et al. (1997), Cloning of the SCA7 gene reveals a highly unstable CAG repeat expansion, Nat Genet, 17(1): p. 65-70.
Dharmavaram RM et al. (1994), Identification of a mutation in type X collagen in a family with Schmid metaphyseal chondrodysplasis, Hum Mol Genet, 3: p. 507-509.
Donoviel DB et al. (1999), Mice lacking both presenllin genes exhibit early embyonic patterning defect, Genes Dev, 13 p. 2801-2810.
Eichler E.E. et al. (1995), Evolution of the cryptic FMR1 CGG repeat, Nat Genet, 11(3): p. 301-8.
Everett, C.M. et al. (2004), Trinucleotide repeats and neurodegenerative disease, Brain, 127 (Pt 11), p. 2385-405.
Fai Poon et al. (2005), Mitochondrial associated metabolic proteins are selectively oxidized in A30P alfa-synuciein transgenic mice—a model of familial Parkinson's disease, Neurobiology of Disease 16:492-498.
Fu, Y.H. et al. (1991), Variation of the CGG repeat at the fragile X site results in genetic instability resolution of the Sherman paradox, Cell, 67(5): p. 1047-58.
Fu, Y.H. et al. (1992), An unstable triplet repeat in a gene related to myotonic muscular dystrophy, Science, 255(5049): p. 1256-58.
Galvao, R. et al. (2001), Triplet repeats RNA secondary structure and toxic gain-of-function models for pathogenesis, Brain Res Bull, 56(3-4): p. 191-201.
Hancock, J.M. et al. (2001), A role for selection in regulating the evolutionary emergence of disease-causing and other coding CAG repeats in humans and mice, Mol Biol Evol, 18(6): p. 1014-23.
Harley, H.G. et al. (1992), Expansion of an unstable DNA region and phenotypic variation in myotonic dystrophy, Nature, 365(6360): p. 545-6.
Holmes S.E. et al. (1999), Expansion of a novel CAG trinucleotide repeat in the 5'region of PPP2R2B is associated with SCA12. Nat Genet 23(4): p. 391-392.
Jin P. et al. (2003), RNA-mediated neurodegeneration caused by the fragile X premutation rCGG repeats in *Drosophila*, Neuron 39(5): p. 739-747.
Kawaguchi Y et al. (1994), CAG expansions in a novel gene for Machado-Joseph disease at chromosome 14q32.1. Nat Genet 8(3): p. 221-228.
Knight S.J. et al. (1993), Trinucleotide repeat amplification and hypermethylation of a CpG island in FRAXE mental retardation, Call 74(1); p. 127-134.
Koide R. et al. (1994), Unstable expansion of CAG repeat in hereditary dentaforubral-pallidoluysian atrophy (DRPLA), Nat Genet 5(1): p. 9-13.
Kulvaniemi H. et al. (1997), Mutations in Fibrillar Collagens (Types I, II, III and XI), Fibril-Associated Collagen (Type IX), and Network-Forming Collagen (Type X) Cause a Spectrum of Diseases of Bone, Cartilage, and Blood Vessels, Hum Mutat, 9: p. 300-315.
Kusafuka K. et al. (2001), Ossification of tracheal cartilage in aged humans a historical and immunohistochemical analysis, J. Bone Miner Metab 19: p. 168-174.
La Sparia A.R. (1992), Meiotic stability and genotype-phenotype correlation of the trinucleotide repeat in X-linked spinal and bulbar muscular atrophy, Nat Genet 2(4); p. 301-304.
Lachman R.S. et al. (1988), Metaphyseal chondrodyspiesia, Schmid type Clinical and radiographic delineation with a review of the literature, Pediatr Radiol 18; p. 93-102.
Lavedan C.N. et al. (1997), Trinucleotide repeats (CGG)22TGG(CGG)43TGG(CGG)21 from the fragile X gene remain stable in transgenic mice, Hum Genet 100(3-4), p. 407-414.
Lavitrano et al. (2006), Sperm-mediated gene transfer, Reprod Fertil Dev 18:19-23.
Lavitrano et al. Sperm-mediated gene transper—(XP002453316)—ABSTRACT, 2005, Mar. 2, 2012.
Lee M.K. et al. (1996), Expression of presenillin 1 and 2 (PS1 and PS2) in human and murine tissues, J Neurosci 16. p. 7513-7525.
Libby R.T. et al (2003), Genomic context drives SCA7 CAG repeat instability, while expressed SCA7 cDNAs are intergenerationally and somatically stable in trangenic mice. Hum Mol Genet 12(1); p. 41-50.
Limprasert P. et al. (1996), Analysis of CAG repeat of the Machado-Joseph gene in human, chimpanzee and monkey populations; a variant nucleotide is associated with the number of CAG repeats, Hum Mol Genet 5(2): p. 207-213.
Limpresert P. et al. (1997), Comparative studies of the CAG repeats in the spinocerebellar ataxia type 1 (SCA1) gene, Am J. Med Genet 74(6); p. 488-493.
Lin Y. et al. (2006), Transcription promotes contraction of CAG repeat tracts in human cells, Nat Struct Nol Biol 13(2): p. 179-180.
Linsenmayer (1998), Type X collagen and other up-regulated components of the avian hypertrophic cartilage program, Prog Nucleic Acid Res Mol Biol. 60: p. 79-109.
Liao A. et al. (2002), Uncommon polymorphism in the presentiln genes in human familiar Alzheimer's disease: not to be mistaken with a pathogenic mutation, Neurosci Lett 318, p. 166-168.
Madsen L.B. (2003), Chromosome location, genomic organization of the porone col. 10A1 gene and model structure of the NC1 domain, Cytogenet Genome Res. 102, p. 173-178.
Mahadevan M. et al. (1992), Myotonic dystrophy mutation: an unstable CTG repeat in the 3' untranslated region of the gene, Science 255(5049): p. 1253-1255.
Marigiarini et al.(Nov. 1996), Exon 1 of the HD Gene with an Expanded CAG Repeat is Sufficient to Cause a Progressive Neurological Phenotype in Transgenic Mice. Cell vol. 87:493-506.
Manzini S. et al. (2006), Genetically modified pigs produced with a nonviral episomal vector, Proc Natl Acad Sci U S A 103: p. 17672-17677.

Marklund (1980), Distribution of CuZn superoxide dismutase and Mn superoxide dismutase in human tissues and extracellular fluids, Acta Physiol Scand Suppl. 492: p. 19-23.
Marklund S.L. (1984), Extracelluar superoxide dismutase in human tissues and human cell lines, J Clin Invest 74, p. 1398-1403.
Matsuyarna et al. (2000), Identification and Characterization of the Miniature Pig Huntington's Disease Gene Homelog: Evidence for Conversation and Polymorphism in the CAG Triplet Repeat, Genomics 69:72-85.
Michlewski G. et al. (2004), Molecular architecture of CAG repeats in human disease related transcripts, J. Mol Biol 340(4): p. 565-579.
Mikkaisen et al. (1999), MPTP-Induced Parkinsonism in Minipigs—A Behavioral, Biochemical, and Histological Study, Neurotoxicology and Teratology vol. 21(2):169-176.
Miller S.A. et al (1988), A simple salting out procedure for extracting DNA from human nucleated cells, Nucleic Acids Res. 16(3): p. 1216.
Mirkin S.M. et al. (2002), Positioned to expand, Nat Genet 31(1): p. 5-6.
Moreno-Flores M.T. et al. (1999), Expression of presenilin 1 in nervous system during at development, J Comp Neurol 410: p. 556-570.
Mulvihill D.J. et al. (2005), Effect of CAT or AGG interruptions and CpG methylationon nucleosome assembly upon trinuclectide repeats on spinacereballar ataxia, type 1 and fragile X syndrome, J Biol Chem 280(5): p. 4498-4503.
Nakamura K. et al. (2001), A novel autosomal dominant cerebeliar ataxia caused by an expanded polglulamine in TATA-binding protein, Hum Mol Genet 10(14): p. 1441-1448.
Neriguke T. et al. (2003), Candidate DNA replication intiation regions at human trinucleotide repeat disease lool, Hum Mol Genet 12(9): p. 1021-1028.
Nielseri et al. (2000), Abnormal growth plate function in pigs carrying a dominant mutation in type X collagen, Mammalian Genome 11:1087-1092.
Orr H.T. et al. (1993), Expansion of an unstable trincieotide CAG repeat in spinocerebellar ataxia type 1. Nat Genet 4(3), p. 221-226.
Orrell R. et al. (1995), A novel SOD mutant ans ALS, Nature 374, p. 504-506.
Orrell R.W. et al. (1999), Clinical characteristics of SOD1 gene mutations in UK families with ALS, Journal of the Neurological Sciences 169, p. 56-60.
Pearson C.E. et al. (2005), Repeat instability mechanisms of dynamic mutations, Nat Rev Genet 6(10): p. 729-742.
Pedersan P.H. et al. (2001), A within litter comparison of muscle fibre characteristics and growth of halothane carrier and halothane free crossbred pigs. Livest Prod Sci 73. p. 15-24.
Pfaffl M.W. et al. (2002), Relative expression software tool (REST) for group-wise comparison and statistical analysis of relative expression results in real-time PCR, Nucleic Acids Res 30(9), e36. p. 1-10.
Prockop D.J. et al. (1995), Collagens molecular biology, dieases, and potentials for therapy, Annu Rev Biochem 64: p. 403-434.
Pulst S.M. et al. (1996), Moderate expansion of a normally bialletic trinucleotide repeat in spinocerabeilar atakia type 2. Nat Genet 14(3), p. 269-276.
Raux G. et al. (2005), Moleculer diagnosis of autosomal dominant early onset Alzeriheimer'S disease an update, J Med Genet 42, p. 793-795.
Sasano Y. et al. (1998), Type X collagen is not localized in hypertrophic or calcified cartilage in the developing at trachea. Anat Embryol (Berl), 197: p. 399-403.
Saveliev A. et al. (2003), DNA triplet repeats mediate heterochromatin-protein-1-sensitive variegated gene silencing. Nature 422(6924), p. 909-913.
Steiner H. et al. (1999), A loss of function mutation of presenilin-2 interferss with amyloid beta-peptide production and noton signaling, J Bio Chem 274, p. 909-913.
Takiyama Y. et al. (1993), The gene for Machado-Joseph disease maps to human chromosome 14q. Nat Genet 4(3); p. 300-304.
The Huntington's Disease Collaborative Research Group (1993), A novel gene containing a trinucleotide repeat that is expanded and unstable on Huntington's disease chromosomes. Cell, 72(6): p. 971-983.
Tailfidle C. et al. (1992), Correlation between CTG trinucleotide repeat length and frequency of severs congential myotonic dystrophy, Nat Genet 1(3), p. 192-195.
Uchida et al. (2001), Production of transgenic miniature pigs by pronuclear microinjection, Transgenic Research 10:577-582.
Verkerk A.J. et al. (1991), Identification of a gene (FMR-1) containing a CGG repeat coincident with a breakpoint cluster region exhibiting lenght variation in fragile X syndrome. Cell 55(5), p. 905-914.
Vodicka et al. (2005), The miniature pig as an animal model in biomedical research. Anti. N.Y. Acad. Sci. 1049:161-171.
Wang J. et al. (2004), Conserved "PAL" sequence in presenilins is essential for gamma-secretase activity, but not required for formation or stabilization of gamma-secretase complexes. Neurobiol Dis 15, p. 654-665.
Wardale R.J. et al. (1994), Characterisation of articular and growth plate cartilage in porchine osteoonondrosis. J Cell Sci 107 (Pt 1), p. 47-59.
Wells R.D. (1996), Molecular basis of genetic instability of triplet repeats. J Biol Chem 271(6), p. 2875-2878.
Wines-Samuelson M. et al. (2005), Presenllins in the developing, adult and aging cerebral cortex. Neuroscientist 11, p. 441-451.
Wolfs M.S. et al. (1999), Two Transmembrane aspartates in presenliln-1 required for presenilin endoproteolysis and gamma-secretase activity, Nature 398, p. 513-517.
Yerie M. et al. (1996), A somatic cell hybrid panel for pig regional gene mapping characterized by molecular cytogenetics. Cytogenet Cell Genet 73; p. 194-202.
Yu F. et al. (2005), Positive selection of a pre-expansion CAG repeat of the human SCA2 gene, PLoS Genet 1(3), p. e41.
Zhuchenko O. et al. (1997), Autosomal dominant cerebellar ataxia (SCAs) associated with small polyglutamine expansions in the alpha 1A-voltage-dependent calcium channel, Nat Genet 15(1), p. 62-69.
Braverman et al., 1997, "Human PEX7 encodes the peroxisomal PTS2 receptor and is responsible for rhizomelic chondrodysplasia punctuata", Nature Genetics, vol. 15, No. 4, pp. 269-376.
Danielsen EH et al. (2000): "The DaNex study of embryonic mesencephalic, dopaminergic tissue grafted to a minipig model of Parkinson's disease: Preliminary findings of effect of MPTPpoisoning on striatal dopaminergic markers"; Cell Transplantation; vol. 9, No. 2, pp. 247-259; Mar. 1, 2000.
Forlino, 2005, "A diastrophic dysplasia sulfate transporter (SLC26A2) mutant mouse: morphological and biochemical characterization of the resulting chondrodysplasia phenotype", Human Molecular Genetics, vol. 14, No. 6, pp. 859-871.
Kragh PM et al.: "Hemizygous minipigs produced by random gene insertion and handmade cloning express the Alzheimer's diseasecausing dominant mutation APPsw"; Transgenic Research; vol. 18, No. 4, pp. 545-558; 2009.
Yang et al., 2010, "Expression of Huntington's disease protein results in apoptotic neurons in the brains of cloned transgenic pigs", Human Molecular Genetics, vol. 19, No. 20, pp. 3983-3994.

* cited by examiner

```
1    ATGGCGACGA AGGCCGTGTG TGTGCTGAAG GGCGACGGCC CGGTGCAGGG CACCATCTAC
61   TTCGAGCTGA AGGGAGAGAA GACAGTGTTA GTAACGGGAA CCATTAAAGG ACTGGCTGAA
121  GGTGATCATG GATTCCATGT CCATCAGTTT GGAGATAATA CACAAGGCTG TACCAGTGCA
181  GGTCCTCACT TCAATCCTGA ATCCAAAAAA CATGGTGGGC CAAAGGATCA AGAGAGGCAC
241  GTTGGAGACC TGGGCAATGT GACTGCTGGC AAAGATGGTG TGGCCACTGT GTACATCGAA
301  GATTCTGTGA TCGCCCTCTC GGGAGACCAT TCCATCATTG GCCGCACAAT GGTGGTCCAT
361  GAAAAACCAG ATGACTTGGG CAGAGGTGGA AATGAAGAAA GTACAAAGAC GGGAAATGCT
421  GGAAGTCGTT TGGCCTGTGG TGTAATTGGG ATCACCCAGT AA
```

Fig. 1

```
1     ATGGCGACGA AGGCCGTGTG TGTGCTGAAG GGCGACGGCC CGGTGCAGGG CACCATCTAC
61    TTCGAGCTGA AGGGAGAGAA GACAGTGTTA GTAACGGGAA CCATTAAAGG ACTGGCTGAA
121   GGTGATCATG GATTCCATGT CCATCAGTTT GGAGATAATA CACAAGGCTG TACCAGTGCA
181   GGTCCTCACT TCAATCCTGA ATCCAAAAAA CATGGTGGGC CAAAGGATCA AGAGAGGCAC
241   GTTGGAGACC TGGGCAATGT GACTGCTGGC AAAGATCGTG TGGCCACTGT GTACATCGAA
301   GATTCTGTGA TCGCCCTCTC GGGAGACCAT TCCATCATTG GCCGCACAAT GGTGGTCCAT
361   GAAAAACCAG ATGACTTGGG CAGAGGTGGA AATGAAGAAA GTACAAAGAC GGGAAATGCT
421   GGAAGTCGTT TGGCCTGTGG TGTAATTGGG ATCACCCAGT AA
```

Fig. 2

```
M.musculus     MAMKAVCVLKGDGPVQGTIHFEQKASGEPVVLSGQITGLTEGQHGFHVHQYGDNTQGCTS 60
R.norvegicus   MAMKAVCVLKGDGPVQGVIHFEQKASGEPVVVSGQITGLTEGEHGFHVHQYGDNTQGCTT 60
H.sapiens      MATKAVCVLKGDGPVQGIINFEQKESNGPVKVWGSIKGLTEGLHGFHVHEFGDNTAGCTS 60
s.scrofa       MATKAVCVLKGDGPVQGTIYFELK-GEKTVLVTGTIKGLAEGDHGFHVHQFGDNTQGCTS 59
               ** ************** * ** *  . .* : * *.**:** ******::**** ***:

M.musculus     AGPHFNPHSKKHGGPADEERHVGDLGNVTAGKDGVANVSIEDRVISLSGEHSIIGRTMVV 120
R.norvegicus   AGPHFNPHSKKHGGPADEERHVGDLGNVAAGKDGVANVSIEDRVISLSGEHSIIGRTMVV 120
H.sapiens      AGPHFNPLSRKHGGPKDEERHVGDLGNVTADKDGVADVSIEDSVISLSGDHCIIGRTLVV 120
S.scrofa       AGPHFNPESKKHGGPKDQERHVGDLGNVTAGKDGVATVYIEDSVIALSGDHSIIGRTMVV 119
               ******* *:***** *:**********:*.***** * *** **:***:*.*****:**

M.musculus     HEKQDDLGKGGNEESTKTGNAGSRLACGVIGIAQ 154
R.norvegicus   HEKQDDLGKGGNEESTKTGNAGSRLACGVIGIAQ 154
H.sapiens      HEKADDLGKGGNEESTKTGNAGSRLACGVIGIAQ 154
S.scrofa       HEKPDDLGRGGNEESTKTGNAGSRLACGVIGITQ 153
                 *** ****:***********************.*
```

Fig. 3

```
1    cagtctgtta gggggaggag cttatttctc cattccggtg tgatccagga acagctgttt
61   tccctccagc tctgaaagtg tggggtaaag gaattcatta gccatggatg tattcatgaa
121  aggactttca aaagccaagg agggagtcgt ggctgctgct gaaaaaacca aacagggtgt
181  ggcagaagca gcgggaaaga caaaagaggg tgtgctctat gtaggatcca aaaccaagga
241  aggagtggtt catggtgtga caacagtggc tgagaagacc aaagagcaag tgacaaatgt
301  tggagaggca gtggtgacag ggggtgacagc ggtagcacag aagacagtgg aaggagcagg
361  gagcattgca gctgccactg gctttggcaa aaaggatcag ctgggcaaga atgaagaagg
421  agccccccag gagggaattc tggaagatat gcctgtggat cctgacaatg aagcttatga
481  aatgccttcc gaggaagggt atcaggacta tgaaccggaa gcctaagggg tatctttgct
541  cccagtttcc tgagatctgc tgacagacgt gccatcctgt ccaagtgccc cgttcccacc
601  tgcccagtcg tgaccttctc tcaacgcttt cacagtgtct tttgaagtct tccatgagca
661  gtgactggag tatctgtacc cgccccacct cggttccggt gcttccctct cactgaatat
721  atggtagcag ggtcttgtgt gctgtggctg ttgtggcttc gaacctaaaa tgtttaatga
781  aaaacaccta agtgactacc acttatttct aaatctattt tttgttgctg ttgagaaatt
841  gtgagtgatt tactctccta agatttaaaa gtgtcttttc aggattccgt cgaagaataa
901  tgatgtatgg cgaaatttgt taatatatac aatacttaaa catgtgagca tggaactatg
961  cacctataaa tattaactat ag
```

Fig. 16

```
                                        ↓
SsSNCA    MDVFMKGLSKAKEGVVAAAEKTKQGVAEAAGKTKEGVLYVGSKTKEGVVHGVTTVAEKTK    60
HsSNCA    MDVFMKGLSKAKEGVVAAAEKTKQGVAEAAGKTKEGVLYVGSKTKEGVVHGVATVAEKTK    60
BtSNCA    MDVFMKGLSKAKEGVVAAAEKTKQGVAEAAGRTKEGVLYVGSKTKEGVVHGVTTVAEKTK    60
MmSNCA    MDVFMKGLSKAKEGVVAAAEKTKQGVAEAAGKTKEGVLYVGSKTKEGVVHGVTTVAETTK    60
RnSNCA    MDVFMKGLSKAKEGVVAAAEKTKQGVAEAAGKTKEGVLYVGSKTKEGVVHGVTTVAEKTK    60
XlSNCA    MDVFMKGLSKAKEGVVAAAEKTKQGVAEAAGKTKEGVLYVGSKTKEGVVHGVTTVAEKTK    60
GgSNCA    MDVFMKGLNKAKEGVVAAAEKTKQGVAEAAGKTKEGVLYVGSRTKEGVVHGVTTVAEKTK    60
          ******** ********************* ********** ********* **** **

SsSNCA    EQVTNVGEAVVTGVTAVAQKTVEGAGSIAAATGFGKKDQLGK-NEEGAPQEGILE---DM   116
HsSNCA    EQVTNVGGAVVTGVTAVAQKTVEGAGSIAAATGFVKKDQLGK-NEEGAPQEGILE---DM   116
BtSNCA    EQVTNVGEAVVTGVTAVAQKTVEGAGSIAAATGFGKKDHMGK-GEEGASQEGILE---DM   116
MmSNCA    EQVTNVGGAVVTGVTAVAQKTVEGAGNIAAATGFVKKDQMGK-GEEGYPQEGILE---DM   116
RnSNCA    EQVTNVGGAVVTGVTAVAQKTVEGAGNIAAATGFVKKDQMGK-GEEGYPQEGILE---DM   116
XlSNCA    EQVSNVGGAVVTGVTAVAHKTVEGAGNFAAATGLVKKDQ-K--NESGFGPEGTMENSENM   117
GgSNCA    EQVSNVGGAVVTGVTAVAQKTVEGAGNIAAATGLVKKDQLAKQNEEGFLQEGMVNNT-DI   119
          *** *** ********** *******  *****  ***       * *   **

SsSNCA    PVDPDNEAYEMPSEEGYQDYEPEA 140
HsSNCA    PVDPDNEAYEMPSEEGYQDYEPEA 140
BtSNCA    PVDPDNEAYEMPSEEGYQDYEPEA 140
MmSNCA    PVDPGSEAYEMPSEEGYQDYEPEA 140
RnSNCA    PVDPSSEAYEMPSEEGYQDYEPEA 140
XlSNCA    PVNPNNETYEMPPEEEYQDYDPEA 141
GgSNCA    PVDPENEAYEMPPEEEYQDYEPEA 143
          ** *  * **** ** **** ***

                                        ↓
```

```
  1   cagtctgtta gggggaggag cttatttctc cattccggtg tgatccagga acagctgttt
 61   tccctccagc tctgaaagtg tggggtaaag gaattcatta gccatggatg tattcatgaa
121   aggactttca aaagccaagg agggagtcgt ggctgctgct gaaaaaacca aacagggtgt
181   ggcagaagca ccgggaaaga caaaagaggg tgtgctctat gtaggatcca aaaccaagga
241   aggagtggtt catggtgtga caacagtggc tgagaagacc aaagagcaag tgacaaatgt
301   tggagaggca gtggtgacag ggtgacagc ggtagcacag aagacagtgg aaggagcagg
361   gagcattgca gctgccactg gctttggcaa aaaggatcag ctgggcaaga atgaagaagg
421   agcccccag gagggaattc tggaagatat gcctgtggat cctgacaatg aagcttatga
481   aatgccttcc gaggaagggt atcaggacta tgaaccggaa gcctaagggg tatctttgct
541   cccagtttcc tgagatctgc tgacagacgt gccatcctgt ccaagtgccc cgttcccacc
601   tgcccagtcg tgaccttctc tcaacgcttt cacagtgtct tttgaagtct tccatgagca
661   gtgactggag tatctgtacc cgccccacct cggttccggt gcttccctct cactgaatat
721   atggtagcag ggtcttgtgt gctgtggctg ttgtggcttc gaacctaaaa tgtttaatga
781   aaaacaccta agtgactacc acttatttct aaatctattt tttgttgctg ttgagaaatt
841   gtgagtgatt tactctccta agatttaaaa gtgtcttttc aggattccgt cgaagaataa
901   tgatgtatgg cgaaatttgt taatatatac aatacttaaa catgtgagca tggaactatg
961   cacctataaa tattaactat ag
```

Fig. 19

A B
Comparison to normal minipig brain
CK1 Minipig
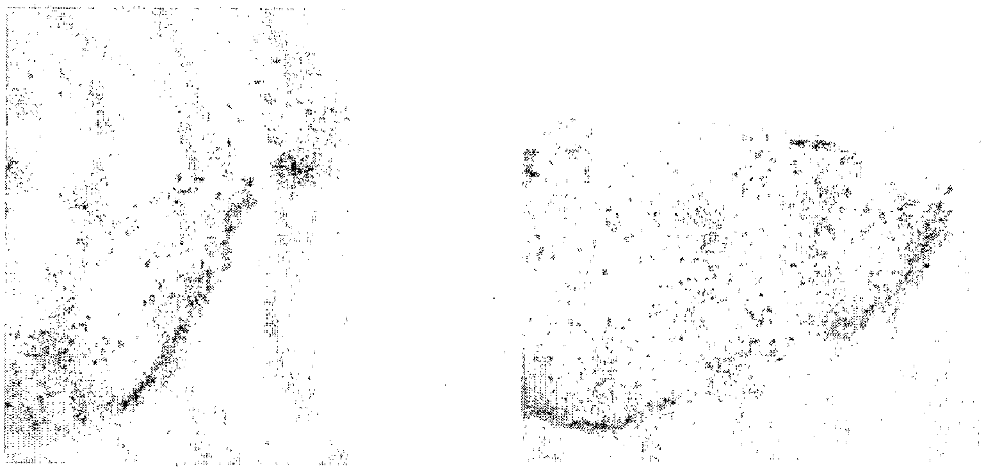
The number of dopaminergic cells seems to be reduced
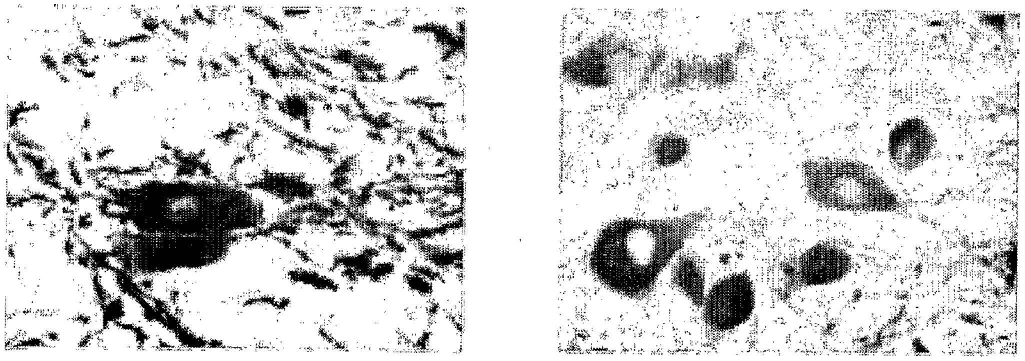
The remaining dopaminergic cells and neuropil seems to be more rough and unordered
Fig. 25

CK1, GFAB-staining
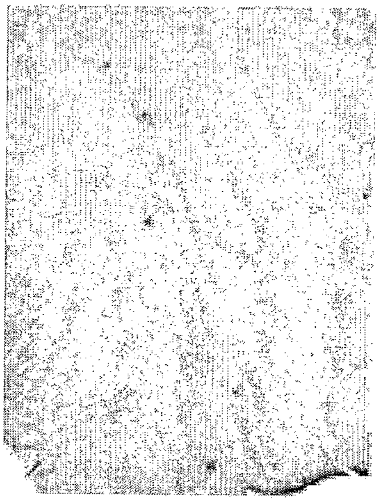
Patches of intense GFAB-staining is noted the mesencephalon.
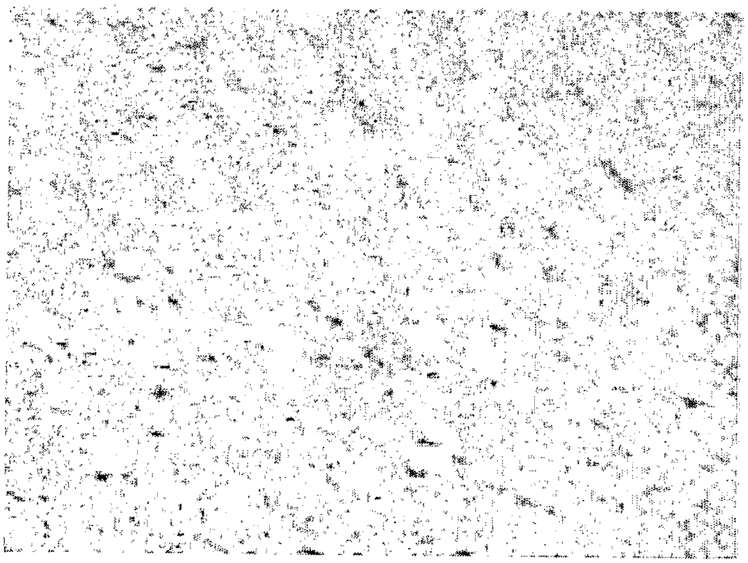
Numerous astrocyttes is noted indicative of active inflammation and reactive gliosis.
Fig. 26

Patches of large alfasynuclein aggregates are visible throughout the mesencephalon Alfasynuclein is located in the cell bodies and extracellular surroundings

```
                                                   Q
S.scrofa   PSEN1 MTELPAPLSYFQNAQMSEDNHVSNNVSSQNDSRERHEHSIERRRRGNSESLSNGGAQGNS 60
B.taurus   PSEN1 MTELPAPLSYFQNAQMSEDNHLSNTVRSQNDSRERHEHGNERRRRGNTESVSNGRAPSSS 60
H.sapiens  PSEN1 MTELPAPLSYFQNAQMSEDNHLSNTVRSQNDNRERQEH-NDRRSLGHPEPLSNGRPQGNS 59
M.musculus PSEN1 MTEIPAPLSYFQNAQMSEDSHSSSAIRSQNDSQERQQQ-HDRQRLDNPEPISNGRPQSNS 59
                 ***:***************.* *. : ****.:**:::  :*:  .:.*.:*** . ..*
                                    +  +  +   +  + + +        +       + +++
S.scrofa   PSEN1 RQVVEQEEEEDEELTLKYGAKHVIMLFVPVTLCMVVVVATIKSVSFYTRKDGQLIYTPFT 120
B.taurus   PSEN1 QQVVEQEEEEDEELTLKYGAKHVIMLFVPVTLCMVVVVATIKSVSFYTRKDGQLIYTPFT 120
H.sapiens  PSEN1 RQVVEQDEEEDEELTLKYGAKHVIMLFVPVTLCMVVVVATIKSVSFYTRKDGQLIYTPFT 119
M.musculus PSEN1 RQVVEQDEEEDEELTLKYGAKHVIMLFVPVTLCMVVVVATIKSVSFYTRKDGQLIYTPFT 119
                 :*****:*****************************************************
                 +  +           +   +   +  ++     ++        + ++  +++ ++S ++
S.scrofa   PSEN1 EDTETVGQRALHSILNAAIMISVIVVMTILLVVLYKYRCYKVIHAWLIISSLLLLFFFSF 180
B.taurus   PSEN1 EDTETVAQRALHSILNAVIMISVIVIMTILLVVLYKYRCYKVIHAWLIVSSLLLLFFFSF 180
H.sapiens  PSEN1 EDTETVGQRALHSILNAAIMISVIVVMTILLVVLYKYRCYKVIHAWLIISSLLLLFFFSF 179
M.musculus PSEN1 EDTETVGQRALHSILNAAIMISVIVIMTILLVVLYKYRCYKVIHAWLIISSLLLLFFFSF 179
                 ******.**********.*******:**********************:***********
                    ++                     +  +   ++  + +  +   +  + + + + +
S.scrofa   PSEN1 IYLGEVFKTYNVAMDYITVALLIWNFGVVGMIAIHWKGPLRLQQAYLIMISALMALVFIK 240
B.taurus   PSEN1 IYLGEVFKTYNVAMDYISVALLIWNFGVVGMIAIHWKGPLRLQQAYLIMISALMALVFIK 240
H.sapiens  PSEN1 IYLGEVFKTYNVAVDYITVALLIWNFGVVGMISIHWKGPLRLQQAYLIMISALMALVFIK 239
M.musculus PSEN1 IYLGEVFKTYNVAVDYVTVALLIWNFGVVGMIAIHWKGPLRLQQAYLIMISALMALVFIK 239
                 *************:**::**************:***************************
                       +   +     +   +++++  + + ++++   + + + +++
S.scrofa   PSEN1 YLPEWTAWLILAVISVYDLVAVLCPNGPLRLLVETAQERNETLFPALIYSSTMVWLVNMA 300
B.taurus   PSEN1 YLPEWTAWLILAVISVYDLVAVLCPKGPLRMLVETAQERNETLFPALIYSSTMVWLVNMA 300
H.sapiens  PSEN1 YLPEWTAWLILAVISVYDLVAVLCPKGPLRMLVETAQERNETLFPALIYSSTMVWLVNMA 299
M.musculus PSEN1 YLPEWTAWLILAVISVYDLVAVLCPKGPLRMLVETAQERNETLFPALIYSSTMVWLVNMA 299
                 *************************:****:*****************************
                                   G
S.scrofa   PSEN1 EGDPEAQRKVSKNSNYNAQSTG-----------ESQDSVTESDDGGFSEEWEAQRDSRLG 349
B.taurus   PSEN1 EGDPEAQRKVSKNSNYNAQRPANSPVTTTGTESESQDPVTESDDGGFSEEWEAQRDSRLG 360
H.sapiens  PSEN1 EGDPEAQRRVSKNSKYNAESTER----------ESQDTVAENDDGGFSEEWEAQRDSHLG 349
M.musculus PSEN1 EGDPEAQRRVPKNPKYNTQRAER----------ETQDSGSGNDDGGFSEEWEAQRDSHLG 349
                 ********:*.**.:**:: .            *:**. : .***************:**
                     +   +      +           ++  +  + +   +++ +          +   +
S.scrofa   PSEN1 PHHSTAESRSAVQDLSRSIPATEDPEERGVKLGLGDFIFYSVLVGKASATASGDWNTTIA 409
B.taurus   PSEN1 PHHSTAESRSAVQDLSSSILASEDPEERGVKLGLGDFIFYSVLVGKASATASGDWNTTIA 420
H.sapiens  PSEN1 PHRSTPESRAAVQELSSSILAGEDPEERGVKLGLGDFIFYSVLVGKASATASGDWNTTIA 409
M.musculus PSEN1 PHRSTPESRAAVQELSGSILTSEDPEERGVKLGLGDFIFYSVLVGKASATASGDWNTTIA 409
                 **:**.***:***:** ** : **************************************
                 +       +     + +    +  +++  +
S.scrofa   PSEN1 CFVAILIGLCLTLLLLAIFKKALPALPISITFGLVFYFATDYLVQPFMDQLAFHQFYI 467
B.taurus   PSEN1 CFVAILIGLCLTLLLLAIFKKALPALPVSITFGLIFYFATDYLVQPFMDQLAFHQFYI 478
H.sapiens  PSEN1 CFVAILIGLCLTLLLLAIFKKALPALPISITFGLVFYFATDYLVQPFMDQLAFHQFYI 467
M.musculus PSEN1 CFVAILIGLCLTLLLLAIFKKALPALPISITFGLVFYFATDYLVQPFMDQLAFHQFYI 467
                 ***************************:******:***********************
```

Fig. 28

```
S.scrofa   PSEN2 MLTFMASDSEEEVCDERTSLMSAESPTPRSCQEGRQGLEDGESAAQWRSQDSEEDHEE-D 59
B.taurus   PSEN2 MLTFMASDSEEEVCDERTSLMSAESPTPRSCQDGRQGLEDGESAAQWRSQESEEDHEEED 60
H.sapiens  PSEN2 MLTFMASDSEEEVCDERTSLMSAESPTPRSCQEGRQGPEDGENTAQWRSQENEEDGEE-D 59
M.musculus PSEN2 MLAFMASDSEEEVCDERTSLMSAESPTSRSCQEGRPGPEDGESTAQWRTQESEEDCEE-D 59
                 **:************************.****:** * ****.:****:*:.*** ** *

                   +
S.scrofa   PSEN2 PDRYVCSGVPGRPPGLEEELTLKYGAKHVIMLFVPVTLCMIVVVATIKSVRFYTEKNGQL 119
B.taurus   PSEN2 PDRYVCSGVPGRPPGLEEELTLKYGAKHVIMLFVPVTLCMIVVVATIKSVRFYTEKNGQL 120
H.sapiens  PSEN2 PDRYVCSGVPGRPPGLEEELTLKYGAKHVIMLFVPVTLCMIVVVATIKSVRFYTEKNGQL 119
M.musculus PSEN2 PDRYACSGAPGRPSGLEEELTLKYGAKRVIMLFVPVTLCMIVVVATIKSVRFYTEKNGQL 119
                 ****.***.****.*************:********************************

                   +       +          +      +
S.scrofa   PSEN2 IYTPFTEDTPSVGQRLLNSVLNTLIMISVIVVMTIFLVVLYKYRCYKFIHGWLITSSLML 179
B.taurus   PSEN2 IYTPFSEDTPSVGQRLLNSVLNTLIMISVIVTMTIFLVVLYKYRCYKFIHGWLIMSSLML 180
H.sapiens  PSEN2 IYTTFTEDTPSVGQRLLNSVLNTLIMISVIVVMTIFLVVLYKYRCYKFIHGWLIMSSLML 179
M.musculus PSEN2 IYTPFTEDTPSVGQRLLNSVLNTLIMISVIVVMTIFLVVLYKYRCYKFIHGWLIMSSLML 179
                 ***.*:*************************.********************** *****

                                                                +          +
S.scrofa   PSEN2 LFLFTYIYLGEVLKTYNVAMDYPTLFLTVWNFGAVGMVCIHWKGPLVLQQAYLIMISALM 239
B.taurus   PSEN2 LFLFTYIYLGEVLKTYNVAMDYPTLFLTVWNFGAVGMVCIHWKGPLVLQQAYLIMISALM 240
H.sapiens  PSEN2 LFLFTYIYLGEVLKTYNVAMDYPTLLLTVWNFGAVGMVCIHWKGPLVLQQAYLIMISALM 239
M.musculus PSEN2 LFLFTYIYLGEVLKTYNVAMDYPTLFLAVWNFGAVGMVCIHWKGPLALQQAYLIVISALM 239
                 *************************:*:******************.*******:*****

S.scrofa   PSEN2 ALVFIKYLPEWSAWVILGAISVYDLVAVLCPKGPLRMLVETAQERNEPIFPALIYSSAMV 299
B.taurus   PSEN2 ALVFIKYLPEWSAWVILGAISVYDLVAVLCPKGPLRMLVETAQERNEPIFPALIYSSAMV 300
H.sapiens  PSEN2 ALVFIKYLPEWSAWVILGAISVYDLVAVLCPKGPLRMLVETAQERNEPIFPALIYSSAMV 299
M.musculus PSEN2 ALVFIKYLPEWSAWVILGAISVYDLVAVLCPKGPLRMLVETAQERNEPIFPALIYSSAMV 299
                 ************************************************************

                                                   R
S.scrofa   PSEN2 WTVGMAKLDPSSQGALQLPYDPEMEEDSYDSFGEPSYPEVFEPPLPGYPGEELEEEEERG 359
B.taurus   PSEN2 WTVGMAKLDPSSQGALQLPYDPEMEEDSYDSFGEPSYPDVFEPPLPGYPGEELEEEEERG 360
H.sapiens  PSEN2 WTVGMAKLDPSSQGALQLPYDPEMEEDSYDSFGEPSYPEVFEPPLTGYPGEELEEEEERG 359
M.musculus PSEN2 WTVGMAKLDPSSQGALQLPYDPEMEEDSYDSFGEPSYPEAFEAPLPGYPGEELEEEEERG 359
                 **************************************:.**.**.**************

S.scrofa   PSEN2 VKLGLGDFIFYSVLVGKAAATGSGDWNTTLACFVAILIGLCLTLLLLAVFKKALPALPIS 419
B.taurus   PSEN2 VKLGLGDFIFYSVLVGKAAAMGSGDWNTTLACFVAILIGLCLTLLLLAVFKKALPALPIS 420
H.sapiens  PSEN2 VKLGLGDFIFYSVLVGKAAATGSGDWNTTLACFVAILIGLCLTLLLLAVFKKALPALPIS 419
M.musculus PSEN2 VKLGLGDFIFYSVLVGKAAATGNGDWNTTLACFIAILIGLCLTLLLLAVFKKALPALPIS 419
                 ******************** *.**********:**************************

                           +        +
S.scrofa   PSEN2 ITFGLIFYFSTDNLVRPFMDTLASHQLYI 448
B.taurus   PSEN2 ITFGLIFYFSTDNLVRPFMDTLASHQLYI 449
H.sapiens  PSEN2 ITFGLIFYFSTDNLVRPFMDTLASHQLYI 448
M.musculus PSEN2 ITFGLIFYFSTDNLVRPFMDTLASHQLYI 448
                 *****************************
```

Fig. 29

*DMPK:*

| | | | | | | |
|---|---|---|---|---|---|---|
| Pig | | (CTG)4 | | | | |
| Human | | (CTG)n | | | | normal n=5-37 / En>50 |
| Chimp | | (CTG)8 | | GTG | | |
| Dog | CCG | CAG | CCG | CTG | CCG | |
| Rat | (CTA)2 | CTG | CAG | | CCC | |
| Mouse | | CTG | (CAG)2 | CTG | | |

*SCA12:*

| | | | | | | | | |
|---|---|---|---|---|---|---|---|---|
| Pig(Duroc) | CTG | (CAG)n | (CTG)2 | | | | | n=8(0.7), 9(0.3) |
| Pig(Hamp) | CTG | (CAG)n | (CTG)2 | | | | | n=8(0.2), 10(0.8) |
| Pig(Land) | CTG | (CAG)n | (CTG)2 | | | | | n=9 |
| Pig(York) | CTG | (CAG)n | (CTG)2 | | | | | n=9 |
| Pig(Mini) | CTG | (CAG)n | (CTG)2 | | | | | n=9 |
| Human | CTG | (CAG)n | CTG | | | | | normal n=7-28 (10) / En>65 |
| Chimp | CTG | (CAG)11 | CTG | | | | | |
| Dog | N.P. | | | | | | | |
| Rat | CTG | (CAG)4 | | | CAC | (CAG)3 | CTG | |
| Mouse | CTG | (CAG)2 | GAG | (CAG)2 | CAC | (CAG)3 | CTG | |

*FMR1/FRAXA:*

| | | | | | | | | |
|---|---|---|---|---|---|---|---|---|
| Pig(Duroc) | (CGG)n | | | | | | | n=12 (<0.1), 13(0.2), 14 (0.9), 15 (<0.1) |
| Pig(Hamp) | (CGG)n | | | | | | | n= 9(0.2), 13(0.1), 14(0.6), 15(0.1) |
| Pig(Land) | (CGG)n | | | | | | | n=14 |
| Pig(York) | (CGG)n | | | | | | | n=13(0.1), 14(0.4), 15(0.5) |
| Pig(Mini) | (CGG)n | | | | | | | n=12(0.3), 13(0.3), 14(0.4) |
| Human | (CGG)14 | AGG | (CGG)n | | | | | normal n=6-52 / En>200 |
| Chimp | (CGG)9 | AGG | CGG | AGG | (CGG)16 | AGG | CGG | |
| Dog | (CGG)12 | | | | | | | |
| Rat | (CGG)4 | CGA | CGG | | | | | |
| Mouse | (CGG)6 | CGA | (CGG)2 | | | | | |

*FMR2/FRAXE:*

| | | | | | | |
|---|---|---|---|---|---|---|
| Pig | | | (CCG)7 | CTG | CCG | |
| Human | CCG | GAC | (CCG)n | CTG | CCG | normal n=6-35 / En>200 |
| Chimp | N.P. | | | | | |
| Dog | N.P. | | | | | |
| Rat | (CCG)2 | CCA | (CCG)2 | CTG | CCG | |
| Mouse | (CCG)4 | | | (CTG)2 | CCG | |

Fig. 32

*SCA1:*

| | | | |
|---|---|---|---|
| Pig(Duroc) | (CAG)n (CCG)4 CCA CCG CCA CCG CAG | n=1 | Q=2, P=8 |
| Pig(Hamp) | (CAG)n (CCG)4 CCA CCG CCA CCG CAG | n=1 | Q=2, P=8 |
| Pig(Land) | (CAG)n (CCG)4 CCA CCG CCA CCG CAG | n=1 | Q=2, P=8 |
| Pig(York) | (CAG)n (CCG)4 CCA CCG CCA CCG CAG | n=1 | Q=2, P=8 |
| Pig(Mini) | (CAG)n (CCG)4 CCA CCG CCA CCG CAG | n=1(0.2), 2(0.8) | Q=3, P=8 |
| Human | (CAG)n CAT CAG CAT (CAG)m | normal n+m=6-39 (15) / E(n+m)>40 | Q=28, H=2 |
| Chimp | (CAG)10 CAT CAG CAT (CAG)10 | | Q=21, H=2 |
| Dog | (CAG)6 | | Q=6 |
| Opossum | CAG CCG CAG | | Q=2, P=1 |
| Rat | CCC CCT CCG (CAG)2 | | Q=2, P=3 |
| Mouse | CCC CCT CCG (CAG)2 | | Q=2, P=3 |

*SCA2:*

| | | | |
|---|---|---|---|
| Pig | (CAG)2 (CAA)2 (CAG)5 | | Q=9 |
| Human | (CAG)n CAA (CAG)4 CAA (CAG)m (CCG)2 | normal n+m=13-33 (15) / E(n+m)>34 | Q=21, P=2 |
| Chimp | (CAG)9 (CAA)6 (CAG)3 CAA (CAG)7 (CCG)2 | | Q=26, P=2 |
| Dog | CAG CAA (CAG)5 (CCG)2 (CAG)2 CCG CAG (CCG)2 | | Q=10, P=5 |
| Opossum | N.P. | | |
| Rat | CAG CCG CAG CCG | | Q=2, P=2 |
| Mouse | CAG CCG CAG CCG | | Q=2, P=2 |

*SCA3:*

| | | | |
|---|---|---|---|
| Pig(Duroc) | (CAG)n CAA | n=6 | Q=7 |
| Pig(Hamp) | (CAG)n CAA | n=6 | Q=7 |
| Pig(Land) | (CAG)n CAA | n=6 | Q=7 |
| Pig(York) | (CAG)n CAA | n=5(0.2), 6(0.8) | Q=6,7 |
| Pig(Mini) | (CAG)n CAA | n=5(0.5), 6(0.5) | Q=6,7 |
| Human | (CAG)2 CAA AAG CAG CAA (CAG)n | normal n=12-36 (15) / En>54 | Q=14 |
| Chimp | (CAG)5 CAA AAG CAG CAA (CAG)11 | | Q=19 |
| Dog | (CAG)2 (CAA)2 (CAG)6 CAA CAG | | Q=12 |
| Opossum | N.P. | | |
| Rat | CAA CAG CAT CAG CAA CAG GAA | | Q=6 |
| Mouse | CAA (CAG)5 GAG | | Q=6 |

*SCA6:*

| | | | |
|---|---|---|---|
| Pig(Duroc) | (CAG)n CAA (CAG)4 | n=5 | Q=10 |
| Pig(Hamp) | (CAG)n CAA (CAG)4 | n=5 | Q=10 |
| Pig(Land) | (CAG)n CAA (CAG)4 | n=5 | Q=10 |
| Pig(York) | (CAG)n CAA (CAG)4 | n=5 | Q=10 |
| Pig(Mini) | (CAG)n CAA (CAG)4 | n=7(0.5), 9(0.5) | Q=12,14 |
| Human | (CAG)n | normal n=4-18 (13) / En>20 | Q=13 |
| Chimp | (CAG)11 | | Q=11 |
| Dog | (CAG)10 | | Q=10 |
| Opossum | CAG (CCG)2 CAG CCG CCA CAG | | Q=3, P=4 |
| Rat | N.P. | | |
| Mouse | N.P. | | |

*SCA7:*

| | | | |
|---|---|---|---|
| Pig | (CAG)5 | | Q=5 |
| Human | (CAG)n | normal n=7-35 (10) / En>37 | Q=10 |
| Chimp | (CAG)8 | | Q=8 |
| Dog | (CAG)8 | | Q=8 |
| Opposum | (CAG)2 CAC CAG CAC CAG (CAC)2 (CAG)4 | | Q=8, H=4 |
| Rat | (CAG)4 | | Q=4 |
| Mouse | (CAG)5 | | Q=5 |

Fig. 33

*DRPLA:*

| | | | |
|---|---|---|---|
| Pig(Duroc) | CAG CAA (CAG)n CAA CAG CAA CAG (CAA)2 | n=6 | Q=14 |
| Pig(Hamp) | CAG CAA (CAG)n CAA CAG CAA CAG (CAA)2 | n=6 | Q=14 |
| Pig(Land) | CAG CAA (CAG)n CAA CAG CAA CAG (CAA)2 | n=6 | Q=14 |
| Pig(York) | CAG CAA (CAG)n CAA CAG CAA CAG (CAA)2 | n=6 | Q=14 |
| Pig(Mini) | CAG CAA (CAG)n CAA CAG CAA CAG (CAA)2 | n=6(0.7), 7(0.3) | Q=14,15 |
| Human | CAG CAA CAG CAA (CAG)n | normal n=3-25 (13) / En>49 | Q=17 |
| Chimp | CAG CAA CAG CAA (CAG)12 | | Q=16 |
| Dog | (CAG)8 CAA CAG CAA CAG | | Q=12 |
| Opossum | (CAG)6 CAA CAG | | Q=8 |
| Rat | (CAG)5 (CCA CAG)4 CCG (CAA)2 | | Q=11, P=5 |
| Mouse | (CAG)3 CCA CAG (CAA)2 | | Q=6, P=1 |

*SCA17:*

| | | | |
|---|---|---|---|
| Pig | (CAG)4 CAA (CAG)6 CAA (CAG)10 CAA | | Q=26 |
| | (CAG)3 | | |
| Human | (CAG)3 (CAA)3 (CAG)8 CAA CAG CAA (CAG)n CAA CAG | n=9-22 (18) En>26 | Q=38 |
| Chimp | (CAG)3 (CAA)3 (CAG)25 CAA CAG | | Q=30 |
| Dog | CAA (CAG)6 GCC (CAG)4 GCC (CAG)5 CAA (CAG)2 GCC | | Q=22 |
| | (CAG)3 | | |
| Opossum | (CAG)8 CAA (CAG)2 CAA | | Q=12 |
| Rat | (CAG)8 CAA (CAG)3 CAA (CAG)2 | | Q=14 |
| Mouse | (CAG)3 CAA CAG CAA (CAG)3 (CAA)2 (CAG)2 | | Q=13 |

*SBMA:*

| | | | |
|---|---|---|---|
| Pig | (CAG)4 CTG (CAG)3 | | Q=7 |
| Human | (CAG)n CAA | normal n=11-37 (22) / En>37 | Q=23 |
| Chimp | (CAG)21 CAA | | Q=22 |
| Dog | (CAG)10 | | Q=10 |
| Opossum | (CAG) CAC (CAG)7 | | Q=8 |
| Rat | (CAG)2 CGG CAG | | Q=3 |
| Mouse | (CAG)2 AGG CAG | | Q=3 |

*Huntingtin:*

| | | | |
|---|---|---|---|
| Pig(Duroc) | (CAG)n CAA (CAG)2 | n=14(0.6), 21(0.2) | Q=17, 24 |
| | (CAG)5 CAA (CAG)8 CAA (CAG)2 | (0.2) | Q=17 |
| Pig(Hamp) | (CAG)n CAA (CAG)2 | N=14(0.7), 15(0.3) | Q=17, 18 |
| Pig(Land) | (CAG)14 CAA (CAG)2 | (0.8) | Q=17 |
| | (CAG)5 CAA (CAG)9 CAA (CAG)2 | (0.2) | Q=18 |
| Pig(York) | (CAG)14 CAA (CAG)2 | (0.5) | Q=17 |
| | (CAG)5 CAA (CAG)n CAA (CAG)2 | n=4(0.2), 7(0.1), 8(0.2) | Q=13,16,17 |
| Pig(Mini) | (CAG)14 CAA (CAG)2 | (0.2) | Q=17 |
| | (CAG)5 CAA (CAG)n CAA (CAG)2 | n=8(0.2), 9(0.6) | Q=17,18 |
| Human | (CAG)n CAA CAG | normal n=6-35 (18) / En>35 | Q=20 |
| Chimp | (CAG)13 CAA CAG | | Q=15 |
| Dog | (CAG)4 CAA (CAG)5 | | Q=10 |
| Opossum | (CAG)6 | | Q=6 |
| Rat | (CAG)2 CAA (CAG)5 | | Q=8 |
| Mouse | (CAG)2 CAA (CAG)4 | | Q=7 |

Fig. 33 continued/

SEQUENCE LISTING

```
<160> NUMBER OF SEQ ID NOS: 159

<210> SEQ ID NO 1
<211> LENGTH: 981
<212> TYPE: DNA
<213> ORGANISM: Homo Sapiens

<400> SEQUENCE: 1

gtttggggcc agagtgggcg aggcgcggag gtctggccta taaagtagtc gcggagacgg      60

ggtgctggtt tgcgtcgtag tctcctgcag cgtctggggt ttccgttgca gtcctcggaa     120

ccaggacctc ggcgtggcct agcgagttat ggcgacgaag gccgtgtgcg tgctgaaggg     180
```

```
cgacggccca gtgcagggca tcatcaattt cgagcagaag gaaagtaatg gaccagtgaa    240

ggtgtgggga agcattaaag gactgactga aggcctgcat ggattccatg ttcatgagtt    300

tggagataat acagcaggct gtaccagtgc aggtcctcac tttaatcctc tatccagaaa    360

acacggtggg ccaaaggatg aagagaggca tgttggagac ttgggcaatg tgactgctga    420

caaagatggt gtggccgatg tgtctattga agattctgtg atctcactct caggagacca    480

ttgcatcatt ggccgcacac tggtggtcca tgaaaaagca gatgacttgg gcaaaggtgg    540

aaatgaagaa agtacaaaga caggaaacgc tggaagtcgt ttggcttgtg gtgtaattgg    600

gatcgcccaa taaacattcc cttggatgta gtctgaggcc ccttaactca tctgttatcc    660

tgctagctgt agaaatgtat cctgataaac attaaacact gtaatcttaa aagtgtaatt    720

gtgtgacttt ttcagagttg ctttaaagta cctgtagtga gaaactgatt tatgatcact    780

tggaagattt gtatagtttt ataaaactca gttaaaatgt ctgtttcaat gacctgtatt    840

ttgccagact taaatcacag atgggtatta aacttgtcag aatttctttg tcattcaagc    900

ctgtgaataa aaaccctgta tggcacttat tatgaggcta ttaaaagaat ccaaattcaa    960

actaaaaaaa aaaaaaaaaa a                                              981


<210> SEQ ID NO 2
<211> LENGTH: 154
<212> TYPE: PRT
<213> ORGANISM: Homo Sapiens

<400> SEQUENCE: 2

Met Ala Thr Lys Ala Val Cys Val Leu Lys Gly Asp Gly Pro Val Gln
1               5                   10                  15

Gly Ile Ile Asn Phe Glu Gln Lys Glu Ser Asn Gly Pro Val Lys Val
            20                  25                  30

Trp Gly Ser Ile Lys Gly Leu Thr Glu Gly Leu His Gly Phe His Val
        35                  40                  45

His Glu Phe Gly Asp Asn Thr Ala Gly Cys Thr Ser Ala Gly Pro His
    50                  55                  60

Phe Asn Pro Leu Ser Arg Lys His Gly Gly Pro Lys Asp Glu Glu Arg
65                  70                  75                  80

His Val Gly Asp Leu Gly Asn Val Thr Ala Asp Lys Asp Gly Val Ala
                85                  90                  95

Asp Val Ser Ile Glu Asp Ser Val Ile Ser Leu Ser Gly Asp His Cys
            100                 105                 110

Ile Ile Gly Arg Thr Leu Val Val His Glu Lys Ala Asp Asp Leu Gly
        115                 120                 125

Lys Gly Gly Asn Glu Glu Ser Thr Lys Thr Gly Asn Ala Gly Ser Arg
    130                 135                 140

Leu Ala Cys Gly Val Ile Gly Ile Ala Gln
145                 150


<210> SEQ ID NO 3
<211> LENGTH: 462
<212> TYPE: DNA
<213> ORGANISM: Porcine

<400> SEQUENCE: 3

atggcgacga aggccgtgtg tgtgctgaag ggcgacggcc cggtgcaggg caccatctac     60

ttcgagctga agggagagaa gacagtgtta gtaacgggaa ccattaaagg actggctgaa    120

ggtgatcatg gattccatgt ccatcagttt ggagataata cacaaggctg taccagtgca    180
```

```
ggtcctcact tcaatcctga atccaaaaaa catggtgggc caaaggatca agagaggcac    240

gttggagacc tgggcaatgt gactgctggc aaagatggtg tggccactgt gtacatcgaa    300

gattctgtga tcgccctctc gggagaccat tccatcattg gccgcacaat ggtggtccat    360

gaaaaaccag atgacttggg cagaggtgga aatgaagaaa gtacaaagac gggaaatgct    420

ggaagtcgtt tggcctgtgg tgtaattggg atcacccagt aa                       462


<210> SEQ ID NO 4
<211> LENGTH: 153
<212> TYPE: PRT
<213> ORGANISM: Porcine

<400> SEQUENCE: 4

Met Ala Thr Lys Ala Val Cys Val Leu Lys Gly Asp Gly Pro Val Gln
1               5                   10                  15

Gly Thr Ile Tyr Phe Glu Leu Lys Gly Glu Lys Thr Val Leu Val Thr
            20                  25                  30

Gly Thr Ile Lys Gly Leu Ala Glu Gly Asp His Gly Phe His Val His
        35                  40                  45

Gln Phe Gly Asp Asn Thr Gln Gly Cys Thr Ser Ala Gly Pro His Phe
    50                  55                  60

Asn Pro Glu Ser Lys Lys His Gly Gly Pro Lys Asp Gln Glu Arg His
65                  70                  75                  80

Val Gly Asp Leu Gly Asn Val Thr Ala Gly Lys Asp Gly Val Ala Thr
                85                  90                  95

Val Tyr Ile Glu Asp Ser Val Ile Ala Leu Ser Gly Asp His Ser Ile
            100                 105                 110

Ile Gly Arg Thr Met Val Val His Glu Lys Pro Asp Asp Leu Gly Arg
        115                 120                 125

Gly Gly Asn Glu Glu Ser Thr Lys Thr Gly Asn Ala Gly Ser Arg Leu
    130                 135                 140

Ala Cys Gly Val Ile Gly Ile Thr Gln
145                 150


<210> SEQ ID NO 5
<211> LENGTH: 462
<212> TYPE: DNA
<213> ORGANISM: Porcine

<400> SEQUENCE: 5

atggcgacga aggccgtgtg tgtgctgaag ggcgacggcc cggtgcaggg caccatctac     60

ttcgagctga agggagagaa gacagtgtta gtaacgggaa ccattaaagg actggctgaa    120

ggtgatcatg gattccatgt ccatcagttt ggagataata cacaaggctg taccagtgca    180

ggtcctcact tcaatcctga atccaaaaaa catggtgggc caaaggatca agagaggcac    240

gttggagacc tgggcaatgt gactgctggc aaagatcgtg tggccactgt gtacatcgaa    300

gattctgtga tcgccctctc gggagaccat tccatcattg gccgcacaat ggtggtccat    360

gaaaaaccag atgacttggg cagaggtgga aatgaagaaa gtacaaagac gggaaatgct    420

ggaagtcgtt tggcctgtgg tgtaattggg atcacccagt aa                       462


<210> SEQ ID NO 6
<211> LENGTH: 153
<212> TYPE: PRT
<213> ORGANISM: Porcine

<400> SEQUENCE: 6
```

-continued

```
Met Ala Thr Lys Ala Val Cys Val Leu Lys Gly Asp Gly Pro Val Gln
1               5                   10                  15

Gly Thr Ile Tyr Phe Glu Leu Lys Gly Glu Lys Thr Val Leu Val Thr
            20                  25                  30

Gly Thr Ile Lys Gly Leu Ala Glu Gly Asp His Gly Phe His Val His
        35                  40                  45

Gln Phe Gly Asp Asn Thr Gln Gly Cys Thr Ser Ala Gly Pro His Phe
    50                  55                  60

Asn Pro Glu Ser Lys Lys His Gly Gly Pro Lys Asp Gln Glu Arg His
65                  70                  75                  80

Val Gly Asp Leu Gly Asn Val Thr Ala Gly Lys Asp Arg Val Ala Thr
                85                  90                  95

Val Tyr Ile Glu Asp Ser Val Ile Ala Leu Ser Gly Asp His Ser Ile
            100                 105                 110

Ile Gly Arg Thr Met Val Val His Glu Lys Pro Asp Asp Leu Gly Arg
        115                 120                 125

Gly Gly Asn Glu Glu Ser Thr Lys Thr Gly Asn Ala Gly Ser Arg Leu
    130                 135                 140

Ala Cys Gly Val Ile Gly Ile Thr Gln
145                 150


<210> SEQ ID NO 7
<211> LENGTH: 2763
<212> TYPE: DNA
<213> ORGANISM: Homo Sapiens

<400> SEQUENCE: 7

tgggacaggc agctccgggg tccgcggttt cacatcggaa acaaaacagc ggctggtctg      60

gaaggaacct gagctacgag ccgcggcggc agcggggcgg cggggaagcg tatacctaat     120

ctgggagcct gcaagtgaca acagcctttg cggtccttag acagcttggc ctggaggaga     180

acacatgaaa gaaagaacct caagaggctt tgttttctgt gaaacagtat ttctatacag     240

ttgctccaat gacagagtta cctgcaccgt tgtcctactt ccagaatgca cagatgtctg     300

aggacaacca cctgagcaat actgtacgta gccagaatga caatagagaa cggcaggagc     360

acaacgacag acggagcctt ggccaccctg agccattatc taatggacga ccccagggta     420

actcccggca ggtggtggag caagatgagg aagaagatga ggagctgaca ttgaaatatg     480

gcgccaagca tgtgatcatg ctctttgtcc ctgtgactct ctgcatggtg gtggtcgtgg     540

ctaccattaa gtcagtcagc ttttataccc ggaaggatgg gcagctaatc tataccccat     600

tcacagaaga taccgagact gtgggccaga gagccctgca ctcaattctg aatgctgcca     660

tcatgatcag tgtcattgtt gtcatgacta tcctcctggt ggttctgtat aaatacaggt     720

gctataaggt catccatgcc tggcttatta tatcatctct attgttgctg ttcttttttt     780

cattcattta cttgggggaa gtgtttaaaa cctataacgt tgctgtggac tacattactg     840

ttgcactcct gatctggaat tttggtgtgg tgggaatgat ttccattcac tggaaaggtc     900

cacttcgact ccagcaggca tatctcatta tgattagtgc cctcatggcc ctggtgttta     960

tcaagtacct ccctgaatgg actgcgtggc tcatcttggc tgtgatttca gtatatgatt    1020

tagtggctgt tttgtgtccg aaaggtccac ttcgtatgct ggttgaaaca gctcaggaga    1080

gaaatgaaac gctttttcca gctctcattt actcctcaac aatggtgtgg ttggtgaata    1140

tggcagaagg agacccggaa gctcaaagga gagtatccaa aaattccaag tataatgcag    1200

aaagcacaga aagggagtca caagacactg ttgcagagaa tgatgatggc gggttcagtg    1260
```

```
aggaatggga agcccagagg gacagtcatc tagggcctca tcgctctaca cctgagtcac   1320

gagctgctgt ccaggaactt tccagcagta tcctcgctgg tgaagaccca gaggaaaggg   1380

gagtaaaact tggattggga gatttcattt tctacagtgt tctggttggt aaagcctcag   1440

caacagccag tggagactgg aacacaacca tagcctgttt cgtagccata ttaattggtt   1500

tgtgccttac attattactc cttgccattt tcaagaaagc attgccagct cttccaatct   1560

ccatcacctt tgggcttgtt ttctactttg ccacagatta tcttgtacag ccttttatgg   1620

accaattagc attccatcaa ttttatatct agcatatttg cggttagaat cccatggatg   1680

tttcttcttt gactataaca aaatctgggg aggacaaagg tgattttcct gtgtccacat   1740

ctaacaaagt caagattccc ggctggactt ttgcagcttc cttccaagtc ttcctgacca   1800

ccttgcacta ttggactttg gaaggaggtg cctatagaaa acgattttga acatacttca   1860

tcgcagtgga ctgtgtccct cggtgcagaa actaccagat ttgagggacg aggtcaagga   1920

gatatgatag gcccggaagt tgctgtgccc catcagcagc ttgacgcgtg gtcacaggac   1980

gatttcactg acactgcgaa ctctcaggac taccgttacc aagaggttag gtgaagtggt   2040

ttaaaccaaa cggaactctt catcttaaac tacacgttga aaatcaaccc aataattctg   2100

tattaactga attctgaact tttcaggagg tactgtgagg aagagcaggc accagcagca   2160

gaatggggaa tggagaggtg ggcaggggtt ccagcttccc tttgattttt tgctgcagac   2220

tcatcctttt taaatgagac ttgttttccc ctctctttga gtcaagtcaa atatgtagat   2280

tgcctttggc aattcttctt ctcaagcact gacactcatt accgtctgtg attgccattt   2340

cttcccaagg ccagtctgaa cctgaggttg ctttatccta aaagttttaa cctcaggttc   2400

caaattcagt aaattttgga aacagtacag ctatttctca tcaattctct atcatgttga   2460

agtcaaattt ggattttcca ccaaattctg aatttgtaga catacttgta cgctcacttg   2520

ccccagatgc ctcctctgtc ctcattcttc tctcccacac aagcagtctt tttctacagc   2580

cagtaaggca gctctgtcgt ggtagcagat ggtcccatta ttctagggtc ttactctttg   2640

tatgatgaaa agaatgtgtt atgaatcggt gctgtcagcc ctgctgtcag accttcttcc   2700

acagcaaatg agatgtatgc ccaaagcggt agaattaaag aagagtaaaa tggctgttga   2760

agc                                                                 2763
```

<210> SEQ ID NO 8
<211> LENGTH: 467
<212> TYPE: PRT
<213> ORGANISM: Homo Sapiens

<400> SEQUENCE: 8

```
Met Thr Glu Leu Pro Ala Pro Leu Ser Tyr Phe Gln Asn Ala Gln Met
1               5                   10                  15

Ser Glu Asp Asn His Leu Ser Asn Thr Val Arg Ser Gln Asn Asp Asn
            20                  25                  30

Arg Glu Arg Gln Glu His Asn Asp Arg Arg Ser Leu Gly His Pro Glu
        35                  40                  45

Pro Leu Ser Asn Gly Arg Pro Gln Gly Asn Ser Arg Gln Val Val Glu
    50                  55                  60

Gln Asp Glu Glu Glu Asp Glu Glu Leu Thr Leu Lys Tyr Gly Ala Lys
65                  70                  75                  80

His Val Ile Met Leu Phe Val Pro Val Thr Leu Cys Met Val Val Val
                85                  90                  95

Val Ala Thr Ile Lys Ser Val Ser Phe Tyr Thr Arg Lys Asp Gly Gln
```

-continued

```
            100                 105                 110

Leu Ile Tyr Thr Pro Phe Thr Glu Asp Thr Glu Thr Val Gly Gln Arg
        115                 120                 125

Ala Leu His Ser Ile Leu Asn Ala Ala Ile Met Ile Ser Val Ile Val
    130                 135                 140

Val Met Thr Ile Leu Leu Val Val Leu Tyr Lys Tyr Arg Cys Tyr Lys
145                 150                 155                 160

Val Ile His Ala Trp Leu Ile Ile Ser Ser Leu Leu Leu Leu Phe Phe
                165                 170                 175

Phe Ser Phe Ile Tyr Leu Gly Glu Val Phe Lys Thr Tyr Asn Val Ala
            180                 185                 190

Val Asp Tyr Ile Thr Val Ala Leu Leu Ile Trp Asn Phe Gly Val Val
        195                 200                 205

Gly Met Ile Ser Ile His Trp Lys Gly Pro Leu Arg Leu Gln Gln Ala
    210                 215                 220

Tyr Leu Ile Met Ile Ser Ala Leu Met Ala Leu Val Phe Ile Lys Tyr
225                 230                 235                 240

Leu Pro Glu Trp Thr Ala Trp Leu Ile Leu Ala Val Ile Ser Val Tyr
                245                 250                 255

Asp Leu Val Ala Val Leu Cys Pro Lys Gly Pro Leu Arg Met Leu Val
            260                 265                 270

Glu Thr Ala Gln Glu Arg Asn Glu Thr Leu Phe Pro Ala Leu Ile Tyr
        275                 280                 285

Ser Ser Thr Met Val Trp Leu Val Asn Met Ala Glu Gly Asp Pro Glu
    290                 295                 300

Ala Gln Arg Arg Val Ser Lys Asn Ser Lys Tyr Asn Ala Glu Ser Thr
305                 310                 315                 320

Glu Arg Glu Ser Gln Asp Thr Val Ala Glu Asn Asp Asp Gly Gly Phe
                325                 330                 335

Ser Glu Glu Trp Glu Ala Gln Arg Asp Ser His Leu Gly Pro His Arg
            340                 345                 350

Ser Thr Pro Glu Ser Arg Ala Ala Val Gln Glu Leu Ser Ser Ser Ile
        355                 360                 365

Leu Ala Gly Glu Asp Pro Glu Glu Arg Gly Val Lys Leu Gly Leu Gly
    370                 375                 380

Asp Phe Ile Phe Tyr Ser Val Leu Val Gly Lys Ala Ser Ala Thr Ala
385                 390                 395                 400

Ser Gly Asp Trp Asn Thr Thr Ile Ala Cys Phe Val Ala Ile Leu Ile
                405                 410                 415

Gly Leu Cys Leu Thr Leu Leu Leu Leu Ala Ile Phe Lys Lys Ala Leu
            420                 425                 430

Pro Ala Leu Pro Ile Ser Ile Thr Phe Gly Leu Val Phe Tyr Phe Ala
        435                 440                 445

Thr Asp Tyr Leu Val Gln Pro Phe Met Asp Gln Leu Ala Phe His Gln
    450                 455                 460

Phe Tyr Ile
465
```

<210> SEQ ID NO 9
<211> LENGTH: 1720
<212> TYPE: DNA
<213> ORGANISM: Porcine

<400> SEQUENCE: 9
aatcggaaac aaaacagcgg ctgctgggga agggacctgg gctgcgagag gtggcggctg     60

-continued

```
cgacgagaaa gaacctaatc cgggagcctg caacctgtga agttcttaga aagcttggcc    120

tggaggagaa cacatgaaag aaagaacccc aggaggctct gatttctgtg aaaaagtatt    180

tctatacggt tgttccaatg acagagttac ctgcaccctt gtcctacttc cagaatgccc    240

agatgtccga ggacaaccac gtgagcaata acgtaagtag ccagaatgac agtagagagc    300

ggcatgagca cagcatcgag aggcggaggc gtggcaactc tgagtcgtta tccaatggcg    360

gagcccaggg aaactcacgc caggtggtgg aacaagaaga agaggaagac gaggagctga    420

cgttgaaata tggcgccaaa catgtgatca tgctctttgt ccctgtgact ctatgtatgg    480

tggtggttgt ggccaccatc aaatcagtca gcttttatac ccggaaggat gggcagctga    540

tctatactcc atttacagaa gacactgaga ctgtagggca gagagccctg cactcaattc    600

tgaatgctgc tatcatgatt agtgtcattg tcgtcatgac tattctcctg gtggttctct    660

ataaatacag gtgctataag gtcatccatg cctggcttat tatttcatcc ctattgttgc    720

tgttcttttt ctcattcatt tacttggggg aagtgtttaa aacctataac gttgccatgg    780

attacattac ggtggcactc ctgatctgga attttggtgt ggtaggaatg attgccattc    840

actggaaagg cccattgcga ctccagcagg catatctcat tatgatcagt gccctcatgg    900

ccctggtgtt tatcaagtac ctcccggaat ggaccgcgtg gctcatcttg gctgtgattt    960

cagtatacga tttagtggct gttttgtgtc caaatggccc acttcgtttg ctggttgaaa   1020

cagctcagga gagaaatgaa actctctttc cagctcttat ttactcgtca acaatggtgt   1080

ggttggtgaa tatggcagaa ggagacccag aagcccaaag gaaggtatcc aaaaactcca   1140

attataatgc acaaagcaca ggtgaatcac aagactctgt gacagagagt gatgatggtg   1200

gcttcagtga agagtgggaa gcccagaggg acagtcgcct gggacctcat cactctacag   1260

ctgagtcacg atctgctgta caggatcttt ccagaagcat cccagccact gaggacccag   1320

aagaaagggg agtaaaactt ggattaggag atttcatttt ctacagtgtt ctggttggta   1380

aagcttctgc aacagccagt ggagactgga acacaaccat tgcctgtttt gtagccatat   1440

taattggttt gtgccttaca ttactgctcc tcgccatttt caagaaagcg ttgccagctc   1500

ttccaatctc tatcaccttt gggcttgttt tctactttgc cacagattat cttgtgcaac   1560

cctttatgga ccaattagca ttccatcaat tttatatcta gcatatttcc agttagaatc   1620

tcatggattt tttctccttt ggctataata aaatctgggg aaagcaaagg tgattttgct   1680

gtgtccacat ctaacaaagt caggattccc agctggacct                          1720
```

```
<210> SEQ ID NO 10
<211> LENGTH: 467
<212> TYPE: PRT
<213> ORGANISM: Porcine

<400> SEQUENCE: 10

Met Thr Glu Leu Pro Ala Pro Leu Ser Tyr Phe Gln Asn Ala Gln Met
1               5                   10                  15

Ser Glu Asp Asn His Val Ser Asn Asn Val Ser Ser Gln Asn Asp Ser
            20                  25                  30

Arg Glu Arg His Glu His Ser Ile Glu Arg Arg Arg Arg Gly Asn Ser
        35                  40                  45

Glu Ser Leu Ser Asn Gly Gly Ala Gln Gly Asn Ser Arg Gln Val Val
    50                  55                  60

Glu Gln Glu Glu Glu Glu Asp Glu Glu Leu Thr Leu Lys Tyr Gly Ala
65                  70                  75                  80
```

-continued

```
Lys His Val Ile Met Leu Phe Val Pro Val Thr Leu Cys Met Val Val
                85                  90                  95

Val Val Ala Thr Ile Lys Ser Val Ser Phe Tyr Thr Arg Lys Asp Gly
            100                 105                 110

Gln Leu Ile Tyr Thr Pro Phe Thr Glu Asp Thr Glu Thr Val Gly Gln
        115                 120                 125

Arg Ala Leu His Ser Ile Leu Asn Ala Ala Ile Met Ile Ser Val Ile
    130                 135                 140

Val Val Met Thr Ile Leu Leu Val Val Leu Tyr Lys Tyr Arg Cys Tyr
145                 150                 155                 160

Lys Val Ile His Ala Trp Leu Ile Ile Ser Ser Leu Leu Leu Leu Phe
                165                 170                 175

Phe Phe Ser Phe Ile Tyr Leu Gly Glu Val Phe Lys Thr Tyr Asn Val
            180                 185                 190

Ala Met Asp Tyr Ile Thr Val Ala Leu Leu Ile Trp Asn Phe Gly Val
        195                 200                 205

Val Gly Met Ile Ala Ile His Trp Lys Gly Pro Leu Arg Leu Gln Gln
    210                 215                 220

Ala Tyr Leu Ile Met Ile Ser Ala Leu Met Ala Leu Val Phe Ile Lys
225                 230                 235                 240

Tyr Leu Pro Glu Trp Thr Ala Trp Leu Ile Leu Ala Val Ile Ser Val
                245                 250                 255

Tyr Asp Leu Val Ala Val Leu Cys Pro Asn Gly Pro Leu Arg Leu Leu
            260                 265                 270

Val Glu Thr Ala Gln Glu Arg Asn Glu Thr Leu Phe Pro Ala Leu Ile
        275                 280                 285

Tyr Ser Ser Thr Met Val Trp Leu Val Asn Met Ala Glu Gly Asp Pro
    290                 295                 300

Glu Ala Gln Arg Lys Val Ser Lys Asn Ser Asn Tyr Asn Ala Gln Ser
305                 310                 315                 320

Thr Gly Glu Ser Gln Asp Ser Val Thr Glu Ser Asp Asp Gly Gly Phe
                325                 330                 335

Ser Glu Glu Trp Glu Ala Gln Arg Asp Ser Arg Leu Gly Pro His His
            340                 345                 350

Ser Thr Ala Glu Ser Arg Ser Ala Val Gln Asp Leu Ser Arg Ser Ile
        355                 360                 365

Pro Ala Thr Glu Asp Pro Glu Glu Arg Gly Val Lys Leu Gly Leu Gly
    370                 375                 380

Asp Phe Ile Phe Tyr Ser Val Leu Val Gly Lys Ala Ser Ala Thr Ala
385                 390                 395                 400

Ser Gly Asp Trp Asn Thr Thr Ile Ala Cys Phe Val Ala Ile Leu Ile
                405                 410                 415

Gly Leu Cys Leu Thr Leu Leu Leu Leu Ala Ile Phe Lys Lys Ala Leu
            420                 425                 430

Pro Ala Leu Pro Ile Ser Ile Thr Phe Gly Leu Val Phe Tyr Phe Ala
        435                 440                 445

Thr Asp Tyr Leu Val Gln Pro Phe Met Asp Gln Leu Ala Phe His Gln
    450                 455                 460

Phe Tyr Ile
465
```

<210> SEQ ID NO 11
<211> LENGTH: 467
<212> TYPE: PRT
<213> ORGANISM: Porcine

<400> SEQUENCE: 11

Met Thr Glu Leu Pro Ala Pro Leu Ser Tyr Phe Gln Asn Ala Gln Met
1 5 10 15

Ser Glu Asp Asn His Val Ser Asn Asn Val Ser Ser Gln Asn Asp Ser
20 25 30

Arg Glu Arg His Glu His Ser Ile Glu Arg Arg Arg Arg Gly Asn Ser
35 40 45

Glu Ser Leu Ser Asn Gly Gly Ala Gln Gly Asn Ser Arg Gln Val Val
50 55 60

Glu Gln Glu Glu Glu Glu Asp Glu Glu Leu Thr Leu Lys Tyr Gly Ala
65 70 75 80

Lys His Val Ile Met Leu Phe Val Pro Val Thr Leu Cys Met Val Val
85 90 95

Val Val Ala Thr Ile Lys Ser Val Ser Phe Tyr Thr Arg Lys Asp Gly
100 105 110

Gln Leu Ile Tyr Thr Pro Phe Thr Glu Asp Thr Glu Thr Val Gly Gln
115 120 125

Arg Ala Leu His Ser Ile Leu Asn Ala Ala Ile Met Thr Ser Val Ile
130 135 140

Val Val Met Thr Ile Leu Leu Val Val Leu Tyr Lys Tyr Arg Cys Tyr
145 150 155 160

Lys Val Ile His Ala Trp Leu Ile Ile Ser Ser Leu Leu Leu Leu Phe
165 170 175

Phe Phe Ser Phe Ile Tyr Leu Gly Glu Val Phe Lys Thr Tyr Asn Val
180 185 190

Ala Met Asp Tyr Ile Thr Val Ala Leu Leu Ile Trp Asn Phe Gly Val
195 200 205

Val Gly Met Ile Ala Ile His Trp Lys Gly Pro Leu Arg Leu Gln Gln
210 215 220

Ala Tyr Leu Ile Met Ile Ser Ala Leu Met Ala Leu Val Phe Ile Lys
225 230 235 240

Tyr Leu Pro Glu Trp Thr Ala Trp Leu Ile Leu Ala Val Ile Ser Val
245 250 255

Tyr Asp Leu Val Ala Val Leu Cys Pro Asn Gly Pro Leu Arg Leu Leu
260 265 270

Val Glu Thr Ala Gln Glu Arg Asn Glu Thr Leu Phe Pro Ala Leu Ile
275 280 285

Tyr Ser Ser Thr Met Val Trp Leu Val Asn Met Ala Glu Gly Asp Pro
290 295 300

Glu Ala Gln Arg Lys Val Ser Lys Asn Ser Asn Tyr Asn Ala Gln Ser
305 310 315 320

Thr Gly Glu Ser Gln Asp Ser Val Thr Glu Ser Asp Asp Gly Gly Phe
325 330 335

Ser Glu Glu Trp Glu Ala Gln Arg Asp Ser Arg Leu Gly Pro His His
340 345 350

Ser Thr Ala Glu Ser Arg Ser Ala Val Gln Asp Leu Ser Arg Ser Ile
355 360 365

Pro Ala Thr Glu Asp Pro Glu Glu Arg Gly Val Lys Leu Gly Leu Gly
370 375 380

Asp Phe Ile Phe Tyr Ser Val Leu Val Gly Lys Ala Ser Ala Thr Ala
385 390 395 400

Ser Gly Asp Trp Asn Thr Thr Ile Ala Cys Phe Val Ala Ile Leu Ile
405 410 415

```
Gly Leu Cys Leu Thr Leu Leu Leu Leu Ala Ile Phe Lys Lys Ala Leu
            420                 425                 430

Pro Ala Leu Pro Ile Ser Ile Thr Phe Gly Leu Val Phe Tyr Phe Ala
        435                 440                 445

Thr Asp Tyr Leu Val Gln Pro Phe Met Asp Gln Leu Ala Phe His Gln
    450                 455                 460

Phe Tyr Ile
465


<210> SEQ ID NO 12
<211> LENGTH: 2236
<212> TYPE: DNA
<213> ORGANISM: Homo Sapiens

<400> SEQUENCE: 12

cgagcggcgg cggagcaggc atttccagca gtgaggagac agccagaagc aagctattgg     60

agctgaagga acctgagaca gaagctagtc ccccctctga attttactga tgaagaaact    120

gaggccacag agctaaagtg acttttccca aggtcgccca gcgaggacgt gggacttctc    180

agacgtcagg agagtgatgt gagggagctg tgtgaccata gaaagtgacg tgttaaaaac    240

cagcgctgcc ctctttgaaa gccagggagc atcattcatt tagcctgctg agaagaagaa    300

accaagtgtc cgggattcag acctctctgc ggccccaagt gttcgtggtg cttccagagg    360

cagggctatg ctcacattca tggcctctga cagcgaggaa gaagtgtgtg atgagcggac    420

gtccctaatg tcggccgaga gccccacgcc gcgctcctgc caggagggca ggcagggccc    480

agaggatgga gagaacactg cccagtggag aagccaggag aacgaggagg acggtgagga    540

ggaccctgac cgctatgtct gtagtggggt tcccgggcgg ccgccaggcc tggaggaaga    600

gctgaccctc aaatacggag cgaagcacgt gatcatgctg tttgtgcctg tcactctgtg    660

catgatcgtg gtggtagcca ccatcaagtc tgtgcgcttc tacacagaga agaatggaca    720

gctcatctac acgacattca ctgaggacac accctcggtg ggccagcgcc tcctcaactc    780

cgtgctgaac accctcatca tgatcagcgt catcgtggtt atgaccatct tcttggtggt    840

gctctacaag taccgctgct acaagttcat ccatggctgg ttgatcatgt cttcactgat    900

gctgctgttc ctcttcacct atatctacct tggggaagtg ctcaagacct acaatgtggc    960

catggactac cccaccctct tgctgactgt ctggaacttc ggggcagtgg gcatggtgtg   1020

catccactgg aagggccctc tggtgctgca gcaggcctac ctcatcatga tcagtgcgct   1080

catggcccta gtgttcatca agtacctccc agagtggtcc gcgtgggtca tcctgggcgc   1140

catctctgtg tatgatctcg tggctgtgct gtgtcccaaa gggcctctga gaatgctggt   1200

agaaactgcc caggagagaa atgagcccat attccctgcc ctgatatact catctgccat   1260

ggtgtggacg gttggcatgg cgaagctgga cccctcctct cagggtgccc tccagctccc   1320

ctacgacccg gagatggaag aagactccta tgacagtttt ggggagcctt cataccccga   1380

agtctttgag cctcccttga ctggctaccc aggggaggag ctggaggaag aggaggaaag   1440

gggcgtgaag cttggcctcg gggacttcat cttctacagt gtgctggtgg gcaaggcggc   1500

tgccacgggc agcggggact ggaataccac gctggcctgc ttcgtggcca tcctcattgg   1560

cttgtgtctg accctcctgc tgcttgctgt gttcaagaag gcgctgcccg ccctccccat   1620

ctccatcacg ttcgggctca tcttttactt ctccacggac aacctggtgc ggccgttcat   1680

ggacaccctg gcctcccatc agctctacat ctgagggaca tggtgtgcca caggctgcaa   1740

gctgcaggga attttcattg gatgcagttg tatagtttta cactctagtg ccatatattt   1800
```

```
ttaagacttt tctttcctta aaaaataaag tacgtgttta cttggtgagg aggaggcaga   1860

accagctctt tggtgccagc tgtttcatca ccagactttg gctcccgctt tggggagcgc   1920

ctcgcttcac ggacaggaag cacagcaggt ttatccagat gaactgagaa ggtcagatta   1980

gggcggggag aagagcatcc ggcatgaggg ctgagatgcg caaagagtgt gctcgggagt   2040

ggcccctggc acctgggtgc tctggctgga gaggaaaagc cagttcccta cgaggagtgt   2100

tcccaatgct ttgtccatga tgtccttgtt attttattgc ctttagaaac tgagtcctgt   2160

tcttgttacg gcagtcacac tgctgggaag tggcttaata gtaatatcaa taaatagatg   2220

agtcctgtta gaaaaa                                                   2236


<210> SEQ ID NO 13
<211> LENGTH: 448
<212> TYPE: PRT
<213> ORGANISM: Homo Sapiens

<400> SEQUENCE: 13

Met Leu Thr Phe Met Ala Ser Asp Ser Glu Glu Glu Val Cys Asp Glu
1               5                   10                  15

Arg Thr Ser Leu Met Ser Ala Glu Ser Pro Thr Pro Arg Ser Cys Gln
            20                  25                  30

Glu Gly Arg Gln Gly Pro Glu Asp Gly Glu Asn Thr Ala Gln Trp Arg
        35                  40                  45

Ser Gln Glu Asn Glu Glu Asp Gly Glu Glu Asp Pro Asp Arg Tyr Val
    50                  55                  60

Cys Ser Gly Val Pro Gly Arg Pro Pro Gly Leu Glu Glu Glu Leu Thr
65                  70                  75                  80

Leu Lys Tyr Gly Ala Lys His Val Ile Met Leu Phe Val Pro Val Thr
                85                  90                  95

Leu Cys Met Ile Val Val Val Ala Thr Ile Lys Ser Val Arg Phe Tyr
            100                 105                 110

Thr Glu Lys Asn Gly Gln Leu Ile Tyr Thr Thr Phe Thr Glu Asp Thr
        115                 120                 125

Pro Ser Val Gly Gln Arg Leu Leu Asn Ser Val Leu Asn Thr Leu Ile
    130                 135                 140

Met Ile Ser Val Ile Val Val Met Thr Ile Phe Leu Val Val Leu Tyr
145                 150                 155                 160

Lys Tyr Arg Cys Tyr Lys Phe Ile His Gly Trp Leu Ile Met Ser Ser
                165                 170                 175

Leu Met Leu Leu Phe Leu Phe Thr Tyr Ile Tyr Leu Gly Glu Val Leu
            180                 185                 190

Lys Thr Tyr Asn Val Ala Met Asp Tyr Pro Thr Leu Leu Leu Thr Val
        195                 200                 205

Trp Asn Phe Gly Ala Val Gly Met Val Cys Ile His Trp Lys Gly Pro
    210                 215                 220

Leu Val Leu Gln Gln Ala Tyr Leu Ile Met Ile Ser Ala Leu Met Ala
225                 230                 235                 240

Leu Val Phe Ile Lys Tyr Leu Pro Glu Trp Ser Ala Trp Val Ile Leu
                245                 250                 255

Gly Ala Ile Ser Val Tyr Asp Leu Val Ala Val Leu Cys Pro Lys Gly
            260                 265                 270

Pro Leu Arg Met Leu Val Glu Thr Ala Gln Glu Arg Asn Glu Pro Ile
        275                 280                 285

Phe Pro Ala Leu Ile Tyr Ser Ser Ala Met Val Trp Thr Val Gly Met
```

-continued

```
    290                 295                 300

Ala Lys Leu Asp Pro Ser Ser Gln Gly Ala Leu Gln Leu Pro Tyr Asp
305                 310                 315                 320

Pro Glu Met Glu Glu Asp Ser Tyr Asp Ser Phe Gly Glu Pro Ser Tyr
                325                 330                 335

Pro Glu Val Phe Glu Pro Pro Leu Thr Gly Tyr Pro Gly Glu Glu Leu
            340                 345                 350

Glu Glu Glu Glu Glu Arg Gly Val Lys Leu Gly Leu Gly Asp Phe Ile
        355                 360                 365

Phe Tyr Ser Val Leu Val Gly Lys Ala Ala Ala Thr Gly Ser Gly Asp
    370                 375                 380

Trp Asn Thr Thr Leu Ala Cys Phe Val Ala Ile Leu Ile Gly Leu Cys
385                 390                 395                 400

Leu Thr Leu Leu Leu Leu Ala Val Phe Lys Lys Ala Leu Pro Ala Leu
                405                 410                 415

Pro Ile Ser Ile Thr Phe Gly Leu Ile Phe Tyr Phe Ser Thr Asp Asn
            420                 425                 430

Leu Val Arg Pro Phe Met Asp Thr Leu Ala Ser His Gln Leu Tyr Ile
        435                 440                 445


<210> SEQ ID NO 14
<211> LENGTH: 1347
<212> TYPE: DNA
<213> ORGANISM: Porcine

<400> SEQUENCE: 14

atgctcactt tcatggcctc tgacagcgag gaagaagtgt gtgacgagcg gacgtccctg      60

atgtcggccg agagccccac gcctcgctcc tgccaggaag gcaggcaggg cctggaggat     120

ggagagagtg ctgctcagtg gagaagccag gacagcgagg aggaccacga ggaagaccct     180

gaccgctatg tctgcagtgg ggttcctggc cggccaccag gcctggagga ggagctgacc     240

ctcaaatatg ggcaaagca cgtgatcatg ctctttgtgc ctgtcacgct gtgtatgatc      300

gtggtagtgg ccaccatcaa gtccgtgcgc ttctacacag agaagaatgg acagctcatc     360

tacacgccgt tcaccgagga cacgccctcc gtgggccagc gcctcctcaa ctccgtgctc     420

aacaccctca tcatgatcag cgtcattgtc gtcatgacca tcttcctggt cgtgctctac     480

aagtaccgct gctacaagtt catccacggc tggctgatca catcctccct gatgctgctc     540

ttcctcttca cctacatcta cctcggggaa gtgctcaaga cctacaacgt ggccatggac     600

taccccaccc tgttcctgac cgtctggaac ttcggggcgg tgggcatggt gtgcatccac     660

tggaagggcc ccctggtgct gcagcaggcc tacctcatca tgatcagcgc gctcatggcc     720

ttggtgttca tcaagtacct cccggagtgg tccgcctggg tcatcctggg cgccatctct     780

gtgtacgatc tcgtggctgt gctgtgcccc aaagggccgc tgagaatgtt ggtagaaact     840

gcccaggaga gaaacgagcc catatttcct gccctgatat actcatctgc catggtgtgg     900

acggtaggca tggccaagct ggacccctcc tctcagggag cccttcagct cccctacgac     960

ccagagatgg aagaggactc ctatgacagt tttggggagc cttcgtaccc tgaagtcttt    1020

gaacccccgc tgcctggcta cccgggcgag gagctggagg aagaggagga aaggggcgtg    1080

aagctgggcc tcggagactt catcttctac agcgtgctgg tgggcaaggc agcggccacg    1140

ggcagcgggg actggaacac cacgctggcc tgcttcgtgg ccatcctcat cggtttgtgt    1200

ctgaccctcc tgctgctcgc ggtgttcaag aaagcgctac ccgcccttcc catctccatc    1260

acgttcggcc tcatcttcta tttctccacc gacaacctgg tacggccttt catggacacg    1320
```

ctggcctccc accagctcta catctga 1347

<210> SEQ ID NO 15
<211> LENGTH: 448
<212> TYPE: PRT
<213> ORGANISM: Porcine

<400> SEQUENCE: 15

Met Leu Thr Phe Met Ala Ser Asp Ser Glu Glu Glu Val Cys Asp Glu
1 5 10 15

Arg Thr Ser Leu Met Ser Ala Glu Ser Pro Thr Pro Arg Ser Cys Gln
20 25 30

Glu Gly Arg Gln Gly Leu Glu Asp Gly Glu Ser Ala Ala Gln Trp Arg
35 40 45

Ser Gln Asp Ser Glu Glu Asp His Glu Glu Asp Pro Asp Arg Tyr Val
50 55 60

Cys Ser Gly Val Pro Gly Arg Pro Pro Gly Leu Glu Glu Glu Leu Thr
65 70 75 80

Leu Lys Tyr Gly Ala Lys His Val Ile Met Leu Phe Val Pro Val Thr
85 90 95

Leu Cys Met Ile Val Val Val Ala Thr Ile Lys Ser Val Arg Phe Tyr
100 105 110

Thr Glu Lys Asn Gly Gln Leu Ile Tyr Thr Pro Phe Thr Glu Asp Thr
115 120 125

Pro Ser Val Gly Gln Arg Leu Leu Asn Ser Val Leu Asn Thr Leu Ile
130 135 140

Met Ile Ser Val Ile Val Val Met Thr Ile Phe Leu Val Val Leu Tyr
145 150 155 160

Lys Tyr Arg Cys Tyr Lys Phe Ile His Gly Trp Leu Ile Thr Ser Ser
165 170 175

Leu Met Leu Leu Phe Leu Phe Thr Tyr Ile Tyr Leu Gly Glu Val Leu
180 185 190

Lys Thr Tyr Asn Val Ala Met Asp Tyr Pro Thr Leu Phe Leu Thr Val
195 200 205

Trp Asn Phe Gly Ala Val Gly Met Val Cys Ile His Trp Lys Gly Pro
210 215 220

Leu Val Leu Gln Gln Ala Tyr Leu Ile Met Ile Ser Ala Leu Met Ala
225 230 235 240

Leu Val Phe Ile Lys Tyr Leu Pro Glu Trp Ser Ala Trp Val Ile Leu
245 250 255

Gly Ala Ile Ser Val Tyr Asp Leu Val Ala Val Leu Cys Pro Lys Gly
260 265 270

Pro Leu Arg Met Leu Val Glu Thr Ala Gln Glu Arg Asn Glu Pro Ile
275 280 285

Phe Pro Ala Leu Ile Tyr Ser Ser Ala Met Val Trp Thr Val Gly Met
290 295 300

Ala Lys Leu Asp Pro Ser Ser Gln Gly Ala Leu Gln Leu Pro Tyr Asp
305 310 315 320

Pro Glu Met Glu Glu Asp Ser Tyr Asp Ser Phe Gly Glu Pro Ser Tyr
325 330 335

Pro Glu Val Phe Glu Pro Pro Leu Pro Gly Tyr Pro Gly Glu Glu Leu
340 345 350

Glu Glu Glu Glu Glu Arg Gly Val Lys Leu Gly Leu Gly Asp Phe Ile
355 360 365

```
Phe Tyr Ser Val Leu Val Gly Lys Ala Ala Ala Thr Gly Ser Gly Asp
    370                 375                 380

Trp Asn Thr Thr Leu Ala Cys Phe Val Ala Ile Leu Ile Gly Leu Cys
385                 390                 395                 400

Leu Thr Leu Leu Leu Leu Ala Val Phe Lys Lys Ala Leu Pro Ala Leu
                405                 410                 415

Pro Ile Ser Ile Thr Phe Gly Leu Ile Phe Tyr Phe Ser Thr Asp Asn
            420                 425                 430

Leu Val Arg Pro Phe Met Asp Thr Leu Ala Ser His Gln Leu Tyr Ile
        435                 440                 445


<210> SEQ ID NO 16
<211> LENGTH: 449
<212> TYPE: PRT
<213> ORGANISM: Porcine

<400> SEQUENCE: 16

Ile Met Leu Thr Phe Met Ala Ser Asp Ser Glu Glu Glu Val Cys Asp
1               5                   10                  15

Glu Arg Thr Ser Leu Met Ser Ala Glu Ser Pro Thr Pro Arg Ser Cys
            20                  25                  30

Gln Glu Gly Arg Gln Gly Leu Glu Asp Gly Glu Ser Ala Ala Gln Trp
        35                  40                  45

Arg Ser Gln Asp Ser Glu Glu Asp His Glu Glu Asp Pro Asp Arg Tyr
    50                  55                  60

Val Cys Ser Gly Val Pro Gly Arg Pro Pro Gly Leu Glu Glu Glu Leu
65                  70                  75                  80

Thr Leu Lys Tyr Gly Ala Lys His Val Ile Met Leu Phe Val Pro Val
                85                  90                  95

Thr Leu Cys Met Ile Val Val Val Ala Thr Ile Lys Ser Val Arg Phe
            100                 105                 110

Tyr Thr Glu Lys Asn Gly Gln Leu Ile Tyr Thr Pro Phe Thr Glu Asp
        115                 120                 125

Thr Pro Ser Val Gly Gln Arg Leu Leu Asn Ser Val Leu Asn Thr Leu
    130                 135                 140

Ile Met Ile Ser Val Ile Val Val Met Thr Ile Phe Leu Val Val Leu
145                 150                 155                 160

Tyr Lys Tyr Arg Cys Tyr Lys Phe Ile His Gly Trp Leu Ile Thr Ser
                165                 170                 175

Ser Leu Met Leu Leu Phe Leu Phe Thr Tyr Ile Tyr Leu Gly Glu Val
            180                 185                 190

Leu Lys Thr Tyr Asn Val Ala Met Asp Tyr Pro Thr Leu Phe Leu Thr
        195                 200                 205

Val Trp Asn Phe Gly Ala Val Gly Met Val Cys Ile His Trp Lys Gly
    210                 215                 220

Pro Leu Val Leu Gln Gln Ala Tyr Leu Ile Met Ile Ser Ala Leu Met
225                 230                 235                 240

Ala Leu Val Phe Ile Lys Tyr Leu Pro Glu Trp Ser Ala Trp Val Ile
                245                 250                 255

Leu Gly Ala Ile Ser Val Tyr Asp Leu Val Ala Val Leu Cys Pro Lys
            260                 265                 270

Gly Pro Leu Arg Met Leu Val Glu Thr Ala Gln Glu Arg Asn Glu Pro
        275                 280                 285

Ile Phe Pro Ala Leu Ile Tyr Ser Ser Ala Met Val Trp Thr Val Gly
    290                 295                 300
```

```
Met Ala Lys Leu Asp Pro Ser Ser Gln Gly Ala Leu Gln Leu Pro Tyr
305                 310                 315                 320

Asp Pro Glu Met Glu Glu Asp Ser Tyr Asp Ser Phe Gly Glu Pro Ser
                325                 330                 335

Tyr Pro Glu Val Phe Glu Pro Pro Leu Pro Gly Tyr Pro Gly Glu Glu
            340                 345                 350

Leu Glu Glu Glu Glu Glu Arg Gly Val Lys Leu Gly Leu Gly Asp Phe
        355                 360                 365

Ile Phe Tyr Ser Val Leu Val Gly Lys Ala Ala Ala Thr Gly Ser Gly
    370                 375                 380

Asp Trp Asn Thr Thr Leu Ala Cys Phe Val Ala Ile Leu Ile Gly Leu
385                 390                 395                 400

Cys Leu Thr Leu Leu Leu Leu Ala Val Phe Lys Lys Ala Leu Pro Ala
                405                 410                 415

Leu Pro Ile Ser Ile Thr Phe Gly Leu Ile Phe Tyr Phe Ser Thr Asp
            420                 425                 430

Asn Leu Val Arg Pro Phe Met Asp Thr Leu Ala Ser His Gln Leu Tyr
        435                 440                 445

Ile


<210> SEQ ID NO 17
<211> LENGTH: 3641
<212> TYPE: DNA
<213> ORGANISM: Homo Sapiens

<400> SEQUENCE: 17

gctgactcgc ctggctctga gccccgccgc cgcgctcggg ctccgtcagt ttcctcggca     60

gcggtaggcg agagcacgcg gaggagcgtg cgcgggggcc ccgggagacg gcggcggtgg    120

cggcgcgggc agagcaagga cgcggcggat cccactcgca cagcagcgca ctcggtgccc    180

cgcgcagggt cgcgatgctg cccggtttgg cactgctcct gctggccgcc tggacggctc    240

gggcgctgga ggtacccact gatggtaatg ctggcctgct ggctgaaccc cagattgcca    300

tgttctgtgg cagactgaac atgcacatga atgtccagaa tgggaagtgg gattcagatc    360

catcagggac caaaacctgc attgatacca aggaaggcat cctgcagtat tgccaagaag    420

tctaccctga actgcagatc accaatgtgg tagaagccaa ccaaccagtg accatccaga    480

actggtgcaa gcggggccgc aagcagtgca agacccatcc ccactttgtg attccctacc    540

gctgcttagt tggtgagttt gtaagtgatg cccttctcgt tcctgacaag tgcaaattct    600

tacaccagga gaggatggat gtttgcgaaa ctcatcttca ctggcacacc gtcgccaaag    660

agacatgcag tgagaagagt accaacttgc atgactacgg catgttgctg ccctgcggaa    720

ttgacaagtt ccgaggggta gagtttgtgt gttgcccact ggctgaagaa agtgacaatg    780

tggattctgc tgatgcggag gaggatgact cggatgtctg gtggggcgga gcagacacag    840

actatgcaga tgggagtgaa gacaaagtag tagaagtagc agaggaggaa gaagtggctg    900

aggtggaaga agaagaagcc gatgatgacg aggacgatga ggatggtgat gaggtagagg    960

aagaggctga ggaaccctac gaagaagcca cagagagaac caccagcatt gccaccacca   1020

ccaccaccac cacagagtct gtggaagagg tggttcgaga ggtgtgctct gaacaagccg   1080

agacggggcc gtgccgagca atgatctccc gctggtactt tgatgtgact gaagggaagt   1140

gtgccccatt cttttacggc ggatgtggcg gcaaccggaa caactttgac acagaagagt   1200

actgcatggc cgtgtgtggc agcgccatgt cccaaagttt actcaagact acccaggaac   1260

ctcttgcccg agatcctgtt aaacttccta caacagcagc cagtacccct gatgccgttg   1320
```

-continued

```
acaagtatct cgagacacct ggggatgaga atgaacatgc ccatttccag aaagccaaag   1380
agaggcttga ggccaagcac cgagagagaa tgtcccaggt catgagagaa tgggaagagg   1440
cagaacgtca agcaaagaac ttgcctaaag ctgataagaa ggcagttatc cagcatttcc   1500
aggagaaagt ggaatctttg gaacaggaag cagccaacga gagacagcag ctggtggaga   1560
cacacatggc cagagtggaa gccatgctca atgaccgccg ccgcctggcc ctggagaact   1620
acatcaccgc tctgcaggct gttcctcctc ggcctcgtca cgtgttcaat atgctaaaga   1680
agtatgtccg cgcagaacag aaggacagac agcacaccct aaagcatttc gagcatgtgc   1740
gcatggtgga tcccaagaaa gccgctcaga tccggtccca ggttatgaca cacctccgtg   1800
tgatttatga gcgcatgaat cagtctctct ccctgctcta caacgtgcct gcagtggccg   1860
aggagattca ggatgaagtt gatgagctgc ttcagaaaga gcaaaactat tcagatgacg   1920
tcttggccaa catgattagt gaaccaagga tcagttacgg aaacgatgct ctcatgccat   1980
ctttgaccga aacgaaaacc accgtggagc tccttcccgt gaatggagag ttcagcctgg   2040
acgatctcca gccgtggcat tcttttgggg ctgactctgt gccagccaac acagaaaacg   2100
aagttgagcc tgttgatgcc cgccctgctg ccgaccgagg actgaccact cgaccaggtt   2160
ctgggttgac aaatatcaag acggaggaga tctctgaagt gaagatggat gcagaattcc   2220
gacatgactc aggatatgaa gttcatcatc aaaaattggt gttctttgca gaagatgtgg   2280
gttcaaacaa aggtgcaatc attggactca tggtgggcgg tgttgtcata gcgacagtga   2340
tcgtcatcac cttggtgatg ctgaagaaga aacagtacac atccattcat catggtgtgg   2400
tggaggttga cgccgctgtc accccagagg agcgccacct gtccaagatg cagcagaacg   2460
gctacgaaaa tccaacctac aagttctttg agcagatgca gaactagacc cccgccacag   2520
cagcctctga agttggacag caaaaccatt gcttcactac ccatcggtgt ccatttatag   2580
aataatgtgg gaagaaacaa acccgtttta tgatttactc attatcgcct tttgacagct   2640
gtgctgtaac acaagtagat gcctgaactt gaattaatcc acacatcagt aatgtattct   2700
atctctcttt acattttggt ctctatacta cattattaat gggttttgtg tactgtaaag   2760
aatttagctg tatcaaacta gtgcatgaat agattctctc ctgattattt atcacatagc   2820
cccttagcca gttgtatatt attcttgtgg tttgtgaccc aattaagtcc tactttacat   2880
atgctttaag aatcgatggg ggatgcttca tgtgaacgtg ggagttcagc tgcttctctt   2940
gcctaagtat tcctttcctg atcactatgc attttaaagt taaacatttt taagtatttc   3000
agatgcttta gagagatttt ttttccatga ctgcatttta ctgtacagat tgctgcttct   3060
gctatatttg tgatatagga attaagagga tacacacgtt tgtttcttcg tgcctgtttt   3120
atgtgcacac attaggcatt gagacttcaa gcttttcttt ttttgtccac gtatctttgg   3180
gtctttgata aagaaaagaa tccctgttca ttgtaagcac ttttacgggg cgggtgggga   3240
ggggtgctct gctggtcttc aattaccaag aattctccaa aacaattttc tgcaggatga   3300
ttgtacagaa tcattgctta tgacatgatc gctttctaca ctgtattaca taaataaatt   3360
aaataaaata accccgggca agacttttct ttgaaggatg actacagaca ttaaataatc   3420
gaagtaattt tgggtgggga gaagaggcag attcaatttt ctttaaccag tctgaagttt   3480
catttatgat acaaaagaag atgaaaatgg aagtggcaat ataaggggat gaggaaggca   3540
tgcctggaca aacccttctt ttaagatgtg tcttcaattt gtataaaatg gtgttttcat   3600
gtaaataaat acattcttgg aggagcaaaa aaaaaaaaaa a                        3641
```

-continued

<210> SEQ ID NO 18
<211> LENGTH: 770
<212> TYPE: PRT
<213> ORGANISM: Homo Sapiens

<400> SEQUENCE: 18

```
Met Leu Pro Gly Leu Ala Leu Leu Leu Leu Ala Ala Trp Thr Ala Arg
1               5                   10                  15

Ala Leu Glu Val Pro Thr Asp Gly Asn Ala Gly Leu Leu Ala Glu Pro
            20                  25                  30

Gln Ile Ala Met Phe Cys Gly Arg Leu Asn Met His Met Asn Val Gln
        35                  40                  45

Asn Gly Lys Trp Asp Ser Asp Pro Ser Gly Thr Lys Thr Cys Ile Asp
    50                  55                  60

Thr Lys Glu Gly Ile Leu Gln Tyr Cys Gln Glu Val Tyr Pro Glu Leu
65                  70                  75                  80

Gln Ile Thr Asn Val Val Glu Ala Asn Gln Pro Val Thr Ile Gln Asn
                85                  90                  95

Trp Cys Lys Arg Gly Arg Lys Gln Cys Lys Thr His Pro His Phe Val
            100                 105                 110

Ile Pro Tyr Arg Cys Leu Val Gly Glu Phe Val Ser Asp Ala Leu Leu
        115                 120                 125

Val Pro Asp Lys Cys Lys Phe Leu His Gln Glu Arg Met Asp Val Cys
    130                 135                 140

Glu Thr His Leu His Trp His Thr Val Ala Lys Glu Thr Cys Ser Glu
145                 150                 155                 160

Lys Ser Thr Asn Leu His Asp Tyr Gly Met Leu Leu Pro Cys Gly Ile
                165                 170                 175

Asp Lys Phe Arg Gly Val Glu Phe Val Cys Cys Pro Leu Ala Glu Glu
            180                 185                 190

Ser Asp Asn Val Asp Ser Ala Asp Ala Glu Glu Asp Asp Ser Asp Val
        195                 200                 205

Trp Trp Gly Gly Ala Asp Thr Asp Tyr Ala Asp Gly Ser Glu Asp Lys
    210                 215                 220

Val Val Glu Val Ala Glu Glu Glu Glu Val Ala Glu Val Glu Glu Glu
225                 230                 235                 240

Glu Ala Asp Asp Asp Glu Asp Asp Glu Asp Gly Asp Glu Val Glu Glu
                245                 250                 255

Glu Ala Glu Glu Pro Tyr Glu Glu Ala Thr Glu Arg Thr Thr Ser Ile
            260                 265                 270

Ala Thr Thr Thr Thr Thr Thr Thr Glu Ser Val Glu Glu Val Val Arg
        275                 280                 285

Glu Val Cys Ser Glu Gln Ala Glu Thr Gly Pro Cys Arg Ala Met Ile
    290                 295                 300

Ser Arg Trp Tyr Phe Asp Val Thr Glu Gly Lys Cys Ala Pro Phe Phe
305                 310                 315                 320

Tyr Gly Gly Cys Gly Gly Asn Arg Asn Asn Phe Asp Thr Glu Glu Tyr
                325                 330                 335

Cys Met Ala Val Cys Gly Ser Ala Met Ser Gln Ser Leu Leu Lys Thr
            340                 345                 350

Thr Gln Glu Pro Leu Ala Arg Asp Pro Val Lys Leu Pro Thr Thr Ala
        355                 360                 365

Ala Ser Thr Pro Asp Ala Val Asp Lys Tyr Leu Glu Thr Pro Gly Asp
    370                 375                 380

Glu Asn Glu His Ala His Phe Gln Lys Ala Lys Glu Arg Leu Glu Ala
```

```
385                 390                 395                 400

Lys His Arg Glu Arg Met Ser Gln Val Met Arg Glu Trp Glu Glu Ala
                405                 410                 415

Glu Arg Gln Ala Lys Asn Leu Pro Lys Ala Asp Lys Lys Ala Val Ile
            420                 425                 430

Gln His Phe Gln Glu Lys Val Glu Ser Leu Glu Gln Glu Ala Ala Asn
        435                 440                 445

Glu Arg Gln Gln Leu Val Glu Thr His Met Ala Arg Val Glu Ala Met
    450                 455                 460

Leu Asn Asp Arg Arg Arg Leu Ala Leu Glu Asn Tyr Ile Thr Ala Leu
465                 470                 475                 480

Gln Ala Val Pro Pro Arg Pro Arg His Val Phe Asn Met Leu Lys Lys
                485                 490                 495

Tyr Val Arg Ala Glu Gln Lys Asp Arg Gln His Thr Leu Lys His Phe
            500                 505                 510

Glu His Val Arg Met Val Asp Pro Lys Lys Ala Ala Gln Ile Arg Ser
        515                 520                 525

Gln Val Met Thr His Leu Arg Val Ile Tyr Glu Arg Met Asn Gln Ser
    530                 535                 540

Leu Ser Leu Leu Tyr Asn Val Pro Ala Val Ala Glu Glu Ile Gln Asp
545                 550                 555                 560

Glu Val Asp Glu Leu Leu Gln Lys Glu Gln Asn Tyr Ser Asp Asp Val
                565                 570                 575

Leu Ala Asn Met Ile Ser Glu Pro Arg Ile Ser Tyr Gly Asn Asp Ala
            580                 585                 590

Leu Met Pro Ser Leu Thr Glu Thr Lys Thr Thr Val Glu Leu Leu Pro
        595                 600                 605

Val Asn Gly Glu Phe Ser Leu Asp Asp Leu Gln Pro Trp His Ser Phe
    610                 615                 620

Gly Ala Asp Ser Val Pro Ala Asn Thr Glu Asn Glu Val Glu Pro Val
625                 630                 635                 640

Asp Ala Arg Pro Ala Ala Asp Arg Gly Leu Thr Thr Arg Pro Gly Ser
                645                 650                 655

Gly Leu Thr Asn Ile Lys Thr Glu Glu Ile Ser Glu Val Lys Met Asp
            660                 665                 670

Ala Glu Phe Arg His Asp Ser Gly Tyr Glu Val His His Gln Lys Leu
        675                 680                 685

Val Phe Phe Ala Glu Asp Val Gly Ser Asn Lys Gly Ala Ile Ile Gly
    690                 695                 700

Leu Met Val Gly Gly Val Val Ile Ala Thr Val Ile Val Ile Thr Leu
705                 710                 715                 720

Val Met Leu Lys Lys Lys Gln Tyr Thr Ser Ile His His Gly Val Val
                725                 730                 735

Glu Val Asp Ala Ala Val Thr Pro Glu Glu Arg His Leu Ser Lys Met
            740                 745                 750

Gln Gln Asn Gly Tyr Glu Asn Pro Thr Tyr Lys Phe Phe Glu Gln Met
        755                 760                 765

Gln Asn
    770
```

<210> SEQ ID NO 19
<211> LENGTH: 2088
<212> TYPE: DNA
<213> ORGANISM: Porcine

<400> SEQUENCE: 19

```
atgctgcccg gtttggcact ggtcctgctg gccgcctgga cggctcgggc gctggaggtg     60
cccactgatg gcaatgccgg cctgcttgca gaaccccagg ttgccatgtt ctgtggcaaa    120
ctcaacatgc acatgaatgt gcagaatggg aagtgggagt cagatccgtc ggggaccaaa    180
acctgcattg gcaccaagga aggcatcttg cagtactgcc aagaagtcta ccctgaactg    240
cagatcacca atgtggtaga agccaaccaa ccagtgacca tccagaactg gtgcaagagg    300
agccggaagc agtgcaagac ccacactcac attgtgattc cgtaccgctg cttagttggc    360
gagtttgtaa gcgatgccct ccttgttccg gacaagtgca agttcttaca ccaggagagg    420
atggatgttt gcgaaaccca ccttcactgg cacactgtgg ccaaagagac ctgtagtgag    480
aagagtacga acttgcatga ctatggcatg ttgctgccct gtggaattga caagttccga    540
ggggtggagt ttgtgtgttg cccactggcc gaggaaagtg acaatatcga ctcagcagat    600
gcagaagagg atgactcgga cgtctggtgg ggtggagcag atacagacta tgcagatggc    660
agtgaagaca aagtcgtgga ggtcgcagag gaggaggaag tggctgatgt cgaggaagaa    720
gaagctgagg atgatgagga tgatgaggat ggtgatgagg tagaagaaga ggctgaggaa    780
ccctatgaag aggccacgga gagaaccacc agcatcgcca caaccaccac caccaccacg    840
gagtctgtgg aagaggtagt ccgagttcct acaacagcag ccagcacccc ggatgccgtt    900
gacaagtatc ttgagacacc tggagatgag aacgaacatg cgcatttcca gaaagccaaa    960
gagaggctgg aggccaagca ccgcgagaga atgtcccagg tcatgagaga gtgggaagag   1020
gcagaacgtc aagcaaagaa cttgcctaaa gctgataaga aagcagtgat ccagcatttc   1080
caggagaaag tggagtctct ggagcaggaa gcagccaacg agaggcagca gttggtggag   1140
acgcacatgg ccagagtgga ggccatgctt aacgaccgcc ggcgcctggc cctggagaat   1200
tacatcacgg ctcttcaggc tgttcctcct cggcctcgtc atgtgttcaa catgctcaag   1260
aagtatgtcc gtgctgaaca gaaagacaga cagcacaccc taaagcattt tgaacacgtt   1320
cgcatggtag atccaaagaa agctgctcag atccgatccc aggttatgac acacctccgt   1380
gtgatttacg agcgcatgaa ccagtctctc tccctgctct acaacgttcc tgctgtggcc   1440
gaggaaattc aggatgaagt tgatgagctg ctgcagaaag agcaaaacta ctcggatgat   1500
gtcttggcca acatgatcag cgaaccgagg atcagttatg gaaacgatgc tctcatgccg   1560
tctctgactg aaaccaaaac caccgtggag cttcttcctg tgaatggaga gttcagcctg   1620
gatgatctcc agccctggca tccttttggg gtagactctg tgcctgccaa cacagaaaat   1680
gaagtcgagc ctgttgacgc ccgccctgca gccgaccgag gactgaccac tcgaccaggt   1740
tccgggttga ccaacatcaa gacggaagag atctctgaag tgaagatgga tgcggagttc   1800
cgacacgatt cgggctatga ggttcatcac caaaaactgg tgttcttcgc agaagatgtg   1860
ggttcaaaca aaggtgccat cattggactc atggtgggtg gtgttgtcat agcaaccgtg   1920
attgtcatca ccttagtgat gctgaagaag aaacagtaca catctatcca tcacggtgtg   1980
gtggaggttg acgcagctgt gaccccggag gagcgccacc tctccaagat gcagcagaat   2040
ggctatgaaa acccaactta caagttcttt gagcagatgc agaactag                2088
```

<210> SEQ ID NO 20
<211> LENGTH: 695
<212> TYPE: PRT
<213> ORGANISM: Porcine

<400> SEQUENCE: 20

-continued

```
Met Leu Pro Gly Leu Ala Leu Val Leu Leu Ala Ala Trp Thr Ala Arg
1               5                   10                  15

Ala Leu Glu Val Pro Thr Asp Gly Asn Ala Gly Leu Leu Ala Glu Pro
            20                  25                  30

Gln Val Ala Met Phe Cys Gly Lys Leu Asn Met His Met Asn Val Gln
        35                  40                  45

Asn Gly Lys Trp Glu Ser Asp Pro Ser Gly Thr Lys Thr Cys Ile Gly
    50                  55                  60

Thr Lys Glu Gly Ile Leu Gln Tyr Cys Gln Glu Val Tyr Pro Glu Leu
65                  70                  75                  80

Gln Ile Thr Asn Val Val Glu Ala Asn Gln Pro Val Thr Ile Gln Asn
                85                  90                  95

Trp Cys Lys Arg Ser Arg Lys Gln Cys Lys Thr His Thr His Ile Val
            100                 105                 110

Ile Pro Tyr Arg Cys Leu Val Gly Glu Phe Val Ser Asp Ala Leu Leu
        115                 120                 125

Val Pro Asp Lys Cys Lys Phe Leu His Gln Glu Arg Met Asp Val Cys
    130                 135                 140

Glu Thr His Leu His Trp His Thr Val Ala Lys Glu Thr Cys Ser Glu
145                 150                 155                 160

Lys Ser Thr Asn Leu His Asp Tyr Gly Met Leu Leu Pro Cys Gly Ile
                165                 170                 175

Asp Lys Phe Arg Gly Val Glu Phe Val Cys Cys Pro Leu Ala Glu Glu
            180                 185                 190

Ser Asp Asn Ile Asp Ser Ala Asp Ala Glu Glu Asp Asp Ser Asp Val
        195                 200                 205

Trp Trp Gly Gly Ala Asp Thr Asp Tyr Ala Asp Gly Ser Glu Asp Lys
    210                 215                 220

Val Val Glu Val Ala Glu Glu Glu Glu Val Ala Asp Val Glu Glu Glu
225                 230                 235                 240

Glu Ala Glu Asp Asp Glu Asp Asp Glu Asp Gly Asp Glu Val Glu Glu
                245                 250                 255

Glu Ala Glu Glu Pro Tyr Glu Glu Ala Thr Glu Arg Thr Thr Ser Ile
            260                 265                 270

Ala Thr Thr Thr Thr Thr Thr Thr Glu Ser Val Glu Glu Val Val Arg
        275                 280                 285

Val Pro Thr Thr Ala Ala Ser Thr Pro Asp Ala Val Asp Lys Tyr Leu
    290                 295                 300

Glu Thr Pro Gly Asp Glu Asn Glu His Ala His Phe Gln Lys Ala Lys
305                 310                 315                 320

Glu Arg Leu Glu Ala Lys His Arg Glu Arg Met Ser Gln Val Met Arg
                325                 330                 335

Glu Trp Glu Glu Ala Glu Arg Gln Ala Lys Asn Leu Pro Lys Ala Asp
            340                 345                 350

Lys Lys Ala Val Ile Gln His Phe Gln Glu Lys Val Glu Ser Leu Glu
        355                 360                 365

Gln Glu Ala Ala Asn Glu Arg Gln Gln Leu Val Glu Thr His Met Ala
    370                 375                 380

Arg Val Glu Ala Met Leu Asn Asp Arg Arg Arg Leu Ala Leu Glu Asn
385                 390                 395                 400

Tyr Ile Thr Ala Leu Gln Ala Val Pro Pro Arg Pro Arg His Val Phe
                405                 410                 415

Asn Met Leu Lys Lys Tyr Val Arg Ala Glu Gln Lys Asp Arg Gln His
            420                 425                 430
```

```
Thr Leu Lys His Phe Glu His Val Arg Met Val Asp Pro Lys Lys Ala
        435                 440                 445

Ala Gln Ile Arg Ser Gln Val Met Thr His Leu Arg Val Ile Tyr Glu
    450                 455                 460

Arg Met Asn Gln Ser Leu Ser Leu Leu Tyr Asn Val Pro Ala Val Ala
465                 470                 475                 480

Glu Glu Ile Gln Asp Glu Val Asp Glu Leu Leu Gln Lys Glu Gln Asn
                485                 490                 495

Tyr Ser Asp Asp Val Leu Ala Asn Met Ile Ser Glu Pro Arg Ile Ser
            500                 505                 510

Tyr Gly Asn Asp Ala Leu Met Pro Ser Leu Thr Glu Thr Lys Thr Thr
        515                 520                 525

Val Glu Leu Leu Pro Val Asn Gly Glu Phe Ser Leu Asp Asp Leu Gln
    530                 535                 540

Pro Trp His Pro Phe Gly Val Asp Ser Val Pro Ala Asn Thr Glu Asn
545                 550                 555                 560

Glu Val Glu Pro Val Asp Ala Arg Pro Ala Ala Asp Arg Gly Leu Thr
                565                 570                 575

Thr Arg Pro Gly Ser Gly Leu Thr Asn Ile Lys Thr Glu Glu Ile Ser
            580                 585                 590

Glu Val Lys Met Asp Ala Glu Phe Arg His Asp Ser Gly Tyr Glu Val
        595                 600                 605

His His Gln Lys Leu Val Phe Phe Ala Glu Asp Val Gly Ser Asn Lys
    610                 615                 620

Gly Ala Ile Ile Gly Leu Met Val Gly Gly Val Val Ile Ala Thr Val
625                 630                 635                 640

Ile Val Ile Thr Leu Val Met Leu Lys Lys Lys Gln Tyr Thr Ser Ile
                645                 650                 655

His His Gly Val Val Glu Val Asp Ala Ala Val Thr Pro Glu Glu Arg
            660                 665                 670

His Leu Ser Lys Met Gln Gln Asn Gly Tyr Glu Asn Pro Thr Tyr Lys
        675                 680                 685

Phe Phe Glu Gln Met Gln Asn
    690                 695


<210> SEQ ID NO 21
<211> LENGTH: 695
<212> TYPE: PRT
<213> ORGANISM: Porcine

<400> SEQUENCE: 21

Met Leu Pro Gly Leu Ala Leu Val Leu Leu Ala Ala Trp Thr Ala Arg
1               5                   10                  15

Ala Leu Glu Val Pro Thr Asp Gly Asn Ala Gly Leu Leu Ala Glu Pro
            20                  25                  30

Gln Val Ala Met Phe Cys Gly Lys Leu Asn Met His Met Asn Val Gln
        35                  40                  45

Asn Gly Lys Trp Glu Ser Asp Pro Ser Gly Thr Lys Thr Cys Ile Gly
    50                  55                  60

Thr Lys Glu Gly Ile Leu Gln Tyr Cys Gln Glu Val Tyr Pro Glu Leu
65                  70                  75                  80

Gln Ile Thr Asn Val Val Glu Ala Asn Gln Pro Val Thr Ile Gln Asn
                85                  90                  95

Trp Cys Lys Arg Ser Arg Lys Gln Cys Lys Thr His Thr His Ile Val
            100                 105                 110
```

-continued

```
Ile Pro Tyr Arg Cys Leu Val Gly Glu Phe Val Ser Asp Ala Leu Leu
        115                 120                 125

Val Pro Asp Lys Cys Lys Phe Leu His Gln Glu Arg Met Asp Val Cys
    130                 135                 140

Glu Thr His Leu His Trp His Thr Val Ala Lys Glu Thr Cys Ser Glu
145                 150                 155                 160

Lys Ser Thr Asn Leu His Asp Tyr Gly Met Leu Leu Pro Cys Gly Ile
                165                 170                 175

Asp Lys Phe Arg Gly Val Glu Phe Val Cys Cys Pro Leu Ala Glu Glu
            180                 185                 190

Ser Asp Asn Ile Asp Ser Ala Asp Ala Glu Glu Asp Asp Ser Asp Val
        195                 200                 205

Trp Trp Gly Gly Ala Asp Thr Asp Tyr Ala Asp Gly Ser Glu Asp Lys
    210                 215                 220

Val Val Glu Val Ala Glu Glu Glu Glu Val Ala Asp Val Glu Glu Glu
225                 230                 235                 240

Glu Ala Glu Asp Asp Glu Asp Asp Glu Asp Gly Asp Glu Val Glu Glu
                245                 250                 255

Glu Ala Glu Glu Pro Tyr Glu Glu Ala Thr Glu Arg Thr Thr Ser Ile
            260                 265                 270

Ala Thr Thr Thr Thr Thr Thr Thr Glu Ser Val Glu Glu Val Val Arg
        275                 280                 285

Val Pro Thr Thr Ala Ala Ser Thr Pro Asp Ala Val Asp Lys Tyr Leu
    290                 295                 300

Glu Thr Pro Gly Asp Glu Asn Glu His Ala His Phe Gln Lys Ala Lys
305                 310                 315                 320

Glu Arg Leu Glu Ala Lys His Arg Glu Arg Met Ser Gln Val Met Arg
                325                 330                 335

Glu Trp Glu Glu Ala Glu Arg Gln Ala Lys Asn Leu Pro Lys Ala Asp
            340                 345                 350

Lys Lys Ala Val Ile Gln His Phe Gln Glu Lys Val Glu Ser Leu Glu
        355                 360                 365

Gln Glu Ala Ala Asn Glu Arg Gln Gln Leu Val Glu Thr His Met Ala
    370                 375                 380

Arg Val Glu Ala Met Leu Asn Asp Arg Arg Arg Leu Ala Leu Glu Asn
385                 390                 395                 400

Tyr Ile Thr Ala Leu Gln Ala Val Pro Pro Arg Pro Arg His Val Phe
                405                 410                 415

Asn Met Leu Lys Lys Tyr Val Arg Ala Glu Gln Lys Asp Arg Gln His
            420                 425                 430

Thr Leu Lys His Phe Glu His Val Arg Met Val Asp Pro Lys Lys Ala
        435                 440                 445

Ala Gln Ile Arg Ser Gln Val Met Thr His Leu Arg Val Ile Tyr Glu
    450                 455                 460

Arg Met Asn Gln Ser Leu Ser Leu Leu Tyr Asn Val Pro Ala Val Ala
465                 470                 475                 480

Glu Glu Ile Gln Asp Glu Val Asp Glu Leu Leu Gln Lys Glu Gln Asn
                485                 490                 495

Tyr Ser Asp Asp Val Leu Ala Asn Met Ile Ser Glu Pro Arg Ile Ser
            500                 505                 510

Tyr Gly Asn Asp Ala Leu Met Pro Ser Leu Thr Glu Thr Lys Thr Thr
        515                 520                 525

Val Glu Leu Leu Pro Val Asn Gly Glu Phe Ser Leu Asp Asp Leu Gln
```

-continued

```
    530                 535                 540

Pro Trp His Pro Phe Gly Val Asp Ser Val Pro Ala Asn Thr Glu Asn
545                 550                 555                 560

Glu Val Glu Pro Val Asp Ala Arg Pro Ala Ala Asp Arg Gly Leu Thr
                565                 570                 575

Thr Arg Pro Gly Ser Gly Leu Thr Asn Ile Lys Thr Glu Glu Ile Ser
            580                 585                 590

Glu Val Lys Met Asp Ala Glu Phe Arg His Asp Ser Gly Tyr Glu Val
        595                 600                 605

His His Gln Lys Leu Val Phe Phe Ala Glu Asp Val Gly Ser Asn Lys
    610                 615                 620

Gly Ala Ile Ile Gly Leu Met Val Gly Gly Val Val Ile Ala Thr Val
625                 630                 635                 640

Ile Val Ile Thr Leu Val Met Leu Lys Lys Lys Gln Tyr Thr Ser Ile
                645                 650                 655

His His Gly Val Val Glu Val Asp Ala Ala Val Thr Pro Glu Glu Arg
            660                 665                 670

His Leu Ser Lys Met Gln Gln Asn Gly Tyr Glu Asn Pro Thr Tyr Lys
        675                 680                 685

Phe Phe Glu Gln Met Gln Asn
    690                 695


<210> SEQ ID NO 22
<211> LENGTH: 1208
<212> TYPE: DNA
<213> ORGANISM: Homo Sapiens

<400> SEQUENCE: 22

agagaggggg cgagcgaccg agcgccgcga cgcggaagtg aggtgcgtgc gggctgcagc     60

gcagaccccg gcccggcccc tccgagagcg tcctgggcgc tccctcacgc cttgccttca    120

agccttctgc ctttccaccc tcgtgagcgg agaactggga gtggccattc gacgacaggt    180

tagcgggttt gcctcccact cccccagcct cgcgtcgccg gctcacagcg gcctcctctg    240

gggacagtcc cccccgggtg ccgcctccgc ccttcctgtg cgctcctttt ccttcttctt    300

tcctattaaa tattatttgg gaattgttta aattttttt ttaaaaaaaa gagagaggcg    360

gggaggagtc ggagttgtgg agaagcagag ggactcagtg tggtgtaaag gaattcatta    420

gccatggatg tattcatgaa aggactttca aaggccaagg agggagttgt ggctgctgct    480

gagaaaacca aacagggtgt ggcagaagca gcaggaaaga caaaagaggg tgttctctat    540

gtaggctcca aaaccaagga gggagtggtg catggtgtgg caacagtggc tgagaagacc    600

aaagagcaag tgacaaatgt tggaggagca gtggtgacgg gtgtgacagc agtagcccag    660

aagacagtgg agggagcagg gagcattgca gcagccactg gctttgtcaa aaaggaccag    720

ttgggcaaga atgaagaagg agccccacag gaaggaattc tggaagatat gcctgtggat    780

cctgacaatg aggcttatga aatgccttct gaggaagggt atcaagacta cgaacctgaa    840

gcctaagaaa tatctttgct cccagtttct tgagatctgc tgacagatgt tccatcctgt    900

acaagtgctc agttccaatg tgcccagtca tgacatttct caaagttttt acagtgtatc    960

tcgaagtctt ccatcagcag tgattgaagt atctgtacct gcccccactc agcatttcgg   1020

tgcttccctt tcactgaagt gaatacatgg tagcagggtc tttgtgtgct gtggattttg   1080

tggcttcaat ctacgatgtt aaaacaaatt aaaaacacct aagtgactac cacttatttc   1140

taaatcctca ctattttttg ttgctgttga aaaaaaaaaa aaaaaaaaaa aaaaaaaaaa   1200
```

aaaaaaaa 1208

<210> SEQ ID NO 23
<211> LENGTH: 140
<212> TYPE: PRT
<213> ORGANISM: Homo Sapiens

<400> SEQUENCE: 23

Met Asp Val Phe Met Lys Gly Leu Ser Lys Ala Lys Glu Gly Val Val
1 5 10 15

Ala Ala Ala Glu Lys Thr Lys Gln Gly Val Ala Glu Ala Ala Gly Lys
20 25 30

Thr Lys Glu Gly Val Leu Tyr Val Gly Ser Lys Thr Lys Glu Gly Val
35 40 45

Val His Gly Val Ala Thr Val Ala Glu Lys Thr Lys Glu Gln Val Thr
50 55 60

Asn Val Gly Gly Ala Val Val Thr Gly Val Thr Ala Val Ala Gln Lys
65 70 75 80

Thr Val Glu Gly Ala Gly Ser Ile Ala Ala Ala Thr Gly Phe Val Lys
85 90 95

Lys Asp Gln Leu Gly Lys Asn Glu Glu Gly Ala Pro Gln Glu Gly Ile
100 105 110

Leu Glu Asp Met Pro Val Asp Pro Asp Asn Glu Ala Tyr Glu Met Pro
115 120 125

Ser Glu Glu Gly Tyr Gln Asp Tyr Glu Pro Glu Ala
130 135 140

<210> SEQ ID NO 24
<211> LENGTH: 982
<212> TYPE: DNA
<213> ORGANISM: Porcine

<400> SEQUENCE: 24
cagtctgtta gggggaggag cttatttctc cattccggtg tgatccagga acagctgttt 60
tccctccagc tctgaaagtg tggggtaaag gaattcatta gccatggatg tattcatgaa 120
aggactttca aaagccaagg agggagtcgt ggctgctgct gaaaaaacca aacagggtgt 180
ggcagaagca gcgggaaaga caaaagaggg tgtgctctat gtaggatcca aaaccaagga 240
aggagtggtt catggtgtga caacagtggc tgagaagacc aaagagcaag tgacaaatgt 300
tggagaggca gtggtgacag ggtgacagc ggtagcacag aagacagtgg aaggagcagg 360
gagcattgca gctgccactg gctttggcaa aaaggatcag ctgggcaaga atgaagaagg 420
agccccccag gagggaattc tggaagatat gcctgtggat cctgacaatg aagcttatga 480
aatgccttcc gaggaagggt atcaggacta tgaaccggaa gcctaagggg tatctttgct 540
cccagtttcc tgagatctgc tgacagacgt gccatcctgt ccaagtgccc cgttcccacc 600
tgcccagtcg tgaccttctc tcaacgcttt cacagtgtct tttgaagtct tccatgagca 660
gtgactggag tatctgtacc cgccccacct cggttccggt gcttccctct cactgaatat 720
atggtagcag ggtcttgtgt gctgtggctg ttgtggcttc gaacctaaaa tgtttaatga 780
aaaacaccta agtgactacc acttatttct aaatctattt tttgttgctg ttgagaaatt 840
gtgagtgatt tactctccta agatttaaaa gtgtcttttc aggattccgt cgaagaataa 900
tgatgtatgg cgaaatttgt taatatatac aatacttaaa catgtgagca tggaactatg 960
cacctataaa tattaactat ag 982

<210> SEQ ID NO 25
<211> LENGTH: 140
<212> TYPE: PRT
<213> ORGANISM: Porcine

<400> SEQUENCE: 25

```
Met Asp Val Phe Met Lys Gly Leu Ser Lys Ala Lys Glu Gly Val Val
1               5                   10                  15

Ala Ala Ala Glu Lys Thr Lys Gln Gly Val Ala Glu Ala Ala Gly Lys
            20                  25                  30

Thr Lys Glu Gly Val Leu Tyr Val Gly Ser Lys Thr Lys Glu Gly Val
        35                  40                  45

Val His Gly Val Thr Thr Val Ala Glu Lys Thr Lys Glu Gln Val Thr
    50                  55                  60

Asn Val Gly Glu Ala Val Val Thr Gly Val Thr Ala Val Ala Gln Lys
65                  70                  75                  80

Thr Val Glu Gly Ala Gly Ser Ile Ala Ala Ala Thr Gly Phe Gly Lys
                85                  90                  95

Lys Asp Gln Leu Gly Lys Asn Glu Glu Gly Ala Pro Gln Glu Gly Ile
            100                 105                 110

Leu Glu Asp Met Pro Val Asp Pro Asp Asn Glu Ala Tyr Glu Met Pro
        115                 120                 125

Ser Glu Glu Gly Tyr Gln Asp Tyr Glu Pro Glu Ala
    130                 135                 140
```

<210> SEQ ID NO 26
<211> LENGTH: 982
<212> TYPE: DNA
<213> ORGANISM: Porcine

<400> SEQUENCE: 26

```
cagtctgtta gggggaggag cttatttctc cattccggtg tgatccagga acagctgttt      60

tccctccagc tctgaaagtg tggggtaaag gaattcatta gccatggatg tattcatgaa     120

aggactttca aaagccaagg agggagtcgt ggctgctgct gaaaaaacca aacagggtgt     180

ggcagaagca ccgggaaaga caaaagaggg tgtgctctat gtaggatcca aaaccaagga     240

aggagtggtt catggtgtga caacagtggc tgagaagacc aaagagcaag tgacaaatgt     300

tggagaggca gtggtgacag ggtgacagc ggtagcacag aagacagtgg aaggagcagg      360

gagcattgca gctgccactg gctttggcaa aaaggatcag ctgggcaaga atgaagaagg     420

agccccccag gagggaattc tggaagatat gcctgtggat cctgacaatg aagcttatga     480

aatgccttcc gaggaagggt atcaggacta tgaaccggaa gcctaagggg tatctttgct     540

cccagtttcc tgagatctgc tgacagacgt gccatcctgt ccaagtgccc cgttcccacc     600

tgcccagtcg tgaccttctc tcaacgcttt cacagtgtct tttgaagtct tccatgagca     660

gtgactggag tatctgtacc cgccccacct cggttccggt gcttccctct cactgaatat     720

atggtagcag ggtcttgtgt gctgtggctg ttgtggcttc gaacctaaaa tgtttaatga     780

aaaacaccta agtgactacc acttatttct aaatctattt tttgttgctg ttgagaaatt     840

gtgagtgatt tactctccta agatttaaaa gtgtcttttc aggattccgt cgaagaataa     900

tgatgtatgg cgaaatttgt taatatatac aatacttaaa catgtgagca tggaactatg     960

cacctataaa tattaactat ag                                              982
```

<210> SEQ ID NO 27
<211> LENGTH: 140
<212> TYPE: PRT

<213> ORGANISM: Porcine

<400> SEQUENCE: 27

```
Met Asp Val Phe Met Lys Gly Leu Ser Lys Ala Lys Glu Gly Val Val
1               5                   10                  15

Ala Ala Ala Glu Lys Thr Lys Gln Gly Val Ala Glu Ala Pro Gly Lys
            20                  25                  30

Thr Lys Glu Gly Val Leu Tyr Val Gly Ser Lys Thr Lys Glu Gly Val
        35                  40                  45

Val His Gly Val Thr Thr Val Ala Glu Lys Thr Lys Glu Gln Val Thr
    50                  55                  60

Asn Val Gly Glu Ala Val Val Thr Gly Val Thr Ala Val Ala Gln Lys
65                  70                  75                  80

Thr Val Glu Gly Ala Gly Ser Ile Ala Ala Ala Thr Gly Phe Gly Lys
                85                  90                  95

Lys Asp Gln Leu Gly Lys Asn Glu Glu Gly Ala Pro Gln Glu Gly Ile
            100                 105                 110

Leu Glu Asp Met Pro Val Asp Pro Asp Asn Glu Ala Tyr Glu Met Pro
        115                 120                 125

Ser Glu Glu Gly Tyr Gln Asp Tyr Glu Pro Glu Ala
    130                 135                 140
```

<210> SEQ ID NO 28
<211> LENGTH: 1109
<212> TYPE: DNA
<213> ORGANISM: Homo Sapiens

<400> SEQUENCE: 28

```
cctgggcggc tccgctagct gtttttcgtc ttccctaggc tatttctgcc gggcgctccg     60

cgaagatgca gctcaagccg atggagatca accccgagat gctgaacaaa gtgctgtccc    120

ggctgggggt cgccggccag tggcgcttcg tggacgtgct ggggctggaa gaggagtctc    180

tgggctcggt gccagcgcct gcctgcgcgc tgctgctgct gtttcccctc acggcccagc    240

atgagaactt caggaaaaag cagattgaag agctgaaggg acaagaagtt agtcctaaag    300

tgtacttcat gaagcagacc attgggaatt cctgtggcac aatcggactt attcacgcag    360

tggccaataa tcaagacaaa ctgggatttg aggatggatc agttctgaaa cagtttcttt    420

ctgaaacaga gaaaattccc ctgaagacag agcaaaatgc tttgaaaaga atgaggccat    480

acaggcagcc catgatgccg tggcacagga aggccaatgt cgggtagatg acaaggtgaa    540

tttccatttt attctgttta acaacgtgga tggccacctc tatgaacttg atggacgaat    600

gccttttccg gtgaaccatg gcgccagttc agaggacacc ctgctgaagg acgctgccaa    660

ggtctgcaga gaattcaccg agcgtgagca aggagaagtc cgcttctctg ccgtggctct    720

ctgcaaggca gcctaatgct ctgtgggagg gactttgctg atttcccctc ttcccttcaa    780

catgaaaata tataccccc catgcagtct aaaatgcttc agtacttgtg aaacacagct    840

gttcttctgt tctgcagaca cgccttcccc tcagccacac ccaggcactt aagcacaagc    900

agagtgcaca gctgtccact gggccattgt ggtgtgagct tcagatggtg aagcattctc    960

cccagtgtat gtcttgtatc cgatatctaa cgctttaaat ggctactttg gtttctgtct   1020

gtaagttaag accttggatg tggtttaatt gtttgtcctc aaaaggaata aaacttttct   1080

gctgataaga taaaaaaaaa aaaaaaaaa                                      1109
```

<210> SEQ ID NO 29
<211> LENGTH: 223

<212> TYPE: PRT
<213> ORGANISM: Homo Sapiens

<400> SEQUENCE: 29

```
Met Gln Leu Lys Pro Met Glu Ile Asn Pro Glu Met Leu Asn Lys Val
1               5                   10                  15

Leu Ser Arg Leu Gly Val Ala Gly Gln Trp Arg Phe Val Asp Val Leu
            20                  25                  30

Gly Leu Glu Glu Glu Ser Leu Gly Ser Val Pro Ala Pro Ala Cys Ala
        35                  40                  45

Leu Leu Leu Leu Phe Pro Leu Thr Ala Gln His Glu Asn Phe Arg Lys
    50                  55                  60

Lys Gln Ile Glu Glu Leu Lys Gly Gln Glu Val Ser Pro Lys Val Tyr
65                  70                  75                  80

Phe Met Lys Gln Thr Ile Gly Asn Ser Cys Gly Thr Ile Gly Leu Ile
                85                  90                  95

His Ala Val Ala Asn Asn Gln Asp Lys Leu Gly Phe Glu Asp Gly Ser
            100                 105                 110

Val Leu Lys Gln Phe Leu Ser Glu Thr Glu Lys Met Ser Pro Glu Asp
        115                 120                 125

Arg Ala Lys Cys Phe Glu Lys Asn Glu Ala Ile Gln Ala Ala His Asp
    130                 135                 140

Ala Val Ala Gln Glu Gly Gln Cys Arg Val Asp Asp Lys Val Asn Phe
145                 150                 155                 160

His Phe Ile Leu Phe Asn Asn Val Asp Gly His Leu Tyr Glu Leu Asp
                165                 170                 175

Gly Arg Met Pro Phe Pro Val Asn His Gly Ala Ser Ser Glu Asp Thr
            180                 185                 190

Leu Leu Lys Asp Ala Ala Lys Val Cys Arg Glu Phe Thr Glu Arg Glu
        195                 200                 205

Gln Gly Glu Val Arg Phe Ser Ala Val Ala Leu Cys Lys Ala Ala
    210                 215                 220
```

<210> SEQ ID NO 30
<211> LENGTH: 9234
<212> TYPE: DNA
<213> ORGANISM: Homo Sapiens

<400> SEQUENCE: 30

```
cgctggctgc gggcggtgag ctgagctcgc ccccggggag ctgtggccgg cgcccctgcc      60

ggttccctga gcagcggacg ttcatgctgg gagggcggcg ggttggaagc aggtgccacc     120

atggctagtg gcagctgtca ggggtgcgaa gaggacgagg aaactctgaa gaagttgata     180

gtcaggctga acaatgtcca ggaaggaaaa cagatagaaa cgctggtcca aatcctggag     240

gatctgctgg tgttcacgta ctccgagcac gcctccaagt tatttcaagg caaaaatatc     300

catgtgcctc tgttgatcgt cttggactcc tatatgagag tcgcgagtgt gcagcaggtg     360

ggttggtcac ttctgtgcaa attaatagaa gtctgtccag gtacaatgca aagcttaatg     420

ggaccccagg atgttggaaa tgattgggaa gtccttggtg ttcaccaatt gattcttaaa     480

atgctaacag ttcataatgc cagtgtaaac ttgtcagtga ttggactgaa gaccttagat     540

ctcctcctaa cttcaggtaa aatcaccttg ctgatattgg atgaagaaag tgatattttc     600

atgttaattt ttgatgccat gcactcattt ccagccaatg atgaagtcca gaaacttgga     660

tgcaaagctt tacatgtgct gtttgagaga gtctcagagg agcaactgac tgaatttgtt     720

gagaacaaag attatatgat attgttaagt gcgtcaacaa attttaaaga tgaagaggaa     780
```

attgtgcttc atgtgctgca ttgtttacat tccctagcga ttccttgcaa taatgtggaa 840
gtcctcatga gtggcaatgt caggtgttat aatattgtgg tggaagctat gaaagcattc 900
cctatgagtg aaagaattca agaagtgagt tgctgtttgc tccataggct tacattaggt 960
aattttttca atatcctggt attaaacgaa gtccatgagt ttgtggtgaa agctgtgcag 1020
cagtacccag agaatgcagc attgcagatc tcagcgctca gctgtttggc cctcctcact 1080
gagactattt tcttaaatca agatttagag gaaaagaatg agaatcaaga gaatgatgat 1140
gagggggaag aagataaatt gttttggctg gaagcctgtt acaaagcatt aacgtggcat 1200
agaaagaaca agcacgtgca ggaggccgca tgctgggcac taaataatct ccttatgtac 1260
caaaacagtt tacatgagaa gattggagat gaagatggcc atttcccagc tcatagggaa 1320
gtgatgctct ccatgctgat gcattcttca tcaaaggaag ttttccaggc atctgcgaat 1380
gcattgtcaa ctctcttaga acaaaatgtt aatttcagaa aaatactgtt atcaaaagga 1440
atacacctga atgttttgga gttaatgcag aagcatatac attctcctga agtggctgaa 1500
agtggctgta aaatgctaaa tcatcttttt gaaggaagca acacttccct ggatataatg 1560
gcagcagtgg tccccaaaat actaacagtt atgaaacgtc atgagacatc attaccagtg 1620
cagctggagg cgcttcgagc tattttacat tttatagtgc ctggcatgcc agaagaatcc 1680
agggaggata cagaatttca tcataagcta aatatggtta aaaaacagtg tttcaagaat 1740
gatattcaca aactggtcct agcagctttg aacaggttca ttggaaatcc tgggattcag 1800
aaatgtggat taaaagtaat ttcttctatt gtacattttc ctgatgcatt agagatgtta 1860
tccctggaag gtgctatgga ttcagtgctt cacacactgc agatgtatcc agatgaccaa 1920
gaaattcagt gtctgggttt aagtcttata ggatacttga ttacaaagaa gaatgtgttc 1980
ataggaactg gacatctgct ggcaaaaatt ctggtttcca gcttataccg atttaaggat 2040
gttgctgaaa tacagactaa aggatttcag acaatcttag caatcctcaa attgtcagca 2100
tctttttcta agctgctggt gcatcattca tttgacttag taatattcca tcaaatgtct 2160
tccaatatca tggaacaaaa ggatcaacag tttctaaacc tctgttgcaa gtgttttgca 2220
aaagtagcta tggatgatta cttaaaaaat gtgatgctag agagagcgtg tgatcagaat 2280
aacagcatca tggttgaatg cttgcttcta ttgggagcag atgccaatca agcaaaggag 2340
ggatcttctt taatttgtca ggtatgtgag aaagagagca gtcccaaatt ggtggaactc 2400
ttactgaata gtggatctcg tgaacaagat gtacgaaaag cgttgacgat aagcattggg 2460
aaaggtgaca gccagatcat cagcttgctc ttaaggaggc tggccctgga tgtggccaac 2520
aatagcattt gccttggagg atttgtata ggaaaagttg aaccttcttg gcttggtcct 2580
ttatttccag ataagacttc taatttaagg aaacaaacaa atatagcatc tacactagca 2640
agaatggtga tcagatatca gatgaaaagt gctgtggaag aaggaacagc ctcaggcagc 2700
gatggaaatt tttctgaaga tgtgctgtct aaatttgatg aatggacctt tattcctgac 2760
tcttctatgg acagtgtgtt tgctcaaagt gatgacctgg atagtgaagg aagtgaaggc 2820
tcatttcttg tgaaaaagaa atctaattca attagtgtag gagaatttta ccgagatgcc 2880
gtattacagc gttgctcacc aaatttgcaa agacattcca attccttggg gcccattttt 2940
gatcatgaag atttactgaa gcgaaaaaga aaaatattat cttcagatga ttcactcagg 3000
tcatcaaaac ttcaatccca tatgaggcat tcagacagca tttcttctct ggcttctgag 3060
agagaatata ttacatcact agacctttca gcaaatgaac taagagatat tgatgcccta 3120
agccagaaat gctgtataag tgttcatttg gagcatcttg aaaagctgga gcttcaccag 3180

```
aatgcactca cgagctttcc acaacagcta tgtgaaactc tgaagagttt gacacatttg   3240
gacttgcaca gtaataaatt tacatcattt ccttcttatt tgttgaaaat gagttgtatt   3300
gctaatcttg atgtctctcg aaatgacatt ggaccctcag tggttttaga tcctacagtg   3360
aaatgtccaa ctctgaaaca gtttaacctg tcatataacc agctgtcttt tgtacctgag   3420
aacctcactg atgtggtaga gaaactggag cagctcattt tagaaggaaa taaaatatca   3480
gggatatgct ccccccttgag actgaaggaa ctgaagattt taaaccttag taagaaccac   3540
atttcatccc tatcagagaa ctttcttgag gcttgtccta aagtggagag tttcagtgcc   3600
agaatgaatt ttcttgctgc tatgcctttc ttgcctcctt ctatgacaat cctaaaatta   3660
tctcagaaca aattttcctg tattccagaa gcaattttaa atcttccaca cttgcggtct   3720
ttagatatga gcagcaatga tattcagtac ctaccaggtc ccgcacactg gaaatctttg   3780
aacttaaggg aactcttatt tagccataat cagatcagca tcttggactt gagtgaaaaa   3840
gcatatttat ggtctagagt agagaaactg catctttctc acaataaact gaaagagatt   3900
cctcctgaga ttggctgtct tgaaaatctg acatctctgg atgtcagtta caacttggaa   3960
ctaagatcct ttcccaatga aatggggaaa ttaagcaaaa tatgggatct tcctttggat   4020
gaactgcatc ttaactttga ttttaaacat ataggatgta aagccaaaga catcataagg   4080
tttcttcaac agcgattaaa aaaggctgtg ccttataacc gaatgaaact tatgattgtg   4140
ggaaatactg ggagtggtaa aaccacctta ttgcagcaat taatgaaaac caagaaatca   4200
gatcttggaa tgcaaagtgc cacagttggc atagatgtga aagactggcc tatccaaata   4260
agagacaaaa gaaagagaga tctcgtccta aatgtgtggg attttgcagg tcgtgaggaa   4320
ttctatagta ctcatcccca ttttatgacg cagcgagcat tgtaccttgc tgtctatgac   4380
ctcagcaagg gacaggctga agttgatgcc atgaagcctt ggctcttcaa tataaaggct   4440
cgcgcttctt cttcccctgt gattctcgtt ggcacacatt tggatgtttc tgatgagaag   4500
caacgcaaag cctgcatgag taaaatcacc aaggaactcc tgaataagcg agggttccct   4560
gccatacgag attaccactt tgtgaatgcc accgaggaat ctgatgcttt ggcaaaactt   4620
cggaaaacca tcataaacga gagccttaat ttcaagatcc gagatcagct tgttgttgga   4680
cagctgattc cagactgcta tgtagaactt gaaaaaatca ttttatcgga gcgtaaaaat   4740
gtgccaattg aatttcccgt aattgaccgg aaacgattat tacaactagt gagagaaaat   4800
cagctgcagt tagatgaaaa tgagcttcct cacgcagttc actttctaaa tgaatcagga   4860
gtccttcttc attttcaaga cccagcactg cagttaagtg acttgtactt tgtggaaccc   4920
aagtggcttt gtaaaatcat ggcacagatt ttgacagtga aagtggaagg ttgtccaaaa   4980
caccctaagg gcattatttc gcgtagagat gtggaaaaat ttctttcaaa aaaaaggaaa   5040
tttccaaaga actacatgtc acagtatttt aagctcctag aaaaattcca gattgctttg   5100
ccaataggag aagaatattt gctggttcca agcagtttgt ctgaccacag gcctgtgata   5160
gagcttcccc attgtgagaa ctctgaaatt atcatccgac tatatgaaat gccttatttt   5220
ccaatgggat tttggtcaag attaatcaat cgattacttg agatttcacc ttacatgctt   5280
tcagggagag aacgagcact tcgcccaaac agaatgtatt ggcgacaagg catttactta   5340
aattggtctc ctgaagctta ttgtctggta ggatctgaag tcttagacaa tcatccagag   5400
agtttcttaa aaattacagt tccttcttgt agaaaaggct gtattctttt gggccaagtt   5460
gtggaccaca ttgattctct catggaagaa tggtttcctg ggttgctgga gattgatatt   5520
tgtggtgaag gagaaactct gttgaagaaa tgggcattat atagttttaa tgatggtgaa   5580
```

```
gaacatcaaa aaatcttact tgatgacttg atgaagaaag cagaggaagg agatctctta   5640
gtaaatccag atcaaccaag gctcaccatt ccaatatctc agattgcccc tgacttgatt   5700
ttggctgacc tgcctagaaa tattatgttg aataatgatg agttggaatt tgaacaagct   5760
ccagagtttc tcctaggtga tggcagtttt ggatcagttt accgagcagc ctatgaagga   5820
gaagaagtgg ctgtgaagat ttttaataaa catacatcac tcaggctgtt aagacaagag   5880
cttgtggtgc tttgccacct ccaccacccc agtttgatat ctttgctggc agctgggatt   5940
cgtccccgga tgttggtgat ggagttagcc tccaagggtt ccttggatcg cctgcttcag   6000
caggacaaag ccagcctcac tagaacccta cagcacagga ttgcactcca cgtagctgat   6060
ggtttgagat acctccactc agccatgatt atataccgag acctgaaacc ccacaatgtg   6120
ctgcttttca cactgtatcc caatgctgcc atcattgcaa agattgctga ctacggcatt   6180
gctcagtact gctgtagaat ggggataaaa acatcagagg gcacaccagg gtttcgtgca   6240
cctgaagttg ccagaggaaa tgtcatttat aaccaacagg ctgatgttta ttcatttggt   6300
ttactactct atgacatttt gacaactgga ggtagaatag tagagggttt gaagtttcca   6360
aatgagtttg atgaattaga aatacaagga aaattacctg atccagttaa agaatatggt   6420
tgtgccccat ggcctatggt tgagaaatta attaaacagt gtttgaaaga aaatcctcaa   6480
gaaaggccta cttctgccca ggtctttgac attttgaatt cagctgaatt agtctgtctg   6540
acgagacgca ttttattacc taaaaacgta attgttgaat gcatggttgc tacacatcac   6600
aacagcagga atgcaagcat ttggctgggc tgtgggcaca ccgacagagg acagctctca   6660
tttcttgact taaatactga aggatacact tctgaggaag ttgctgatag tagaatattg   6720
tgcttagcct tggtgcatct tcctgttgaa aaggaaagct ggattgtgtc tgggacacag   6780
tctggtactc tcctggtcat caataccgaa gatgggaaaa agagacatac cctagaaaag   6840
atgactgatt ctgtcacttg tttgtattgc aattcctttt ccaagcaaag caaacaaaaa   6900
aattttcttt tggttggaac cgctgatggc aagttagcaa tttttgaaga taagactgtt   6960
aagcttaaag gagctgctcc tttgaagata ctaaatatag gaaatgtcag tactccattg   7020
atgtgtttga gtgaatccac aaattcaacg gaaagaaatg taatgtgggg aggatgtggc   7080
acaaagattt tctccttttc taatgatttc accattcaga aactcattga gacaagaaca   7140
agccaactgt tttcttatgc agctttcagt gattccaaca tcataacagt ggtggtagac   7200
actgctctct atattgctaa gcaaaatagc cctgttgtgg aagtgtggga taagaaaact   7260
gaaaaactct gtggactaat agactgcgtg cactttttaa gggaggtaat ggtaaaagaa   7320
aacaaggaat caaaacacaa aatgtcttat tctgggagag tgaaaaccct ctgccttcag   7380
aagaacactg ctctttggat aggaactgga ggaggccata ttttactcct ggatctttca   7440
actcgtcgac ttatacgtgt aatttacaac ttttgtaatt cggtcagagt catgatgaca   7500
gcacagctag gaagccttaa aaatgtcatg ctggtattgg gctacaaccg gaaaaatact   7560
gaaggtacac aaaagcagaa agagatacaa tcttgcttga ccgtttggga catcaatctt   7620
ccacatgaag tgcaaaattt agaaaaacac attgaagtga gaaaagaatt agctgaaaaa   7680
atgagacgaa catctgttga gtaagagaga aataggaatt gtctttggat aggaaaatta   7740
ttctctcctc ttgtaaatat ttattttaaa aatgttcaca tggaaagggt actcacattt   7800
tttgaaatag ctcgtgtgta tgaaggaatg ttattatttt taatttaaat atatgtaaaa   7860
atacttacca gtaaatgtgt attttaaaga actatttaaa acacaatgtt atatttctta   7920
taaataccag ttactttcgt tcattaatta atgaaaataa atctgtgaag tacctaattt   7980
```

-continued

```
aagtactcat actaaaattt ataaggccga taattttttg ttttcttgtc tgtaatggag   8040

gtaaacttta ttttaaattc tgtgcttaag acaggactat tgcttgtcga tttttctaga   8100

aatctgcacg gtataatgaa aatattaaga cagtttccca tgtaatgtat tccttcttag   8160

attgcatcga aatgcactat catatatgct tgtaaatatt caaatgaatt tgcactaata   8220

aagtcctttg ttggtatgtg aattctcttt gttgctgttg caaacagtgc atcttacaca   8280

acttcactca attcaaaaga aaactccatt aaaagtacta atgaaaaaac atgacatact   8340

gtcaaagtcc tcatatctag gaaagacaca gaaactctct ttgtcacaga aactctctgt   8400

gtctttccta gacataatag agttgttttt caactctatg tttgaatgtg gataccctga   8460

attttgtata attagtgtaa atacagtgtt cagtccttca agtgatattt ttattttttt   8520

attcatacca ctagctactt gttttctaat ctgcttcatt ctaatgctta tattcatctt   8580

ttccctaaat ttgtgatgct gcagatccta catcattcag atagaaacct tttttttttt   8640

cagaattata gaattccaca gctcctacca agaccatgag gataaatatc taacactttt   8700

cagttgctga aggagaaagg agctttagtt atgatggata aaaatatctg ccaccctagg   8760

cttccaaatt atacttaaat tgtttacata gcttaccaca ataggagtat cagggccaaa   8820

tacctatgta ataatttgag gtcatttctg ctttaggaaa agtactttcg gtaaattctt   8880

tggccctgac cagtattcat tatttcagat aattccctgt gataggacaa ctagtacatt   8940

taatattctc agaacttatg gcattttact atgtgaaaac tttaaattta tttatattaa   9000

gggtaatcaa attcttaaag atgaaagatt ttctgtattt taaaggaagc tatgctttaa   9060

cttgttatgt aattaacaaa aaaatcatat ataatagagc tctttgttcc agtgttatct   9120

ctttcattgt tactttgtat ttgcaatttt ttttaccaaa gacaaattaa aaaaatgaat   9180

accatattta aatggaataa taaaggtttt ttaaaaactt taaaaaaaaa aaaa         9234
```

<210> SEQ ID NO 31
<211> LENGTH: 2505
<212> TYPE: PRT
<213> ORGANISM: Homo Sapiens

<400> SEQUENCE: 31

```
Met Ala Ser Gly Ser Cys Gln Gly Cys Glu Glu Asp Glu Glu Thr Leu
1               5                   10                  15

Lys Lys Leu Ile Val Arg Leu Asn Asn Val Gln Glu Gly Lys Gln Ile
            20                  25                  30

Glu Thr Leu Val Gln Ile Leu Glu Asp Leu Leu Val Phe Thr Tyr Ser
        35                  40                  45

Glu His Ala Ser Lys Leu Phe Gln Gly Lys Asn Ile His Val Pro Leu
    50                  55                  60

Leu Ile Val Leu Asp Ser Tyr Met Arg Val Ala Ser Val Gln Gln Val
65                  70                  75                  80

Gly Trp Ser Leu Leu Cys Lys Leu Ile Glu Val Cys Pro Gly Thr Met
                85                  90                  95

Gln Ser Leu Met Gly Pro Gln Asp Val Gly Asn Asp Trp Glu Val Leu
            100                 105                 110

Gly Val His Gln Leu Ile Leu Lys Met Leu Thr Val His Asn Ala Ser
        115                 120                 125

Val Asn Leu Ser Val Ile Gly Leu Lys Thr Leu Asp Leu Leu Leu Thr
    130                 135                 140

Ser Gly Lys Ile Thr Leu Leu Ile Leu Asp Glu Glu Ser Asp Ile Phe
145                 150                 155                 160
```

-continued

```
Met Leu Ile Phe Asp Ala Met His Ser Phe Pro Ala Asn Asp Glu Val
                165                 170                 175

Gln Lys Leu Gly Cys Lys Ala Leu His Val Leu Phe Glu Arg Val Ser
            180                 185                 190

Glu Glu Gln Leu Thr Glu Phe Val Glu Asn Lys Asp Tyr Met Ile Leu
        195                 200                 205

Leu Ser Ala Ser Thr Asn Phe Lys Asp Glu Glu Glu Ile Val Leu His
    210                 215                 220

Val Leu His Cys Leu His Ser Leu Ala Ile Pro Cys Asn Asn Val Glu
225                 230                 235                 240

Val Leu Met Ser Gly Asn Val Arg Cys Tyr Asn Ile Val Val Glu Ala
                245                 250                 255

Met Lys Ala Phe Pro Met Ser Glu Arg Ile Gln Glu Val Ser Cys Cys
            260                 265                 270

Leu Leu His Arg Leu Thr Leu Gly Asn Phe Phe Asn Ile Leu Val Leu
        275                 280                 285

Asn Glu Val His Glu Phe Val Val Lys Ala Val Gln Gln Tyr Pro Glu
    290                 295                 300

Asn Ala Ala Leu Gln Ile Ser Ala Leu Ser Cys Leu Ala Leu Leu Thr
305                 310                 315                 320

Glu Thr Ile Phe Leu Asn Gln Asp Leu Glu Glu Lys Asn Glu Asn Gln
                325                 330                 335

Glu Asn Asp Asp Glu Gly Glu Glu Asp Lys Leu Phe Trp Leu Glu Ala
            340                 345                 350

Cys Tyr Lys Ala Leu Thr Trp His Arg Lys Asn Lys His Val Gln Glu
        355                 360                 365

Ala Ala Cys Trp Ala Leu Asn Asn Leu Leu Met Tyr Gln Asn Ser Leu
    370                 375                 380

His Glu Lys Ile Gly Asp Glu Asp Gly His Phe Pro Ala His Arg Glu
385                 390                 395                 400

Val Met Leu Ser Met Leu Met His Ser Ser Ser Lys Glu Val Phe Gln
                405                 410                 415

Ala Ser Ala Asn Ala Leu Ser Thr Leu Leu Glu Gln Asn Val Asn Phe
            420                 425                 430

Arg Lys Ile Leu Leu Ser Lys Gly Ile His Leu Asn Val Leu Glu Leu
        435                 440                 445

Met Gln Lys His Ile His Ser Pro Glu Val Ala Glu Ser Gly Cys Lys
    450                 455                 460

Met Leu Asn His Leu Phe Glu Gly Ser Asn Thr Ser Leu Asp Ile Met
465                 470                 475                 480

Ala Ala Val Val Pro Lys Ile Leu Thr Val Met Lys Arg His Glu Thr
                485                 490                 495

Ser Leu Pro Val Gln Leu Glu Ala Leu Arg Ala Ile Leu His Phe Ile
            500                 505                 510

Val Pro Gly Met Pro Glu Glu Ser Arg Glu Asp Thr Glu Phe His His
        515                 520                 525

Lys Leu Asn Met Val Lys Lys Gln Cys Phe Lys Asn Asp Ile His Lys
    530                 535                 540

Leu Val Leu Ala Ala Leu Asn Arg Phe Ile Gly Asn Pro Gly Ile Gln
545                 550                 555                 560

Lys Cys Gly Leu Lys Val Ile Ser Ser Ile Val His Phe Pro Asp Ala
                565                 570                 575

Leu Glu Met Leu Ser Leu Glu Gly Ala Met Asp Ser Val Leu His Thr
```

-continued

```
            580                 585                 590

Leu Gln Met Tyr Pro Asp Asp Gln Glu Ile Gln Cys Leu Gly Leu Ser
        595                 600                 605

Leu Ile Gly Tyr Leu Ile Thr Lys Lys Asn Val Phe Ile Gly Thr Gly
    610                 615                 620

His Leu Leu Ala Lys Ile Leu Val Ser Ser Leu Tyr Arg Phe Lys Asp
625                 630                 635                 640

Val Ala Glu Ile Gln Thr Lys Gly Phe Gln Thr Ile Leu Ala Ile Leu
                645                 650                 655

Lys Leu Ser Ala Ser Phe Ser Lys Leu Leu Val His His Ser Phe Asp
            660                 665                 670

Leu Val Ile Phe His Gln Met Ser Ser Asn Ile Met Glu Gln Lys Asp
        675                 680                 685

Gln Gln Phe Leu Asn Leu Cys Cys Lys Cys Phe Ala Lys Val Ala Met
    690                 695                 700

Asp Asp Tyr Leu Lys Asn Val Met Leu Glu Arg Ala Cys Asp Gln Asn
705                 710                 715                 720

Asn Ser Ile Met Val Glu Cys Leu Leu Leu Leu Gly Ala Asp Ala Asn
                725                 730                 735

Gln Ala Lys Glu Gly Ser Ser Leu Ile Cys Gln Val Cys Glu Lys Glu
            740                 745                 750

Ser Ser Pro Lys Leu Val Glu Leu Leu Leu Asn Ser Gly Ser Arg Glu
        755                 760                 765

Gln Asp Val Arg Lys Ala Leu Thr Ile Ser Ile Gly Lys Gly Asp Ser
    770                 775                 780

Gln Ile Ile Ser Leu Leu Leu Arg Arg Leu Ala Leu Asp Val Ala Asn
785                 790                 795                 800

Asn Ser Ile Cys Leu Gly Gly Phe Cys Ile Gly Lys Val Glu Pro Ser
                805                 810                 815

Trp Leu Gly Pro Leu Phe Pro Asp Lys Thr Ser Asn Leu Arg Lys Gln
            820                 825                 830

Thr Asn Ile Ala Ser Thr Leu Ala Arg Met Val Ile Arg Tyr Gln Met
        835                 840                 845

Lys Ser Ala Val Glu Glu Gly Thr Ala Ser Gly Ser Asp Gly Asn Phe
    850                 855                 860

Ser Glu Asp Val Leu Ser Lys Phe Asp Glu Trp Thr Phe Ile Pro Asp
865                 870                 875                 880

Ser Ser Met Asp Ser Val Phe Ala Gln Ser Asp Asp Leu Asp Ser Glu
                885                 890                 895

Gly Ser Glu Gly Ser Phe Leu Val Lys Lys Lys Ser Asn Ser Ile Ser
            900                 905                 910

Val Gly Glu Phe Tyr Arg Asp Ala Val Leu Gln Arg Cys Ser Pro Asn
        915                 920                 925

Leu Gln Arg His Ser Asn Ser Leu Gly Pro Ile Phe Asp His Glu Asp
    930                 935                 940

Leu Leu Lys Arg Lys Arg Lys Ile Leu Ser Ser Asp Asp Ser Leu Arg
945                 950                 955                 960

Ser Ser Lys Leu Gln Ser His Met Arg His Ser Asp Ser Ile Ser Ser
                965                 970                 975

Leu Ala Ser Glu Arg Glu Tyr Ile Thr Ser Leu Asp Leu Ser Ala Asn
            980                 985                 990

Glu Leu Arg Asp Ile Asp Ala Leu  Ser Gln Lys Cys Cys  Ile Ser Val
        995                 1000                1005
```

-continued

```
His Leu  Glu His Leu Glu Lys  Leu Glu Leu His Gln  Asn Ala Leu
    1010                 1015                 1020

Thr Ser  Phe Pro Gln Gln Leu  Cys Glu Thr Leu Lys  Ser Leu Thr
    1025                 1030                 1035

His Leu  Asp Leu His Ser Asn  Lys Phe Thr Ser Phe  Pro Ser Tyr
    1040                 1045                 1050

Leu Leu  Lys Met Ser Cys Ile  Ala Asn Leu Asp Val  Ser Arg Asn
    1055                 1060                 1065

Asp Ile  Gly Pro Ser Val Val  Leu Asp Pro Thr Val  Lys Cys Pro
    1070                 1075                 1080

Thr Leu  Lys Gln Phe Asn Leu  Ser Tyr Asn Gln Leu  Ser Phe Val
    1085                 1090                 1095

Pro Glu  Asn Leu Thr Asp Val  Val Glu Lys Leu Glu  Gln Leu Ile
    1100                 1105                 1110

Leu Glu  Gly Asn Lys Ile Ser  Gly Ile Cys Ser Pro  Leu Arg Leu
    1115                 1120                 1125

Lys Glu  Leu Lys Ile Leu Asn  Leu Ser Lys Asn His  Ile Ser Ser
    1130                 1135                 1140

Leu Ser  Glu Asn Phe Leu Glu  Ala Cys Pro Lys Val  Glu Ser Phe
    1145                 1150                 1155

Ser Ala  Arg Met Asn Phe Leu  Ala Ala Met Pro Phe  Leu Pro Pro
    1160                 1165                 1170

Ser Met  Thr Ile Leu Lys Leu  Ser Gln Asn Lys Phe  Ser Cys Ile
    1175                 1180                 1185

Pro Glu  Ala Ile Leu Asn Leu  Pro His Leu Arg Ser  Leu Asp Met
    1190                 1195                 1200

Ser Ser  Asn Asp Ile Gln Tyr  Leu Pro Gly Pro Ala  His Trp Lys
    1205                 1210                 1215

Ser Leu  Asn Leu Arg Glu Leu  Leu Phe Ser His Asn  Gln Ile Ser
    1220                 1225                 1230

Ile Leu  Asp Leu Ser Glu Lys  Ala Tyr Leu Trp Ser  Arg Val Glu
    1235                 1240                 1245

Lys Leu  His Leu Ser His Asn  Lys Leu Lys Glu Ile  Pro Pro Glu
    1250                 1255                 1260

Ile Gly  Cys Leu Glu Asn Leu  Thr Ser Leu Asp Val  Ser Tyr Asn
    1265                 1270                 1275

Leu Glu  Leu Arg Ser Phe Pro  Asn Glu Met Gly Lys  Leu Ser Lys
    1280                 1285                 1290

Ile Trp  Asp Leu Pro Leu Asp  Glu Leu His Leu Asn  Phe Asp Phe
    1295                 1300                 1305

Lys His  Ile Gly Cys Lys Ala  Lys Asp Ile Ile Arg  Phe Leu Gln
    1310                 1315                 1320

Gln Arg  Leu Lys Lys Ala Val  Pro Tyr Asn Arg Met  Lys Leu Met
    1325                 1330                 1335

Ile Val  Gly Asn Thr Gly Ser  Gly Lys Thr Thr Leu  Leu Gln Gln
    1340                 1345                 1350

Leu Met  Lys Thr Lys Lys Ser  Asp Leu Gly Met Gln  Ser Ala Thr
    1355                 1360                 1365

Val Gly  Ile Asp Val Lys Asp  Trp Pro Ile Gln Ile  Arg Asp Lys
    1370                 1375                 1380

Arg Lys  Arg Asp Leu Val Leu  Asn Val Trp Asp Phe  Ala Gly Arg
    1385                 1390                 1395

Glu Glu  Phe Tyr Ser Thr His  Pro His Phe Met Thr  Gln Arg Ala
    1400                 1405                 1410
```

Leu Tyr Leu Ala Val Tyr Asp Leu Ser Lys Gly Gln Ala Glu Val
1415 1420 1425

Asp Ala Met Lys Pro Trp Leu Phe Asn Ile Lys Ala Arg Ala Ser
1430 1435 1440

Ser Ser Pro Val Ile Leu Val Gly Thr His Leu Asp Val Ser Asp
1445 1450 1455

Glu Lys Gln Arg Lys Ala Cys Met Ser Lys Ile Thr Lys Glu Leu
1460 1465 1470

Leu Asn Lys Arg Gly Phe Pro Ala Ile Arg Asp Tyr His Phe Val
1475 1480 1485

Asn Ala Thr Glu Glu Ser Asp Ala Leu Ala Lys Leu Arg Lys Thr
1490 1495 1500

Ile Ile Asn Glu Ser Leu Asn Phe Lys Ile Arg Asp Gln Leu Val
1505 1510 1515

Val Gly Gln Leu Ile Pro Asp Cys Tyr Val Glu Leu Glu Lys Ile
1520 1525 1530

Ile Leu Ser Glu Arg Lys Asn Val Pro Ile Glu Phe Pro Val Ile
1535 1540 1545

Asp Arg Lys Arg Leu Leu Gln Leu Val Arg Glu Asn Gln Leu Gln
1550 1555 1560

Leu Asp Glu Asn Glu Leu Pro His Ala Val His Phe Leu Asn Glu
1565 1570 1575

Ser Gly Val Leu Leu His Phe Gln Asp Pro Ala Leu Gln Leu Ser
1580 1585 1590

Asp Leu Tyr Phe Val Glu Pro Lys Trp Leu Cys Lys Ile Met Ala
1595 1600 1605

Gln Ile Leu Thr Val Lys Val Glu Gly Cys Pro Lys His Pro Lys
1610 1615 1620

Gly Ile Ile Ser Arg Arg Asp Val Glu Lys Phe Leu Ser Lys Lys
1625 1630 1635

Arg Lys Phe Pro Lys Asn Tyr Met Ser Gln Tyr Phe Lys Leu Leu
1640 1645 1650

Glu Lys Phe Gln Ile Ala Leu Pro Ile Gly Glu Glu Tyr Leu Leu
1655 1660 1665

Val Pro Ser Ser Leu Ser Asp His Arg Pro Val Ile Glu Leu Pro
1670 1675 1680

His Cys Glu Asn Ser Glu Ile Ile Ile Arg Leu Tyr Glu Met Pro
1685 1690 1695

Tyr Phe Pro Met Gly Phe Trp Ser Arg Leu Ile Asn Arg Leu Leu
1700 1705 1710

Glu Ile Ser Pro Tyr Met Leu Ser Gly Arg Glu Arg Ala Leu Arg
1715 1720 1725

Pro Asn Arg Met Tyr Trp Arg Gln Gly Ile Tyr Leu Asn Trp Ser
1730 1735 1740

Pro Glu Ala Tyr Cys Leu Val Gly Ser Glu Val Leu Asp Asn His
1745 1750 1755

Pro Glu Ser Phe Leu Lys Ile Thr Val Pro Ser Cys Arg Lys Gly
1760 1765 1770

Cys Ile Leu Leu Gly Gln Val Val Asp His Ile Asp Ser Leu Met
1775 1780 1785

Glu Glu Trp Phe Pro Gly Leu Leu Glu Ile Asp Ile Cys Gly Glu
1790 1795 1800

Gly Glu Thr Leu Leu Lys Lys Trp Ala Leu Tyr Ser Phe Asn Asp

-continued

```
    1805                1810                1815

Gly Glu  Glu His Gln Lys Ile  Leu Leu Asp Asp Leu  Met Lys Lys
    1820                1825                1830

Ala Glu  Glu Gly Asp Leu Leu  Val Asn Pro Asp Gln  Pro Arg Leu
    1835                1840                1845

Thr Ile  Pro Ile Ser Gln Ile  Ala Pro Asp Leu Ile  Leu Ala Asp
    1850                1855                1860

Leu Pro  Arg Asn Ile Met Leu  Asn Asn Asp Glu Leu  Glu Phe Glu
    1865                1870                1875

Gln Ala  Pro Glu Phe Leu Leu  Gly Asp Gly Ser Phe  Gly Ser Val
    1880                1885                1890

Tyr Arg  Ala Ala Tyr Glu Gly  Glu Glu Val Ala Val  Lys Ile Phe
    1895                1900                1905

Asn Lys  His Thr Ser Leu Arg  Leu Leu Arg Gln Glu  Leu Val Val
    1910                1915                1920

Leu Cys  His Leu His His Pro  Ser Leu Ile Ser Leu  Leu Ala Ala
    1925                1930                1935

Gly Ile  Arg Pro Arg Met Leu  Val Met Glu Leu Ala  Ser Lys Gly
    1940                1945                1950

Ser Leu  Asp Arg Leu Leu Gln  Gln Asp Lys Ala Ser  Leu Thr Arg
    1955                1960                1965

Thr Leu  Gln His Arg Ile Ala  Leu His Val Ala Asp  Gly Leu Arg
    1970                1975                1980

Tyr Leu  His Ser Ala Met Ile  Ile Tyr Arg Asp Leu  Lys Pro His
    1985                1990                1995

Asn Val  Leu Leu Phe Thr Leu  Tyr Pro Asn Ala Ala  Ile Ile Ala
    2000                2005                2010

Lys Ile  Ala Asp Tyr Gly Ile  Ala Gln Tyr Cys Cys  Arg Met Gly
    2015                2020                2025

Ile Lys  Thr Ser Glu Gly Thr  Pro Gly Phe Arg Ala  Pro Glu Val
    2030                2035                2040

Ala Arg  Gly Asn Val Ile Tyr  Asn Gln Gln Ala Asp  Val Tyr Ser
    2045                2050                2055

Phe Gly  Leu Leu Leu Tyr Asp  Ile Leu Thr Thr Gly  Gly Arg Ile
    2060                2065                2070

Val Glu  Gly Leu Lys Phe Pro  Asn Glu Phe Asp Glu  Leu Glu Ile
    2075                2080                2085

Gln Gly  Lys Leu Pro Asp Pro  Val Lys Glu Tyr Gly  Cys Ala Pro
    2090                2095                2100

Trp Pro  Met Val Glu Lys Leu  Ile Lys Gln Cys Leu  Lys Glu Asn
    2105                2110                2115

Pro Gln  Glu Arg Pro Thr Ser  Ala Gln Val Phe Asp  Ile Leu Asn
    2120                2125                2130

Ser Ala  Glu Leu Val Cys Leu  Thr Arg Arg Ile Leu  Leu Pro Lys
    2135                2140                2145

Asn Val  Ile Val Glu Cys Met  Val Ala Thr His His  Asn Ser Arg
    2150                2155                2160

Asn Ala  Ser Ile Trp Leu Gly  Cys Gly His Thr Asp  Arg Gly Gln
    2165                2170                2175

Leu Ser  Phe Leu Asp Leu Asn  Thr Glu Gly Tyr Thr  Ser Glu Glu
    2180                2185                2190

Val Ala  Asp Ser Arg Ile Leu  Cys Leu Ala Leu Val  His Leu Pro
    2195                2200                2205
```

-continued

Val Glu Lys Glu Ser Trp Ile Val Ser Gly Thr Gln Ser Gly Thr
2210 2215 2220

Leu Leu Val Ile Asn Thr Glu Asp Gly Lys Lys Arg His Thr Leu
2225 2230 2235

Glu Lys Met Thr Asp Ser Val Thr Cys Leu Tyr Cys Asn Ser Phe
2240 2245 2250

Ser Lys Gln Ser Lys Gln Lys Asn Phe Leu Leu Val Gly Thr Ala
2255 2260 2265

Asp Gly Lys Leu Ala Ile Phe Glu Asp Lys Thr Val Lys Leu Lys
2270 2275 2280

Gly Ala Ala Pro Leu Lys Ile Leu Asn Ile Gly Asn Val Ser Thr
2285 2290 2295

Pro Leu Met Cys Leu Ser Glu Ser Thr Asn Ser Thr Glu Arg Asn
2300 2305 2310

Val Met Trp Gly Gly Cys Gly Thr Lys Ile Phe Ser Phe Ser Asn
2315 2320 2325

Asp Phe Thr Ile Gln Lys Leu Ile Glu Thr Arg Thr Ser Gln Leu
2330 2335 2340

Phe Ser Tyr Ala Ala Phe Ser Asp Ser Asn Ile Ile Thr Val Val
2345 2350 2355

Val Asp Thr Ala Leu Tyr Ile Ala Lys Gln Asn Ser Pro Val Val
2360 2365 2370

Glu Val Trp Asp Lys Lys Thr Glu Lys Leu Cys Gly Leu Ile Asp
2375 2380 2385

Cys Val His Phe Leu Arg Glu Val Met Val Lys Glu Asn Lys Glu
2390 2395 2400

Ser Lys His Lys Met Ser Tyr Ser Gly Arg Val Lys Thr Leu Cys
2405 2410 2415

Leu Gln Lys Asn Thr Ala Leu Trp Ile Gly Thr Gly Gly Gly His
2420 2425 2430

Ile Leu Leu Leu Asp Leu Ser Thr Arg Arg Leu Ile Arg Val Ile
2435 2440 2445

Tyr Asn Phe Cys Asn Ser Val Arg Val Met Met Thr Ala Gln Leu
2450 2455 2460

Gly Ser Leu Lys Asn Val Met Leu Val Leu Gly Tyr Asn Arg Lys
2465 2470 2475

Asn Thr Glu Gly Thr Gln Lys Gln Lys Glu Ile Gln Ser Cys Leu
2480 2485 2490

Thr Val Trp Asp Ile Asn Leu Pro His Glu Val Gln
2495 2500 2505

<210> SEQ ID NO 32
<211> LENGTH: 3261
<212> TYPE: DNA
<213> ORGANISM: Homo Sapiens

<400> SEQUENCE: 32
gccacaagcc tccaccccag ctggtccccc acccaggctg cccagtttaa cattcctagt 60
cataggacct tgacttctga gaggcctgat tgtcatctgt aaataagggg taggactaaa 120
gcactcctcc tggaggactg agagatgggc tggaccggag cacttgagtc tgggatatgt 180
gaccatgcta cctttgtctc cctgtcctgt tccttccccc agccccaaat ccagggtttt 240
ccaaagtgtg gttcaagaac cacctgcatc tgaatctaga ggtactggat acaaccccac 300
gtctgggccg ttacccagga cattctacat gagaacgtgg gggtggggcc ctggctgcac 360

-continued

```
ctgaactgtc acctggagtc agggtggaag gtggaagaac tgggtcttat ttccttctcc    420
ccttgttctt tagggtctgt ccttctgcag actccgttac cccaccctaa ccatcctgca    480
caccccttgga gccctctggg ccaatgccct gtcccgcaaa gggcttctca ggcatctcac    540
ctctatggga gggcattttt ggcccccaga accttacacg gtgtttatgt ggggaagccc    600
ctgggaagca gacagtccta gggtgaagct gagaggcaga gagaagggga gacagacaga    660
gggtggggct ttcccccttg tctccagtgc cctttctggt gaccctcggt tcttttcccc    720
caccaccccc ccagcggagc ccatcgtggt gaggcttaag gaggtccgac tgcagaggga    780
cgacttcgag attctgaagg tgatcggacg cggggcgttc agcgaggtag cggtagtgaa    840
gatgaagcag acgggccagg tgtatgccat gaagatcatg aacaagtggg acatgctgaa    900
gaggggcgag gtgtcgtgct tccgtgagga gagggacgtg ttggtgaatg gggaccggcg    960
gtggatcacg cagctgcact tcgccttcca ggatgagaac tacctgtacc tggtcatgga   1020
gtattacgtg ggcggggacc tgctgacact gctgagcaag tttggggagc ggattccggc   1080
cgagatggcg cgcttctacc tggcggagat tgtcatggcc atagactcgg tgcaccggct   1140
tggctacgtg cacagggaca tcaaacccga caacatcctg ctggaccgct gtggccacat   1200
ccgcctggcc gacttcggct cttgcctcaa gctgcgggca gatggaacgg tgcggtcgct   1260
ggtggctgtg ggcaccccag actacctgtc ccccgagatc ctgcaggctg tgggcggtgg   1320
gcctgggaca ggcagctacg ggcccgagtg tgactggtgg gcgctgggtg tattcgccta   1380
tgaaatgttc tatgggcaga cgcccttcta cgcggattcc acggcggaga cctatggcaa   1440
gatcgtccac tacaaggagc acctctctct gccgctggtg gacgaagggg tccctgagga   1500
ggctcgagac ttcattcagc ggttgctgtg tcccccggag acacggctgg gccggggtgg   1560
agcaggcgac ttccggacac atcccttctt ctttggcctc gactgggatg gtctccggga   1620
cagcgtgccc ccctttacac cggatttcga aggtgccacc gacacatgca acttcgactt   1680
ggtggaggac gggctcactg ccatggtgag cgggggcggg gagacactgt cggacattcg   1740
ggaaggtgcg ccgctagggg tccacctgcc ttttgtgggc tactcctact cctgcatggc   1800
cctcagggac agtgaggtcc caggccccac acccatggaa ctggaggccg agcagctgct   1860
tgagccacac gtgcaagcgc ccagcctgga gccctcggtg tccccacagg atgaaacagc   1920
tgaagtggca gttccagcgg ctgtccctgc ggcagaggct gaggccgagg tgacgctgcg   1980
ggagctccag gaagccctgg aggaggaggt gctcacccgg cagagcctga gccgggagat   2040
ggaggccatc cgcacggaca accagaactt cgccagtcaa ctacgcgagg cagaggctcg   2100
gaaccgggac ctagaggcac acgtccggca gttgcaggag cggatggagt tgctgcaggc   2160
agagggagcc acagctgtca cgggggtccc cagtccccgg gccacggatc caccttccca   2220
tctagatggc ccccccggccg tggctgtggg ccagtgcccg ctggtggggc caggccccat   2280
gcaccgccgc cacctgctgc tccctgccag ggtccctagg cctggcctat cggaggcgct   2340
ttccctgctc ctgttcgccg ttgttctgtc tcgtgccgcc gccctgggct gcattgggtt   2400
ggtggcccac gccggccaac tcaccgcagt ctggcgccgc ccaggagccg cccgcgctcc   2460
ctgaacccta gaactgtctt cgactccggg gccccgttgg aagactgagt gcccggggca   2520
cggcacagaa gccgcgccca ccgcctgcca gttcacaacc gctccgagcg tgggtctccg   2580
cccagctcca gtcctgtgat ccgggcccgc cccctagcgg ccggggaggg aggggccggg   2640
tccgcggccg gcgaacgggg ctcgaagggt ccttgtagcc gggaatgctg ctgctgctgc   2700
tgctgctgct gctgctgctg ctgctgctgc tgctgctgct gctgctgggg ggatcacaga   2760
```

```
ccatttcttt ctttcggcca ggctgaggcc ctgacgtgga tgggcaaact gcaggcctgg   2820

gaaggcagca agccgggccg tccgtgttcc atcctccacg cacccccacc tatcgttggt   2880

tcgcaaagtg caaagctttc ttgtgcatga cgccctgctc tggggagcgt ctggcgcgat   2940

ctctgcctgc ttactcggga aatttgcttt tgccaaaccc gctttttcgg ggatcccgcg   3000

ccccccctcct cacttgcgct gctctcggag ccccagccgg ctccgcccgc ttcggcggtt   3060

tggatattta ttgacctcgt cctccgactc gctgacaggc tacaggaccc ccaacaaccc   3120

caatccacgt tttggatgca ctgagacccc gacattcctc ggtatttatt gtctgtcccc   3180

acctaggacc cccacccccg accctcgcga ataaaaggcc ctccatctgc ccaaaaaaaa   3240

aaaaaaaaaa aaaaaaaaaa a                                              3261
```

<210> SEQ ID NO 33
<211> LENGTH: 639
<212> TYPE: PRT
<213> ORGANISM: Homo Sapiens

<400> SEQUENCE: 33

```
Met Gly Gly His Phe Trp Pro Pro Glu Pro Tyr Thr Val Phe Met Trp
1               5                   10                  15

Gly Ser Pro Trp Glu Ala Asp Ser Pro Arg Val Lys Leu Arg Gly Arg
            20                  25                  30

Glu Lys Gly Arg Gln Thr Glu Gly Gly Ala Phe Pro Leu Val Ser Ser
        35                  40                  45

Ala Leu Ser Gly Asp Pro Arg Phe Phe Ser Pro Thr Thr Pro Pro Ala
    50                  55                  60

Glu Pro Ile Val Val Arg Leu Lys Glu Val Arg Leu Gln Arg Asp Asp
65                  70                  75                  80

Phe Glu Ile Leu Lys Val Ile Gly Arg Gly Ala Phe Ser Glu Val Ala
                85                  90                  95

Val Val Lys Met Lys Gln Thr Gly Gln Val Tyr Ala Met Lys Ile Met
            100                 105                 110

Asn Lys Trp Asp Met Leu Lys Arg Gly Glu Val Ser Cys Phe Arg Glu
        115                 120                 125

Glu Arg Asp Val Leu Val Asn Gly Asp Arg Arg Trp Ile Thr Gln Leu
    130                 135                 140

His Phe Ala Phe Gln Asp Glu Asn Tyr Leu Tyr Leu Val Met Glu Tyr
145                 150                 155                 160

Tyr Val Gly Gly Asp Leu Leu Thr Leu Leu Ser Lys Phe Gly Glu Arg
                165                 170                 175

Ile Pro Ala Glu Met Ala Arg Phe Tyr Leu Ala Glu Ile Val Met Ala
            180                 185                 190

Ile Asp Ser Val His Arg Leu Gly Tyr Val His Arg Asp Ile Lys Pro
        195                 200                 205

Asp Asn Ile Leu Leu Asp Arg Cys Gly His Ile Arg Leu Ala Asp Phe
    210                 215                 220

Gly Ser Cys Leu Lys Leu Arg Ala Asp Gly Thr Val Arg Ser Leu Val
225                 230                 235                 240

Ala Val Gly Thr Pro Asp Tyr Leu Ser Pro Glu Ile Leu Gln Ala Val
                245                 250                 255

Gly Gly Gly Pro Gly Thr Gly Ser Tyr Gly Pro Glu Cys Asp Trp Trp
            260                 265                 270

Ala Leu Gly Val Phe Ala Tyr Glu Met Phe Tyr Gly Gln Thr Pro Phe
        275                 280                 285
```

-continued

```
Tyr Ala Asp Ser Thr Ala Glu Thr Tyr Gly Lys Ile Val His Tyr Lys
    290                 295                 300

Glu His Leu Ser Leu Pro Leu Val Asp Glu Gly Val Pro Glu Glu Ala
305                 310                 315                 320

Arg Asp Phe Ile Gln Arg Leu Leu Cys Pro Pro Glu Thr Arg Leu Gly
                325                 330                 335

Arg Gly Gly Ala Gly Asp Phe Arg Thr His Pro Phe Phe Phe Gly Leu
            340                 345                 350

Asp Trp Asp Gly Leu Arg Asp Ser Val Pro Pro Phe Thr Pro Asp Phe
        355                 360                 365

Glu Gly Ala Thr Asp Thr Cys Asn Phe Asp Leu Val Glu Asp Gly Leu
    370                 375                 380

Thr Ala Met Val Ser Gly Gly Gly Glu Thr Leu Ser Asp Ile Arg Glu
385                 390                 395                 400

Gly Ala Pro Leu Gly Val His Leu Pro Phe Val Gly Tyr Ser Tyr Ser
                405                 410                 415

Cys Met Ala Leu Arg Asp Ser Glu Val Pro Gly Pro Thr Pro Met Glu
            420                 425                 430

Leu Glu Ala Glu Gln Leu Leu Glu Pro His Val Gln Ala Pro Ser Leu
        435                 440                 445

Glu Pro Ser Val Ser Pro Gln Asp Glu Thr Ala Glu Val Ala Val Pro
    450                 455                 460

Ala Ala Val Pro Ala Ala Glu Ala Glu Ala Glu Val Thr Leu Arg Glu
465                 470                 475                 480

Leu Gln Glu Ala Leu Glu Glu Glu Val Leu Thr Arg Gln Ser Leu Ser
                485                 490                 495

Arg Glu Met Glu Ala Ile Arg Thr Asp Asn Gln Asn Phe Ala Ser Gln
            500                 505                 510

Leu Arg Glu Ala Glu Ala Arg Asn Arg Asp Leu Glu Ala His Val Arg
        515                 520                 525

Gln Leu Gln Glu Arg Met Glu Leu Leu Gln Ala Glu Gly Ala Thr Ala
    530                 535                 540

Val Thr Gly Val Pro Ser Pro Arg Ala Thr Asp Pro Pro Ser His Leu
545                 550                 555                 560

Asp Gly Pro Pro Ala Val Ala Val Gly Gln Cys Pro Leu Val Gly Pro
                565                 570                 575

Gly Pro Met His Arg Arg His Leu Leu Leu Pro Ala Arg Val Pro Arg
            580                 585                 590

Pro Gly Leu Ser Glu Ala Leu Ser Leu Leu Leu Phe Ala Val Val Leu
        595                 600                 605

Ser Arg Ala Ala Ala Leu Gly Cys Ile Gly Leu Val Ala His Ala Gly
    610                 615                 620

Gln Leu Thr Ala Val Trp Arg Arg Pro Gly Ala Ala Arg Ala Pro
625                 630                 635
```

<210> SEQ ID NO 34
<211> LENGTH: 4362
<212> TYPE: DNA
<213> ORGANISM: Homo Sapiens

<400> SEQUENCE: 34

```
acggcgagcg cgggcggcgg cggtgacgga ggcgccgctg ccagggggcg tgcggcagcg      60

cggcggcggc ggcggcggcg gcggcggcgg aggcggcggc ggcggcggcg gcggcggcgg     120

aggcggcggc ggcggcggcg gcggcggcgg ctgggcctcg agcgcccgca gcccacctct     180
```

-continued

```
cgggggcggg ctcccggcgc tagcagggct gaagagaaga tggaggagct ggtggtggaa    240
gtgcggggct ccaatggcgc tttctacaag gcatttgtaa aggatgttca tgaagattca    300
ataacagttg catttgaaaa caactggcag cctgataggc agattccatt tcatgatgtc    360
agattcccac ctcctgtagg ttataataaa gatataaatg aaagtgatga agttgaggtg    420
tattccagag caaatgaaaa agagccttgc tgttggtggt tagctaaagt gaggatgata    480
aagggtgagt tttatgtgat agaatatgca gcatgtgatg caacttacaa tgaaattgtc    540
acaattgaac gtctaagatc tgttaatccc aacaaacctg ccacaaaaga tactttccat    600
aagatcaagc tggatgtgcc agaagactta cggcaaatgt gtgccaaaga ggcggcacat    660
aaggatttta aaaaggcagt tggtgccttt tctgtaactt atgatccaga aaattatcag    720
cttgtcattt tgtccatcaa tgaagtcacc tcaaagcgag cacatatgct gattgacatg    780
cactttcgga gtctgcgcac taagttgtct ctgataatga gaaatgaaga agctagtaag    840
cagctggaga gttcaaggca gcttgcctcg agatttcatg aacagtttat cgtaagagaa    900
gatctgatgg gtctagctat tggtactcat ggtgctaata ttcagcaagc tagaaaagta    960
cctggggtca ctgctattga tctagatgaa gatacctgca catttcatat ttatggagag   1020
gatcaggatg cagtgaaaaa agctagaagc tttctcgaat ttgctgaaga tgtaatacaa   1080
gttccaagga acttagtagg caaagtaata ggaaaaaatg gaaagctgat tcaggagatt   1140
gtggacaagt caggagttgt gagggtgagg attgaggctg aaaatgagaa aaatgttcca   1200
caagaagagg aaattatgcc accaaattcc cttccttcca ataattcaag ggttggacct   1260
aatgccccag aagaaaaaaa acatttagat ataaaggaaa acagcaccca tttttctcaa   1320
cctaacagta caaaagtcca gagggtgtta gtggcttcat cagttgtagc aggggaatcc   1380
cagaaacctg aactcaaggc ttggcagggt atggtaccat ttgtttttgt gggaacaaag   1440
gacagcatcg ctaatgccac tgttcttttg gattatcacc tgaactattt aaaggaagta   1500
gaccagttgc gtttggagag attacaaatt gatgagcagt tgcgacagat tggagctagt   1560
tctagaccac caccaaatcg tacagataag gaaaaaagct atgtgactga tgatggtcaa   1620
ggaatgggtc gaggtagtag accttacaga aatagggggc acggcagacg cggtcctgga   1680
tatacttcag gaactaattc tgaagcatca aatgcttctg aaacagaatc tgaccacaga   1740
gacgaactca gtgattggtc attagctcca acagaggaag agagggagag cttcctgcgc   1800
agaggagacg gacggcggcg tggagggggga ggaagaggac aaggaggaag aggacgtgga   1860
ggaggcttca aggaaaacga cgatcactcc cgaacagata atcgtccacg taatccaaga   1920
gaggctaaag gaagaacaac agatggatcc cttcagatca gagttgactg caataatgaa   1980
aggagtgtcc acactaaaac attacagaat acctccagtg aaggtagtcg gctgcgcacg   2040
ggtaaagatc gtaaccagaa gaaagagaag ccagacagcg tggatggtca gcaaccactc   2100
gtgaatggag taccctaaac tgcataattc tgaagttata tttcctatac catttccgta   2160
attcttattc catattagaa aactttgtta ggccaaagac aaatagtagg caagatggca   2220
cagggcatga aatgaacaca aattatgcta agaatttttt attttttggt attggccata   2280
agcaacaatt ttcagatttg cacaaaaaga taccttaaaa tttgaaacat tgcttttaaa   2340
actacttagc acttcagggc agattttagt tttattttct aaagtactga gcagtgatat   2400
tctttgttaa tttggaccat tttcctgcat tgggtgatca ttcaccagta cattctcagt   2460
ttttcttaat atatagcatt tatggtaatc atattagact tctgttttca atctcgtata   2520
gaagtcttca tgaaatgcta tgtcatttca tgtcctgtgt cagtttatgt tttggtccac   2580
```

```
ttttccagta ttttagtgga ccctgaaatg tgtgtgatgt gacatttgtc attttcatta   2640

gcaaaaaaag ttgtatgatc tgtgcctttt ttatatcttg gcaggtagga atattatatt   2700

tggatgcaga gttcagggaa gataagttgg aaacactaaa tgttaaagat gtagcaaacc   2760

ctgtcaaaca ttagtacttt atagaagaat gcatgctttc catatttttt tccttacata   2820

aacatcaggt taggcagtat aaagaatagg acttgttttt gtttttgttt tgttgcactg   2880

aagtttgata aatagtgtta ttgagagaga tgtgtaattt ttctgtatag acaggagaag   2940

aaagaactat cttcatctga gagaggctaa aatgttttca gctaggaaca aatcttcctg   3000

gtcgaaagtt agtaggatat gcctgctctt tggcctgatg accaatttta acttagagct   3060

ttttttttta attttgtctg ccccaagttt tgtgaaattt ttcatatttt aatttcaagc   3120

ttattttgga gagataggaa ggtcatttcc atgtatgcat aataatcctg caaagtacag   3180

gtactttgtc taagaaacat tggaagcagg ttaaatgttt tgtaaacttt gaaatatatg   3240

gtctaatgtt taagcagaat tggaaaagac taagatcggt taacaaataa caactttttt   3300

ttcttttttt cttttgtttt ttgaagtgtt ggggtttggt tttgtttttt gagtcttttt   3360

tttttaagtg aaatttattg aggaaaaata tgtgaaggac cttcactcta agatgttata   3420

tttttcttaa aaagtaactc ctagtagggg taccactgaa tctgtacaga gccgtaaaaa   3480

ctgaagttct gcctctgatg tattttgtga gtttgtttct ttgaattttc attttacagt   3540

tacttttcct tgcatacaaa caagcatata aaatggcaac aaactgcaca tgatttcaca   3600

aatattaaaa agtcttttaa aaagtattgc caaacattaa tgttgatttc tagttattta   3660

ttctgggaat gtatagtatt tgaaaacaga aattggtacc ttgcacacat catctgtaag   3720

ctgtttggtt ttaaaatact gtagataatt aaccaaggta gaatgacctt gtaatgtaac   3780

tgctcttggg caatattctc tgtacatatt agcgacaaca gattggattt tatgttgaca   3840

tttgtttggt tatagtgcaa tatattttgt atgcaagcag tttcaataaa gtttgatctt   3900

cctctgctaa attgatgttg atgcaatcct tacaaatgat tgcttttaaa attttaagct   3960

aggaaaagaa atctatagaa agtgttctgt tacaaaatgt aactgttacc attggaaatt   4020

tcacgtcata ggaagttagc ctttatctac ccaactttca agaaggttct ttaataaagc   4080

gaaaactcaa ccaaatggta cttttccaca gtgtaccatt aaaatatgca ctagtctctt   4140

tttacaaggc tgtattcagc aagggcctaa cttgcttaaa gtgtaattac taacttctaa   4200

aactgtactt tgattcacat gttttcaaat ggagttggag ttcattcata ttacaatatt   4260

tgtgtgctaa acgtgtatgt ttttcagttc aaagtcatga tgtttttaaa atcttattaa   4320

agtttcaaaa atctgaagat tgtttatcta gatgtaaatt tt                      4362
```

<210> SEQ ID NO 35
<211> LENGTH: 632
<212> TYPE: PRT
<213> ORGANISM: Homo Sapiens

<400> SEQUENCE: 35

```
Met Glu Glu Leu Val Val Glu Val Arg Gly Ser Asn Gly Ala Phe Tyr
1               5                   10                  15

Lys Ala Phe Val Lys Asp Val His Glu Asp Ser Ile Thr Val Ala Phe
            20                  25                  30

Glu Asn Asn Trp Gln Pro Asp Arg Gln Ile Pro Phe His Asp Val Arg
        35                  40                  45

Phe Pro Pro Pro Val Gly Tyr Asn Lys Asp Ile Asn Glu Ser Asp Glu
    50                  55                  60
```

-continued

```
Val Glu Val Tyr Ser Arg Ala Asn Glu Lys Glu Pro Cys Cys Trp Trp
65                  70                  75                  80

Leu Ala Lys Val Arg Met Ile Lys Gly Glu Phe Tyr Val Ile Glu Tyr
                85                  90                  95

Ala Ala Cys Asp Ala Thr Tyr Asn Glu Ile Val Thr Ile Glu Arg Leu
            100                 105                 110

Arg Ser Val Asn Pro Asn Lys Pro Ala Thr Lys Asp Thr Phe His Lys
        115                 120                 125

Ile Lys Leu Asp Val Pro Glu Asp Leu Arg Gln Met Cys Ala Lys Glu
    130                 135                 140

Ala Ala His Lys Asp Phe Lys Lys Ala Val Gly Ala Phe Ser Val Thr
145                 150                 155                 160

Tyr Asp Pro Glu Asn Tyr Gln Leu Val Ile Leu Ser Ile Asn Glu Val
                165                 170                 175

Thr Ser Lys Arg Ala His Met Leu Ile Asp Met His Phe Arg Ser Leu
            180                 185                 190

Arg Thr Lys Leu Ser Leu Ile Met Arg Asn Glu Glu Ala Ser Lys Gln
        195                 200                 205

Leu Glu Ser Ser Arg Gln Leu Ala Ser Arg Phe His Glu Gln Phe Ile
    210                 215                 220

Val Arg Glu Asp Leu Met Gly Leu Ala Ile Gly Thr His Gly Ala Asn
225                 230                 235                 240

Ile Gln Gln Ala Arg Lys Val Pro Gly Val Thr Ala Ile Asp Leu Asp
                245                 250                 255

Glu Asp Thr Cys Thr Phe His Ile Tyr Gly Glu Asp Gln Asp Ala Val
            260                 265                 270

Lys Lys Ala Arg Ser Phe Leu Glu Phe Ala Glu Asp Val Ile Gln Val
        275                 280                 285

Pro Arg Asn Leu Val Gly Lys Val Ile Gly Lys Asn Gly Lys Leu Ile
    290                 295                 300

Gln Glu Ile Val Asp Lys Ser Gly Val Val Arg Val Arg Ile Glu Ala
305                 310                 315                 320

Glu Asn Glu Lys Asn Val Pro Gln Glu Glu Glu Ile Met Pro Pro Asn
                325                 330                 335

Ser Leu Pro Ser Asn Asn Ser Arg Val Gly Pro Asn Ala Pro Glu Glu
            340                 345                 350

Lys Lys His Leu Asp Ile Lys Glu Asn Ser Thr His Phe Ser Gln Pro
        355                 360                 365

Asn Ser Thr Lys Val Gln Arg Val Leu Val Ala Ser Ser Val Val Ala
    370                 375                 380

Gly Glu Ser Gln Lys Pro Glu Leu Lys Ala Trp Gln Gly Met Val Pro
385                 390                 395                 400

Phe Val Phe Val Gly Thr Lys Asp Ser Ile Ala Asn Ala Thr Val Leu
                405                 410                 415

Leu Asp Tyr His Leu Asn Tyr Leu Lys Glu Val Asp Gln Leu Arg Leu
            420                 425                 430

Glu Arg Leu Gln Ile Asp Glu Gln Leu Arg Gln Ile Gly Ala Ser Ser
        435                 440                 445

Arg Pro Pro Pro Asn Arg Thr Asp Lys Glu Lys Ser Tyr Val Thr Asp
    450                 455                 460

Asp Gly Gln Gly Met Gly Arg Gly Ser Arg Pro Tyr Arg Asn Arg Gly
465                 470                 475                 480

His Gly Arg Arg Gly Pro Gly Tyr Thr Ser Gly Thr Asn Ser Glu Ala
                485                 490                 495
```

```
Ser Asn Ala Ser Glu Thr Glu Ser Asp His Arg Asp Glu Leu Ser Asp
            500                 505                 510

Trp Ser Leu Ala Pro Thr Glu Glu Glu Arg Glu Ser Phe Leu Arg Arg
        515                 520                 525

Gly Asp Gly Arg Arg Arg Gly Gly Gly Gly Arg Gly Gln Gly Gly Arg
    530                 535                 540

Gly Arg Gly Gly Gly Phe Lys Gly Asn Asp Asp His Ser Arg Thr Asp
545                 550                 555                 560

Asn Arg Pro Arg Asn Pro Arg Glu Ala Lys Gly Arg Thr Thr Asp Gly
                565                 570                 575

Ser Leu Gln Ile Arg Val Asp Cys Asn Asn Glu Arg Ser Val His Thr
            580                 585                 590

Lys Thr Leu Gln Asn Thr Ser Ser Glu Gly Ser Arg Leu Arg Thr Gly
        595                 600                 605

Lys Asp Arg Asn Gln Lys Lys Glu Lys Pro Asp Ser Val Asp Gly Gln
    610                 615                 620

Gln Pro Leu Val Asn Gly Val Pro
625                 630


<210> SEQ ID NO 36
<211> LENGTH: 3819
<212> TYPE: DNA
<213> ORGANISM: Homo Sapiens

<400> SEQUENCE: 36

atggatctat tcgacttttt cagagactgg gacttggagc agcagtgtca ctatgaacaa     60

gaccgtagtg cacttaaaaa aagggaatgg gagcggagga atcaagaagt ccagcaagaa    120

gacgatctct tttcttcagg ctttgatctt tttggggagc catacaagac aaacaaaggt    180

gatgcacttg ccaaccgagt ccagaacacg cttggaaact atgatgaaat gaagaatttg    240

ctaactaacc attctaatca gaatcaccta gtgggaattc caaagaattc tgtgccccag    300

aatcccaaca acaaaaatga accaagcttt tttccagaac aaaagaacag aataattcca    360

cctcaccagg ataataccca tccttcagca ccaatgcctc caccttctgt tgtgatactg    420

aattcaactc taatacacag caacagaaaa tcaaaacctg agtggtcacg tgatagtcat    480

aaccctagca ctgtactggc aagccaggcc agtggtcagc caaacaagat gcagactttg    540

acacaggacc agtctcaagc caaactggaa gacttctttg tctacccagc tgaacagccc    600

cagattggag aagttgaaga gtcaaaccca tctgcaaagg aagacagtaa ccctaattct    660

agtggagaag atgctttcaa agaaatcttt caatccaatt caccggaaga atctgaattc    720

gccgtgcaag cgcctgggtc tcccctagtg gcttcctctt tattagctcc tagcagtggc    780

ctttcagttc aaaacttccc accagggctt tactgcaaaa caagcatggg gcagcaaaag    840

ccaactgcat acgtcagacc catggatggc caggaccagg caccggacat ctcaccaaca    900

ctgaaacctt caattgaatt tgagaacagc tttgggaatc tgtcatttgg aacactcttg    960

gatggaaaac ccagtgcagc cagttcaaag actaaactgc caaagttcac catcctccaa   1020

acaagtgaag taagccttcc cagtgatcca agctgtgttg aagaaatctt gcgggaatcg   1080

cagcatctga ccccaggatt caccttacaa aagtggaatg acccaaccac cagagcttct   1140

acaaagatgc ttgaggatga cctgaagctg agcagtgatg aagatgacct tgagcctgtg   1200

aagaccttga ccactcagtg cactgccact gagctctacc aggctgttga aaaggcaaaa   1260

cctaggaata atcctgtgaa cccacccttg gccactcccc agcccccacc tgcagtgcaa   1320
```

-continued

```
gccagcgggg gttctggcag ctccagcgaa tcggagagca gctctgagtc ggattcagac   1380
actgaaagta gcaccactga cagcgaatct aatgaggcac ctcgtgtggc aactccagag   1440
cctgagccac cctcaaccaa caagtggcaa ctggataaat ggcttaacaa agtgacatcc   1500
cagaacaagt cttttatttg tggccaaaat gaaacaccca tggagactat ttctctgcct   1560
cctccaatca tccaaccaat ggaagtccag atgaaagtga agacgaatgc cagtcaggtc   1620
ccagctgaac ccaaagaaag gcctctcctc agtctcatta gggagaaagc ccgtccacgg   1680
cccactcaga aaattccaga aacaaaggct ttgaagcata agttgtcaac aactagtgag   1740
acagtgtctc aaaggacaat tggagaaaaa cagcccaaaa aagttgagaa gaacaccagc   1800
actgacgagt ttacctggcc caaaccaaat attaccagca gcactcccaa agaaaaagaa   1860
agtgtggagc ttcatgaccc accaagaggc cgcaacaaag ccactgccca caaaccagcc   1920
cctaggaaag aaccaagacc taacatccct ttggctcccg agaagaagaa gtacagaggg   1980
cctggcaaga ttgtgccaaa gtctcgggaa ttcattgaaa cagattcatc tacatctgac   2040
tccaacacag atcaggaaga gaccctgcaa atcaaagtcc tgcctccgtg cattatttct   2100
ggaggtaata ctgccaaatc caaggaaatc tgtggtgcca gcctgaccct cagcacctta   2160
atgagtagca gtggcagcaa caacaactta tccatcagta atgaagagcc aacattttca   2220
cctattcctg tcatgcaaac tgaaatcctg tcccctctgc gagatcatga gaacctgaaa   2280
aacctctggg tgaagattga ccttgactta ctctctagag tacctggcca cagctcactc   2340
catgcagcac ctgccaagcc agaccacaag gagactgcca caaaacccaa gcgtcagaca   2400
gctgtcacag ctgtggagaa accagcccct aagggcaaac gtaagcacaa gccaatagaa   2460
gttgcagaga agatccctga gaagaagcag cgcctggagg aggccacaac tatctgcttg   2520
ctccctcctt gcatctcacc agccccaccc cacaagcctc ccaacactag agaaaataat   2580
tcatccagga gagcaaatag aagaaaggaa gaaaaactat ttcctcctcc actttcccca   2640
ctgccagagg accctccacg ccgcagaaat gtcagtggca ataatggtcc ctttggtcaa   2700
gacaaaaaca tcgccatgac tggacaaatc acatctacca aacctaagag aactgaaggc   2760
aaattctgtg ctactttcaa agggatatcg gtaaatgagg gagacactcc aaaaaaggca   2820
tcctctgcca ccatcactgt caccaatact gctattgcca ctgctactgt cactgctact   2880
gccattgtca ccaccactgt cacagctact gccaccgcca cggccaccac cacaactact   2940
accactacca tttccaccat cacctctacc atcactactg gcctcatgga tagcagtcac   3000
ctggagatga cgtcctgggc ggctctgccc cttctatcca gcagcagcac taatgtccgg   3060
agacccaagc tcacttttga tgactcggtt cacaatgctg attattacat gcaagaagct   3120
aagaagctga agcacaaagc tgatgcactg ttcgagaaat ttggcaaagc tgtgaattat   3180
gctgatgccg ccctctcctt cactgaatgt ggcaatgcca tggaacgcga ccctctggaa   3240
gcaaagtccc catacaccat gtactctgag actgtggagc tcctcaggta tgcaatgagg   3300
ctgaagaact ttgcaagtcc cttggcttcg gatggggaca aaaagctagc agtactatgc   3360
taccgatgtt tatcactcct ctatttgaga atgtttaagc tgaagaagga ccatgctatg   3420
aagtactcca gatcactgat ggaatatttt aagcaaaatg cttcaaaagt cgcacagata   3480
ccctctccat gggtaagcaa tggaaagaac actccatccc cagtgtctct caacaacgtc   3540
tcccccatca acgcaatggg gaactgtaac aatggcccag tcaccattcc ccagcgcatt   3600
caccacatgg ctgccagcca cgtcaacatc actagcaatg tgttacgggg ctatgaacac   3660
tgggatatgg ccgacaaact gacaagagaa aacaaagaat tctttggtga tctggacacg   3720
```

ctgatggggc ctctgaccca gcacagcagc atgaccaatc ttgtccgcta cgttcgccaa 3780
ggactgtgtt ggctgcgcat cgatgcccac ttgttgtag 3819

<210> SEQ ID NO 37
<211> LENGTH: 1272
<212> TYPE: PRT
<213> ORGANISM: Homo Sapiens

<400> SEQUENCE: 37

Met Asp Leu Phe Asp Phe Phe Arg Asp Trp Asp Leu Glu Gln Gln Cys
1 5 10 15

His Tyr Glu Gln Asp Arg Ser Ala Leu Lys Lys Arg Glu Trp Glu Arg
20 25 30

Arg Asn Gln Glu Val Gln Gln Glu Asp Asp Leu Phe Ser Ser Gly Phe
35 40 45

Asp Leu Phe Gly Glu Pro Tyr Lys Thr Asn Lys Gly Asp Ala Leu Ala
50 55 60

Asn Arg Val Gln Asn Thr Leu Gly Asn Tyr Asp Glu Met Lys Asn Leu
65 70 75 80

Leu Thr Asn His Ser Asn Gln Asn His Leu Val Gly Ile Pro Lys Asn
85 90 95

Ser Val Pro Gln Asn Pro Asn Asn Lys Asn Glu Pro Ser Phe Phe Pro
100 105 110

Glu Gln Lys Asn Arg Ile Ile Pro Pro His Gln Asp Asn Thr His Pro
115 120 125

Ser Ala Pro Met Pro Pro Pro Ser Val Val Ile Leu Asn Ser Thr Leu
130 135 140

Ile His Ser Asn Arg Lys Ser Lys Pro Glu Trp Ser Arg Asp Ser His
145 150 155 160

Asn Pro Ser Thr Val Leu Ala Ser Gln Ala Ser Gly Gln Pro Asn Lys
165 170 175

Met Gln Thr Leu Thr Gln Asp Gln Ser Gln Ala Lys Leu Glu Asp Phe
180 185 190

Phe Val Tyr Pro Ala Glu Gln Pro Gln Ile Gly Glu Val Glu Glu Ser
195 200 205

Asn Pro Ser Ala Lys Glu Asp Ser Asn Pro Asn Ser Ser Gly Glu Asp
210 215 220

Ala Phe Lys Glu Ile Phe Gln Ser Asn Ser Pro Glu Glu Ser Glu Phe
225 230 235 240

Ala Val Gln Ala Pro Gly Ser Pro Leu Val Ala Ser Ser Leu Leu Ala
245 250 255

Pro Ser Ser Gly Leu Ser Val Gln Asn Phe Pro Pro Gly Leu Tyr Cys
260 265 270

Lys Thr Ser Met Gly Gln Gln Lys Pro Thr Ala Tyr Val Arg Pro Met
275 280 285

Asp Gly Gln Asp Gln Ala Pro Asp Ile Ser Pro Thr Leu Lys Pro Ser
290 295 300

Ile Glu Phe Glu Asn Ser Phe Gly Asn Leu Ser Phe Gly Thr Leu Leu
305 310 315 320

Asp Gly Lys Pro Ser Ala Ala Ser Ser Lys Thr Lys Leu Pro Lys Phe
325 330 335

Thr Ile Leu Gln Thr Ser Glu Val Ser Leu Pro Ser Asp Pro Ser Cys
340 345 350

Val Glu Glu Ile Leu Arg Glu Ser Gln His Leu Thr Pro Gly Phe Thr
355 360 365

```
Leu Gln Lys Trp Asn Asp Pro Thr Thr Arg Ala Ser Thr Lys Met Leu
    370                 375                 380

Glu Asp Asp Leu Lys Leu Ser Ser Asp Glu Asp Asp Leu Glu Pro Val
385                 390                 395                 400

Lys Thr Leu Thr Thr Gln Cys Thr Ala Thr Glu Leu Tyr Gln Ala Val
                405                 410                 415

Glu Lys Ala Lys Pro Arg Asn Asn Pro Val Asn Pro Pro Leu Ala Thr
            420                 425                 430

Pro Gln Pro Pro Pro Ala Val Gln Ala Ser Gly Gly Ser Gly Ser Ser
        435                 440                 445

Ser Glu Ser Glu Ser Ser Ser Glu Ser Asp Ser Asp Thr Glu Ser Ser
    450                 455                 460

Thr Thr Asp Ser Glu Ser Asn Glu Ala Pro Arg Val Ala Thr Pro Glu
465                 470                 475                 480

Pro Glu Pro Pro Ser Thr Asn Lys Trp Gln Leu Asp Lys Trp Leu Asn
                485                 490                 495

Lys Val Thr Ser Gln Asn Lys Ser Phe Ile Cys Gly Gln Asn Glu Thr
            500                 505                 510

Pro Met Glu Thr Ile Ser Leu Pro Pro Pro Ile Ile Gln Pro Met Glu
        515                 520                 525

Val Gln Met Lys Val Lys Thr Asn Ala Ser Gln Val Pro Ala Glu Pro
    530                 535                 540

Lys Glu Arg Pro Leu Leu Ser Leu Ile Arg Glu Lys Ala Arg Pro Arg
545                 550                 555                 560

Pro Thr Gln Lys Ile Pro Glu Thr Lys Ala Leu Lys His Lys Leu Ser
                565                 570                 575

Thr Thr Ser Glu Thr Val Ser Gln Arg Thr Ile Gly Lys Lys Gln Pro
            580                 585                 590

Lys Lys Val Glu Lys Asn Thr Ser Thr Asp Glu Phe Thr Trp Pro Lys
        595                 600                 605

Pro Asn Ile Thr Ser Ser Thr Pro Lys Glu Lys Glu Ser Val Glu Leu
    610                 615                 620

His Asp Pro Pro Arg Gly Arg Asn Lys Ala Thr Ala His Lys Pro Ala
625                 630                 635                 640

Pro Arg Lys Glu Pro Arg Pro Asn Ile Pro Leu Ala Pro Glu Lys Lys
                645                 650                 655

Lys Tyr Arg Gly Pro Gly Lys Ile Val Pro Lys Ser Arg Glu Phe Ile
            660                 665                 670

Glu Thr Asp Ser Ser Thr Ser Asp Ser Asn Thr Asp Gln Glu Glu Thr
        675                 680                 685

Leu Gln Ile Lys Val Leu Pro Pro Cys Ile Ile Ser Gly Gly Asn Thr
    690                 695                 700

Ala Lys Ser Lys Glu Ile Cys Gly Ala Ser Leu Thr Leu Ser Thr Leu
705                 710                 715                 720

Met Ser Ser Ser Gly Ser Asn Asn Asn Leu Ser Ile Ser Asn Glu Glu
                725                 730                 735

Pro Thr Phe Ser Pro Ile Pro Val Met Gln Thr Glu Ile Leu Ser Pro
            740                 745                 750

Leu Arg Asp His Glu Asn Leu Lys Asn Leu Trp Val Lys Ile Asp Leu
        755                 760                 765

Asp Leu Leu Ser Arg Val Pro Gly His Ser Ser Leu His Ala Ala Pro
    770                 775                 780

Ala Lys Pro Asp His Lys Glu Thr Ala Thr Lys Pro Lys Arg Gln Thr
```

-continued

```
785                 790                 795                 800

Ala Val Thr Ala Val Glu Lys Pro Ala Pro Lys Gly Lys Arg Lys His
                805                 810                 815

Lys Pro Ile Glu Val Ala Glu Lys Ile Pro Glu Lys Lys Gln Arg Leu
            820                 825                 830

Glu Glu Ala Thr Thr Ile Cys Leu Leu Pro Pro Cys Ile Ser Pro Ala
        835                 840                 845

Pro Pro His Lys Pro Pro Asn Thr Arg Glu Asn Asn Ser Ser Arg Arg
    850                 855                 860

Ala Asn Arg Arg Lys Glu Glu Lys Leu Phe Pro Pro Pro Leu Ser Pro
865                 870                 875                 880

Leu Pro Glu Asp Pro Pro Arg Arg Arg Asn Val Ser Gly Asn Asn Gly
                885                 890                 895

Pro Phe Gly Gln Asp Lys Asn Ile Ala Met Thr Gly Gln Ile Thr Ser
            900                 905                 910

Thr Lys Pro Lys Arg Thr Glu Gly Lys Phe Cys Ala Thr Phe Lys Gly
        915                 920                 925

Ile Ser Val Asn Glu Gly Asp Thr Pro Lys Lys Ala Ser Ser Ala Thr
    930                 935                 940

Ile Thr Val Thr Asn Thr Ala Ile Ala Thr Ala Thr Val Thr Ala Thr
945                 950                 955                 960

Ala Ile Val Thr Thr Thr Val Thr Ala Thr Ala Thr Ala Thr Ala Thr
                965                 970                 975

Thr Thr Thr Thr Thr Thr Thr Ile Ser Thr Ile Thr Ser Thr Ile Thr
            980                 985                 990

Thr Gly Leu Met Asp Ser Ser His  Leu Glu Met Thr Ser  Trp Ala Ala
        995                 1000                1005

Leu Pro  Leu Leu Ser Ser Ser  Ser Thr Asn Val Arg  Arg Pro Lys
    1010                1015                1020

Leu Thr  Phe Asp Asp Ser Val  His Asn Ala Asp Tyr  Tyr Met Gln
    1025                1030                1035

Glu Ala  Lys Lys Leu Lys His  Lys Ala Asp Ala Leu  Phe Glu Lys
    1040                1045                1050

Phe Gly  Lys Ala Val Asn Tyr  Ala Asp Ala Ala Leu  Ser Phe Thr
    1055                1060                1065

Glu Cys  Gly Asn Ala Met Glu  Arg Asp Pro Leu Glu  Ala Lys Ser
    1070                1075                1080

Pro Tyr  Thr Met Tyr Ser Glu  Thr Val Glu Leu Leu  Arg Tyr Ala
    1085                1090                1095

Met Arg  Leu Lys Asn Phe Ala  Ser Pro Leu Ala Ser  Asp Gly Asp
    1100                1105                1110

Lys Lys  Leu Ala Val Leu Cys  Tyr Arg Cys Leu Ser  Leu Leu Tyr
    1115                1120                1125

Leu Arg  Met Phe Lys Leu Lys  Lys Asp His Ala Met  Lys Tyr Ser
    1130                1135                1140

Arg Ser  Leu Met Glu Tyr Phe  Lys Gln Asn Ala Ser  Lys Val Ala
    1145                1150                1155

Gln Ile  Pro Ser Pro Trp Val  Ser Asn Gly Lys Asn  Thr Pro Ser
    1160                1165                1170

Pro Val  Ser Leu Asn Asn Val  Ser Pro Ile Asn Ala  Met Gly Asn
    1175                1180                1185

Cys Asn  Asn Gly Pro Val Thr  Ile Pro Gln Arg Ile  His His Met
    1190                1195                1200
```

```
Ala Ala  Ser His Val Asn Ile  Thr Ser Asn Val Leu  Arg Gly Tyr
    1205                 1210                 1215

Glu His  Trp Asp Met Ala Asp  Lys Leu Thr Arg Glu  Asn Lys Glu
    1220                 1225                 1230

Phe Phe  Gly Asp Leu Asp Thr  Leu Met Gly Pro Leu  Thr Gln His
    1235                 1240                 1245

Ser Ser  Met Thr Asn Leu Val  Arg Tyr Val Arg Gln  Gly Leu Cys
    1250                 1255                 1260

Trp Leu  Arg Ile Asp Ala His  Leu Leu
    1265                 1270


<210> SEQ ID NO 38
<211> LENGTH: 2300
<212> TYPE: DNA
<213> ORGANISM: Homo Sapiens

<400> SEQUENCE: 38

ggccaggcaa gcctgaatcc tgtccctgcc atctcgccac tgcagctcgg gtccagaaag     60

gcaccatttt gtcgcggctg cccgctctcc caggggggagg agggatcttt tttgcatttt    120

ggagcggctg ccaaggaggg gaacctgttg ggcatctccc cagacccgct tgtgagcgcc    180

tccggggcgg gcgggcggga ccagacccct cggggcacgg cgtatcttgg cacccggagg    240

cagcggaggc aggcgcagca tcctcgctgg gaactggagc tggagtgagc gcaccgcgcg    300

ggaggagccg ccgcagcctc gcagaacccg agtggaggag gtgacagctc cattgccggg    360

tttttatttt ttttctctcc gcctccccgt ctcctcctca ggctcggacc atggtgcagt    420

cccactggct cccctgcccc cctctcctgt gagactggct gcggggaggg atcatggata    480

cttgtctgcc ggcttctggt tcccacgcaa gtaagcctgc tgtcaatgga ggaggacatt    540

gatacccgca aaatcaacaa cagtttcctg cgcgaccaca gctatgcgac cgaagctgac    600

attatctcta cggtagaatt caaccacacg ggagaattac tagcgacagg ggacaagggg    660

ggtcgggttg taatatttca acgagagcag gagagtaaaa atcaggttca tcgtaggggt    720

gaatacaatg tttacagcac attccagagc catgaacccg agttcgatta cctgaagagt    780

ttagaaatag aagaaaaaat caataaaata agatggctcc cccagcagaa tgcagcttac    840

tttcttctgt ctactaatga taaaactgtg aagctgtgga aagtcagcga gcgtgataag    900

aggccagaag gctacaatct gaaagatgag gagggccggc tccgggatcc tgccaccatc    960

acaaccctgc gggtgcctgt cctgagaccc atggacctga tggtggaggc caccccacga   1020

agagtatttg ccaacgcaca cacatatcac atcaactcca tatctgtcaa cagcgactat   1080

gaaacctaca tgtccgctga tgacctgagg attaacctat ggaactttga aataaccaat   1140

caaagtttta atattgtgga cattaagcca gccaacatgg aggagctcac ggaggtgatc   1200

acagcagccg agttccaccc ccatcattgc aacaccttcg tgtacagcag cagcaaaggg   1260

acaatccggc tgtgtgacat gcgggcatct gccctgtgtg acaggcacac caaatttttt   1320

gaagagccgg aagatccaag caacagatca tttttctctg aaattatctc ttcgatttcg   1380

gatgtgaagt tcagccacag tgggaggtat atcatgacca gggactactt gaccgtcaaa   1440

gtctgggatc tcaacatgga aaaccgcccc atcgagactt accaggttca tgactacctc   1500

cgcagcaagc tgtgttccct ctatgaaaat gactgcattt ttgataaatt tgagtgtgtg   1560

tggaatgggt cagacagtgt catcatgaca ggctcctaca acaacttctt caggatgttc   1620

gacagaaaca ccaagcgtga tgtgaccctt gaggcttcga gggaaaacag caagccccgg   1680

gctatcctca aaccccgaaa agtgtgtgtg gggggcaagc ggagaaaaga cgagatcagt   1740
```

```
gtcgacagtc tggactttag caaaaagatc ttgcatacag cttggcatcc ttcagaaaat   1800

attatagcag tggcggctac aaataaccta tatatattcc aggacaaggt taactaggtg   1860

gacaagttat tacttaataa tctcacatac tgaatactag tcaaacaagt ttttaaatgt   1920

ttctttgggt cttcatttga tgcattgact ttaatttccc tatacaggaa atgattggaa   1980

tagaattaaa aggagtccaa cattcccagc tccccagttc taagaaactt ttgtcaaacc   2040

caataggttt gggacacttc tgtttagaat tgaaagctgc cagctaacag taattcttcc   2100

atagttgact tgaacttctg atgcttttat tgcccagttt tctctggtgg gtccagtgtt   2160

ttgttcctag gtgtctgctg cgataaaatg aggttgtctg tagtatttaa ggagaaaaga   2220

gataagtttt ttttaattaa gcaattccat ttgattgaaa aaaatcaaca aaaaataaac   2280

accgtttact cttagacaaa                                                2300


<210> SEQ ID NO 39
<211> LENGTH: 443
<212> TYPE: PRT
<213> ORGANISM: Homo Sapiens

<400> SEQUENCE: 39

Met Glu Glu Asp Ile Asp Thr Arg Lys Ile Asn Asn Ser Phe Leu Arg
1               5                   10                  15

Asp His Ser Tyr Ala Thr Glu Ala Asp Ile Ile Ser Thr Val Glu Phe
            20                  25                  30

Asn His Thr Gly Glu Leu Leu Ala Thr Gly Asp Lys Gly Gly Arg Val
        35                  40                  45

Val Ile Phe Gln Arg Glu Gln Glu Ser Lys Asn Gln Val His Arg Arg
    50                  55                  60

Gly Glu Tyr Asn Val Tyr Ser Thr Phe Gln Ser His Glu Pro Glu Phe
65                  70                  75                  80

Asp Tyr Leu Lys Ser Leu Glu Ile Glu Glu Lys Ile Asn Lys Ile Arg
                85                  90                  95

Trp Leu Pro Gln Gln Asn Ala Ala Tyr Phe Leu Leu Ser Thr Asn Asp
            100                 105                 110

Lys Thr Val Lys Leu Trp Lys Val Ser Glu Arg Asp Lys Arg Pro Glu
        115                 120                 125

Gly Tyr Asn Leu Lys Asp Glu Glu Gly Arg Leu Arg Asp Pro Ala Thr
    130                 135                 140

Ile Thr Thr Leu Arg Val Pro Val Leu Arg Pro Met Asp Leu Met Val
145                 150                 155                 160

Glu Ala Thr Pro Arg Arg Val Phe Ala Asn Ala His Thr Tyr His Ile
                165                 170                 175

Asn Ser Ile Ser Val Asn Ser Asp Tyr Glu Thr Tyr Met Ser Ala Asp
            180                 185                 190

Asp Leu Arg Ile Asn Leu Trp Asn Phe Glu Ile Thr Asn Gln Ser Phe
        195                 200                 205

Asn Ile Val Asp Ile Lys Pro Ala Asn Met Glu Glu Leu Thr Glu Val
    210                 215                 220

Ile Thr Ala Ala Glu Phe His Pro His His Cys Asn Thr Phe Val Tyr
225                 230                 235                 240

Ser Ser Ser Lys Gly Thr Ile Arg Leu Cys Asp Met Arg Ala Ser Ala
                245                 250                 255

Leu Cys Asp Arg His Thr Lys Phe Phe Glu Glu Pro Glu Asp Pro Ser
            260                 265                 270
```

-continued

```
Asn Arg Ser Phe Phe Ser Glu Ile Ile Ser Ser Ile Ser Asp Val Lys
        275                 280                 285

Phe Ser His Ser Gly Arg Tyr Ile Met Thr Arg Asp Tyr Leu Thr Val
    290                 295                 300

Lys Val Trp Asp Leu Asn Met Glu Asn Arg Pro Ile Glu Thr Tyr Gln
305                 310                 315                 320

Val His Asp Tyr Leu Arg Ser Lys Leu Cys Ser Leu Tyr Glu Asn Asp
                325                 330                 335

Cys Ile Phe Asp Lys Phe Glu Cys Val Trp Asn Gly Ser Asp Ser Val
            340                 345                 350

Ile Met Thr Gly Ser Tyr Asn Asn Phe Phe Arg Met Phe Asp Arg Asn
        355                 360                 365

Thr Lys Arg Asp Val Thr Leu Glu Ala Ser Arg Glu Asn Ser Lys Pro
    370                 375                 380

Arg Ala Ile Leu Lys Pro Arg Lys Val Cys Val Gly Gly Lys Arg Arg
385                 390                 395                 400

Lys Asp Glu Ile Ser Val Asp Ser Leu Asp Phe Ser Lys Lys Ile Leu
                405                 410                 415

His Thr Ala Trp His Pro Ser Glu Asn Ile Ile Ala Val Ala Ala Thr
            420                 425                 430

Asn Asn Leu Tyr Ile Phe Gln Asp Lys Val Asn
        435                 440


<210> SEQ ID NO 40
<211> LENGTH: 10692
<212> TYPE: DNA
<213> ORGANISM: Homo Sapiens

<400> SEQUENCE: 40

gaggagagag cagagtatac cgcagacatc atttctacta cagtggcgga gccgtacagg      60

acctgtttca ctgcaggggg atccaaaaca agccccgtgg agcagcagcc agagcaacag     120

cagccgcaag acattgtttc tctccctctg cccccccttc cccacgcaac cccagatcca     180

tttacacttt acagttttac ctcacaaaaa ctactacaag caccaagctc cctgatggaa     240

aggagcatcg tgcatcaagt caccagggtg gtccattcaa gctgcagatt tgtttgtcat     300

ccttgtacag caatctcctc ctccactgcc actacaggga agtgcatcac atgtcagcat     360

actggagcat agtgaaagag tctattttga agcttcaaac ttagtgctgc tgcagaccag     420

gaacaagaga gaaagagtgg atttcagcct gcacggatgg tcttgaaaca caaatggttt     480

ttggtctagg cgttttacac tgagattctc cactgccacc ctttctactc aagcaaaatc     540

ttcgtgaaaa gatctgctgc aaggaactga tagcttatgg ttctccattg tgatgaaagc     600

acatggtaca gttttccaaa gaaattagac cattttcttc gtgagaaaga aatcgacgtg     660

ctgttttcat agggtatttc tcacttctct gtgaaaggaa gaaagaacac gcctgagccc     720

aagagccctc aggagccctc cagagcctgt gggaagtctc catggtgaag tataggctga     780

ggctacctgt gaacagtacg cagtgaatgt tcatccagag ctgctgttgg cggattgtac     840

ccacggggag atgattcctc atgaagagcc tggatcccct acagaaatca aatgtgactt     900

tccgtttatc agactaaaat cagagccatc cagacagtga aacagtcacc gtggaggggg     960

gacggcgaaa aatgaaatcc aaccaagagc ggagcaacga atgcctgcct cccaagaagc    1020

gcgagatccc cgccaccagc cggtcctccg aggagaaggc ccctaccctg cccagcgaca    1080

accaccgggt ggagggcaca gcatggctcc cgggcaaccc tggtggccgg ggccacgggg    1140

gcgggaggca tgggccggca gggacctcgg tggagcttgg tttacaacag ggaataggtt    1200
```

-continued

```
tacacaaagc attgtccaca gggctggact actccccgcc cagcgctccc aggtctgtcc   1260
ccgtggccac cacgctgcct gccgcgtacg ccaccccgca gccagggacc ccggtgtccc   1320
ccgtgcagta cgctcacctg ccgcacacct tccagttcat tgggtcctcc caatacagtg   1380
gaacctatgc cagcttcatc ccatcacagc tgatcccccc aaccgccaac cccgtcacca   1440
gtgcagtggc ctcggccgca ggggccacca ctccatccca gcgctcccag ctggaggcct   1500
attccactct gctggccaac atgggcagtc tgagccagac gccgggacac aaggctgagc   1560
agcagcagca gcagcagcag cagcagcagc agcagcatca gcatcagcag cagcagcagc   1620
agcagcagca gcagcagcag cagcagcacc tcagcagggc tccggggctc atcaccccgg   1680
ggtccccccc accagcccag cagaaccagt acgtccacat ttccagttct ccgcagaaca   1740
ccggccgcac cgcctctcct ccggccatcc ccgtccacct ccacccccac cagacgatga   1800
tcccacacac gctcaccctg gggcccccct cccaggtcgt catgcaatac gccgactccg   1860
gcagccactt tgtccctcgg gaggccacca agaaagctga gagcagccgg ctgcagcagg   1920
ccatccaggc caaggaggtc ctgaacggtg agatggagaa gagccggcgg tacggggccc   1980
cgtcctcagc cgacctgggc ctgggcaagg caggcggcaa gtcggttcct cacccgtacg   2040
agtccaggca cgtggtggtc cacccgagcc cctcagacta cagcagtcgt gatccttcgg   2100
gggtccgggc ctctgtgatg gtcctgccca acagcaacac gcccgcagct gacctggagg   2160
tgcaacaggc cactcatcgt gaagcctccc cttctaccct caacgacaaa agtggcctgc   2220
atttagggaa gcctggccac cggtcctacg cgctctcacc ccacacggtc attcagacca   2280
cacacagtgc ttcagagcca ctcccggtgg gactgccagc cacggccttc tacgcaggga   2340
ctcaaccccc tgtcatcggc tacctgagcg gccagcagca agcaatcacc tacgccggca   2400
gcctgcccca gcacctggtg atccccggca cacagcccct gctcatcccg gtcggcagca   2460
ctgacatgga agcgtcgggg gcagccccgg ccatagtcac gtcatccccc cagtttgctg   2520
cagtgcctca cacgttcgtc accaccgccc ttcccaagag cgagaacttc aaccctgagg   2580
ccctggtcac ccaggccgcc tacccagcca tggtgcaggc ccagatccac ctgcctgtgg   2640
tgcagtccgt ggcctccccg gcggcggctc cccctacgct gcctccctac ttcatgaaag   2700
gctccatcat ccagttggcc aacggggagc taaagaaggt ggaagactta aaaacagaag   2760
atttcatcca gagtgcagag ataagcaacg acctgaagat cgactccagc accgtagaga   2820
ggattgaaga cagccatagc ccgggcgtgg ccgtgataca gttcgccgtc ggggagcacc   2880
gagcccaggt cagcgttgaa gttttggtag agtatccttt ttttgtgttt ggacagggct   2940
ggtcatcctg ctgtccggag agaaccagcc agctctttga tttgccgtgt tccaaactct   3000
cagttgggga tgtctgcatc tcgcttaccc tcaagaacct gaagaacggc tctgttaaaa   3060
agggccagcc cgtggatccc gccagcgtcc tgctgaagca ctcaaaggcc gacggcctgg   3120
cgggcagcag acacaggtat gccgagcagg aaaacggaat caaccagggg agtgcccaga   3180
tgctctctga gaatggcgaa ctgaagtttc cagagaaaat gggattgcct gcagcgccct   3240
tcctcaccaa aatagaaccc agcaagcccg cggcaacgag gaagaggagg tggtcggcgc   3300
cagagagccg caaactggag aagtcagaag acgaaccacc tttgactctt cctaagcctt   3360
ctctaattcc tcaggaggtt aagatttgca ttgaaggccg gtctaatgta ggcaagtaga   3420
ggcagcgtgg gggaaaggaa acgtggctct cccttatcat ttgtatccag attactgtac   3480
tgtaggctaa aataacacag tatttacatg ttatcttctt aattttaggt ttctgttcta   3540
accttgtcat tagagttaca gcaggtgtgt cgcaggagac tggtgcatat gctttttcca   3600
```

-continued

```
cgagtgtctg tcagtgagcg ggcgggagga agggcacagc aggagcggtc agggctccag   3660
gcatccccgg ggaagaaagg aacggggctt cacagtgcct gccttctcta gcggcacaga   3720
agcagccggg ggcgctgact cccgctagtg tcaggagaaa agtcccgtgg gaagagtcct   3780
gcaggggtgc agggttgcac gcatgtgggg gtgcacaggc gctgtggcgg cgagtgaggg   3840
tctcttttc tctgcctccc tctgcctcac tctcttgcta tcggcatggg ccgggggggt   3900
tcagagcagt gtcctcctgg ggttcccacg tgcaaaatca acatcaggaa cccagcttca   3960
gggcatcgcg gagacgcgtc agatggcaga tttggaaagt taaccattta aaagaacatt   4020
tttctctcca acatatttta caataaaagc aacttttaat tgtatagata tatatttccc   4080
cctatggggc ctgactgcac tgatatatat tttttttaaa gagcaactgc cacatgcggg   4140
atttcatttc tgctttttac tagtgcagcg atgtcaccag ggtgttgtgg tggacaggga   4200
agcccctgct gtcatggccc cacatggggt aagggggggtt gggggtgggg gagagggaga   4260
gagcgaacac ccacgctggt ttctgtgcag tgttaggaaa accaatcagg ttattgcatt   4320
gacttcactc ccaagaggta gatgcaaact gcccttcagt gagagcaaca gaagctcttc   4380
acgttgagtt tgcgaaatct ttttgtcttt gaactctagt actgtttata gttcatgact   4440
atggacaact cgggtgccac tttttttttt tttcagattc cagtgtgaca tgaggaatta   4500
gattttgaag atgagcatat attactatct ttaagcattt aaaaatactg ttcacacttt   4560
attaccaagc atcttggtct ctcattcaac aagtactgta tctcacttta aactctttgg   4620
ggaaaaaaca aaaacaaaaa aaactaagtt gctttctttt tttcaacact gtaactacat   4680
ttcagctctg cagaattgct gaagagcaag atattgaaag tttcaatgtg gtttaaaggg   4740
atgaatgtga attatgaact agtatgtgac aataaatgac caccaagtac tacctgacgg   4800
gaggcacttt tcactttgat gtctgagaat cagttcaagg catatgcaga gttggcagag   4860
aaactgagag aaaagggatg gagaagagaa tactcatttt tgtccagtgt ttttcttttt   4920
aagatgaact tttaaagaac cttgcgattt gcacatattg agtttataac ttgtgtgata   4980
ttcctgcagt ttttatccaa taacattgtg ggaaaggttt gggggactga acgagcataa   5040
ataaatgtag caaaatttct ttctaacctg cctaaactct aggccatttt ataaggttat   5100
gttcctttga aaattcattt tggtcttttt accacatctg tcacaaaaag ccaggtctta   5160
gcgggctctt agaaactctg agaattttct tcagattcat tgagagagtt ttccataaag   5220
acatttatat atgtgagcaa gatttttttt aaacaattac tttattattg ttgttattaa   5280
tgttattttc agaatggctt tttttttct attcaaaatc aaatcgagat ttaatgtttg   5340
gtacaaaccc agaaagggta tttcatagtt tttaaacctt tcattcccag agatccgaaa   5400
tatcatttgt gggttttgaa tgcatcttta aagtgcttta aaaaaaagtt ttataagtag   5460
ggagaaattt ttaaatattc ttacttggat ggctgcaact aaactgaaca aatacctgac   5520
ttttctttta ccccattgaa aatagtactt tcttcgtttc acaaattaaa aaaaaaatct   5580
ggtatcaacc cacattttgg ctgtctagta ttcatttaca tttagggttc accaggacta   5640
atgattttta taaaccgttt tctggggtgt accaaaaaca tttgaatagg tttagaatag   5700
ctagaatagt tccttgactt tcctcgaatt tcattaccct ctcagcatgc ttgcagagag   5760
ctgggtgggc tcattcttgc agtcatactg cttatttagt gctgtatttt ttaaacgttt   5820
ctgttcagag aacttgctta atcttccata tattctgctc agggcacttg caattattag   5880
gttttgtttt tctttttgtt ttttagcctt tgatggtaag aggaatacgg gctgccacat   5940
agactttgtt ctcattaata tcactattta caactcatgt ggactcagaa aaacacacac   6000
```

-continued

```
caccttttgg cttacttcga gtattgaatt gactggatcc actaaaccaa cactaagatg   6060
ggaaaacaca catggtttgg agcaatagga acatcatcat aatttttgtg gttctatttc   6120
aggtatagga attataaaat aattggttct ttctaaacac ttgtcccatt tcattctctt   6180
gctttttag catgtgcaat actttctgtg ccaatagagt ctgaccagtg tgctatatag    6240
ttaaagctca ttcccttttg gctttttcct tgtttggttg atcttcccca ttctggccag   6300
agcagggctg gagggaagga gccaggaggg agagagcctc ccacctttcc cctgctgcgg   6360
atgctgagtg ctggggcggg gagccttcag gagccccgtg cgtctgccgc cacgttgcag   6420
aaagagccag ccaaggagac ccgggggagg aaccgcagtg tcccctgtca ccacacggaa   6480
tagtgaatgt ggagtgtgga gaggaaggag gcagattcat ttctaagacg cactctggag   6540
ccatgtagcc tggagtcaac ccattttcca cggtcttttc tgcaagtggg caggcccctc   6600
ctcggggtct gtgtccttga gacttggagc cctgcctctg agcctggacg ggaagtgtgg   6660
cctgttgtgt gtgtgcgttc tgagcgtgtt ggccagtggc tgtggagggg accacctgcc   6720
acccacggtc accactccct tgtggcagct ttctcttcaa ataggaagaa cgcacagagg   6780
gcaggagcct cctgtttgca gacgttggcg ggccccgagg ctcccagagc agcctctgtc   6840
accgcttctg tgtagcaaac attaacgatg acaggggtag aaattcttcg gtgccgttca   6900
gcttacaagg atcagccatg tgcctctgta ctatgtccac tttgcaatat ttaccgacag   6960
ccgtcttttg ttctttcttt cctgttttcc atttttaaac tagtaacagc aggccttttg   7020
cgtttacaat ggaacacaat caccaagaaa ttagtcaggg cgaaaagaaa aaaataatac   7080
tattaataag aaaccaacaa acaagaacct ctctttctag ggatttctaa atatataaaa   7140
tgactgttcc ttagaatgtt taacttaaga attatttcag tttgtctggg ccacactggg   7200
gcagaggggg gagggaggga tacagagatg gatgccactt acctcagatc ttttaaagtg   7260
gaaatccaaa ttgaatttc atttggactt tcaggataat tttctatgtt ggtcaacttt    7320
tcgttttccc taactcaccc agtttagttt gggatgattt gatttctgtt gttgttgatc   7380
ccatttctaa cttggaattg tgagcctcta tgttttctgt taggtgagtg tgttgggttt   7440
tttcccccca ccaggaagtg gcagcatccc tccttctccc ctaaagggac tctgcggaac   7500
ctttcacacc tctttctcag ggacggggca ggtgtgtgtg tggtacactg acgtgtccag   7560
aagcagcact ttgactgctc tggagtaggg ttgtacaatt tcaaggaatg tttggatttc   7620
ctgcatcttg tggattactc cttagatacc gcatagattg caatataatg ctgcatgttc   7680
aagatgaaca gtagctccta gtaatcataa aatccactct ttgcacagtt tgatctttac   7740
tgaaatatgt tgccaaaatt tatttttgtt gttgtagctc tggattttgt tttgttttgt   7800
tttttaagga aacgattgac aataccettt aacatctgtg actactaagg aaacctattt   7860
ctttcataga gagaaaaatc tccaatgctt ttgaagacac taataccgtg ctatttcaga   7920
tatgggtgag gaagcagagc tctcggtacc gaaggccggg cttcttgagc tgtgttggtt   7980
gtcatggcta ctgtttcatg aaccacaagc agctcaacag actggtctgt tgccttctga   8040
aaccctttgc acttcaattt gcaccaggtg aaaacagggc cagcagactc catggcccaa   8100
ttcggtttct tcggtggtga tgtgaaagga gagaattaca cttttttttt ttttaagtgg   8160
cgtggaggcc tttgcttcca catttgtttt taacccagaa tttctgaaat agagaattta   8220
agaacacatc aagtaataaa tatacagaga atatactttt ttataaagca catgcatctg   8280
ctattgtgtt gggttggttt cctctctttt ccacggacag tgttgtgttt ctggcatagg   8340
gaaactccaa acaacttgca cacctctact ccggagctga gatttctttt acatagatga   8400
```

```
cctcgcttca aatacgttac cttactgatg ataggatctt ttcttgtagc actatacctt   8460
gtgggaattt ttttttaaat gtacacctga tttgagaagc tgaagaaaac aaaattttga   8520
agcactcact ttgaggagta caggtaatgt tttaaaaaat tgcacaaaag aaaaatgaat   8580
gtcgaaatga ttcattcagt gtttgaaaga tatggctctg ttgaaacaat gagtttcata   8640
ctttgtttgt aaaaaaaaaa aagcagagaa gggttgaaag ttacatgttt ttttgtatat   8700
agaaatttgt catgtctaaa tgatcagatt tgtatggtta tggcctggaa gaattactac   8760
gtaaaaggct cttaaactat acctatgctt attgttattt ttgttacata tagccctcgt   8820
ctgagggagg ggaactcggt attctgcgat ttgagaatac tgttcattcc tatgctgaaa   8880
gtacttctct gagctccctt cttagtctaa actcttaagc cattgcaact tctttttctt   8940
cagagatgat gtttgacatt ttcagcactt cctgttccta taaacccaaa gaatataatc   9000
ttgaacacga agtgtttgta acaagggatc caggctacca atcaaacagg actcattatg   9060
gggacaaaaa aaaaaattat ttcaccttct ttccccccac acctcattta aatgggggga   9120
gtaaaaacat gatttcaatg taaatgcctc attttatttt agttttattt tgatttttat   9180
ttaatataaa gaggccagaa taaatacgga gcatcttctc agaatagtat tcctgtccaa   9240
aaatcaagcc ggacagtgga aactggacag ctgtggggat attaagcacc cccacttaca   9300
attcttaaat tcagaatctc gtcccctccc ttctcgttga aggcaactgt tctggtagct   9360
aactttctcc tgtgtaatgg cgggagggaa caccggcttc agtttttcat gtccccatga   9420
cttgcataca aatggttcaa ctgtattaaa attaagtgca tttggccaat aggtagtatc   9480
tatacaataa caacaatctc taagaatttc cataactttt cttatctgaa aggactcaag   9540
tcttccactg cagatacatt ggaggcttca cccacgtttt ctttcccttt agtttgtttg   9600
ctgtctggat ggccaatgag cctgtctcct tttctgtggc caatctgaag gccttcgttg   9660
gaagtgttgt ttacagtaat ccttaccaag ataacatact gtcctccaga ataccaagta   9720
ttaggtgaca ctagctcaag ctgttgtctt cagagcagtt accaagaagc tcggtgcaca   9780
ggttttctct ggttcttaca ggaaccacct actctttcag ttttctggcc caggagtggg   9840
gtaaatcctt tagttagtgc atttgaactt gatacctgtg cattcagttc tgtgaatact   9900
gcccttttg gcggggtttc ctcatctccc cagcctgaac tgctcaactc taaacccaaa   9960
ttagtgtcag ccgaaaggag gtttcaagat agtcctgtca gtatttgtgg tgaccttcag  10020
attagacagt cttcatttcc agccagtgga gtcctggctc cagagccatc tctgagactc  10080
gtactactgg atgttttaat atcagatcat tacccaccat atgcctccca caggccaagg  10140
gaaaacagac accagaactt gggttgaggg cactaccaga ctgacatggc cagtacagag  10200
gagaactagg gaaggaatga tgttttgcac cttattgaaa agaaaatttt aagtgcatac  10260
ataatagtta agagctttta ttgtgacagg agaacttttt tccatatgcg tgcatactct  10320
ctgtaattcc agtgtaaaat attgtacttg cactagcttt tttaaacaaa tattaaaaaa  10380
tggaagaatt catattctat tttctaatcg tggtgtgtct atttgtagga tacactcgag  10440
tctgtttatt gaattttatg gtccctttct ttgatggtgc ttgcaggttt tctaggtaga  10500
aattatttca ttattataat aaaacaatgt ttgattcaaa atttgaacaa aattgtttta  10560
aataaattgt ctgtatacca gtacaagttt attgtttcag tatactcgta ctaataaaat  10620
aacagtgcca attgcaaaaa aaaaaaaaaa aaaaaaaaaa aaaaaaaaaa aaaaaaaaaa  10680
aaaaaaaaaa aa                                                      10692
```

<210> SEQ ID NO 41
<211> LENGTH: 798
<212> TYPE: PRT
<213> ORGANISM: Homo Sapiens

<400> SEQUENCE: 41

Met Lys Ser Asn Gln Glu Arg Ser Asn Glu Cys Leu Pro Pro Lys Lys
1               5                   10                  15

Arg Glu Ile Pro Ala Thr Ser Arg Ser Ser Glu Glu Lys Ala Pro Thr
            20                  25                  30

Leu Pro Ser Asp Asn His Arg Val Glu Gly Thr Ala Trp Leu Pro Gly
        35                  40                  45

Asn Pro Gly Gly Arg Gly His Gly Gly Gly Arg His Gly Pro Ala Gly
    50                  55                  60

Thr Ser Val Glu Leu Gly Leu Gln Gln Gly Ile Gly Leu His Lys Ala
65                  70                  75                  80

Leu Ser Thr Gly Leu Asp Tyr Ser Pro Pro Ser Ala Pro Arg Ser Val
                85                  90                  95

Pro Val Ala Thr Thr Leu Pro Ala Ala Tyr Ala Thr Pro Gln Pro Gly
            100                 105                 110

Thr Pro Val Ser Pro Val Gln Tyr Ala His Leu Pro His Thr Phe Gln
        115                 120                 125

Phe Ile Gly Ser Ser Gln Tyr Ser Gly Thr Tyr Ala Ser Phe Ile Pro
    130                 135                 140

Ser Gln Leu Ile Pro Pro Thr Ala Asn Pro Val Thr Ser Ala Val Ala
145                 150                 155                 160

Ser Ala Ala Gly Ala Thr Thr Pro Ser Gln Arg Ser Gln Leu Glu Ala
                165                 170                 175

Tyr Ser Thr Leu Leu Ala Asn Met Gly Ser Leu Ser Gln Thr Pro Gly
            180                 185                 190

His Lys Ala Glu Gln Gln Gln Gln Gln Gln Gln Gln Gln Gln Gln Gln
        195                 200                 205

His Gln His Gln Gln Gln Gln Gln Gln Gln Gln Gln Gln Gln Gln Gln
    210                 215                 220

Gln His Leu Ser Arg Ala Pro Gly Leu Ile Thr Pro Gly Ser Pro Pro
225                 230                 235                 240

Pro Ala Gln Gln Asn Gln Tyr Val His Ile Ser Ser Ser Pro Gln Asn
                245                 250                 255

Thr Gly Arg Thr Ala Ser Pro Pro Ala Ile Pro Val His Leu His Pro
            260                 265                 270

His Gln Thr Met Ile Pro His Thr Leu Thr Leu Gly Pro Pro Ser Gln
        275                 280                 285

Val Val Met Gln Tyr Ala Asp Ser Gly Ser His Phe Val Pro Arg Glu
    290                 295                 300

Ala Thr Lys Lys Ala Glu Ser Ser Arg Leu Gln Gln Ala Ile Gln Ala
305                 310                 315                 320

Lys Glu Val Leu Asn Gly Glu Met Glu Lys Ser Arg Arg Tyr Gly Ala
                325                 330                 335

Pro Ser Ser Ala Asp Leu Gly Leu Gly Lys Ala Gly Gly Lys Ser Val
            340                 345                 350

Pro His Pro Tyr Glu Ser Arg His Val Val Val His Pro Ser Pro Ser
        355                 360                 365

Asp Tyr Ser Ser Arg Asp Pro Ser Gly Val Arg Ala Ser Val Met Val
    370                 375                 380

Leu Pro Asn Ser Asn Thr Pro Ala Ala Asp Leu Glu Val Gln Gln Ala

```
385                 390                 395                 400

Thr His Arg Glu Ala Ser Pro Ser Thr Leu Asn Asp Lys Ser Gly Leu
                405                 410                 415

His Leu Gly Lys Pro Gly His Arg Ser Tyr Ala Leu Ser Pro His Thr
            420                 425                 430

Val Ile Gln Thr Thr His Ser Ala Ser Glu Pro Leu Pro Val Gly Leu
        435                 440                 445

Pro Ala Thr Ala Phe Tyr Ala Gly Thr Gln Pro Pro Val Ile Gly Tyr
    450                 455                 460

Leu Ser Gly Gln Gln Gln Ala Ile Thr Tyr Ala Gly Ser Leu Pro Gln
465                 470                 475                 480

His Leu Val Ile Pro Gly Thr Gln Pro Leu Leu Ile Pro Val Gly Ser
                485                 490                 495

Thr Asp Met Glu Ala Ser Gly Ala Ala Pro Ala Ile Val Thr Ser Ser
            500                 505                 510

Pro Gln Phe Ala Ala Val Pro His Thr Phe Val Thr Thr Ala Leu Pro
        515                 520                 525

Lys Ser Glu Asn Phe Asn Pro Glu Ala Leu Val Thr Gln Ala Ala Tyr
    530                 535                 540

Pro Ala Met Val Gln Ala Gln Ile His Leu Pro Val Val Gln Ser Val
545                 550                 555                 560

Ala Ser Pro Ala Ala Ala Pro Pro Thr Leu Pro Pro Tyr Phe Met Lys
                565                 570                 575

Gly Ser Ile Ile Gln Leu Ala Asn Gly Glu Leu Lys Lys Val Glu Asp
            580                 585                 590

Leu Lys Thr Glu Asp Phe Ile Gln Ser Ala Glu Ile Ser Asn Asp Leu
        595                 600                 605

Lys Ile Asp Ser Ser Thr Val Glu Arg Ile Glu Asp Ser His Ser Pro
    610                 615                 620

Gly Val Ala Val Ile Gln Phe Ala Val Gly Glu His Arg Ala Gln Val
625                 630                 635                 640

Ser Val Glu Val Leu Val Glu Tyr Pro Phe Phe Val Phe Gly Gln Gly
                645                 650                 655

Trp Ser Ser Cys Cys Pro Glu Arg Thr Ser Gln Leu Phe Asp Leu Pro
            660                 665                 670

Cys Ser Lys Leu Ser Val Gly Asp Val Cys Ile Ser Leu Thr Leu Lys
        675                 680                 685

Asn Leu Lys Asn Gly Ser Val Lys Lys Gly Gln Pro Val Asp Pro Ala
    690                 695                 700

Ser Val Leu Leu Lys His Ser Lys Ala Asp Gly Leu Ala Gly Ser Arg
705                 710                 715                 720

His Arg Tyr Ala Glu Gln Glu Asn Gly Ile Asn Gln Gly Ser Ala Gln
                725                 730                 735

Met Leu Ser Glu Asn Gly Glu Leu Lys Phe Pro Glu Lys Met Gly Leu
            740                 745                 750

Pro Ala Ala Pro Phe Leu Thr Lys Ile Glu Pro Ser Lys Pro Ala Ala
        755                 760                 765

Thr Arg Lys Arg Arg Trp Ser Ala Pro Glu Ser Arg Lys Leu Glu Lys
    770                 775                 780

Ser Glu Asp Glu Pro Pro Leu Thr Leu Pro Lys Pro Ser Leu
785                 790                 795
```

<210> SEQ ID NO 42
<211> LENGTH: 4702

<212> TYPE: DNA
<213> ORGANISM: Homo Sapiens

<400> SEQUENCE: 42

```
acccccgaga aagcaaccca gcgcgccgcc cgctcctcac gtgtccctcc cggccccggg     60
gccacctcac gttctgcttc cgtctgaccc ctccgacttc cggtaaagag tccctatccg    120
cacctccgct cccacccggc gcctcggcgc gcccgccctc cgatgcgctc agcggccgca    180
gctcctcgga gtcccgcggt ggccaccgag tctcgccgct tcgccgcagc caggtggccc    240
gggtggcgct cgctccagcg gccggcgcgg cggagcgggc ggggcggcgg tggcgcggcc    300
ccgggaccgt atccctccgc cgcccctccc ccgcccggcc ccggcccccc tccctcccgg    360
cagagctcgc ctccctccgc ctcagactgt tttggtagca acggcaacgg cggcggcgcg    420
tttcggcccg gctcccggcg gctccttggt ctcggcgggc ctccccgccc cttcgtcgtc    480
gtccttctcc ccctcgccag cccgggcgcc cctccggccg cgccaacccg cgcctccccg    540
ctcggcgccc gtgcgtcccc gccgcgttcc ggcgtctcct tggcgcgccc ggctcccggc    600
tgtccccgcc cggcgtgcga gccggtgtat gggcccctca ccatgtcgct gaagccccag    660
cagcagcagc agcagcagca gcagcagcag cagcagcaac agcagcagca gcagcagcag    720
cagcagccgc cgcccgcggc tgccaatgtc cgcaagcccg gcggcagcgg ccttctagcg    780
tcgcccgccg ccgcgccttc gccgtcctcg tcctcggtct cctcgtcctc ggccacggct    840
ccctcctcgg tggtcgcggc gacctccggc ggcgggaggc ccggcctggg cagaggtcga    900
aacagtaaca aaggactgcc tcagtctacg atttcttttg atggaatcta tgcaaatatg    960
aggatggttc atatacttac atcagttgtt ggctccaaat gtgaagtaca agtgaaaaat   1020
ggaggtatat atgaaggagt ttttaaaact tacagtccga agtgtgattt ggtacttgat   1080
gccgcacatg agaaaagtac agaatccagt tcggggccga aacgtgaaga aataatggag   1140
agtattttgt tcaaatgttc agactttgtt gtggtacagt ttaaagatat ggactccagt   1200
tatgcaaaaa gagatgcttt tactgactct gctatcagtg ctaaagtgaa tggcgaacac   1260
aaagagaagg acctggagcc ctgggatgca ggtgaactca cagccaatga ggaacttgag   1320
gctttggaaa atgacgtatc taatggatgg gatcccaatg atatgtttcg atataatgaa   1380
gaaaattatg gtgtagtgtc tacgtatgat agcagtttat cttcgtatac agtgccctta   1440
gaaagagata actcagaaga atttttaaaa cgggaagcaa gggcaaacca gttagcagaa   1500
gaaattgagt caagtgccca gtacaaagct cgagtggccc tggaaaatga tgataggagt   1560
gaggaagaaa aatacacagc agttcagaga aattccagtg aacgtgaggg gcacagcata   1620
aacactaggg aaaataaata tattcctcct ggacaaagaa atagagaagt catatcctgg   1680
ggaagtggga gacagaattc accgcgtatg ggccagcctg gatcgggctc catgccatca   1740
agatccactt ctcacacttc agatttcaac ccgaattctg gttcagacca aagagtagtt   1800
aatggaggtg ttccctggcc atcgccttgc ccatctcctt cctctcgccc accttctcgc   1860
taccagtcag gtcccaactc tcttccacct cgggcagcca cccctacacg gccgccctcc   1920
aggccccccct cgcggccatc cagacccccg tctcacccct ctgctcatgg ttctccagct   1980
cctgtctcta ctatgcctaa acgcatgtct tcagaagggc ctccaaggat gtccccaaag   2040
gcccagcgac atcctcgaaa tcacagagtt tctgctggga ggggttccat atccagtggc   2100
ctagaatttg tatcccacaa cccacccagt gaagcagcta ctcctccagt agcaaggacc   2160
agtccctcgg ggggaacgtg gtcatcagtg gtcagtgggg ttccaagatt atcccctaaa   2220
actcatagac ccaggtctcc cagacagaac agtattggaa atacccccag tgggccagtt   2280
```

```
cttgcttctc cccaagctgg tattattcca actgaagctg ttgccatgcc tattccagct   2340
gcatctccta cgcctgctag tcctgcatcg aacagagctg ttaccccttc tagtgaggct   2400
aaagattcca ggcttcaaga tcagaggcag aactctcctg cagggaataa agaaaatatt   2460
aaacccaatg aaacatcacc tagcttctca aaagctgaaa acaaaggtat atcaccagtt   2520
gtttctgaac atagaaaaca gattgatgat ttaaagaaat ttaagaatga ttttaggtta   2580
cagccaagtt ctacttctga atctatggat caactactaa acaaaaatag agagggagaa   2640
aaatcaagag atttgatcaa agacaaaatt gaaccaagtg ctaaggattc tttcattgaa   2700
aatagcagca gcaactgtac cagtggcagc agcaagccga atagccccag catttcccct   2760
tcaatactta gtaacacgga gcacaagagg ggacctgagg tcacttccca aggggttcag   2820
acttccagcc cagcatgtaa acaagagaaa gacgataagg aagagaagaa agacgcagct   2880
gagcaagtta ggaaatcaac attgaatccc aatgcaaagg agttcaaccc acgttccttc   2940
tctcagccaa agccttctac taccccaact tcacctcggc ctcaagcaca acctagccca   3000
tctatggtgg gtcatcaaca gccaactcca gtttatactc agcctgtttg ttttgcacca   3060
aatatgatgt atccagtccc agtgagccca ggcgtgcaac ctttataccc aatacctatg   3120
acgcccatgc cagtgaatca agccaagaca tatagagcag taccaaatat gccccaacag   3180
cggcaagacc agcatcatca gagtgccatg atgcacccag cgtcagcagc gggcccaccg   3240
attgcagcca ccccaccagc ttactccacg caatatgttg cctacagtcc tcagcagttc   3300
ccaaatcagc cccttgttca gcatgtgcca cattatcagt ctcagcatcc tcatgtctat   3360
agtcctgtaa tacagggtaa tgctagaatg atggcaccac caacacacgc ccagcctggt   3420
ttagtatctt cttcagcaac tcagtacggg gctcatgagc agacgcatgc gatgtatgca   3480
tgtcccaaat taccatacaa caaggagaca agcccttctt tctactttgc catttccacg   3540
ggctcccttg ctcagcagta tgcgcaccct aacgctaccc tgcacccaca tactccacac   3600
cctcagcctt cagctacccc cactggacag cagcaaagcc aacatggtgg aagtcatcct   3660
gcacccagtc ctgttcagca ccatcagcac caggccgccc aggctctcca tctggccagt   3720
ccacagcagc agtcagccat ttaccacgcg gggcttgcgc caactccacc ctccatgaca   3780
cctgcctcca acacgcagtc gccacagaat agtttcccag cagcacaaca gactgtcttt   3840
acgatccatc cttctcacgt tcagccggcg tataccaacc caccccacat ggcccacgta   3900
cctcaggctc atgtacagtc aggaatggtt ccttctcatc caactgccca tgcgccaatg   3960
atgctaatga cgacacagcc acccggcggt ccccaggccg ccctcgctca aagtgcacta   4020
cagcccattc cagtctcgac aacagcgcat ttccccctata tgacgcaccc ttcagtacaa   4080
gcccaccacc aacagcagtt gtaaggctgc cctggaggaa ccgaaaggcc aaattccctc   4140
ctcccttcta ctgcttctac caactggaag cacagaaaac tagaatttca tttattttgt   4200
ttttaaaata tatatgttga tttcttgtaa catccaatag gaatgctaac agttcacttg   4260
cagtggaaga tacttggacc gagtagaggc atttaggaac ttgggggcta ttccataatt   4320
ccatatgctg tttcagagtc ccgcaggtac cccagctctg cttgccgaaa ctggaagtta   4380
tttattttttt aataaccctt gaaagtcatg aacacatcag ctagcaaaag aagtaacaag   4440
agtgattctt gctgctatta ctgctaaaaa aaaaaaaaaa aaaaaatcaa gacttggaac   4500
gcccttttac taaacttgac aaagtttcag taaattctta ccgtcaaact gacggattat   4560
tatttataaa tcaagtttga tgaggtgatc actgtctaca gtggttcaac ttttaagtta   4620
agggaaaaac ttttactttg tagataatat aaaataaaaa cttaaaaaaa atttaaaaaa   4680
```

taaaaaaagt tttaaaaact ga 4702

<210> SEQ ID NO 43
<211> LENGTH: 1313
<212> TYPE: PRT
<213> ORGANISM: Homo Sapiens

<400> SEQUENCE: 43

Met Arg Ser Ala Ala Ala Ala Pro Arg Ser Pro Ala Val Ala Thr Glu
1 5 10 15

Ser Arg Arg Phe Ala Ala Ala Arg Trp Pro Gly Trp Arg Ser Leu Gln
20 25 30

Arg Pro Ala Arg Arg Ser Gly Arg Gly Gly Gly Gly Ala Ala Pro Gly
35 40 45

Pro Tyr Pro Ser Ala Ala Pro Pro Pro Pro Gly Pro Gly Pro Pro Pro
50 55 60

Ser Arg Gln Ser Ser Pro Pro Ser Ala Ser Asp Cys Phe Gly Ser Asn
65 70 75 80

Gly Asn Gly Gly Gly Ala Phe Arg Pro Gly Ser Arg Arg Leu Leu Gly
85 90 95

Leu Gly Gly Pro Pro Arg Pro Phe Val Val Val Leu Leu Pro Leu Ala
100 105 110

Ser Pro Gly Ala Pro Pro Ala Ala Pro Thr Arg Ala Ser Pro Leu Gly
115 120 125

Ala Arg Ala Ser Pro Pro Arg Ser Gly Val Ser Leu Ala Arg Pro Ala
130 135 140

Pro Gly Cys Pro Arg Pro Ala Cys Glu Pro Val Tyr Gly Pro Leu Thr
145 150 155 160

Met Ser Leu Lys Pro Gln Gln Gln Gln Gln Gln Gln Gln Gln Gln Gln
165 170 175

Gln Gln Gln Gln Gln Gln Gln Gln Gln Gln Gln Gln Pro Pro Pro Ala
180 185 190

Ala Ala Asn Val Arg Lys Pro Gly Gly Ser Gly Leu Leu Ala Ser Pro
195 200 205

Ala Ala Ala Pro Ser Pro Ser Ser Ser Ser Val Ser Ser Ser Ser Ala
210 215 220

Thr Ala Pro Ser Ser Val Val Ala Ala Thr Ser Gly Gly Gly Arg Pro
225 230 235 240

Gly Leu Gly Arg Gly Arg Asn Ser Asn Lys Gly Leu Pro Gln Ser Thr
245 250 255

Ile Ser Phe Asp Gly Ile Tyr Ala Asn Met Arg Met Val His Ile Leu
260 265 270

Thr Ser Val Val Gly Ser Lys Cys Glu Val Gln Val Lys Asn Gly Gly
275 280 285

Ile Tyr Glu Gly Val Phe Lys Thr Tyr Ser Pro Lys Cys Asp Leu Val
290 295 300

Leu Asp Ala Ala His Glu Lys Ser Thr Glu Ser Ser Ser Gly Pro Lys
305 310 315 320

Arg Glu Glu Ile Met Glu Ser Ile Leu Phe Lys Cys Ser Asp Phe Val
325 330 335

Val Val Gln Phe Lys Asp Met Asp Ser Ser Tyr Ala Lys Arg Asp Ala
340 345 350

Phe Thr Asp Ser Ala Ile Ser Ala Lys Val Asn Gly Glu His Lys Glu
355 360 365

-continued

```
Lys Asp Leu Glu Pro Trp Asp Ala Gly Glu Leu Thr Ala Asn Glu Glu
    370                 375                 380

Leu Glu Ala Leu Glu Asn Asp Val Ser Asn Gly Trp Asp Pro Asn Asp
385                 390                 395                 400

Met Phe Arg Tyr Asn Glu Glu Asn Tyr Gly Val Val Ser Thr Tyr Asp
                405                 410                 415

Ser Ser Leu Ser Ser Tyr Thr Val Pro Leu Glu Arg Asp Asn Ser Glu
            420                 425                 430

Glu Phe Leu Lys Arg Glu Ala Arg Ala Asn Gln Leu Ala Glu Glu Ile
        435                 440                 445

Glu Ser Ser Ala Gln Tyr Lys Ala Arg Val Ala Leu Glu Asn Asp Asp
    450                 455                 460

Arg Ser Glu Glu Glu Lys Tyr Thr Ala Val Gln Arg Asn Ser Ser Glu
465                 470                 475                 480

Arg Glu Gly His Ser Ile Asn Thr Arg Glu Asn Lys Tyr Ile Pro Pro
                485                 490                 495

Gly Gln Arg Asn Arg Glu Val Ile Ser Trp Gly Ser Gly Arg Gln Asn
            500                 505                 510

Ser Pro Arg Met Gly Gln Pro Gly Ser Gly Ser Met Pro Ser Arg Ser
        515                 520                 525

Thr Ser His Thr Ser Asp Phe Asn Pro Asn Ser Gly Ser Asp Gln Arg
    530                 535                 540

Val Val Asn Gly Gly Val Pro Trp Pro Ser Pro Cys Pro Ser Pro Ser
545                 550                 555                 560

Ser Arg Pro Pro Ser Arg Tyr Gln Ser Gly Pro Asn Ser Leu Pro Pro
                565                 570                 575

Arg Ala Ala Thr Pro Thr Arg Pro Pro Ser Arg Pro Pro Ser Arg Pro
            580                 585                 590

Ser Arg Pro Pro Ser His Pro Ser Ala His Gly Ser Pro Ala Pro Val
        595                 600                 605

Ser Thr Met Pro Lys Arg Met Ser Ser Glu Gly Pro Pro Arg Met Ser
    610                 615                 620

Pro Lys Ala Gln Arg His Pro Arg Asn His Arg Val Ser Ala Gly Arg
625                 630                 635                 640

Gly Ser Ile Ser Ser Gly Leu Glu Phe Val Ser His Asn Pro Pro Ser
                645                 650                 655

Glu Ala Ala Thr Pro Pro Val Ala Arg Thr Ser Pro Ser Gly Gly Thr
            660                 665                 670

Trp Ser Ser Val Val Ser Gly Val Pro Arg Leu Ser Pro Lys Thr His
        675                 680                 685

Arg Pro Arg Ser Pro Arg Gln Asn Ser Ile Gly Asn Thr Pro Ser Gly
    690                 695                 700

Pro Val Leu Ala Ser Pro Gln Ala Gly Ile Ile Pro Thr Glu Ala Val
705                 710                 715                 720

Ala Met Pro Ile Pro Ala Ala Ser Pro Thr Pro Ala Ser Pro Ala Ser
                725                 730                 735

Asn Arg Ala Val Thr Pro Ser Ser Glu Ala Lys Asp Ser Arg Leu Gln
            740                 745                 750

Asp Gln Arg Gln Asn Ser Pro Ala Gly Asn Lys Glu Asn Ile Lys Pro
        755                 760                 765

Asn Glu Thr Ser Pro Ser Phe Ser Lys Ala Glu Asn Lys Gly Ile Ser
    770                 775                 780

Pro Val Val Ser Glu His Arg Lys Gln Ile Asp Asp Leu Lys Lys Phe
785                 790                 795                 800
```

```
Lys Asn Asp Phe Arg Leu Gln Pro Ser Ser Thr Ser Glu Ser Met Asp
            805                 810                 815

Gln Leu Leu Asn Lys Asn Arg Glu Gly Glu Lys Ser Arg Asp Leu Ile
            820                 825                 830

Lys Asp Lys Ile Glu Pro Ser Ala Lys Asp Ser Phe Ile Glu Asn Ser
        835                 840                 845

Ser Ser Asn Cys Thr Ser Gly Ser Ser Lys Pro Asn Ser Pro Ser Ile
    850                 855                 860

Ser Pro Ser Ile Leu Ser Asn Thr Glu His Lys Arg Gly Pro Glu Val
865                 870                 875                 880

Thr Ser Gln Gly Val Gln Thr Ser Ser Pro Ala Cys Lys Gln Glu Lys
                885                 890                 895

Asp Asp Lys Glu Glu Lys Lys Asp Ala Ala Glu Gln Val Arg Lys Ser
            900                 905                 910

Thr Leu Asn Pro Asn Ala Lys Glu Phe Asn Pro Arg Ser Phe Ser Gln
        915                 920                 925

Pro Lys Pro Ser Thr Thr Pro Thr Ser Pro Arg Pro Gln Ala Gln Pro
    930                 935                 940

Ser Pro Ser Met Val Gly His Gln Gln Pro Thr Pro Val Tyr Thr Gln
945                 950                 955                 960

Pro Val Cys Phe Ala Pro Asn Met Met Tyr Pro Val Pro Val Ser Pro
                965                 970                 975

Gly Val Gln Pro Leu Tyr Pro Ile Pro Met Thr Pro Met Pro Val Asn
            980                 985                 990

Gln Ala Lys Thr Tyr Arg Ala Val  Pro Asn Met Pro Gln  Gln Arg Gln
        995                 1000                1005

Asp Gln  His His Gln Ser Ala  Met Met His Pro Ala  Ser Ala Ala
    1010                1015                1020

Gly Pro  Pro Ile Ala Ala Thr  Pro Pro Ala Tyr Ser  Thr Gln Tyr
    1025                1030                1035

Val Ala  Tyr Ser Pro Gln Gln  Phe Pro Asn Gln Pro  Leu Val Gln
    1040                1045                1050

His Val  Pro His Tyr Gln Ser  Gln His Pro His Val  Tyr Ser Pro
    1055                1060                1065

Val Ile  Gln Gly Asn Ala Arg  Met Met Ala Pro Pro  Thr His Ala
    1070                1075                1080

Gln Pro  Gly Leu Val Ser Ser  Ser Ala Thr Gln Tyr  Gly Ala His
    1085                1090                1095

Glu Gln  Thr His Ala Met Tyr  Ala Cys Pro Lys Leu  Pro Tyr Asn
    1100                1105                1110

Lys Glu  Thr Ser Pro Ser Phe  Tyr Phe Ala Ile Ser  Thr Gly Ser
    1115                1120                1125

Leu Ala  Gln Gln Tyr Ala His  Pro Asn Ala Thr Leu  His Pro His
    1130                1135                1140

Thr Pro  His Pro Gln Pro Ser  Ala Thr Pro Thr Gly  Gln Gln Gln
    1145                1150                1155

Ser Gln  His Gly Gly Ser His  Pro Ala Pro Ser Pro  Val Gln His
    1160                1165                1170

His Gln  His Gln Ala Ala Gln  Ala Leu His Leu Ala  Ser Pro Gln
    1175                1180                1185

Gln Gln  Ser Ala Ile Tyr His  Ala Gly Leu Ala Pro  Thr Pro Pro
    1190                1195                1200

Ser Met  Thr Pro Ala Ser Asn  Thr Gln Ser Pro Gln  Asn Ser Phe
```

```
    1205                1210                1215

Pro Ala  Ala Gln Gln Thr Val  Phe Thr Ile His Pro  Ser His Val
    1220                1225                1230

Gln Pro  Ala Tyr Thr Asn Pro  Pro His Met Ala His  Val Pro Gln
    1235                1240                1245

Ala His  Val Gln Ser Gly Met  Val Pro Ser His Pro  Thr Ala His
    1250                1255                1260

Ala Pro  Met Met Leu Met Thr  Thr Gln Pro Pro Gly  Gly Pro Gln
    1265                1270                1275

Ala Ala  Leu Ala Gln Ser Ala  Leu Gln Pro Ile Pro  Val Ser Thr
    1280                1285                1290

Thr Ala  His Phe Pro Tyr Met  Thr His Pro Ser Val  Gln Ala His
    1295                1300                1305

His Gln  Gln Gln Leu
    1310


<210> SEQ ID NO 44
<211> LENGTH: 2678
<212> TYPE: DNA
<213> ORGANISM: Homo Sapiens

<400> SEQUENCE: 44

ggggcggagc tggagggggt ggttcggcgt gggggccgtt ggctccagac aaataaacat     60

ggagtccatc ttccacgaga aacaagaagg ctcactttgt gctcaacatt gcctgaataa    120

cttattgcaa ggagaatatt ttagccctgt ggaattatcc tcaattgcac atcagctgga    180

tgaggaggag aggatgagaa tggcagaagg aggagttact agtgaagatt atcgcacgtt    240

tttacagcag ccttctggaa atatggatga cagtggtttt ttctctattc aggttataag    300

caatgccttg aaagtttggg gtttagaact aatcctgttc aacagtccag agtatcagag    360

gctcaggatc gatcctataa atgaaagatc atttatatgc aattataagg aacactggtt    420

tacagttaga aaattaggaa aacagtggtt taacttgaat tctctcttga cgggtccaga    480

attaatatca gatacatatc ttgcactttt cttggctcaa ttacaacagg aaggttattc    540

tatatttgtc gttaagggtg atctgccaga ttgcgaagct gaccaactcc tgcagatgat    600

tagggtccaa cagatgcatc gaccaaaact tattggagaa gaattagcac aactaaaaga    660

gcaaagagtc cataaaacag acctggaacg agtgttagaa gcaaatgatg gctcaggaat    720

gttagacgaa gatgaggagg atttgcagag ggctctggca ctaagtcgcc aagaaattga    780

catggaagat gaggaagcag atctccgcag ggctattcag ctaagtatgc aaggtagttc    840

cagaaacata tctcaagata tgacacagac atcaggtaca aatcttactt cagaagagct    900

tcggaagaga cgagaagcct actttgaaaa acagcagcaa aagcagcaac agcagcagca    960

gcagcagcag caggggggacc tatcaggaca gagttcacat ccatgtgaaa ggccagccac   1020

cagttcagga gcacttggga gtgatctagg tgatgctatg agtgaagaag acatgcttca   1080

ggcagctgtg accatgtctt tagaaactgt cagaaatgat ttgaaaacag aaggaaaaaa   1140

ataatacctt taaaaaataa tttagatatt catactttcc aacattatcc tgtgtgatta   1200

cagcataggg tccactttgg taatgtgtca aagagatgag gaaataagac ttttagcggt   1260

ttgcaaacaa aatgatggga aagtggaaca atgcgtcggt tgtaggacta aataatgatc   1320

ttccaaatat tagccaaaga ggcattcagc aattaaagac atttaaaata gttttctaaa   1380

tgtttctttt tctttttga gtgtgcaata tgtaacatgt ctaaagttag ggcatttttc   1440

ttggatcttt ttgcagacta gctaattagc tctcgcctca ggctttttcc atatagtttg   1500
```

```
ttttcttttt ctgtcttgta ggtaagttgg ctcacatcat gtaatagtgg ctttcatttc   1560

ttattaacca aattaacctt tcaggaaagt atctctactt tcctgatgtt gataatagta   1620

atggttctag aaggatgaac agttctccct tcaactgtat accgtgtgct ccagtgtttt   1680

cttgtgttgt tttctctgat cacaactttt ctgctacctg gttttcatta ttttcccaca   1740

attcttttga aagatggtaa tcttttctga ggtttagcgt tttaagccct acgatgggat   1800

cattatttca tgactggtgc gttcctaaac tctgaaatca gccttgcaca agtacttgag   1860

aataaatgag catttttttaa aatgtgtgag catgtgcttt cccagatgct ttatgaatgt   1920

cttttcactt atatcaaaac cttacagctt tgttgcaacc ccttcttcct gcgccttatt   1980

ttttcctttc ttctccaatt gagaaaacta ggagaagcat agtatgcagg caagtctcct   2040

tctgttagaa gactaaacat acgtacccac catgaatgta tgatacatga aatttggcct   2100

tcaattttaa tagcagtttt attttatttt ttctcctatg actggagctt tgtgttctct   2160

ttacagttga gtcatggaat gtaggtgtct gcttcacatc ttttagtagg tatagcttgt   2220

caaagatggt gatctggaac atgaaaataa tttactaatg aaaatatgtt taaatttata   2280

ctgtgatttg acacttgcat catgtttaga tagcttaaga acaatggaag tcacagtact   2340

tagtggatct ataaataaga aagtccatag ttttgataaa tattctcttt aattgagatg   2400

tacagagagt ttcttgctgg gtcaatagga tagtatcatt ttggtgaaaa ccatgtctct   2460

gaaattgatg ttttagtttc agtgttccct atccctcatt ctccatctcc ttttgaagct   2520

cttttgaatg ttgaattgtt cataagctaa aatccaagaa atttcagctg acaacttcga   2580

aaattataat atggtatatt gccctcctgg tgtgtggctg cacacatttt atcagggaaa   2640

gtttttgat ctaggattta ttgctaacta actgaaaa                            2678
```

<210> SEQ ID NO 45
<211> LENGTH: 361
<212> TYPE: PRT
<213> ORGANISM: Homo Sapiens

<400> SEQUENCE: 45

```
Met Glu Ser Ile Phe His Glu Lys Gln Glu Gly Ser Leu Cys Ala Gln
1               5                   10                  15

His Cys Leu Asn Asn Leu Leu Gln Gly Glu Tyr Phe Ser Pro Val Glu
            20                  25                  30

Leu Ser Ser Ile Ala His Gln Leu Asp Glu Glu Glu Arg Met Arg Met
        35                  40                  45

Ala Glu Gly Gly Val Thr Ser Glu Asp Tyr Arg Thr Phe Leu Gln Gln
    50                  55                  60

Pro Ser Gly Asn Met Asp Asp Ser Gly Phe Phe Ser Ile Gln Val Ile
65                  70                  75                  80

Ser Asn Ala Leu Lys Val Trp Gly Leu Glu Leu Ile Leu Phe Asn Ser
                85                  90                  95

Pro Glu Tyr Gln Arg Leu Arg Ile Asp Pro Ile Asn Glu Arg Ser Phe
            100                 105                 110

Ile Cys Asn Tyr Lys Glu His Trp Phe Thr Val Arg Lys Leu Gly Lys
        115                 120                 125

Gln Trp Phe Asn Leu Asn Ser Leu Leu Thr Gly Pro Glu Leu Ile Ser
    130                 135                 140

Asp Thr Tyr Leu Ala Leu Phe Leu Ala Gln Leu Gln Gln Glu Gly Tyr
145                 150                 155                 160

Ser Ile Phe Val Val Lys Gly Asp Leu Pro Asp Cys Glu Ala Asp Gln
```

```
                165                 170                 175

Leu Leu Gln Met Ile Arg Val Gln Gln Met His Arg Pro Lys Leu Ile
            180                 185                 190

Gly Glu Glu Leu Ala Gln Leu Lys Glu Gln Arg Val His Lys Thr Asp
        195                 200                 205

Leu Glu Arg Val Leu Glu Ala Asn Asp Gly Ser Gly Met Leu Asp Glu
    210                 215                 220

Asp Glu Glu Asp Leu Gln Arg Ala Leu Ala Leu Ser Arg Gln Glu Ile
225                 230                 235                 240

Asp Met Glu Asp Glu Glu Ala Asp Leu Arg Arg Ala Ile Gln Leu Ser
                245                 250                 255

Met Gln Gly Ser Ser Arg Asn Ile Ser Gln Asp Met Thr Gln Thr Ser
            260                 265                 270

Gly Thr Asn Leu Thr Ser Glu Glu Leu Arg Lys Arg Arg Glu Ala Tyr
        275                 280                 285

Phe Glu Lys Gln Gln Gln Lys Gln Gln Gln Gln Gln Gln Gln Gln Gln
    290                 295                 300

Gln Gly Asp Leu Ser Gly Gln Ser Ser His Pro Cys Glu Arg Pro Ala
305                 310                 315                 320

Thr Ser Ser Gly Ala Leu Gly Ser Asp Leu Gly Asp Ala Met Ser Glu
                325                 330                 335

Glu Asp Met Leu Gln Ala Ala Val Thr Met Ser Leu Glu Thr Val Arg
            340                 345                 350

Asn Asp Leu Lys Thr Glu Gly Lys Lys
        355                 360


<210> SEQ ID NO 46
<211> LENGTH: 7807
<212> TYPE: DNA
<213> ORGANISM: Homo Sapiens

<400> SEQUENCE: 46

cgcaccctcc ttccgcccct ccttctccgg ggtcagccag gaagatgtcc cgagctgcta     60

tccccggctc ggcccgggca gccgccttct gagcccccga cccgaggcgc cgagccgccg    120

ccgcccgatg ggctgggccg tggagcgtct ccgcagtcgt agctccagcc gccgcgctcc    180

cagccccggc agcctcagca tcagcggcgg cggcggcggc ggcggcggcg tcttccgcat    240

cgttcgccgc agcgtaaccc ggagcccttt gctctttgca gaatggcccg cttcggagac    300

gagatgccgg cccgctacgg gggaggaggc tccggggcag ccgccggggt ggtcgtgggc    360

agcggaggcg ggcgaggagc cgggggcagc cggcagggcg ggcagcccgg ggcgcaaagg    420

atgtacaagc agtcaatggc gcagagagcg cggaccatgg cactctacaa ccccatcccc    480

gtccgacaga actgcctcac ggttaaccgg tctctcttcc tcttcagcga agacaacgtg    540

gtgagaaaat acgccaaaaa gatcaccgaa tggcctccct ttgaatatat gattttagcc    600

accatcatag cgaattgcat cgtcctcgca ctggagcagc atctgcctga tgatgacaag    660

accccgatgt ctgaacggct ggatgacaca gaaccatact tcattggaat tttttgtttc    720

gaggctggaa ttaaaatcat tgcccttggg tttgccttcc acaaaggctc ctacttgagg    780

aatggctgga atgtcatgga ctttgtggtg gtgctaacgg gcatcttggc gacagttggg    840

acggagtttg acctacggac gctgagggca gttcgagtgc tgcggccgct caagctggtg    900

tctggaatcc caagtttaca agtcgtcctg aagtcgatca tgaaggcgat gatccctttg    960

ctgcagatcg gcctcctcct attttttgca atccttattt ttgcaatcat agggttagaa   1020
```

-continued ttttatatgg gaaaatttca taccacctgc tttgaagagg ggacagatga cattcagggt 1080
gagtctccgg ctccatgtgg gacagaagag cccgcccgca cctgccccaa tgggaccaaa 1140
tgtcagccct actgggaagg gcccaacaac gggatcactc agttcgacaa catcctgttt 1200
gcagtgctga ctgttttcca gtgcataacc atggaagggt ggactgatct cctctacaat 1260
agcaacgatg cctcagggaa cacttggaac tggttgtact tcatcccccct catcatcatc 1320 ggctcctttt ttatgctgaa ccttgtgctg ggtgtgctgt caggggagtt tgccaaagaa 1380
agggaacggg tggagaaccg gcgggctttt ctgaagctga ggcggcaaca acagattgaa 1440
cgtgagctca atgggtacat ggaatggatc tcaaaagcag aagaggtgat cctcgccgag 1500
gatgaaactg acggggagca gaggcatccc tttgatggag ctctgcggag aaccaccata 1560
aagaaaagca agacagattt gctcaacccc gaagaggctg aggatcagct ggctgatata 1620
gcctctgtgg gttctccctt cgcccgagcc agcattaaaa gtgccaagct ggagaactcg 1680 acctttttttc acaaaaagga gaggaggatg cgtttctaca tccgccgcat ggtcaaaact 1740
caggccttct actggactgt actcagtttg gtagctctca acacgctgtg tgttgctatt 1800
gttcactaca accagcccga gtggctctcc gacttccttt actatgcaga attcattttc 1860
ttaggactct ttatgtccga aatgtttata aaaatgtacg ggcttgggac gcggccttac 1920
ttccactctt ccttcaactg ctttgactgt ggggttatca ttgggagcat cttcgaggtc 1980
atctgggctg tcataaaacc tggcacatcc tttggaatca gcgtgttacg agccctcagg 2040
ttattgcgta ttttcaaagt cacaaagtac tgggcatctc tcagaaacct ggtcgtctct 2100
ctcctcaact ccatgaagtc catcatcagc ctgttgtttc tccttttcct gttcattgtc 2160
gtcttcgccc ttttgggaat gcaactcttc ggcggccagt ttaatttcga tgaagggact 2220
cctcccacca acttcgatac ttttccagca gcaataatga cggtgtttca gatcctgacg 2280
ggcgaagact ggaacgaggt catgtacgac gggatcaagt ctcagggggg cgtgcagggc 2340
ggcatggtgt tctccatcta tttcattgta ctgacgctct ttgggaacta caccctcctg 2400
aatgtgttct tggccatcgc tgtggacaat ctggccaacg cccaggagct caccaaggac 2460
gagcaagagg aagaagaagc agcgaaccag aaacttgccc tacagaaagc caaggaggtg 2520
gcagaagtga gtcctctgtc cgcggccaac atgtctatag ctgtgaaaga gcaacagaag 2580
aatcaaaagc cagccaagtc cgtgtgggag cagcggacca gtgagatgcg aaagcagaac 2640
ttgctggcca gccgggaggc cctgtataac gaaatggacc cggacgagcg ctggaaggct 2700
gcctacacgc ggcacctgcg gccagacatg aagacgcact tggaccggcc gctggtggtg 2760
gacccgcagg agaaccgcaa caacaacacc aacaagagcc gggcggccga gcccaccgtg 2820
gaccagcgcc tcggccagca gcgcgccgag gacttcctca ggaaacaggc ccgctaccac 2880
gatcgggccc gggaccccag cggctcggcg ggcctggacg cacggaggcc ctgggcggga 2940
agccaggagg ccgagctgag ccgggaggga ccctacggcc gcgagtcgga ccaccacgcc 3000
cgggagggca gcctggagca acccgggttc tgggagggcg aggccgagcg aggcaaggcc 3060
ggggaccccc accggaggca cgtgcaccgg caggggggca gcagggagag ccgcagcggg 3120
tccccgcgca cgggcgcgga cggggagcat cgacgtcatc gcgcgcaccg caggcccggg 3180
gaggagggtc cggaggacaa ggcggagcgg agggcgcggc accgcgaggg cagccggccg 3240
gcccggggcg gcgagggcga gggcgagggc cccgacgggg gcgagcgcag gagaaggcac 3300
cggcatggcg ctccagccac gtacgagggg gacgcgcgga gggaggacaa ggagcggagg 3360
catcggagga ggaaagagaa ccagggctcc ggggtccctg tgtcgggccc caacctgtca 3420

-continued accacccggc caatccagca ggacctgggc cgccaagacc cacccctggc agaggatatt 3480
gacaacatga agaacaacaa gctggccacc gcggagtcgg ccgctcccca cggcagcctt 3540
ggccacgccg gcctgcccca gagcccagcc aagatgggaa acagcaccga ccccggcccc 3600
atgctggcca tccctgccat ggccaccaac ccccagaacg ccgccagccg ccggacgccc 3660
aacaacccgg ggaacccatc caatcccggc ccccccaaga cccccgagaa tagccttatc 3720
gtcaccaacc ccagcggcac ccagaccaat tcagctaaga ctgccaggaa acccgaccac 3780
accacagtgg acatcccccc agcctgccca cccccccctca accacaccgt cgtacaagtg 3840
aacaaaaacg ccaacccaga cccactgcca aaaaaagagg aagagaagaa ggaggaggag 3900
gaagacgacc gtggggaaga cggccctaag ccaatgcctc cctatagctc catgttcatc 3960
ctgtccacga ccaacccccct tcgccgcctg tgccattaca tcctgaacct gcgctacttt 4020
gagatgtgca tcctcatggt cattgccatg agcagcatcg ccctggccgc cgaggaccct 4080
gtgcagccca acgcacctcg gaacaacgtg ctgcgatact ttgactacgt ttttacaggc 4140
gtctttacct ttgagatggt gatcaagatg attgacctgg ggctcgtcct gcatcagggt 4200
gcctacttcc gtgacctctg gaatattctc gacttcatag tggtcagtgg ggccctggta 4260
gcctttgcct tcactggcaa tagcaaagga aaagacatca acacgattaa atccctccga 4320
gtcctccggg tgctacgacc tcttaaaacc atcaagcggc tgccaaagct caaggctgtg 4380
tttgactgtg tggtgaactc acttaaaaac gtcttcaaca tcctcatcgt ctacatgcta 4440
ttcatgttca tcttcgccgt ggtggctgtg cagctcttca aggggaaatt cttccactgc 4500
actgacgagt ccaaagagtt tgagaaagat tgtcgaggca aatacctcct ctacgagaag 4560
aatgaggtga aggcgcgaga ccgggagtgg aagaagtatg aattccatta cgacaatgtg 4620
ctgtgggctc tgctgaccct cttcaccgtg tccacgggag aaggctggcc acaggtcctc 4680
aagcattcgg tggacgccac ctttgagaac cagggcccca gccccgggta ccgcatggag 4740
atgtccattt tctacgtcgt ctactttgtg gtgttcccct tcttctttgt caatatcttt 4800
gtggccttga tcatcatcac cttccaggag caaggggaca agatgatgga ggaatacagc 4860
ctggagaaaa atgagagggc ctgcattgat ttcgccatca gcgccaagcc gctgacccga 4920
cacatgccgc agaacaagca gagcttccag taccgcatgt ggcagttcgt ggtgtctccg 4980
cctttcgagt acacgatcat ggccatgatc gccctcaaca ccatcgtgct tatgatgaag 5040
ttctatgggg cttctgttgc ttatgaaaat gccctgcggg tgttcaacat cgtcttcacc 5100
tccctcttct ctctggaatg tgtgctgaaa gtcatggctt ttgggattct gaattatttc 5160
cgcgatgcct ggaacatctt cgactttgtg actgttctgg gcagcatcac cgatatcctc 5220
gtgactgagt ttgggaataa cttcatcaac ctgagctttc tccgcctctt ccgagctgcc 5280
cggctcatca aacttctccg tcagggttac accatccgca ttcttctctg gacctttgtg 5340
cagtccttca aggccctgcc ttatgtctgt ctgctgatcg ccatgctctt cttcatctat 5400
gccatcattg ggatgcaggt gtttggtaac attggcatcg acgtggagga cgaggacagt 5460
gatgaagatg agttccaaat cactgagcac aataacttcc ggaccttctt ccaggccctc 5520
atgcttctct tccggagtgc caccggggaa gcttggcaca acatcatgct ttcctgcctc 5580
agcgggaaac cgtgtgataa gaactctggc atcctgactc gagagtgtgg caatgaattt 5640
gcttattttt actttgtttc cttcatcttc ctctgctcgt ttctgatgct gaatctcttt 5700
gtcgccgtca tcatggacaa ctttgagtac ctcacccgag actcctccat cctgggcccc 5760
caccacctgg atgagtacgt gcgtgtctgg gccgagtatg accccgcagc ttgcggtcgg 5820

-continued

```
attcattata aggatatgta cagtttatta cgagtaatat ctccccctct cggcttaggc   5880

aagaaatgtc ctcatagggt tgcttgcaag cggcttctgc ggatggacct gcccgtcgca   5940

gatgacaaca ccgtccactt caattccacc ctcatggctc tgatccgcac agccctggac   6000

atcaagattg ccaagggagg agccgacaaa cagcagatgg acgctgagct gcggaaggag   6060

atgatggcga tttggcccaa tctgtcccag aagacgctag acctgctggt cacacctcac   6120

aagtccacgg acctcaccgt ggggaagatc tacgcagcca tgatgatcat ggagtactac   6180

cggcagagca aggccaagaa gctgcaggcc atgcgcgagg agcaggaccg gacacccctc   6240

atgttccagc gcatggagcc cccgtcccca acgcaggaag gggcacctgg ccagaacgcc   6300

ctcccctcca cccagctgga cccaggagga gccctgatgg ctcacgaaag cggcctcaag   6360

gagagcccgt cctgggtgac ccagcgtgcc caggagatgt tccagaagac gggcacatgg   6420

agtccggaac aaggcccccc taccgacatg cccaacagcc agcctaactc tcagtccgtg   6480

gagatgcgag agatgggcag agatggctac tccgacagcg agcactacct ccccatggaa   6540

ggccagggcc gggctgcctc catgccccgc ctccctgcag agaaccagag gagaaggggc   6600

cggccacgtg ggaataacct cagtaccatc tcagacacca gccccatgaa gcgttcagcc   6660

tccgtgctgg gccccaaggc ccgacgcctg gacgattact cgctggagcg ggtcccgccc   6720

gaggagaacc agcggcacca ccagcggcgc cgcgaccgca gccaccgcgc ctctgagcgc   6780

tccctgggcc gctacaccga tgtggacaca ggcttgggga cagacctgag catgaccacc   6840

caatccgggg acctgccgtc gaaggagcgg gaccaggagc ggggccggcc caaggatcgg   6900

aagcatcgac agcaccacca ccaccaccac caccaccacc atcccccgcc ccccgacaag   6960

gaccgctatg cccaggaacg gccggaccac ggccgggcac gggctcggga ccagcgctgg   7020

tcccgctcgc ccagcgaggg ccgagagcac atggcgcacc ggcagtagtt ccgtaagtgg   7080

aagcccagcc ccctcaacat ctggtaccag cactccgcgg cggggccgcc gccagctccc   7140

ccagaccccc tccacccccc ggccacacgt gtcctattcc cctgtgatcc gtaaggccgg   7200

cggctcgggg cccccgcagc agcagcagca gcagcagcag cagcagcagg cggtggccag   7260

gccgggccgg gcggccacca gcggccctcg gaggtaccca ggccccacgg ccgagcctct   7320

ggccggagat cggccgccca cggggggcca cagcagcggc cgctcgccca ggatggagag   7380

gcgggtccca ggcccggccc ggagcgagtc cccccagggcc tgtcgacacg gcggggcccg  7440

gtggccggca tctggcccgc acgtgtccga ggggcccccg ggtccccggc accatggcta   7500

ctaccggggc tccgactacg acgaggccga tggcccgggc agcgggggcg gcgaggaggc   7560

catggccggg gcctacgacg cgccaccccc cgtacgacac gcgtcctcgg gcgccaccgg   7620

gcgctcgccc aggactcccc gggcctcggg cccggcctgc gcctcgcctt ctcggcacgg   7680

ccggcgactc cccaacggct actacccggc gcacggactg gccaggcccc gcgggccggg   7740

ctccaggaag ggcctgcacg aaccctacag cgagagtgac gatgattggt gctaagcccg   7800

ggcgagg                                                             7807
```

<210> SEQ ID NO 47
<211> LENGTH: 2261
<212> TYPE: PRT
<213> ORGANISM: Homo Sapiens

<400> SEQUENCE: 47

```
Met Ala Arg Phe Gly Asp Glu Met Pro Ala Arg Tyr Gly Gly Gly Gly
1               5                   10                  15

Ser Gly Ala Ala Ala Gly Val Val Val Gly Ser Gly Gly Gly Arg Gly
```

-continued

```
            20                  25                  30

Ala Gly Gly Ser Arg Gln Gly Gly Gln Pro Gly Ala Gln Arg Met Tyr
        35                  40                  45

Lys Gln Ser Met Ala Gln Arg Ala Arg Thr Met Ala Leu Tyr Asn Pro
    50                  55                  60

Ile Pro Val Arg Gln Asn Cys Leu Thr Val Asn Arg Ser Leu Phe Leu
65                  70                  75                  80

Phe Ser Glu Asp Asn Val Val Arg Lys Tyr Ala Lys Lys Ile Thr Glu
                85                  90                  95

Trp Pro Pro Phe Glu Tyr Met Ile Leu Ala Thr Ile Ile Ala Asn Cys
            100                 105                 110

Ile Val Leu Ala Leu Glu Gln His Leu Pro Asp Asp Asp Lys Thr Pro
        115                 120                 125

Met Ser Glu Arg Leu Asp Asp Thr Glu Pro Tyr Phe Ile Gly Ile Phe
    130                 135                 140

Cys Phe Glu Ala Gly Ile Lys Ile Ile Ala Leu Gly Phe Ala Phe His
145                 150                 155                 160

Lys Gly Ser Tyr Leu Arg Asn Gly Trp Asn Val Met Asp Phe Val Val
                165                 170                 175

Val Leu Thr Gly Ile Leu Ala Thr Val Gly Thr Glu Phe Asp Leu Arg
            180                 185                 190

Thr Leu Arg Ala Val Arg Val Leu Arg Pro Leu Lys Leu Val Ser Gly
        195                 200                 205

Ile Pro Ser Leu Gln Val Val Leu Lys Ser Ile Met Lys Ala Met Ile
    210                 215                 220

Pro Leu Leu Gln Ile Gly Leu Leu Leu Phe Phe Ala Ile Leu Ile Phe
225                 230                 235                 240

Ala Ile Ile Gly Leu Glu Phe Tyr Met Gly Lys Phe His Thr Thr Cys
                245                 250                 255

Phe Glu Glu Gly Thr Asp Asp Ile Gln Gly Glu Ser Pro Ala Pro Cys
            260                 265                 270

Gly Thr Glu Glu Pro Ala Arg Thr Cys Pro Asn Gly Thr Lys Cys Gln
        275                 280                 285

Pro Tyr Trp Glu Gly Pro Asn Asn Gly Ile Thr Gln Phe Asp Asn Ile
    290                 295                 300

Leu Phe Ala Val Leu Thr Val Phe Gln Cys Ile Thr Met Glu Gly Trp
305                 310                 315                 320

Thr Asp Leu Leu Tyr Asn Ser Asn Asp Ala Ser Gly Asn Thr Trp Asn
                325                 330                 335

Trp Leu Tyr Phe Ile Pro Leu Ile Ile Ile Gly Ser Phe Phe Met Leu
            340                 345                 350

Asn Leu Val Leu Gly Val Leu Ser Gly Glu Phe Ala Lys Glu Arg Glu
        355                 360                 365

Arg Val Glu Asn Arg Arg Ala Phe Leu Lys Leu Arg Arg Gln Gln Gln
    370                 375                 380

Ile Glu Arg Glu Leu Asn Gly Tyr Met Glu Trp Ile Ser Lys Ala Glu
385                 390                 395                 400

Glu Val Ile Leu Ala Glu Asp Glu Thr Asp Gly Glu Gln Arg His Pro
                405                 410                 415

Phe Asp Gly Ala Leu Arg Arg Thr Thr Ile Lys Lys Ser Lys Thr Asp
            420                 425                 430

Leu Leu Asn Pro Glu Glu Ala Glu Asp Gln Leu Ala Asp Ile Ala Ser
        435                 440                 445
```

```
Val Gly Ser Pro Phe Ala Arg Ala Ser Ile Lys Ser Ala Lys Leu Glu
    450                 455                 460

Asn Ser Thr Phe Phe His Lys Lys Glu Arg Arg Met Arg Phe Tyr Ile
465                 470                 475                 480

Arg Arg Met Val Lys Thr Gln Ala Phe Tyr Trp Thr Val Leu Ser Leu
                485                 490                 495

Val Ala Leu Asn Thr Leu Cys Val Ala Ile Val His Tyr Asn Gln Pro
            500                 505                 510

Glu Trp Leu Ser Asp Phe Leu Tyr Tyr Ala Glu Phe Ile Phe Leu Gly
        515                 520                 525

Leu Phe Met Ser Glu Met Phe Ile Lys Met Tyr Gly Leu Gly Thr Arg
    530                 535                 540

Pro Tyr Phe His Ser Ser Phe Asn Cys Phe Asp Cys Gly Val Ile Ile
545                 550                 555                 560

Gly Ser Ile Phe Glu Val Ile Trp Ala Val Ile Lys Pro Gly Thr Ser
                565                 570                 575

Phe Gly Ile Ser Val Leu Arg Ala Leu Arg Leu Leu Arg Ile Phe Lys
            580                 585                 590

Val Thr Lys Tyr Trp Ala Ser Leu Arg Asn Leu Val Val Ser Leu Leu
        595                 600                 605

Asn Ser Met Lys Ser Ile Ile Ser Leu Leu Phe Leu Leu Phe Leu Phe
    610                 615                 620

Ile Val Val Phe Ala Leu Leu Gly Met Gln Leu Phe Gly Gly Gln Phe
625                 630                 635                 640

Asn Phe Asp Glu Gly Thr Pro Pro Thr Asn Phe Asp Thr Phe Pro Ala
                645                 650                 655

Ala Ile Met Thr Val Phe Gln Ile Leu Thr Gly Glu Asp Trp Asn Glu
            660                 665                 670

Val Met Tyr Asp Gly Ile Lys Ser Gln Gly Gly Val Gln Gly Gly Met
        675                 680                 685

Val Phe Ser Ile Tyr Phe Ile Val Leu Thr Leu Phe Gly Asn Tyr Thr
    690                 695                 700

Leu Leu Asn Val Phe Leu Ala Ile Ala Val Asp Asn Leu Ala Asn Ala
705                 710                 715                 720

Gln Glu Leu Thr Lys Asp Glu Gln Glu Glu Glu Glu Ala Ala Asn Gln
                725                 730                 735

Lys Leu Ala Leu Gln Lys Ala Lys Glu Val Ala Glu Val Ser Pro Leu
            740                 745                 750

Ser Ala Ala Asn Met Ser Ile Ala Val Lys Glu Gln Gln Lys Asn Gln
        755                 760                 765

Lys Pro Ala Lys Ser Val Trp Glu Gln Arg Thr Ser Glu Met Arg Lys
    770                 775                 780

Gln Asn Leu Leu Ala Ser Arg Glu Ala Leu Tyr Asn Glu Met Asp Pro
785                 790                 795                 800

Asp Glu Arg Trp Lys Ala Ala Tyr Thr Arg His Leu Arg Pro Asp Met
                805                 810                 815

Lys Thr His Leu Asp Arg Pro Leu Val Val Asp Pro Gln Glu Asn Arg
            820                 825                 830

Asn Asn Asn Thr Asn Lys Ser Arg Ala Ala Glu Pro Thr Val Asp Gln
        835                 840                 845

Arg Leu Gly Gln Gln Arg Ala Glu Asp Phe Leu Arg Lys Gln Ala Arg
    850                 855                 860

Tyr His Asp Arg Ala Arg Asp Pro Ser Gly Ser Ala Gly Leu Asp Ala
865                 870                 875                 880
```

```
Arg Arg Pro Trp Ala Gly Ser Gln Glu Ala Glu Leu Ser Arg Glu Gly
                885                 890                 895

Pro Tyr Gly Arg Glu Ser Asp His His Ala Arg Glu Gly Ser Leu Glu
            900                 905                 910

Gln Pro Gly Phe Trp Glu Gly Glu Ala Glu Arg Gly Lys Ala Gly Asp
        915                 920                 925

Pro His Arg Arg His Val His Arg Gln Gly Gly Ser Arg Glu Ser Arg
    930                 935                 940

Ser Gly Ser Pro Arg Thr Gly Ala Asp Gly Glu His Arg Arg His Arg
945                 950                 955                 960

Ala His Arg Arg Pro Gly Glu Glu Gly Pro Glu Asp Lys Ala Glu Arg
                965                 970                 975

Arg Ala Arg His Arg Glu Gly Ser Arg Pro Ala Arg Gly Gly Glu Gly
            980                 985                 990

Glu Gly Glu Gly Pro Asp Gly Gly  Glu Arg Arg Arg Arg  His Arg His
        995                 1000                1005

Gly Ala  Pro Ala Thr Tyr Glu  Gly Asp Ala Arg Arg  Glu Asp Lys
    1010                1015                1020

Glu Arg  Arg His Arg Arg Arg  Lys Glu Asn Gln Gly  Ser Gly Val
    1025                1030                1035

Pro Val  Ser Gly Pro Asn Leu  Ser Thr Thr Arg Pro  Ile Gln Gln
    1040                1045                1050

Asp Leu  Gly Arg Gln Asp Pro  Pro Leu Ala Glu Asp  Ile Asp Asn
    1055                1060                1065

Met Lys  Asn Asn Lys Leu Ala  Thr Ala Glu Ser Ala  Ala Pro His
    1070                1075                1080

Gly Ser  Leu Gly His Ala Gly  Leu Pro Gln Ser Pro  Ala Lys Met
    1085                1090                1095

Gly Asn  Ser Thr Asp Pro Gly  Pro Met Leu Ala Ile  Pro Ala Met
    1100                1105                1110

Ala Thr  Asn Pro Gln Asn Ala  Ala Ser Arg Arg Thr  Pro Asn Asn
    1115                1120                1125

Pro Gly  Asn Pro Ser Asn Pro  Gly Pro Pro Lys Thr  Pro Glu Asn
    1130                1135                1140

Ser Leu  Ile Val Thr Asn Pro  Ser Gly Thr Gln Thr  Asn Ser Ala
    1145                1150                1155

Lys Thr  Ala Arg Lys Pro Asp  His Thr Thr Val Asp  Ile Pro Pro
    1160                1165                1170

Ala Cys  Pro Pro Pro Leu Asn  His Thr Val Val Gln  Val Asn Lys
    1175                1180                1185

Asn Ala  Asn Pro Asp Pro Leu  Pro Lys Lys Glu Glu  Glu Lys Lys
    1190                1195                1200

Glu Glu  Glu Glu Asp Asp Arg  Gly Glu Asp Gly Pro  Lys Pro Met
    1205                1210                1215

Pro Pro  Tyr Ser Ser Met Phe  Ile Leu Ser Thr Thr  Asn Pro Leu
    1220                1225                1230

Arg Arg  Leu Cys His Tyr Ile  Leu Asn Leu Arg Tyr  Phe Glu Met
    1235                1240                1245

Cys Ile  Leu Met Val Ile Ala  Met Ser Ser Ile Ala  Leu Ala Ala
    1250                1255                1260

Glu Asp  Pro Val Gln Pro Asn  Ala Pro Arg Asn Asn  Val Leu Arg
    1265                1270                1275

Tyr Phe  Asp Tyr Val Phe Thr  Gly Val Phe Thr Phe  Glu Met Val
```

1280 1285 1290

Ile Lys Met Ile Asp Leu Gly Leu Val Leu His Gln Gly Ala Tyr
1295 1300 1305

Phe Arg Asp Leu Trp Asn Ile Leu Asp Phe Ile Val Val Ser Gly
1310 1315 1320

Ala Leu Val Ala Phe Ala Phe Thr Gly Asn Ser Lys Gly Lys Asp
1325 1330 1335

Ile Asn Thr Ile Lys Ser Leu Arg Val Leu Arg Val Leu Arg Pro
1340 1345 1350

Leu Lys Thr Ile Lys Arg Leu Pro Lys Leu Lys Ala Val Phe Asp
1355 1360 1365

Cys Val Val Asn Ser Leu Lys Asn Val Phe Asn Ile Leu Ile Val
1370 1375 1380

Tyr Met Leu Phe Met Phe Ile Phe Ala Val Val Ala Val Gln Leu
1385 1390 1395

Phe Lys Gly Lys Phe Phe His Cys Thr Asp Glu Ser Lys Glu Phe
1400 1405 1410

Glu Lys Asp Cys Arg Gly Lys Tyr Leu Leu Tyr Glu Lys Asn Glu
1415 1420 1425

Val Lys Ala Arg Asp Arg Glu Trp Lys Lys Tyr Glu Phe His Tyr
1430 1435 1440

Asp Asn Val Leu Trp Ala Leu Leu Thr Leu Phe Thr Val Ser Thr
1445 1450 1455

Gly Glu Gly Trp Pro Gln Val Leu Lys His Ser Val Asp Ala Thr
1460 1465 1470

Phe Glu Asn Gln Gly Pro Ser Pro Gly Tyr Arg Met Glu Met Ser
1475 1480 1485

Ile Phe Tyr Val Val Tyr Phe Val Val Phe Pro Phe Phe Phe Val
1490 1495 1500

Asn Ile Phe Val Ala Leu Ile Ile Ile Thr Phe Gln Glu Gln Gly
1505 1510 1515

Asp Lys Met Met Glu Glu Tyr Ser Leu Glu Lys Asn Glu Arg Ala
1520 1525 1530

Cys Ile Asp Phe Ala Ile Ser Ala Lys Pro Leu Thr Arg His Met
1535 1540 1545

Pro Gln Asn Lys Gln Ser Phe Gln Tyr Arg Met Trp Gln Phe Val
1550 1555 1560

Val Ser Pro Pro Phe Glu Tyr Thr Ile Met Ala Met Ile Ala Leu
1565 1570 1575

Asn Thr Ile Val Leu Met Met Lys Phe Tyr Gly Ala Ser Val Ala
1580 1585 1590

Tyr Glu Asn Ala Leu Arg Val Phe Asn Ile Val Phe Thr Ser Leu
1595 1600 1605

Phe Ser Leu Glu Cys Val Leu Lys Val Met Ala Phe Gly Ile Leu
1610 1615 1620

Asn Tyr Phe Arg Asp Ala Trp Asn Ile Phe Asp Phe Val Thr Val
1625 1630 1635

Leu Gly Ser Ile Thr Asp Ile Leu Val Thr Glu Phe Gly Asn Asn
1640 1645 1650

Phe Ile Asn Leu Ser Phe Leu Arg Leu Phe Arg Ala Ala Arg Leu
1655 1660 1665

Ile Lys Leu Leu Arg Gln Gly Tyr Thr Ile Arg Ile Leu Leu Trp
1670 1675 1680

-continued

```
Thr Phe Val Gln Ser Phe Lys Ala Leu Pro Tyr Val Cys Leu Leu
    1685                1690                1695

Ile Ala Met Leu Phe Phe Ile Tyr Ala Ile Ile Gly Met Gln Val
    1700                1705                1710

Phe Gly Asn Ile Gly Ile Asp Val Glu Asp Glu Asp Ser Asp Glu
    1715                1720                1725

Asp Glu Phe Gln Ile Thr Glu His Asn Asn Phe Arg Thr Phe Phe
    1730                1735                1740

Gln Ala Leu Met Leu Leu Phe Arg Ser Ala Thr Gly Glu Ala Trp
    1745                1750                1755

His Asn Ile Met Leu Ser Cys Leu Ser Gly Lys Pro Cys Asp Lys
    1760                1765                1770

Asn Ser Gly Ile Leu Thr Arg Glu Cys Gly Asn Glu Phe Ala Tyr
    1775                1780                1785

Phe Tyr Phe Val Ser Phe Ile Phe Leu Cys Ser Phe Leu Met Leu
    1790                1795                1800

Asn Leu Phe Val Ala Val Ile Met Asp Asn Phe Glu Tyr Leu Thr
    1805                1810                1815

Arg Asp Ser Ser Ile Leu Gly Pro His His Leu Asp Glu Tyr Val
    1820                1825                1830

Arg Val Trp Ala Glu Tyr Asp Pro Ala Ala Cys Gly Arg Ile His
    1835                1840                1845

Tyr Lys Asp Met Tyr Ser Leu Leu Arg Val Ile Ser Pro Pro Leu
    1850                1855                1860

Gly Leu Gly Lys Lys Cys Pro His Arg Val Ala Cys Lys Arg Leu
    1865                1870                1875

Leu Arg Met Asp Leu Pro Val Ala Asp Asp Asn Thr Val His Phe
    1880                1885                1890

Asn Ser Thr Leu Met Ala Leu Ile Arg Thr Ala Leu Asp Ile Lys
    1895                1900                1905

Ile Ala Lys Gly Gly Ala Asp Lys Gln Gln Met Asp Ala Glu Leu
    1910                1915                1920

Arg Lys Glu Met Met Ala Ile Trp Pro Asn Leu Ser Gln Lys Thr
    1925                1930                1935

Leu Asp Leu Leu Val Thr Pro His Lys Ser Thr Asp Leu Thr Val
    1940                1945                1950

Gly Lys Ile Tyr Ala Ala Met Met Ile Met Glu Tyr Tyr Arg Gln
    1955                1960                1965

Ser Lys Ala Lys Lys Leu Gln Ala Met Arg Glu Glu Gln Asp Arg
    1970                1975                1980

Thr Pro Leu Met Phe Gln Arg Met Glu Pro Pro Ser Pro Thr Gln
    1985                1990                1995

Glu Gly Gly Pro Gly Gln Asn Ala Leu Pro Ser Thr Gln Leu Asp
    2000                2005                2010

Pro Gly Gly Ala Leu Met Ala His Glu Ser Gly Leu Lys Glu Ser
    2015                2020                2025

Pro Ser Trp Val Thr Gln Arg Ala Gln Glu Met Phe Gln Lys Thr
    2030                2035                2040

Gly Thr Trp Ser Pro Glu Gln Gly Pro Pro Thr Asp Met Pro Asn
    2045                2050                2055

Ser Gln Pro Asn Ser Gln Ser Val Glu Met Arg Glu Met Gly Arg
    2060                2065                2070

Asp Gly Tyr Ser Asp Ser Glu His Tyr Leu Pro Met Glu Gly Gln
    2075                2080                2085
```

```
Gly Arg  Ala Ala Ser Met Pro  Arg Leu Pro Ala Glu  Asn Gln Arg
    2090                 2095                 2100

Arg Arg  Gly Arg Pro Arg Gly  Asn Asn Leu Ser Thr  Ile Ser Asp
    2105                 2110                 2115

Thr Ser  Pro Met Lys Arg Ser  Ala Ser Val Leu Gly  Pro Lys Ala
    2120                 2125                 2130

Arg Arg  Leu Asp Asp Tyr Ser  Leu Glu Arg Val Pro  Pro Glu Glu
    2135                 2140                 2145

Asn Gln  Arg His His Gln Arg  Arg Arg Asp Arg Ser  His Arg Ala
    2150                 2155                 2160

Ser Glu  Arg Ser Leu Gly Arg  Tyr Thr Asp Val Asp  Thr Gly Leu
    2165                 2170                 2175

Gly Thr  Asp Leu Ser Met Thr  Thr Gln Ser Gly Asp  Leu Pro Ser
    2180                 2185                 2190

Lys Glu  Arg Asp Gln Glu Arg  Gly Arg Pro Lys Asp  Arg Lys His
    2195                 2200                 2205

Arg Gln  His His His His His  His His His His His  Pro Pro Pro
    2210                 2215                 2220

Pro Asp  Lys Asp Arg Tyr Ala  Gln Glu Arg Pro Asp  His Gly Arg
    2225                 2230                 2235

Ala Arg  Ala Arg Asp Gln Arg  Trp Ser Arg Ser Pro  Ser Glu Gly
    2240                 2245                 2250

Arg Glu  His Met Ala His Arg  Gln
    2255                 2260
```

<210> SEQ ID NO 48
<211> LENGTH: 4416
<212> TYPE: DNA
<213> ORGANISM: Homo Sapiens

<400> SEQUENCE: 48

```
gaaaaagggt gaaagagaaa cttggcgacc tcccggagga gttcgcgaag cgaccaggag     60

cgtgttgcca tcgtcctcac ccggcaccca attccaccac agagtcggga tttcgtcggt    120

gatcgtgatg gggtgctttt atttttctct ttgattttca aaaaatgtct atgtgactgt    180

ccctatctta aggggaagtt gaaagtgggg gcgggggtgc tcaatgagaa acgttgcctt    240

gtgtgtagtt gtttggagca cactgcaaat tatattggca tctctttcca aaagtcactt    300

tgattcaact tcgatagctt tctcgtaaat ggcacgttta ggtggtgaga ggtggatgag    360

gaaacaggca ccagtgcagc tgatttgacc tccagtggga tagatacgat tagcaccagg    420

atcgtgtctc attttgaacc cagatctgaa cagaattaag acgaacgagc tttcacaatt    480

gcagcagatg aagatccatt ggtaaattga tcaggatttt tggcctaccc tccaaagaaa    540

aggagcggaa agaatgtcgg agcgggccgc ggatgacgtc aggggggagc cgcgccgcgc    600

ggcggcggcg gcgggcggag cagcggccgc ggccgcccgg cagcagcagc agcagcagca    660

gcagcagcag ccgccgcctc cgcagcccca gcggcagcag cacccgccac cgccgccacg    720

gcgcacacgg ccggaggacg gcgggcccgg cgccgcctcc acctcggccg ccgcaatggc    780

gacggtcggg gagcgcaggc ctctgcccag tcctgaagtg atgctgggac agtcgtggaa    840

tctgtgggtt gaggcttcca aacttcctgg gaaggacggg acagaattgg acgaaagttt    900

caaggagttt gggaaaaacc gcgaagtcat ggggctctgt cgggaagaca tgccaatatt    960

tggtttctgt ccagcccatg atgatttcta cttggtggtg tgtaacgact gtaatcaggt   1020

tgtcaaaccg caggcatttc aatcacatta tgaaagaaga catagctcat ccagcaagcc   1080
```

```
gcctttggcc gttcctccca cttcagtatt ttccttcttc ccttctctgt ccaaaagcaa   1140
aggaggcagt gcaagtggaa gcaaccgttc ttccagtgga ggtgttctta gcgcatcctc   1200
atcaagttcc aagttgttga aatcacccaa agagaaactg cagctcaggg ggaacaccag   1260
gccaatgcat cccattcagc aaagtagagt tccccatggt agaatcatga caccctctgt   1320
gaaagtggaa aagattcatc cgaaaatgga tggcacacta ctgaaatctg cggtggggcc   1380
aacctgtcct gctactgtga gttccttagt caagcctggc cttaactgcc cctcaatacc   1440
aaagccaacc ttgccttcac ctggacagat tctgaatggc aaagggcttc ctgcaccgcc   1500
cactctggaa aagaaacctg aagacaattc caataatagg aaatttttaa ataagagatt   1560
atcagaaaga gagtttgatc ctgacatcca ctgtggggtt attgatctcg acaccaagaa   1620
gccctgcacc cggtctttga catgcaagac acattcctta acccagcgca gggctgtcca   1680
gggtagaaga aaacgatttg atgtgttatt agccgagcac aaaaacaaaa ccagggaaaa   1740
ggaattgatt cgccatccgg actctcagca accaccgcag cctctcaggg acccgcatcc   1800
cgcccctcct agaacgtcac aggagccgca ccaaaaccct cacggagtga ttccttccga   1860
atcaaagcct tttgtagcta gtaaacctaa acctcacacc cccagtcttc caaggcctcc   1920
aggctgccct gctcagcaag gtgggagtgc ccccattgac cctcctccag tccatgaatc   1980
tccacaccct cccctgcctg ccactgagcc agcttctcgg ttatccagtg aggagggcga   2040
aggcgatgac aaagaagagt ctgttgaaaa actggactgt cattattcag gtcatcatcc   2100
tcagccagca tctttttgca catttgggag ccggcagata ggaagaggct attacgtgtt   2160
tgactccagg tggaatcgac ttcgctgcgc cctcaacctc atggtggaga agcatctgaa   2220
tgcacagcta tggaagaaaa tcccaccagt gcccagtacc acctcaccca tctccacacg   2280
tattcctcac cggacaaact ctgtgccgac atcacaatgt ggagtcagct atctggcagc   2340
agccaccgtc tctacatccc cagtcctgct ctcatctacc tgcatctccc caaatagcaa   2400
atcggtacca gctcatggaa ccacactaaa tgcacagcct gctgcttcag ggcgatgga    2460
tcctgtgtgc agtatgcaat ccagacaagt gtcctcttca tcctcatccc cttccacgcc   2520
ctctggcctt tcctcggttc cttcctcccc catgtccagg aaacctcaga aattgaaatc   2580
cagcaaatct ttgaggccca aggagtcttc tggtaacagc actaactgtc aaaatgccag   2640
tagcagtacc agtggcggct caggaaagaa acgcaaaaac agttccccac tgttggttca   2700
ctcttcctcc tcctcttcct cctcctcctc ttcttctcat tccatggagt cttttaggaa   2760
aaactgtgtg gctcactctg ggcctcccta cccctcaacg gtaacatctt cccatagcat   2820
cggcctcaac tgtgtgacga ataaagcaaa tgcggtgaac gtccggcatg accagtcagg   2880
gaggggcccc cccaccggga gccctgctga atccatcaag aggatgagtg tgatggtgaa   2940
cagcagtgat tctactcttt ctcttgggcc attcattcac cagtccaatg aactgcctgt   3000
caactcccac ggcagttttt cccactcaca cactcctcta gacaaactca taggaaagaa   3060
aagaaagtgc tcacccagct cgagcagcat caacaacagc agcagcaaac ccacaaaggt   3120
tgccaaagtg ccagccgtga acaatgtcca catgaaacac acaggcacca tcccaggggc   3180
acaaggactg atgaacagtt ccctccttca tcagccaaag gcacgtccct gacagctgaa   3240
aatagcacgg ggaggaataa tgcggacact tttgaggaca agttacacct ccactcagca   3300
ctctggactc cacgatgcct ttgagtctgt tttcccaacc tcctgtgggc ctcaagggta   3360
gaaacctgcc gggctgttgt tttaacgagg atttccctga agctatgtct ctagcagtga   3420
gtactcataa aggacactgg atcaagttca gccaccgaat tgcttttatc agtgttaaag   3480
```

tggtctgaac tgcttgctac caatctgtga gaagtttttg tttttgtttt gtttttttaac 3540 ttgcagtata tcacagagcc actcttcaag tagattggct gggcaaaaga atgttttggc 3600
aagagcgtta ctgtagacct ttctccctcc ttcctttttac taccattttt ttttaacact 3660
gtcatctgta ggtcactctc cagcagttag gcaccttaac tggagaccag aaaccttcca 3720
gagaacacag ggctgcatcc cgagcaaccc tctgaagaag ggaattaggc tttagatttt 3780
gatagcaatg ttccaggaat gaaatataga tgttagccca agacaccatg acaaaatagc 3840
ccagcctttt gagagtaatt tgggaaaaga agctgtcaga agtttctaac ttacaaactg 3900
gtttgaaatt tttgatgccc agacagcaag tataaatcat tttggaggct tacttttcat 3960
gatacaaaag caattctgtg tgattttttt ttttaagaag aaagaaaatg caagctagtt 4020
ttgagaaagg aaggccaaat tgggtcgggg gagggtggga gtgaggaagt taaaatcact 4080
atagggagaa aaaacttttt tcaagatttc caaagagatg aaatttttctt aatcctttta 4140 agttttcata gtaaacagta tggcagattg ggttggttgt cctacctggt ctatttttaa 4200
aagtcacctt ttaaagtgac attattagat acacttaaat gtttccaagg cactctctac 4260 attaccctttg tttttctctt tggatactgt cctgggacta agtgtagatt tctgcttcaa 4320
gcacttctgg cattgtgtgt ttttgtatgc actccccttc atgccacttc agatgtttat 4380
ttggatgtgg ttggggacga gagcagacac caagga 4416

<210> SEQ ID NO 49
<211> LENGTH: 892
<212> TYPE: PRT
<213> ORGANISM: Homo Sapiens

<400> SEQUENCE: 49

Met Ser Glu Arg Ala Ala Asp Asp Val Arg Gly Glu Pro Arg Arg Ala
1 5 10 15

Ala Ala Ala Ala Gly Gly Ala Ala Ala Ala Ala Ala Arg Gln Gln Gln
20 25 30

Gln Gln Gln Gln Gln Gln Gln Pro Pro Pro Pro Gln Pro Gln Arg Gln
35 40 45

Gln His Pro Pro Pro Pro Pro Arg Arg Thr Arg Pro Glu Asp Gly Gly
50 55 60

Pro Gly Ala Ala Ser Thr Ser Ala Ala Ala Met Ala Thr Val Gly Glu
65 70 75 80

Arg Arg Pro Leu Pro Ser Pro Glu Val Met Leu Gly Gln Ser Trp Asn
85 90 95

Leu Trp Val Glu Ala Ser Lys Leu Pro Gly Lys Asp Gly Thr Glu Leu
100 105 110

Asp Glu Ser Phe Lys Glu Phe Gly Lys Asn Arg Glu Val Met Gly Leu
115 120 125

Cys Arg Glu Asp Met Pro Ile Phe Gly Phe Cys Pro Ala His Asp Asp
130 135 140

Phe Tyr Leu Val Val Cys Asn Asp Cys Asn Gln Val Val Lys Pro Gln
145 150 155 160

Ala Phe Gln Ser His Tyr Glu Arg Arg His Ser Ser Ser Ser Lys Pro
165 170 175

Pro Leu Ala Val Pro Pro Thr Ser Val Phe Ser Phe Phe Pro Ser Leu
180 185 190

Ser Lys Ser Lys Gly Gly Ser Ala Ser Gly Ser Asn Arg Ser Ser Ser
195 200 205

-continued

```
Gly Gly Val Leu Ser Ala Ser Ser Ser Ser Ser Lys Leu Leu Lys Ser
    210                 215                 220

Pro Lys Glu Lys Leu Gln Leu Arg Gly Asn Thr Arg Pro Met His Pro
225                 230                 235                 240

Ile Gln Gln Ser Arg Val Pro His Gly Arg Ile Met Thr Pro Ser Val
                245                 250                 255

Lys Val Glu Lys Ile His Pro Lys Met Asp Gly Thr Leu Leu Lys Ser
            260                 265                 270

Ala Val Gly Pro Thr Cys Pro Ala Thr Val Ser Ser Leu Val Lys Pro
        275                 280                 285

Gly Leu Asn Cys Pro Ser Ile Pro Lys Pro Thr Leu Pro Ser Pro Gly
    290                 295                 300

Gln Ile Leu Asn Gly Lys Gly Leu Pro Ala Pro Pro Thr Leu Glu Lys
305                 310                 315                 320

Lys Pro Glu Asp Asn Ser Asn Asn Arg Lys Phe Leu Asn Lys Arg Leu
                325                 330                 335

Ser Glu Arg Glu Phe Asp Pro Asp Ile His Cys Gly Val Ile Asp Leu
            340                 345                 350

Asp Thr Lys Lys Pro Cys Thr Arg Ser Leu Thr Cys Lys Thr His Ser
        355                 360                 365

Leu Thr Gln Arg Arg Ala Val Gln Gly Arg Arg Lys Arg Phe Asp Val
    370                 375                 380

Leu Leu Ala Glu His Lys Asn Lys Thr Arg Glu Lys Glu Leu Ile Arg
385                 390                 395                 400

His Pro Asp Ser Gln Gln Pro Pro Gln Pro Leu Arg Asp Pro His Pro
                405                 410                 415

Ala Pro Pro Arg Thr Ser Gln Glu Pro His Gln Asn Pro His Gly Val
            420                 425                 430

Ile Pro Ser Glu Ser Lys Pro Phe Val Ala Ser Lys Pro Lys Pro His
        435                 440                 445

Thr Pro Ser Leu Pro Arg Pro Pro Gly Cys Pro Ala Gln Gln Gly Gly
    450                 455                 460

Ser Ala Pro Ile Asp Pro Pro Pro Val His Glu Ser Pro His Pro Pro
465                 470                 475                 480

Leu Pro Ala Thr Glu Pro Ala Ser Arg Leu Ser Ser Glu Glu Gly Glu
                485                 490                 495

Gly Asp Asp Lys Glu Glu Ser Val Glu Lys Leu Asp Cys His Tyr Ser
            500                 505                 510

Gly His His Pro Gln Pro Ala Ser Phe Cys Thr Phe Gly Ser Arg Gln
        515                 520                 525

Ile Gly Arg Gly Tyr Tyr Val Phe Asp Ser Arg Trp Asn Arg Leu Arg
    530                 535                 540

Cys Ala Leu Asn Leu Met Val Glu Lys His Leu Asn Ala Gln Leu Trp
545                 550                 555                 560

Lys Lys Ile Pro Pro Val Pro Ser Thr Thr Ser Pro Ile Ser Thr Arg
                565                 570                 575

Ile Pro His Arg Thr Asn Ser Val Pro Thr Ser Gln Cys Gly Val Ser
            580                 585                 590

Tyr Leu Ala Ala Ala Thr Val Ser Thr Ser Pro Val Leu Leu Ser Ser
        595                 600                 605

Thr Cys Ile Ser Pro Asn Ser Lys Ser Val Pro Ala His Gly Thr Thr
    610                 615                 620

Leu Asn Ala Gln Pro Ala Ala Ser Gly Ala Met Asp Pro Val Cys Ser
625                 630                 635                 640
```

```
Met Gln Ser Arg Gln Val Ser Ser Ser Ser Ser Ser Pro Ser Thr Pro
                645                 650                 655

Ser Gly Leu Ser Ser Val Pro Ser Ser Pro Met Ser Arg Lys Pro Gln
            660                 665                 670

Lys Leu Lys Ser Ser Lys Ser Leu Arg Pro Lys Glu Ser Ser Gly Asn
        675                 680                 685

Ser Thr Asn Cys Gln Asn Ala Ser Ser Ser Thr Ser Gly Gly Ser Gly
    690                 695                 700

Lys Lys Arg Lys Asn Ser Ser Pro Leu Leu Val His Ser Ser Ser Ser
705                 710                 715                 720

Ser Ser Ser Ser Ser Ser Ser Ser His Ser Met Glu Ser Phe Arg Lys
                725                 730                 735

Asn Cys Val Ala His Ser Gly Pro Pro Tyr Pro Ser Thr Val Thr Ser
            740                 745                 750

Ser His Ser Ile Gly Leu Asn Cys Val Thr Asn Lys Ala Asn Ala Val
        755                 760                 765

Asn Val Arg His Asp Gln Ser Gly Arg Gly Pro Pro Thr Gly Ser Pro
    770                 775                 780

Ala Glu Ser Ile Lys Arg Met Ser Val Met Val Asn Ser Ser Asp Ser
785                 790                 795                 800

Thr Leu Ser Leu Gly Pro Phe Ile His Gln Ser Asn Glu Leu Pro Val
                805                 810                 815

Asn Ser His Gly Ser Phe Ser His Ser His Thr Pro Leu Asp Lys Leu
            820                 825                 830

Ile Gly Lys Lys Arg Lys Cys Ser Pro Ser Ser Ser Ser Ile Asn Asn
        835                 840                 845

Ser Ser Ser Lys Pro Thr Lys Val Ala Lys Val Pro Ala Val Asn Asn
    850                 855                 860

Val His Met Lys His Thr Gly Thr Ile Pro Gly Ala Gln Gly Leu Met
865                 870                 875                 880

Asn Ser Ser Leu Leu His Gln Pro Lys Ala Arg Pro
                885                 890


<210> SEQ ID NO 50
<211> LENGTH: 1867
<212> TYPE: DNA
<213> ORGANISM: Homo Sapiens

<400> SEQUENCE: 50

ggttcgctgt ggcgggcgcc tgggccgccg gctgtttaac ttcgcttccg ctggcccata      60

gtgatctttg cagtgaccca gcagcatcac tgtttcttgg cgtgtgaaga taacccaagg     120

aattgaggaa gttgctgaga agagtgtgct ggagatgctc taggaaaaaa ttgaatagtg     180

agacgagttc cagcgcaagg gtttctggtt tgccaagaag aaagtgaaca tcatggatca     240

gaacaacagc ctgccacctt acgctcaggg cttggcctcc cctcagggtg ccatgactcc     300

cggaatccct atctttagtc caatgatgcc ttatggcact ggactgaccc cacagcctat     360

tcagaacacc aatagtctgt ctattttgga agagcaacaa aggcagcagc agcaacaaca     420

acagcagcag cagcagcagc agcagcaaca gcaacagcag cagcagcagc agcagcagca     480

gcagcagcag cagcagcagc agcagcagca gcaacaggca gtggcagctg cagccgttca     540

gcagtcaacg tcccagcagg caacacaggg aacctcaggc caggcaccac agctcttcca     600

ctcacagact ctcacaactg cacccttgcc gggcaccact ccactgtatc cctcccccat     660

gactcccatg acccccatca ctcctgccac gccagcttcg gagagttctg ggattgtacc     720
```

```
gcagctgcaa aatattgtat ccacagtgaa tcttggttgt aaacttgacc taaagaccat    780

tgcacttcgt gcccgaaacg ccgaatataa tcccaagcgg tttgctgcgg taatcatgag    840

gataagagag ccacgaacca cggcactgat tttcagttct gggaaaatgg tgtgcacagg    900

agccaagagt gaagaacagt ccagactggc agcaagaaaa tatgctagag ttgtacagaa    960

gttgggtttt ccagctaagt tcttggactt caagattcag aatatggtgg ggagctgtga   1020

tgtgaagttt cctataaggt tagaaggcct tgtgctcacc caccaacaat ttagtagtta   1080

tgagccagag ttatttcctg gtttaatcta cagaatgatc aaacccagaa ttgttctcct   1140

tatttttgtt tctggaaaag ttgtattaac aggtgctaaa gtcagagcag aaatttatga   1200

agcatttgaa aacatctacc ctattctaaa gggattcagg aagacgacgt aatggctctc   1260

atgtaccctt gcctccccca ccccccttctt ttttttttt taaacaaatc agtttgtttt   1320

ggtaccttta aatggtggtg ttgtgagaag atggatgttg agttgcaggg tgtggcacca   1380

ggtgatgccc ttctgtaagt gcccaccgcg ggatgccggg aaggggcatt atttgtgcac   1440

tgagaacacc gcgcagcgtg actgtgagtt gctcataccg tgctgctatc tgggcagcgc   1500

tgcccattta tttatatgta gattttaaac actgctgttg acaagttggt ttgagggaga   1560

aaactttaag tgttaaagcc acctctataa ttgattggac tttttaattt taatgttttt   1620

ccccatgaac cacagttttt atatttctac cagaaaagta aaaatctttt ttaaaagtgt   1680

tgtttttcta atttataact cctaggggtt atttctgtgc cagacacatt ccacctctcc   1740

agtattgcag gacagaatat atgtgttaat gaaaatgaat ggctgtacat attttttttct   1800

ttcttcagag tactctgtac aataaatgca gtttataaaa gtgttaaaaa aaaaaaaaaa   1860

aaaaaaa                                                             1867


<210> SEQ ID NO 51
<211> LENGTH: 344
<212> TYPE: PRT
<213> ORGANISM: Homo Sapiens

<400> SEQUENCE: 51

Met Asp Gln Asn Asn Ser Leu Pro Pro Tyr Ala Gln Gly Leu Ala Ser
1               5                   10                  15

Pro Gln Gly Ala Met Thr Pro Gly Ile Pro Ile Phe Ser Pro Met Met
            20                  25                  30

Pro Tyr Gly Thr Gly Leu Thr Pro Gln Pro Ile Gln Asn Thr Asn Ser
        35                  40                  45

Leu Ser Ile Leu Glu Glu Gln Gln Arg Gln Gln Gln Gln Gln Gln
    50                  55                  60

Gln Gln Gln Gln Gln Gln Gln Gln Gln Gln Gln Gln Gln Gln Gln Gln
65                  70                  75                  80

Gln Gln Gln Gln Gln Gln Gln Gln Gln Gln Gln Gln Gln Gln Gln Ala
                85                  90                  95

Val Ala Ala Ala Ala Val Gln Gln Ser Thr Ser Gln Gln Ala Thr Gln
            100                 105                 110

Gly Thr Ser Gly Gln Ala Pro Gln Leu Phe His Ser Gln Thr Leu Thr
        115                 120                 125

Thr Ala Pro Leu Pro Gly Thr Thr Pro Leu Tyr Pro Ser Pro Met Thr
    130                 135                 140

Pro Met Thr Pro Ile Thr Pro Ala Thr Pro Ala Ser Glu Ser Ser Gly
145                 150                 155                 160

Ile Val Pro Gln Leu Gln Asn Ile Val Ser Thr Val Asn Leu Gly Cys
```

```
                165                 170                 175

Lys Leu Asp Leu Lys Thr Ile Ala Leu Arg Ala Arg Asn Ala Glu Tyr
            180                 185                 190

Asn Pro Lys Arg Phe Ala Ala Val Ile Met Arg Ile Arg Glu Pro Arg
        195                 200                 205

Thr Thr Ala Leu Ile Phe Ser Ser Gly Lys Met Val Cys Thr Gly Ala
    210                 215                 220

Lys Ser Glu Glu Gln Ser Arg Leu Ala Ala Arg Lys Tyr Ala Arg Val
225                 230                 235                 240

Val Gln Lys Leu Gly Phe Pro Ala Lys Phe Leu Asp Phe Lys Ile Gln
                245                 250                 255

Asn Met Val Gly Ser Cys Asp Val Lys Phe Pro Ile Arg Leu Glu Gly
            260                 265                 270

Leu Val Leu Thr His Gln Gln Phe Ser Ser Tyr Glu Pro Glu Leu Phe
        275                 280                 285

Pro Gly Leu Ile Tyr Arg Met Ile Lys Pro Arg Ile Val Leu Leu Ile
    290                 295                 300

Phe Val Ser Gly Lys Val Val Leu Thr Gly Ala Lys Val Arg Ala Glu
305                 310                 315                 320

Ile Tyr Glu Ala Phe Glu Asn Ile Tyr Pro Ile Leu Lys Gly Phe Arg
                325                 330                 335

Lys Thr Thr Asp Arg Asx Pro Leu
            340


<210> SEQ ID NO 52
<211> LENGTH: 4367
<212> TYPE: DNA
<213> ORGANISM: Homo Sapiens

<400> SEQUENCE: 52

gacgccatac tggacgccaa gtgggaggaa cttcaaggct gtcccctgcg ggcctcccgc      60

tctgcttctg cgaaggtttc attgaaaaca gatcctgcaa aagttccagg tgcccacact     120

ggaaacttgg agatcctgct tcccagacca cagctgtggg gaacttgggg tggagcagag     180

aagtttctgt attcagctgc ccaggcagag gagaatgggg tctccacagc ctgaagaatg     240

aagacacgac agaataaaga ctcgatgtca atgaggagtg gacggaagaa agaggcccct     300

gggccccggg aagaactgag atcgaggggc cgggcctccc ctggaggggt cagcacgtcc     360

agcagtgatg gcaaagctga gaagtccagg cagacagcca agaaggcccg agtagaggaa     420

gcctccaccc caaaggtcaa caagcagggt cggagtgagg agatctcaga gagtgaaagt     480

gaggagacca atgcaccaaa aaagaccaaa actgagcagg aactccctcg gccacagtct     540

ccctccgatc tggatagctt ggacgggcgg agccttaatg atgatggcag cagcgaccct     600

agggatatcg accaggacaa ccgaagcacg tcccccagta tctacagccc tggaagtgtg     660

gagaatgact ctgactcatc ttctggcctg tcccagggcc cagcccgccc ctaccaccca     720

cctccactct ttcctccttc ccctcaaccg ccagacagca cccctcgaca gccagaggct     780

agctttgaac cccatccttc tgtgacaccc actggatatc atgctcccat ggagcccccc     840

acatctcgaa tgttccaggc tcctcctggg gcccctcccc ctcacccaca gctctatcct     900

gggggcactg gtggagtttt gtctggaccc ccaatgggtc ccaagggggg aggggctgcc     960

tcatcagtgg ggggccctaa tgggggtaag cagcaccccc cacccactac tcccatttca    1020

gtatcaagct ctggggctag tggtgctccc ccaacaaagc cgcctaccac tccagtgggt    1080

ggtgggaacc taccttctgc tccaccacca gccaacttcc cccatgtgac accgaacctg    1140
```

cctcccccac ctgccctgag accccctcaac aatgcatcag cctctccccc tggcctgggg 1200
gcccaaccac tacctggtca tctgccctct ccccacgcca tgggacaggg tatgggtgga 1260
cttcctcctg gcccagagaa gggcccaact ctggctcctt caccccactc tctgcctcct 1320
gcttcctctt ctgctccagc gccccccatg aggtttcctt attcatcctc tagtagtagc 1380
tctgcagcag cctcctcttc cagttcttcc tcctcttcct ctgcctcccc cttcccagct 1440
tcccaggcat tgcccagcta cccccactct ttccctcccc caacaagcct ctctgtctcc 1500
aatcagcccc ccaagtatac tcagccttct ctcccatccc aggctgtgtg gagccagggt 1560
cccccaccac ctcctcccta tggccgcctc ttagccaaca gcaatgccca tccaggcccc 1620
ttccctccct ctactggggc ccagtccacc gcccacccac cagtctcaac acatcaccat 1680
caccaccagc aacagcaaca gcagcagcag cagcagcagc agcagcagca gcagcagcag 1740
cagcatcacg gaaactctgg gccccctcct cctggagcat ttccccaccc actggagggc 1800
ggtagctccc accacgcaca cccttacgcc atgtctccct ccctggggtc tctgaggccc 1860
tacccaccag ggccagcaca cctgccccca cctcacagcc aggtgtccta cagccaagca 1920
ggccccaatg gccctccagt ctcttcctct tccaactctt cctcttccac ttctcaaggg 1980
tcctacccat gttcacaccc ctccccttcc cagggccctc aaggggcgcc ctaccctttc 2040
ccaccggtgc ctacggtcac cacctcttcg gctacccttt ccacggtcat tgccaccgtg 2100
gcttcctcgc cagcaggcta caaaaacggcc tccccacctg ggcccccacc gtacggaaag 2160
agagccccgt ccccgggggc ctacaagaca gccaccccac ccggatacaa acccgggtcg 2220
cctccctcct tccgaacggg gaccccaccg ggctatcgag gaacctcgcc acctgcaggc 2280
ccagggacct tcaagccggg ctcgcccacc gtgggacctg ggcccctgcc acctgcgggg 2340
ccctcaggcc tgccatcgct gccaccacca cctgcggccc ctgcctcagg gccgcccctg 2400
agcgccacgc agatcaaaca ggagccggct gaggagtatg agacccccga gagcccggtg 2460
cccccagccc gcagcccctc gccccctccc aaggtggtag atgtacccag ccatgccagt 2520
cagtctgcca ggttcaacaa acacctggat cgcggcttca actcgtgcgc gcgcagcgac 2580
ctgtacttcg tgccactgga gggctccaag ctggccaaga agcgggccga cctggtggag 2640
aaggtgcggc gcgaggccga gcagcgcgcg cgcgaagaaa aggagcgcga gcgcgagcgg 2700
gaacgcgaga aagagcgcga gcgcgagaag gagcgcgagc ttgaacgcag cgtgaagttg 2760
gctcaggagg gccgtgctcc ggtggaatgc ccatctctgg gcccagtgcc ccatcgccct 2820
ccatttgaac cgggcagtgc ggtggctaca gtgccccccct acctgggtcc tgacactcca 2880
gccttgcgca ctctcagtga atatgcccgg cctcatgtca tgtctcctgg caatcgcaac 2940
catccattct acgtgcccct gggggcagtg gacccggggc tcctgggtta caatgtcccg 3000
gccctgtaca gcagtgatcc agctgcccgg gagagggaac gggaagcccg tgaacgagac 3060
ctccgtgacc gcctcaagcc tggctttgag gtgaagccta gtgagctgga accccctacat 3120 ggggtccctg ggccgggctt ggatcccttt ccccgacatg ggggcctggc tctgcagcct 3180
ggcccacctg gcctgcaccc tttccccttt catccgagcc tggggcccct ggagcgagaa 3240
cgtctagcgc tggcagctgg gccagccctg cggcctgaca tgtcctatgc tgagcggctg 3300
gcagctgaga ggcagcacgc agaaagggtg gcggccctgg gcaatgaccc actggcccgg 3360
ctgcagatgc tcaatgtgac tccccatcac caccagcact cccacatcca ctcgcacctg 3420
cacctgcacc agcaagatgc tatccatgca gcctctgcct cggtgcaccc tctcattgac 3480
cccctggcct cagggtctca ccttacccgg atcccctacc cagctggaac tctccctaac 3540

```
cccctgcttc ctcaccctct gcacgagaac gaagttcttc gtcaccagct ctttgctgcc   3600

ccttaccggg acctgccggc ctccctttct gccccgatgt cagcagctca tcagctgcag   3660

gccatgcacg cacagtcagc tgagctgcag cgcttggcgc tggaacagca gcagtggctg   3720

catgcccatc acccgctgca cagtgtgccg ctgcctgccc aggaggacta ctacagtcac   3780

ctgaagaagg aaagcgacaa gccactgtag aacctgcgat caagagagca ccatggctcc   3840

tacattggac cttggagcac ccccaccctc cccccaccgt gcccttggcc tgccacccag   3900

agccaagagg gtgctgctca gttgcagggc ctccgcagct ggacagagag tgggggaggg   3960

agggacagac agaaggccaa ggcccgatgt ggtgtgcaga ggtggggagg tggcgaggat   4020

ggggacagaa agcgcacaga atcttggacc aggtctctct tccttgtccc ccctgctttt   4080

ctcctccccc atgcccaacc cctgtggccg ccgcccctcc cctgccccgt tggtgtgatt   4140

atttcatctg ttagatgtgg ctgttttgcg tagcatcgtg tgccacccct gcccctcccc   4200

gatccctgtg tgcgcgcccc ctctgcaatg tatgcccctt gcccccttccc cacactaata   4260

atttatatat ataaatatct atatgacgct cttaaaaaaa catcccaacc aaaaccaacc   4320

aaacaaaaac atcctcacaa ctccccagga aaaaaaaaaa aaaaaaa                 4367


<210> SEQ ID NO 53
<211> LENGTH: 1194
<212> TYPE: PRT
<213> ORGANISM: Homo Sapiens

<400> SEQUENCE: 53

Met Lys Thr Arg Gln Asn Lys Asp Ser Met Ser Met Arg Ser Gly Arg
1               5                   10                  15

Lys Lys Glu Ala Pro Gly Pro Arg Glu Glu Leu Arg Ser Arg Gly Arg
            20                  25                  30

Ala Ser Pro Gly Gly Val Ser Thr Ser Ser Ser Asp Gly Lys Ala Glu
        35                  40                  45

Lys Ser Arg Gln Thr Ala Lys Lys Ala Arg Val Glu Glu Ala Ser Thr
    50                  55                  60

Pro Lys Val Asn Lys Gln Gly Arg Ser Glu Glu Ile Ser Glu Ser Glu
65                  70                  75                  80

Ser Glu Glu Thr Asn Ala Pro Lys Lys Thr Lys Thr Glu Gln Glu Leu
                85                  90                  95

Pro Arg Pro Gln Ser Pro Ser Asp Leu Asp Ser Leu Asp Gly Arg Ser
            100                 105                 110

Leu Asn Asp Asp Gly Ser Ser Asp Pro Arg Asp Ile Asp Gln Asp Asn
        115                 120                 125

Arg Ser Thr Ser Pro Ser Ile Tyr Ser Pro Gly Ser Val Glu Asn Asp
    130                 135                 140

Ser Asp Ser Ser Ser Gly Leu Ser Gln Gly Pro Ala Arg Pro Tyr His
145                 150                 155                 160

Pro Pro Pro Leu Phe Pro Pro Ser Pro Gln Pro Pro Asp Ser Thr Pro
                165                 170                 175

Arg Gln Pro Glu Ala Ser Phe Glu Pro His Pro Ser Val Thr Pro Thr
            180                 185                 190

Gly Tyr His Ala Pro Met Glu Pro Pro Thr Ser Arg Met Phe Gln Ala
        195                 200                 205

Pro Pro Gly Ala Pro Pro Pro His Pro Gln Leu Tyr Pro Gly Gly Thr
    210                 215                 220

Gly Gly Val Leu Ser Gly Pro Pro Met Gly Pro Lys Gly Gly Gly Ala
```

```
225                 230                 235                 240

Ala Ser Ser Val Gly Gly Pro Asn Gly Gly Lys Gln His Pro Pro Pro
                245                 250                 255

Thr Thr Pro Ile Ser Val Ser Ser Ser Gly Ala Ser Gly Ala Pro Pro
            260                 265                 270

Thr Lys Pro Pro Thr Thr Pro Val Gly Gly Gly Asn Leu Pro Ser Ala
        275                 280                 285

Pro Pro Pro Ala Asn Phe Pro His Val Thr Pro Asn Leu Pro Pro Pro
    290                 295                 300

Pro Ala Leu Arg Pro Leu Asn Asn Ala Ser Ala Ser Pro Pro Gly Leu
305                 310                 315                 320

Gly Ala Gln Pro Leu Pro Gly His Leu Pro Ser Pro His Ala Met Gly
                325                 330                 335

Gln Gly Met Gly Gly Leu Pro Pro Gly Pro Glu Lys Gly Pro Thr Leu
            340                 345                 350

Ala Pro Ser Pro His Ser Leu Pro Pro Ala Ser Ser Ser Ala Pro Ala
        355                 360                 365

Pro Pro Met Arg Phe Pro Tyr Ser Ser Ser Ser Ser Ser Ser Ala Ala
    370                 375                 380

Ala Ser Ser Ser Ser Ser Ser Ser Ser Ser Ser Ala Ser Pro Phe Pro
385                 390                 395                 400

Ala Ser Gln Ala Leu Pro Ser Tyr Pro His Ser Phe Pro Pro Pro Thr
                405                 410                 415

Ser Leu Ser Val Ser Asn Gln Pro Pro Lys Tyr Thr Gln Pro Ser Leu
            420                 425                 430

Pro Ser Gln Ala Val Trp Ser Gln Gly Pro Pro Pro Pro Pro Pro Tyr
        435                 440                 445

Gly Arg Leu Leu Ala Asn Ser Asn Ala His Pro Gly Pro Phe Pro Pro
    450                 455                 460

Ser Thr Gly Ala Gln Ser Thr Ala His Pro Pro Val Ser Thr His His
465                 470                 475                 480

His His His Gln Gln Gln Gln Gln Gln Gln Gln Gln Gln Gln Gln Gln
                485                 490                 495

Gln Gln Gln Gln Gln Gln His His Gly Asn Ser Gly Pro Pro Pro Pro
            500                 505                 510

Gly Ala Phe Pro His Pro Leu Glu Gly Gly Ser Ser His His Ala His
        515                 520                 525

Pro Tyr Ala Met Ser Pro Ser Leu Gly Ser Leu Arg Pro Tyr Pro Pro
    530                 535                 540

Gly Pro Ala His Leu Pro Pro Pro His Ser Gln Val Ser Tyr Ser Gln
545                 550                 555                 560

Ala Gly Pro Asn Gly Pro Pro Val Ser Ser Ser Ser Asn Ser Ser Ser
                565                 570                 575

Ser Thr Ser Gln Gly Ser Tyr Pro Cys Ser His Pro Ser Pro Ser Gln
            580                 585                 590

Gly Pro Gln Gly Ala Pro Tyr Pro Phe Pro Pro Val Pro Thr Val Thr
        595                 600                 605

Thr Ser Ser Ala Thr Leu Ser Thr Val Ile Ala Thr Val Ala Ser Ser
    610                 615                 620

Pro Ala Gly Tyr Lys Thr Ala Ser Pro Pro Gly Pro Pro Pro Tyr Gly
625                 630                 635                 640

Lys Arg Ala Pro Ser Pro Gly Ala Tyr Lys Thr Ala Thr Pro Pro Gly
                645                 650                 655
```

-continued

```
Tyr Lys Pro Gly Ser Pro Pro Ser Phe Arg Thr Gly Thr Pro Pro Gly
            660                 665                 670

Tyr Arg Gly Thr Ser Pro Pro Ala Gly Pro Gly Thr Phe Lys Pro Gly
        675                 680                 685

Ser Pro Thr Val Gly Pro Gly Pro Leu Pro Pro Ala Gly Pro Ser Gly
    690                 695                 700

Leu Pro Ser Leu Pro Pro Pro Pro Ala Ala Pro Ala Ser Gly Pro Pro
705                 710                 715                 720

Leu Ser Ala Thr Gln Ile Lys Gln Glu Pro Ala Glu Glu Tyr Glu Thr
                725                 730                 735

Pro Glu Ser Pro Val Pro Pro Ala Arg Ser Pro Ser Pro Pro Pro Lys
            740                 745                 750

Val Val Asp Val Pro Ser His Ala Ser Gln Ser Ala Arg Phe Asn Lys
        755                 760                 765

His Leu Asp Arg Gly Phe Asn Ser Cys Ala Arg Ser Asp Leu Tyr Phe
    770                 775                 780

Val Pro Leu Glu Gly Ser Lys Leu Ala Lys Lys Arg Ala Asp Leu Val
785                 790                 795                 800

Glu Lys Val Arg Arg Glu Ala Glu Gln Arg Ala Arg Glu Glu Lys Glu
                805                 810                 815

Arg Glu Arg Glu Arg Glu Arg Glu Lys Glu Arg Glu Arg Glu Lys Glu
            820                 825                 830

Arg Glu Leu Glu Arg Ser Val Lys Leu Ala Gln Glu Gly Arg Ala Pro
        835                 840                 845

Val Glu Cys Pro Ser Leu Gly Pro Val Pro His Arg Pro Pro Phe Glu
    850                 855                 860

Pro Gly Ser Ala Val Ala Thr Val Pro Pro Tyr Leu Gly Pro Asp Thr
865                 870                 875                 880

Pro Ala Leu Arg Thr Leu Ser Glu Tyr Ala Arg Pro His Val Met Ser
                885                 890                 895

Pro Gly Asn Arg Asn His Pro Phe Tyr Val Pro Leu Gly Ala Val Asp
            900                 905                 910

Pro Gly Leu Leu Gly Tyr Asn Val Pro Ala Leu Tyr Ser Ser Asp Pro
        915                 920                 925

Ala Ala Arg Glu Arg Glu Arg Glu Ala Arg Glu Arg Asp Leu Arg Asp
    930                 935                 940

Arg Leu Lys Pro Gly Phe Glu Val Lys Pro Ser Glu Leu Glu Pro Leu
945                 950                 955                 960

His Gly Val Pro Gly Pro Gly Leu Asp Pro Phe Pro Arg His Gly Gly
                965                 970                 975

Leu Ala Leu Gln Pro Gly Pro Pro Gly Leu His Pro Phe Pro Phe His
            980                 985                 990

Pro Ser Leu Gly Pro Leu Glu Arg  Glu Arg Leu Ala Leu  Ala Ala Gly
        995                 1000                1005

Pro Ala  Leu Arg Pro Asp Met  Ser Tyr Ala Glu Arg  Leu Ala Ala
    1010                 1015                1020

Glu Arg  Gln His Ala Glu Arg  Val Ala Ala Leu Gly  Asn Asp Pro
    1025                 1030                1035

Leu Ala  Arg Leu Gln Met Leu  Asn Val Thr Pro His  His His Gln
    1040                 1045                1050

His Ser  His Ile His Ser His  Leu His Leu His Gln  Gln Asp Ala
    1055                 1060                1065

Ile His  Ala Ala Ser Ala Ser  Val His Pro Leu Ile  Asp Pro Leu
    1070                 1075                1080
```

```
Ala Ser  Gly Ser His Leu Thr  Arg Ile Pro Tyr Pro  Ala Gly Thr
    1085                 1090                 1095

Leu Pro  Asn Pro Leu Leu Pro  His Pro Leu His Glu  Asn Glu Val
    1100                 1105                 1110

Leu Arg  His Gln Leu Phe Ala  Ala Pro Tyr Arg Asp  Leu Pro Ala
    1115                 1120                 1125

Ser Leu  Ser Ala Pro Met Ser  Ala Ala His Gln Leu  Gln Ala Met
    1130                 1135                 1140

His Ala  Gln Ser Ala Glu Leu  Gln Arg Leu Ala Leu  Glu Gln Gln
    1145                 1150                 1155

Gln Trp  Leu His Ala His His  Pro Leu His Ser Val  Pro Leu Pro
    1160                 1165                 1170

Ala Gln  Glu Asp Tyr Tyr Ser  His Leu Lys Lys Glu  Ser Asp Lys
    1175                 1180                 1185

Pro Leu  Ser Asx Met Ala
    1190
```

<210> SEQ ID NO 54
<211> LENGTH: 4314
<212> TYPE: DNA
<213> ORGANISM: Homo Sapiens

<400> SEQUENCE: 54

```
cgagatcccg gggagccagc ttgctgggag agcgggacgg tccggagcaa gcccagaggc     60

agaggaggcg acagagggaa aaagggccga gctagccgct ccagtgctgt acaggagccg    120

aagggacgca ccacgccagc cccagcccgg ctccagcgac agccaacgcc tcttgcagcg    180

cggcggcttc gaagccgccg cccggagctg ccctttcctc ttcggtgaag tttttaaaag    240

ctgctaaaga ctcggaggaa gcaaggaaag tgcctggtag gactgacggc tgcctttgtc    300

ctcctcctct ccaccccgcc tccccccacc ctgccttccc cccctccccc gtcttctctc    360

ccgcagctgc ctcagtcggc tactctcagc caacccccct caccaccctt ctccccaccc    420

gcccccccgc ccccgtcggc ccagcgctgc cagcccgagt ttgcagagag gtaactccct    480

ttggctgcga gcgggcgagc tagctgcaca ttgcaaagaa ggctcttagg agccaggcga    540

ctggggagcg gcttcagcac tgcagccacg acccgcctgg ttaggctgca cgcggagaga    600

accctctgtt ttcccccact ctctctccac ctcctcctgc cttccccacc ccgagtgcgg    660

agccagagat caaaagatga aaaggcagtc aggtcttcag tagccaaaaa acaaaacaaa    720

caaaaacaaa aaagccgaaa taaaagaaaa agataataac tcagttctta tttgcaccta    780

cttcagtgga cactgaattt ggaaggtgga ggattttgtt tttttctttt aagatctggg    840

catcttttga atctaccctt caagtattaa gagacagact gtgagcctag cagggcagat    900

cttgtccacc gtgtgtcttc ttctgcacga gactttgagg ctgtcagagc gctttttgcg    960

tggttgctcc cgcaagtttc cttctctgga gcttcccgca ggtgggcagc tagctgcagc   1020

gactaccgca tcatcacagc ctgttgaact cttctgagca agagaagggg aggcggggta   1080

agggaagtag gtggaagatt cagccaagct caaggatgga agtgcagtta gggctgggaa   1140

gggtctaccc tcggccgccg tccaagacct accgaggagc tttccagaat ctgttccaga   1200

gcgtgcgcga agtgatccag aacccgggcc ccaggcaccc agaggccgcg agcgcagcac   1260

ctcccggcgc cagtttgctg ctgctgcagc agcagcagca gcagcagcag cagcagcagc   1320

agcagcagca gcagcagcag cagcagcagc agcaagagac tagccccagg cagcagcagc   1380

agcagcaggg tgaggatggt tctccccaag cccatcgtag aggccccaca ggctacctgg   1440
```

-continued

```
tcctggatga ggaacagcaa ccttcacagc cgcagtcggc cctggagtgc caccccgaga   1500
gaggttgcgt cccagagcct ggagccgccg tggccgccag caaggggctg ccgcagcagc   1560
tgccagcacc tccggacgag gatgactcag ctgccccatc cacgttgtcc ctgctgggcc   1620
ccactttccc cggcttaagc agctgctccg ctgaccttaa agacatcctg agcgaggcca   1680
gcaccatgca actccttcag caacagcagc aggaagcagt atccgaaggc agcagcagcg   1740
ggagagcgag ggaggcctcg ggggctccca cttcctccaa ggacaattac ttagggggca   1800
cttcgaccat ttctgacaac gccaaggagt tgtgtaaggc agtgtcggtg tccatgggcc   1860
tgggtgtgga ggcgttggag catctgagtc caggggaaca gcttcggggg gattgcatgt   1920
acgccccact tttgggagtt ccacccgctg tgcgtcccac tccttgtgcc ccattggccg   1980
aatgcaaagg ttctctgcta gacgacagcg caggcaagag cactgaagat actgctgagt   2040
attccccttt caagggaggt tacaccaaag ggctagaagg cgagagccta ggctgctctg   2100
gcagcgctgc agcagggagc tccgggacac ttgaactgcc gtctaccctg tctctctaca   2160
agtccggagc actggacgag gcagctgcgt accagagtcg cgactactac aactttccac   2220
tggctctggc cggaccgccg ccccctccgc cgcctcccca tccccacgct cgcatcaagc   2280
tggagaaccc gctggactac ggcagcgcct gggcggctgc ggcggcgcag tgccgctatg   2340
gggacctggc gagcctgcat ggcgcgggtg cagcgggacc cggttctggg tcaccctcag   2400
ccgccgcttc ctcatcctgg cacactctct tcacagccga agaaggccag ttgtatggac   2460
cgtgtggtgg tggtgggggt ggtggcggcg gcggcggcgg cggcggcggc ggcggcggcg   2520
gcggcggcgg cggcgaggcg ggagctgtag ccccctacgg ctacactcgg ccccctcagg   2580
ggctggcggg ccaggaaagc gacttcaccg cacctgatgt gtggtaccct ggcggcatgg   2640
tgagcagagt gccctatccc agtcccactt gtgtcaaaag cgaaatgggc ccctggatgg   2700
atagctactc cggaccttac ggggacatgc gtttggagac tgccagggac catgttttgc   2760
ccattgacta ttactttcca ccccagaaga cctgcctgat ctgtggagat gaagcttctg   2820
ggtgtcacta tggagctctc acatgtggaa gctgcaaggt cttcttcaaa agagccgctg   2880
aagggaaaca gaagtacctg tgcgccagca gaaatgattg cactattgat aaattccgaa   2940
ggaaaaattg tccatcttgt cgtcttcgga aatgttatga agcagggatg actctgggag   3000
cccggaagct gaagaaactt ggtaatctga aactacagga ggaaggagag gcttccagca   3060
ccaccagccc cactgaggag acaacccaga agctgacagt gtcacacatt gaaggctatg   3120
aatgtcagcc catctttctg aatgtcctgg aagccattga gccaggtgta gtgtgtgctg   3180
gacacgacaa caaccagccc gactcctttg cagccttgct ctctagcctc aatgaactgg   3240
gagagagaca gcttgtacac gtggtcaagt gggccaaggc cttgcctggc ttccgcaact   3300
tacacgtgga cgaccagatg gctgtcattc agtactcctg gatggggctc atggtgtttg   3360
ccatgggctg gcgatccttc accaatgtca actccaggat gctctacttc gcccctgatc   3420
tggttttcaa tgagtaccgc atgcacaagt cccggatgta cagccagtgt gtccgaatga   3480
ggcacctctc tcaagagttt ggatggctcc aaatcacccc ccaggaattc ctgtgcatga   3540
aagcactgct actcttcagc attattccag tggatgggct gaaaaatcaa aaattctttg   3600
atgaacttcg aatgaactac atcaaggaac tcgatcgtat cattgcatgc aaaagaaaaa   3660
atcccacatc ctgctcaaga cgcttctacc agctcaccaa gctcctggac tccgtgcagc   3720
ctattgcgag agagctgcat cagttcactt ttgacctgct aatcaagtca cacatggtga   3780
gcgtggactt tccggaaatg atggcagaga tcatctctgt gcaagtgccc aagatccttt   3840
```

```
ctgggaaagt caagcccatc tatttccaca cccagtgaag cattggaaac cctatttccc   3900

caccccagct catgcccccct ttcagatgtc ttctgcctgt tataactctg cactactcct   3960

ctgcagtgcc ttggggaatt tcctctattg atgtacagtc tgtcatgaac atgttcctga   4020

attctatttg ctgggctttt tttttctctt tctctccttt ctttttcttc ttccctccct   4080

atctaaccct cccatggcac cttcagactt tgcttcccat tgtggctcct atctgtgttt   4140

tgaatggtgt tgtatgcctt taaatctgtg atgatcctca tatggcccag tgtcaagttg   4200

tgcttgttta cagcactact ctgtgccagc cacacaaacg tttacttatc ttatgccacg   4260

ggaagtttag agagctaaga ttatctgggg aaatcaaaac aaaaacaagc aaac         4314


<210> SEQ ID NO 55
<211> LENGTH: 920
<212> TYPE: PRT
<213> ORGANISM: Homo Sapiens

<400> SEQUENCE: 55

Met Glu Val Gln Leu Gly Leu Gly Arg Val Tyr Pro Arg Pro Pro Ser
1               5                   10                  15

Lys Thr Tyr Arg Gly Ala Phe Gln Asn Leu Phe Gln Ser Val Arg Glu
            20                  25                  30

Val Ile Gln Asn Pro Gly Pro Arg His Pro Glu Ala Ala Ser Ala Ala
        35                  40                  45

Pro Pro Gly Ala Ser Leu Leu Leu Leu Gln Gln Gln Gln Gln Gln Gln
    50                  55                  60

Gln Gln Gln Gln Gln Gln Gln Gln Gln Gln Gln Gln Gln Gln Gln Gln
65                  70                  75                  80

Glu Thr Ser Pro Arg Gln Gln Gln Gln Gln Gln Gly Glu Asp Gly Ser
                85                  90                  95

Pro Gln Ala His Arg Arg Gly Pro Thr Gly Tyr Leu Val Leu Asp Glu
            100                 105                 110

Glu Gln Gln Pro Ser Gln Pro Gln Ser Ala Leu Glu Cys His Pro Glu
        115                 120                 125

Arg Gly Cys Val Pro Glu Pro Gly Ala Ala Val Ala Ala Ser Lys Gly
    130                 135                 140

Leu Pro Gln Gln Leu Pro Ala Pro Pro Asp Glu Asp Asp Ser Ala Ala
145                 150                 155                 160

Pro Ser Thr Leu Ser Leu Leu Gly Pro Thr Phe Pro Gly Leu Ser Ser
                165                 170                 175

Cys Ser Ala Asp Leu Lys Asp Ile Leu Ser Glu Ala Ser Thr Met Gln
            180                 185                 190

Leu Leu Gln Gln Gln Gln Gln Glu Ala Val Ser Glu Gly Ser Ser Ser
        195                 200                 205

Gly Arg Ala Arg Glu Ala Ser Gly Ala Pro Thr Ser Ser Lys Asp Asn
    210                 215                 220

Tyr Leu Gly Gly Thr Ser Thr Ile Ser Asp Asn Ala Lys Glu Leu Cys
225                 230                 235                 240

Lys Ala Val Ser Val Ser Met Gly Leu Gly Val Glu Ala Leu Glu His
                245                 250                 255

Leu Ser Pro Gly Glu Gln Leu Arg Gly Asp Cys Met Tyr Ala Pro Leu
            260                 265                 270

Leu Gly Val Pro Pro Ala Val Arg Pro Thr Pro Cys Ala Pro Leu Ala
        275                 280                 285

Glu Cys Lys Gly Ser Leu Leu Asp Asp Ser Ala Gly Lys Ser Thr Glu
```

-continued

```
    290                 295                 300

Asp Thr Ala Glu Tyr Ser Pro Phe Lys Gly Gly Tyr Thr Lys Gly Leu
305                 310                 315                 320

Glu Gly Glu Ser Leu Gly Cys Ser Gly Ser Ala Ala Ala Gly Ser Ser
                325                 330                 335

Gly Thr Leu Glu Leu Pro Ser Thr Leu Ser Leu Tyr Lys Ser Gly Ala
            340                 345                 350

Leu Asp Glu Ala Ala Ala Tyr Gln Ser Arg Asp Tyr Tyr Asn Phe Pro
        355                 360                 365

Leu Ala Leu Ala Gly Pro Pro Pro Pro Pro Pro Pro Pro His Pro His
    370                 375                 380

Ala Arg Ile Lys Leu Glu Asn Pro Leu Asp Tyr Gly Ser Ala Trp Ala
385                 390                 395                 400

Ala Ala Ala Ala Gln Cys Arg Tyr Gly Asp Leu Ala Ser Leu His Gly
                405                 410                 415

Ala Gly Ala Ala Gly Pro Gly Ser Gly Ser Pro Ser Ala Ala Ala Ser
            420                 425                 430

Ser Ser Trp His Thr Leu Phe Thr Ala Glu Glu Gly Gln Leu Tyr Gly
        435                 440                 445

Pro Cys Gly Gly Gly Gly Gly Gly Gly Gly Gly Gly Gly Gly Gly Gly
    450                 455                 460

Gly Gly Gly Gly Gly Gly Gly Gly Gly Glu Ala Gly Ala Val Ala Pro
465                 470                 475                 480

Tyr Gly Tyr Thr Arg Pro Pro Gln Gly Leu Ala Gly Gln Glu Ser Asp
                485                 490                 495

Phe Thr Ala Pro Asp Val Trp Tyr Pro Gly Gly Met Val Ser Arg Val
            500                 505                 510

Pro Tyr Pro Ser Pro Thr Cys Val Lys Ser Glu Met Gly Pro Trp Met
        515                 520                 525

Asp Ser Tyr Ser Gly Pro Tyr Gly Asp Met Arg Leu Glu Thr Ala Arg
    530                 535                 540

Asp His Val Leu Pro Ile Asp Tyr Tyr Phe Pro Pro Gln Lys Thr Cys
545                 550                 555                 560

Leu Ile Cys Gly Asp Glu Ala Ser Gly Cys His Tyr Gly Ala Leu Thr
                565                 570                 575

Cys Gly Ser Cys Lys Val Phe Phe Lys Arg Ala Ala Glu Gly Lys Gln
            580                 585                 590

Lys Tyr Leu Cys Ala Ser Arg Asn Asp Cys Thr Ile Asp Lys Phe Arg
        595                 600                 605

Arg Lys Asn Cys Pro Ser Cys Arg Leu Arg Lys Cys Tyr Glu Ala Gly
    610                 615                 620

Met Thr Leu Gly Ala Arg Lys Leu Lys Lys Leu Gly Asn Leu Lys Leu
625                 630                 635                 640

Gln Glu Glu Gly Glu Ala Ser Ser Thr Thr Ser Pro Thr Glu Glu Thr
                645                 650                 655

Thr Gln Lys Leu Thr Val Ser His Ile Glu Gly Tyr Glu Cys Gln Pro
            660                 665                 670

Ile Phe Leu Asn Val Leu Glu Ala Ile Glu Pro Gly Val Val Cys Ala
        675                 680                 685

Gly His Asp Asn Asn Gln Pro Asp Ser Phe Ala Ala Leu Leu Ser Ser
    690                 695                 700

Leu Asn Glu Leu Gly Glu Arg Gln Leu Val His Val Val Lys Trp Ala
705                 710                 715                 720
```

-continued

```
Lys Ala Leu Pro Gly Phe Arg Asn Leu His Val Asp Asp Gln Met Ala
                725                 730                 735

Val Ile Gln Tyr Ser Trp Met Gly Leu Met Val Phe Ala Met Gly Trp
            740                 745                 750

Arg Ser Phe Thr Asn Val Asn Ser Arg Met Leu Tyr Phe Ala Pro Asp
        755                 760                 765

Leu Val Phe Asn Glu Tyr Arg Met His Lys Ser Arg Met Tyr Ser Gln
    770                 775                 780

Cys Val Arg Met Arg His Leu Ser Gln Glu Phe Gly Trp Leu Gln Ile
785                 790                 795                 800

Thr Pro Gln Glu Phe Leu Cys Met Lys Ala Leu Leu Leu Phe Ser Ile
                805                 810                 815

Ile Pro Val Asp Gly Leu Lys Asn Gln Lys Phe Phe Asp Glu Leu Arg
            820                 825                 830

Met Asn Tyr Ile Lys Glu Leu Asp Arg Ile Ile Ala Cys Lys Arg Lys
        835                 840                 845

Asn Pro Thr Ser Cys Ser Arg Arg Phe Tyr Gln Leu Thr Lys Leu Leu
    850                 855                 860

Asp Ser Val Gln Pro Ile Ala Arg Glu Leu His Gln Phe Thr Phe Asp
865                 870                 875                 880

Leu Leu Ile Lys Ser His Met Val Ser Val Asp Phe Pro Glu Met Met
                885                 890                 895

Ala Glu Ile Ile Ser Val Gln Val Pro Lys Ile Leu Ser Gly Lys Val
            900                 905                 910

Lys Pro Ile Tyr Phe His Thr Gln
        915                 920
```

<210> SEQ ID NO 56
<211> LENGTH: 9435
<212> TYPE: DNA
<213> ORGANISM: Homo Sapiens

<400> SEQUENCE: 56

```
atggcgaccc tggaaaagct gatgaaggcc ttcgagtccc tcaagtcctt ccagcagcag      60

cagcagcagc agcagcagca gcagcagcag cagcagcagc agcagcagca gcagcaacag     120

ccgccaccgc cgccgccgcc gccgccgcct cctcagcttc ctcagccgcc gccgcaggca     180

cagccgctgc tgcctcagcc gcagccgccc ccgccgccgc ccccgccgcc acccggcccg     240

gctgtggctg aggagccgct gcaccgacca aagaaagaac tttcagctac caagaaagac     300

cgtgtgaatc attgtctgac aatatgtgaa aacatagtgg cacagtctgt cagaaattct     360

ccagaatttc agaaacttct gggcatcgct atggaacttt ttctgctgtg cagtgatgac     420

gcagagtcag atgtcaggat ggtggctgac gaatgcctca acaaagttat caaagctttg     480

atggattcta atcttccaag gttacagctc gagctctata aggaaattaa aaagaatggt     540

gcccctcgga gtttgcgtgc tgccctgtgg aggtttgctg agctggctca cctggttcgg     600

cctcagaaat gcaggcctta cctggtgaac cttctgccgt gcctgactcg aacaagcaag     660

agacccgaag aatcagtcca ggagaccttg gctgcagctg ttcccaaaat tatggcttct     720

tttggcaatt ttgcaaatga caatgaaatt aaggttttgt taaaggcctt catagcgaac     780

ctgaagtcaa gctcccccac cattcggcgg acagcggctg gatcagcagt gagcatctgc     840

cagcactcaa gaaggacaca atatttctat agttggctac taaatgtgct cttaggctta     900

ctcgttcctg tcgaggatga acactccact ctgctgattc ttggcgtgct gctcaccctg     960

aggtatttgg tgcccttgct gcagcagcag gtcaaggaca caagcctgaa aggcagcttc    1020
```

-continued

```
ggagtgacaa ggaaagaaat ggaagtctct ccttctgcag agcagcttgt ccaggtttat   1080
gaactgacgt tacatcatac acagcaccaa gaccacaatg ttgtgaccgg agccctggag   1140
ctgttgcagc agctcttcag aacgcctcca cccgagcttc tgcaaaccct gaccgcagtc   1200
gggggcattg ggcagctcac cgctgctaag gaggagtctg gtggccgaag ccgtagtggg   1260
agtattgtgg aacttatagc tggagggggt tcctcatgca gccctgtcct ttcaagaaaa   1320
caaaaaggca aagtgctctt aggagaagaa gaagccttgg aggatgactc tgaatcgaga   1380
tcggatgtca gcagctctgc cttaacagcc tcagtgaagg atgagatcag tggagagctg   1440
gctgcttctt caggggtttc cactccaggg tcagcaggtc atgacatcat cacagaacag   1500
ccacggtcac agcacacact gcaggcggac tcagtggatc tggccagctg tgacttgaca   1560
agctctgcca ctgatgggga tgaggaggat atcttgagcc acagctccag ccaggtcagc   1620
gccgtcccat ctgaccctgc catggacctg aatgatggga cccaggcctc gtcgcccatc   1680
agcgacagct cccagaccac caccgaaggg cctgattcag ctgttacccc ttcagacagt   1740
tctgaaattg tgttagacgg taccgacaac cagtatttgg gcctgcagat tggacagccc   1800
caggatgaag atgaggaagc cacaggtatt cttcctgatg aagcctcgga ggccttcagg   1860
aactcttcca tggcccttca acaggcacat ttattgaaaa acatgagtca ctgcaggcag   1920
ccttctgaca gcagtgttga taaatttgtg ttgagagatg aagctactga accgggtgat   1980
caagaaaaca agccttgccg catcaaaggt gacattggac agtccactga tgatgactct   2040
gcacctcttg tccattgtgt ccgccttta tctgcttcgt tttgctaac aggggggaaaa   2100
aatgtgctgg ttccggacag ggatgtgagg gtcagcgtga aggccctggc cctcagctgt   2160
gtgggagcag ctgtggccct ccacccggaa tctttcttca gcaaactcta taaagttcct   2220
cttgacacca cggaataccc tgaggaacag tatgtctcag acatcttgaa ctacatcgat   2280
catggagacc cacaggttcg aggagccact gccattctct gtgggaccct catctgctcc   2340
atcctcagca ggtcccgctt ccacgtggga gattggatgg gcaccattag aaccctcaca   2400
ggaaatacat tttctttggc ggattgcatt cctttgctgc ggaaaacact gaaggatgag   2460
tcttctgtta cttgcaagtt agcttgtaca gctgtgagga actgtgtcat gagtctctgc   2520
agcagcagct acagtgagtt aggactgcag ctgatcatcg atgtgctgac tctgaggaac   2580
agttcctatt ggctggtgag gacagagctt ctggaaaccc ttgcagagat tgacttcagg   2640
ctggtgagct tttggaggc aaaagcagaa aacttacaca gaggggctca tcattataca   2700
gggcttttaa aactgcaaga acgagtgctc aataatgttg tcatccattt gcttggagat   2760
gaagacccca gggtgcgaca tgttgccgca gcatcactaa ttaggcttgt cccaaagctg   2820
ttttataaat gtgaccaagg acaagctgat ccagtagtgg ccgtggcaag agatcaaagc   2880
agtgtttacc tgaaacttct catgcatgag acgcagcctc catctcattt ctccgtcagc   2940
acaataacca gaatatatag aggctataac ctactaccaa gcataacaga cgtcactatg   3000
gaaaataacc tttcaagagt tattgcagca gtttctcatg aactaatcac atcaaccacc   3060
agagcactca catttggatg ctgtgaagct ttgtgtcttc tttccactgc cttcccagtt   3120
tgcatttgga gtttaggttg gcactgtgga gtgcctccac tgagtgcctc agatgagtct   3180
aggaagagct gtaccgttgg gatggccaca atgattctga ccctgctctc gtcagcttgg   3240
ttcccattgg atctctcagc ccatcaagat gctttgattt tggccggaaa cttgcttgca   3300
gccagtgctc ccaaatctct gagaagttca tgggcctctg aagaagaagc caacccagca   3360
gccaccaagc aagaggaggt ctggccagcc ctgggggacc gggccctggt gcccatggtg   3420
```

```
gagcagctct tctctcacct gctgaaggtg attaacattt gtgcccacgt cctggatgac   3480
gtggctcctg gacccgcaat aaaggcagcc ttgccttctc taacaaaccc cccttctcta   3540
agtcccatcc gacgaaaggg gaaggagaaa gaaccaggag aacaagcatc tgtaccgttg   3600
agtcccaaga aaggcagtga ggccagtgca gcttctagac aatctgatac ctcaggtcct   3660
gttacaacaa gtaaatcctc atcactgggg agtttctatc atcttccttc atacctcaaa   3720
ctgcatgatg tcctgaaagc tacacacgct aactacaagg tcacgctgga tcttcagaac   3780
agcacggaaa agtttggagg gtttctccgc tcagccttgg atgttctttc tcagatacta   3840
gagctggcca cactgcagga cattgggaag tgtgttgaag agatcctagg atacctgaaa   3900
tcctgcttta gtcgagaacc aatgatggca actgtttgtg ttcaacaatt gttgaagact   3960
ctctttggca caaacttggc ctcccagttt gatggcttat cttccaaccc cagcaagtca   4020
caaggccgag cacagcgcct tggctcctcc agtgtgaggc caggcttgta ccactactgc   4080
ttcatggccc cgtacaccca cttcacccag gccctcgctg acgccagcct gaggaacatg   4140
gtgcaggcgg agcaggagaa cgacacctcg ggatggtttg atgtcctcca gaaagtgtct   4200
acccagttga agacaaacct cacgagtgtc acaaagaacc gtgcagataa gaatgctatt   4260
cataatcaca ttcgtttgtt tgaacctctt gttataaaag ctttaaaaca gtacacgact   4320
acaacatgtg tgcagttaca gaagcaggtt ttagatttgc tggcgcagct ggttcagtta   4380
cgggttaatt actgtcttct ggattcagat caggtgttta ttggctttgt attgaaacag   4440
tttgaataca ttgaagtggg ccagttcagg gaatcagagg caatcattcc aaacatcttt   4500
ttcttcttgg tattactatc ttatgaacgc tatcattcaa aacagatcat tggaattcct   4560
aaaatcattc agctctgtga tggcatcatg gccagtggaa ggaaggctgt gacacatgcc   4620
ataccggctc tgcagcccat agtccacgac ctctttgtat taagaggaac aaataaagct   4680
gatgcaggaa aagagcttga aacccaaaaa gaggtggtgg tgtcaatgtt actgagactc   4740
atccagtacc atcaggtgtt ggagatgttc attcttgtcc tgcagcagtg ccacaaggag   4800
aatgaagaca agtggaagcg actgtctcga cagatagctg acatcatcct cccaatgtta   4860
gccaaacagc agatgcacat tgactctcat gaagcccttg gagtgttaaa tacattattt   4920
gagattttgg ccccttcctc cctccgtccg gtagacatgc ttttacggag tatgttcgtc   4980
actccaaaca caatggcgtc cgtgagcact gttcaactgt ggatatcggg aattctggcc   5040
attttgaggg ttctgatttc ccagtcaact gaagatattg ttctttctcg tattcaggag   5100
ctctccttct ctccgtattt aatctcctgt acagtaatta ataggttaag agatggggac   5160
agtacttcaa cgctagaaga acacagtgaa gggaaacaaa taaagaattt gccagaagaa   5220
acattttcaa ggtttctatt acaactggtt ggtattcttt tagaagacat tgttacaaaa   5280
cagctgaagg tggaaatgag tgagcagcaa catactttct attgccagga actaggcaca   5340
ctgctaatgt gtctgatcca catcttcaag tctggaatgt tccggagaat cacagcagct   5400
gccactaggc tgttccgcag tgatggctgt ggcggcagtt tctacaccct ggacagcttg   5460
aacttgcggg ctcgttccat gatcaccacc cacccggccc tggtgctgct ctggtgtcag   5520
atactgctgc ttgtcaacca caccgactac cgctggtggg cagaagtgca gcagaccccg   5580
aaaagacaca gtctgtccag cacaaagtta cttagtcccc agatgtctgg agaagaggag   5640
gattctgact tggcagccaa acttggaatg tgcaatagag aaatagtacg aagaggggct   5700
ctcattctct tctgtgatta tgtctgtcag aacctccatg actccgagca cttaacgtgg   5760
ctcattgtaa atcacattca agatctgatc agcctttccc acgagcctcc agtacaggac   5820
```

-continued

```
ttcatcagtg ccgttcatcg gaactctgct gccagcggcc tgttcatcca ggcaattcag   5880
tctcgttgtg aaaacctttc aactccaacc atgctgaaga aaactcttca gtgcttggag   5940
gggatccatc tcagccagtc gggagctgtg ctcacgctgt atgtggacag gcttctgtgc   6000
accccttcc gtgtgctggc tcgcatggtc gacatccttg cttgtcgccg ggtagaaatg   6060
cttctggctg caaatttaca gagcagcatg gcccagttgc caatggaaga actcaacaga   6120
atccaggaat accttcagag cagcgggctc gctcagagac accaaaggct ctattccctg   6180
ctggacaggt ttcgtctctc caccatgcaa gactcactta gtccctctcc tccagtctct   6240
tcccacccgc tggacgggga tgggcacgtg tcactggaaa cagtgagtcc ggacaaagac   6300
tggtacgttc atcttgtcaa atcccagtgt tggaccaggt cagattctgc actgctggaa   6360
ggtgcagagc tggtgaatcg gattcctgct gaagatatga atgccttcat gatgaactcg   6420
gagttcaacc taagcctgct agctccatgc ttaagcctag ggatgagtga aatttctggt   6480
ggccagaaga gtgccctttt tgaagcagcc cgtgaggtga ctctggcccg tgtgagcggc   6540
accgtgcagc agctccctgc tgtccatcat gtcttccagc ccgagctgcc tgcagagccg   6600
gcggcctact ggagcaagtt gaatgatctg tttggggatg ctgcactgta tcagtccctg   6660
cccactctgg cccgggccct ggcacagtac ctggtggtgg tctccaaact gcccagtcat   6720
ttgcaccttc ctcctgagaa agagaaggac attgtgaaat tcgtggtggc aacccttgag   6780
gccctgtcct ggcatttgat ccatgagcag atcccgctga gtctggatct ccaggcaggg   6840
ctggactgct gctgcctggc cctgcagctg cctggcctct ggagcgtggt ctcctccaca   6900
gagtttgtga cccacgcctg ctccctcatc tactgtgtgc acttcatcct ggaggccgtt   6960
gcagtgcagc ctggagagca gcttcttagt ccagaaagaa ggacaaatac cccaaaagcc   7020
atcagcgagg aggaggagga agtagatcca aacacacaga atcctaagta tatcactgca   7080
gcctgtgaga tggtggcaga aatggtggag tctctgcagt cggtgttggc cttgggtcat   7140
aaaaggaata gcggcgtgcc ggcgtttctc acgccattgc taaggaacat catcatcagc   7200
ctggcccgcc tgccccttgt caacagctac acacgtgtgc ccccactggt gtggaagctt   7260
ggatggtcac ccaaaccggg aggggatttt ggcacagcat tccctgagat ccccgtggag   7320
ttcctccagg aaaaggaagt ctttaaggag ttcatctacc gcatcaacac actaggctgg   7380
accagtcgta ctcagtttga agaaacttgg gccaccctcc ttggtgtcct ggtgacgcag   7440
cccctcgtga tggagcagga ggagagccca ccagaagaag acacagagag gacccagatc   7500
aacgtcctgg ccgtgcaggc catcacctca ctggtgctca gtgcaatgac tgtgcctgtg   7560
gccggcaacc cagctgtaag ctgcttggag cagcagcccc ggaacaagcc tctgaaagct   7620
ctcgacacca ggtttgggag gaagctgagc attatcagag ggattgtgga gcaagagatt   7680
caagcaatgg tttcaaagag agagaatatt gccacccatc atttatatca ggcatgggat   7740
cctgtccctt ctctgtctcc ggctactaca ggtgccctca tcagccacga gaagctgctg   7800
ctacagatca accccgagcg ggagctgggg agcatgagct acaaactcgg ccaggtgtcc   7860
atacactccg tgtggctggg gaacagcatc acacccctga gggaggagga atgggacgag   7920
gaagaggagg aggaggccga cgcccctgca ccttcgtcac cacccacgtc tccagtcaac   7980
tccaggaaac accgggctgg agttgacatc cactcctgtt cgcagttttt gcttgagttg   8040
tacagccgct ggatcctgcc gtccagctca gccaggagga ccccggccat cctgatcagt   8100
gaggtggtca gatcccttct agtggtctca gacttgttca ccgagcgcaa ccagtttgag   8160
ctgatgtatg tgacgctgac agaactgcga agggtgcacc cttcagaaga cgagatcctc   8220
```

```
gctcagtacc tggtgcctgc cacctgcaag gcagctgccg tccttgggat ggacaaggcc   8280

gtggcggagc ctgtcagccg cctgctggag agcacgctca ggagcagcca cctgcccagc   8340

agggttggag ccctgcacgg cgtcctctat gtgctggagt gcgacctgct ggacgacact   8400

gccaagcagc tcatcccggt catcagcgac tatctcctct ccaacctgaa agggatcgcc   8460

cactgcgtga acattcacag ccagcagcac gtactggtca tgtgtgccac tgcgttttac   8520

ctcattgaga actatcctct ggacgtaggg ccggaatttt cagcatcaat aatacagatg   8580

tgtggggtga tgctgtctgg aagtgaggag tccacccccct ccatcattta ccactgtgcc   8640

ctcagaggcc tggagcgcct cctgctctct gagcagctct cccgcctgga tgcagaatcg   8700

ctggtcaagc tgagtgtgga cagagtgaac gtgcacagcc cgcaccgggc catggcggct   8760

ctgggcctga tgctcacctg catgtacaca ggaaaggaga aagtcagtcc gggtagaact   8820

tcagacccta atcctgcagc ccccgacagc gagtcagtga ttgttgctat ggagcgggta   8880

tctgttcttt ttgataggat caggaaaggc tttccttgtg aagccagagt ggtggccagg   8940

atcctgcccc agtttctaga cgacttcttc ccaccccagg acatcatgaa caaagtcatc   9000

ggagagtttc tgtccaacca gcagccatac ccccagttca tggccaccgt ggtgtataag   9060

gtgtttcaga ctctgcacag caccgggcag tcgtccatgg tccgggactg ggtcatgctg   9120

tccctctcca acttcacgca gagggccccg gtcgccatgg ccacgtggag cctctcctgc   9180

ttctttgtca gcgcgtccac cagcccgtgg gtcgcggcga tcctcccaca tgtcatcagc   9240

aggatgggca agctggagca ggtggacgtg aacctttttct gcctggtcgc cacagacttc   9300

tacagacacc agatagagga ggagctcgac cgcagggcct tccagtctgt gcttgaggtg   9360

gttgcagccc caggaagccc atatcaccgg ctgctgactt gtttacgaaa tgtccacaag   9420

gtcaccacct gctga                                                    9435
```

<210> SEQ ID NO 57
<211> LENGTH: 3144
<212> TYPE: PRT
<213> ORGANISM: Homo Sapiens

<400> SEQUENCE: 57

```
Met Ala Thr Leu Glu Lys Leu Met Lys Ala Phe Glu Ser Leu Lys Ser
1               5                   10                  15

Phe Gln Gln Gln Gln Gln Gln Gln Gln Gln Gln Gln Gln Gln Gln Gln
            20                  25                  30

Gln Gln Gln Gln Gln Gln Gln Gln Pro Pro Pro Pro Pro Pro Pro Pro
        35                  40                  45

Pro Pro Pro Gln Leu Pro Gln Pro Pro Pro Gln Ala Gln Pro Leu Leu
    50                  55                  60

Pro Gln Pro Gln Pro Pro Pro Pro Pro Pro Pro Pro Pro Pro Gly Pro
65                  70                  75                  80

Ala Val Ala Glu Glu Pro Leu His Arg Pro Lys Lys Glu Leu Ser Ala
                85                  90                  95

Thr Lys Lys Asp Arg Val Asn His Cys Leu Thr Ile Cys Glu Asn Ile
            100                 105                 110

Val Ala Gln Ser Val Arg Asn Ser Pro Glu Phe Gln Lys Leu Leu Gly
        115                 120                 125

Ile Ala Met Glu Leu Phe Leu Leu Cys Ser Asp Asp Ala Glu Ser Asp
    130                 135                 140

Val Arg Met Val Ala Asp Glu Cys Leu Asn Lys Val Ile Lys Ala Leu
145                 150                 155                 160
```

-continued

```
Met Asp Ser Asn Leu Pro Arg Leu Gln Leu Glu Leu Tyr Lys Glu Ile
                165                 170                 175

Lys Lys Asn Gly Ala Pro Arg Ser Leu Arg Ala Ala Leu Trp Arg Phe
            180                 185                 190

Ala Glu Leu Ala His Leu Val Arg Pro Gln Lys Cys Arg Pro Tyr Leu
        195                 200                 205

Val Asn Leu Leu Pro Cys Leu Thr Arg Thr Ser Lys Arg Pro Glu Glu
    210                 215                 220

Ser Val Gln Glu Thr Leu Ala Ala Ala Val Pro Lys Ile Met Ala Ser
225                 230                 235                 240

Phe Gly Asn Phe Ala Asn Asp Asn Glu Ile Lys Val Leu Leu Lys Ala
                245                 250                 255

Phe Ile Ala Asn Leu Lys Ser Ser Ser Pro Thr Ile Arg Arg Thr Ala
            260                 265                 270

Ala Gly Ser Ala Val Ser Ile Cys Gln His Ser Arg Arg Thr Gln Tyr
        275                 280                 285

Phe Tyr Ser Trp Leu Leu Asn Val Leu Leu Gly Leu Leu Val Pro Val
    290                 295                 300

Glu Asp Glu His Ser Thr Leu Leu Ile Leu Gly Val Leu Leu Thr Leu
305                 310                 315                 320

Arg Tyr Leu Val Pro Leu Leu Gln Gln Gln Val Lys Asp Thr Ser Leu
                325                 330                 335

Lys Gly Ser Phe Gly Val Thr Arg Lys Glu Met Glu Val Ser Pro Ser
            340                 345                 350

Ala Glu Gln Leu Val Gln Val Tyr Glu Leu Thr Leu His His Thr Gln
        355                 360                 365

His Gln Asp His Asn Val Val Thr Gly Ala Leu Glu Leu Leu Gln Gln
    370                 375                 380

Leu Phe Arg Thr Pro Pro Pro Glu Leu Leu Gln Thr Leu Thr Ala Val
385                 390                 395                 400

Gly Gly Ile Gly Gln Leu Thr Ala Ala Lys Glu Glu Ser Gly Gly Arg
                405                 410                 415

Ser Arg Ser Gly Ser Ile Val Glu Leu Ile Ala Gly Gly Gly Ser Ser
            420                 425                 430

Cys Ser Pro Val Leu Ser Arg Lys Gln Lys Gly Lys Val Leu Leu Gly
        435                 440                 445

Glu Glu Glu Ala Leu Glu Asp Asp Ser Glu Ser Arg Ser Asp Val Ser
    450                 455                 460

Ser Ser Ala Leu Thr Ala Ser Val Lys Asp Glu Ile Ser Gly Glu Leu
465                 470                 475                 480

Ala Ala Ser Ser Gly Val Ser Thr Pro Gly Ser Ala Gly His Asp Ile
                485                 490                 495

Ile Thr Glu Gln Pro Arg Ser Gln His Thr Leu Gln Ala Asp Ser Val
            500                 505                 510

Asp Leu Ala Ser Cys Asp Leu Thr Ser Ser Ala Thr Asp Gly Asp Glu
        515                 520                 525

Glu Asp Ile Leu Ser His Ser Ser Ser Gln Val Ser Ala Val Pro Ser
    530                 535                 540

Asp Pro Ala Met Asp Leu Asn Asp Gly Thr Gln Ala Ser Ser Pro Ile
545                 550                 555                 560

Ser Asp Ser Ser Gln Thr Thr Thr Glu Gly Pro Asp Ser Ala Val Thr
                565                 570                 575

Pro Ser Asp Ser Ser Glu Ile Val Leu Asp Gly Thr Asp Asn Gln Tyr
```

```
            580                 585                 590

Leu Gly Leu Gln Ile Gly Gln Pro Gln Asp Glu Asp Glu Glu Ala Thr
        595                 600                 605

Gly Ile Leu Pro Asp Glu Ala Ser Glu Ala Phe Arg Asn Ser Ser Met
    610                 615                 620

Ala Leu Gln Gln Ala His Leu Leu Lys Asn Met Ser His Cys Arg Gln
625                 630                 635                 640

Pro Ser Asp Ser Ser Val Asp Lys Phe Val Leu Arg Asp Glu Ala Thr
                645                 650                 655

Glu Pro Gly Asp Gln Glu Asn Lys Pro Cys Arg Ile Lys Gly Asp Ile
            660                 665                 670

Gly Gln Ser Thr Asp Asp Asp Ser Ala Pro Leu Val His Cys Val Arg
        675                 680                 685

Leu Leu Ser Ala Ser Phe Leu Leu Thr Gly Gly Lys Asn Val Leu Val
    690                 695                 700

Pro Asp Arg Asp Val Arg Val Ser Val Lys Ala Leu Ala Leu Ser Cys
705                 710                 715                 720

Val Gly Ala Ala Val Ala Leu His Pro Glu Ser Phe Phe Ser Lys Leu
                725                 730                 735

Tyr Lys Val Pro Leu Asp Thr Thr Glu Tyr Pro Glu Glu Gln Tyr Val
            740                 745                 750

Ser Asp Ile Leu Asn Tyr Ile Asp His Gly Asp Pro Gln Val Arg Gly
        755                 760                 765

Ala Thr Ala Ile Leu Cys Gly Thr Leu Ile Cys Ser Ile Leu Ser Arg
    770                 775                 780

Ser Arg Phe His Val Gly Asp Trp Met Gly Thr Ile Arg Thr Leu Thr
785                 790                 795                 800

Gly Asn Thr Phe Ser Leu Ala Asp Cys Ile Pro Leu Leu Arg Lys Thr
                805                 810                 815

Leu Lys Asp Glu Ser Ser Val Thr Cys Lys Leu Ala Cys Thr Ala Val
            820                 825                 830

Arg Asn Cys Val Met Ser Leu Cys Ser Ser Ser Tyr Ser Glu Leu Gly
        835                 840                 845

Leu Gln Leu Ile Ile Asp Val Leu Thr Leu Arg Asn Ser Ser Tyr Trp
    850                 855                 860

Leu Val Arg Thr Glu Leu Leu Glu Thr Leu Ala Glu Ile Asp Phe Arg
865                 870                 875                 880

Leu Val Ser Phe Leu Glu Ala Lys Ala Glu Asn Leu His Arg Gly Ala
                885                 890                 895

His His Tyr Thr Gly Leu Leu Lys Leu Gln Glu Arg Val Leu Asn Asn
            900                 905                 910

Val Val Ile His Leu Leu Gly Asp Glu Asp Pro Arg Val Arg His Val
        915                 920                 925

Ala Ala Ala Ser Leu Ile Arg Leu Val Pro Lys Leu Phe Tyr Lys Cys
    930                 935                 940

Asp Gln Gly Gln Ala Asp Pro Val Val Ala Val Ala Arg Asp Gln Ser
945                 950                 955                 960

Ser Val Tyr Leu Lys Leu Leu Met His Glu Thr Gln Pro Pro Ser His
                965                 970                 975

Phe Ser Val Ser Thr Ile Thr Arg Ile Tyr Arg Gly Tyr Asn Leu Leu
            980                 985                 990

Pro Ser Ile Thr Asp Val Thr Met  Glu Asn Asn Leu Ser  Arg Val Ile
        995                 1000                1005
```

```
Ala Ala  Val Ser His Glu Leu  Ile Thr Ser Thr Thr  Arg Ala Leu
    1010                 1015                 1020

Thr Phe  Gly Cys Cys Glu Ala  Leu Cys Leu Leu Ser  Thr Ala Phe
    1025                 1030                 1035

Pro Val  Cys Ile Trp Ser Leu  Gly Trp His Cys Gly  Val Pro Pro
    1040                 1045                 1050

Leu Ser  Ala Ser Asp Glu Ser  Arg Lys Ser Cys Thr  Val Gly Met
    1055                 1060                 1065

Ala Thr  Met Ile Leu Thr Leu  Leu Ser Ser Ala Trp  Phe Pro Leu
    1070                 1075                 1080

Asp Leu  Ser Ala His Gln Asp  Ala Leu Ile Leu Ala  Gly Asn Leu
    1085                 1090                 1095

Leu Ala  Ala Ser Ala Pro Lys  Ser Leu Arg Ser Ser  Trp Ala Ser
    1100                 1105                 1110

Glu Glu  Glu Ala Asn Pro Ala  Ala Thr Lys Gln Glu  Glu Val Trp
    1115                 1120                 1125

Pro Ala  Leu Gly Asp Arg Ala  Leu Val Pro Met Val  Glu Gln Leu
    1130                 1135                 1140

Phe Ser  His Leu Leu Lys Val  Ile Asn Ile Cys Ala  His Val Leu
    1145                 1150                 1155

Asp Asp  Val Ala Pro Gly Pro  Ala Ile Lys Ala Ala  Leu Pro Ser
    1160                 1165                 1170

Leu Thr  Asn Pro Pro Ser Leu  Ser Pro Ile Arg Arg  Lys Gly Lys
    1175                 1180                 1185

Glu Lys  Glu Pro Gly Glu Gln  Ala Ser Val Pro Leu  Ser Pro Lys
    1190                 1195                 1200

Lys Gly  Ser Glu Ala Ser Ala  Ala Ser Arg Gln Ser  Asp Thr Ser
    1205                 1210                 1215

Gly Pro  Val Thr Thr Ser Lys  Ser Ser Ser Leu Gly  Ser Phe Tyr
    1220                 1225                 1230

His Leu  Pro Ser Tyr Leu Lys  Leu His Asp Val Leu  Lys Ala Thr
    1235                 1240                 1245

His Ala  Asn Tyr Lys Val Thr  Leu Asp Leu Gln Asn  Ser Thr Glu
    1250                 1255                 1260

Lys Phe  Gly Gly Phe Leu Arg  Ser Ala Leu Asp Val  Leu Ser Gln
    1265                 1270                 1275

Ile Leu  Glu Leu Ala Thr Leu  Gln Asp Ile Gly Lys  Cys Val Glu
    1280                 1285                 1290

Glu Ile  Leu Gly Tyr Leu Lys  Ser Cys Phe Ser Arg  Glu Pro Met
    1295                 1300                 1305

Met Ala  Thr Val Cys Val Gln  Gln Leu Leu Lys Thr  Leu Phe Gly
    1310                 1315                 1320

Thr Asn  Leu Ala Ser Gln Phe  Asp Gly Leu Ser Ser  Asn Pro Ser
    1325                 1330                 1335

Lys Ser  Gln Gly Arg Ala Gln  Arg Leu Gly Ser Ser  Ser Val Arg
    1340                 1345                 1350

Pro Gly  Leu Tyr His Tyr Cys  Phe Met Ala Pro Tyr  Thr His Phe
    1355                 1360                 1365

Thr Gln  Ala Leu Ala Asp Ala  Ser Leu Arg Asn Met  Val Gln Ala
    1370                 1375                 1380

Glu Gln  Glu Asn Asp Thr Ser  Gly Trp Phe Asp Val  Leu Gln Lys
    1385                 1390                 1395

Val Ser  Thr Gln Leu Lys Thr  Asn Leu Thr Ser Val  Thr Lys Asn
    1400                 1405                 1410
```

-continued

```
Arg Ala  Asp Lys Asn Ala Ile  His Asn His Ile Arg  Leu Phe Glu
    1415                 1420                 1425

Pro Leu  Val Ile Lys Ala Leu  Lys Gln Tyr Thr Thr  Thr Thr Cys
    1430                 1435                 1440

Val Gln  Leu Gln Lys Gln Val  Leu Asp Leu Leu Ala  Gln Leu Val
    1445                 1450                 1455

Gln Leu  Arg Val Asn Tyr Cys  Leu Leu Asp Ser Asp  Gln Val Phe
    1460                 1465                 1470

Ile Gly  Phe Val Leu Lys Gln  Phe Glu Tyr Ile Glu  Val Gly Gln
    1475                 1480                 1485

Phe Arg  Glu Ser Glu Ala Ile  Ile Pro Asn Ile Phe  Phe Phe Leu
    1490                 1495                 1500

Val Leu  Leu Ser Tyr Glu Arg  Tyr His Ser Lys Gln  Ile Ile Gly
    1505                 1510                 1515

Ile Pro  Lys Ile Ile Gln Leu  Cys Asp Gly Ile Met  Ala Ser Gly
    1520                 1525                 1530

Arg Lys  Ala Val Thr His Ala  Ile Pro Ala Leu Gln  Pro Ile Val
    1535                 1540                 1545

His Asp  Leu Phe Val Leu Arg  Gly Thr Asn Lys Ala  Asp Ala Gly
    1550                 1555                 1560

Lys Glu  Leu Glu Thr Gln Lys  Glu Val Val Val Ser  Met Leu Leu
    1565                 1570                 1575

Arg Leu  Ile Gln Tyr His Gln  Val Leu Glu Met Phe  Ile Leu Val
    1580                 1585                 1590

Leu Gln  Gln Cys His Lys Glu  Asn Glu Asp Lys Trp  Lys Arg Leu
    1595                 1600                 1605

Ser Arg  Gln Ile Ala Asp Ile  Ile Leu Pro Met Leu  Ala Lys Gln
    1610                 1615                 1620

Gln Met  His Ile Asp Ser His  Glu Ala Leu Gly Val  Leu Asn Thr
    1625                 1630                 1635

Leu Phe  Glu Ile Leu Ala Pro  Ser Ser Leu Arg Pro  Val Asp Met
    1640                 1645                 1650

Leu Leu  Arg Ser Met Phe Val  Thr Pro Asn Thr Met  Ala Ser Val
    1655                 1660                 1665

Ser Thr  Val Gln Leu Trp Ile  Ser Gly Ile Leu Ala  Ile Leu Arg
    1670                 1675                 1680

Val Leu  Ile Ser Gln Ser Thr  Glu Asp Ile Val Leu  Ser Arg Ile
    1685                 1690                 1695

Gln Glu  Leu Ser Phe Ser Pro  Tyr Leu Ile Ser Cys  Thr Val Ile
    1700                 1705                 1710

Asn Arg  Leu Arg Asp Gly Asp  Ser Thr Ser Thr Leu  Glu Glu His
    1715                 1720                 1725

Ser Glu  Gly Lys Gln Ile Lys  Asn Leu Pro Glu Glu  Thr Phe Ser
    1730                 1735                 1740

Arg Phe  Leu Leu Gln Leu Val  Gly Ile Leu Leu Glu  Asp Ile Val
    1745                 1750                 1755

Thr Lys  Gln Leu Lys Val Glu  Met Ser Glu Gln Gln  His Thr Phe
    1760                 1765                 1770

Tyr Cys  Gln Glu Leu Gly Thr  Leu Leu Met Cys Leu  Ile His Ile
    1775                 1780                 1785

Phe Lys  Ser Gly Met Phe Arg  Arg Ile Thr Ala Ala  Ala Thr Arg
    1790                 1795                 1800

Leu Phe  Arg Ser Asp Gly Cys  Gly Gly Ser Phe Tyr  Thr Leu Asp
```

```
    1805                1810                1815

Ser Leu  Asn Leu Arg Ala Arg  Ser Met Ile Thr Thr  His Pro Ala
    1820                1825                1830

Leu Val  Leu Leu Trp Cys Gln  Ile Leu Leu Leu Val  Asn His Thr
    1835                1840                1845

Asp Tyr  Arg Trp Trp Ala Glu  Val Gln Gln Thr Pro  Lys Arg His
    1850                1855                1860

Ser Leu  Ser Ser Thr Lys Leu  Leu Ser Pro Gln Met  Ser Gly Glu
    1865                1870                1875

Glu Glu  Asp Ser Asp Leu Ala  Ala Lys Leu Gly Met  Cys Asn Arg
    1880                1885                1890

Glu Ile  Val Arg Arg Gly Ala  Leu Ile Leu Phe Cys  Asp Tyr Val
    1895                1900                1905

Cys Gln  Asn Leu His Asp Ser  Glu His Leu Thr Trp  Leu Ile Val
    1910                1915                1920

Asn His  Ile Gln Asp Leu Ile  Ser Leu Ser His Glu  Pro Pro Val
    1925                1930                1935

Gln Asp  Phe Ile Ser Ala Val  His Arg Asn Ser Ala  Ala Ser Gly
    1940                1945                1950

Leu Phe  Ile Gln Ala Ile Gln  Ser Arg Cys Glu Asn  Leu Ser Thr
    1955                1960                1965

Pro Thr  Met Leu Lys Lys Thr  Leu Gln Cys Leu Glu  Gly Ile His
    1970                1975                1980

Leu Ser  Gln Ser Gly Ala Val  Leu Thr Leu Tyr Val  Asp Arg Leu
    1985                1990                1995

Leu Cys  Thr Pro Phe Arg Val  Leu Ala Arg Met Val  Asp Ile Leu
    2000                2005                2010

Ala Cys  Arg Arg Val Glu Met  Leu Leu Ala Ala Asn  Leu Gln Ser
    2015                2020                2025

Ser Met  Ala Gln Leu Pro Met  Glu Glu Leu Asn Arg  Ile Gln Glu
    2030                2035                2040

Tyr Leu  Gln Ser Ser Gly Leu  Ala Gln Arg His Gln  Arg Leu Tyr
    2045                2050                2055

Ser Leu  Leu Asp Arg Phe Arg  Leu Ser Thr Met Gln  Asp Ser Leu
    2060                2065                2070

Ser Pro  Ser Pro Pro Val Ser  Ser His Pro Leu Asp  Gly Asp Gly
    2075                2080                2085

His Val  Ser Leu Glu Thr Val  Ser Pro Asp Lys Asp  Trp Tyr Val
    2090                2095                2100

His Leu  Val Lys Ser Gln Cys  Trp Thr Arg Ser Asp  Ser Ala Leu
    2105                2110                2115

Leu Glu  Gly Ala Glu Leu Val  Asn Arg Ile Pro Ala  Glu Asp Met
    2120                2125                2130

Asn Ala  Phe Met Met Asn Ser  Glu Phe Asn Leu Ser  Leu Leu Ala
    2135                2140                2145

Pro Cys  Leu Ser Leu Gly Met  Ser Glu Ile Ser Gly  Gly Gln Lys
    2150                2155                2160

Ser Ala  Leu Phe Glu Ala Ala  Arg Glu Val Thr Leu  Ala Arg Val
    2165                2170                2175

Ser Gly  Thr Val Gln Gln Leu  Pro Ala Val His His  Val Phe Gln
    2180                2185                2190

Pro Glu  Leu Pro Ala Glu Pro  Ala Ala Tyr Trp Ser  Lys Leu Asn
    2195                2200                2205
```

```
Asp Leu  Phe Gly Asp Ala Ala  Leu Tyr Gln Ser Leu  Pro Thr Leu
    2210                 2215                 2220

Ala Arg  Ala Leu Ala Gln Tyr  Leu Val Val Val Ser  Lys Leu Pro
    2225                 2230                 2235

Ser His  Leu His Leu Pro Pro  Glu Lys Glu Lys Asp  Ile Val Lys
    2240                 2245                 2250

Phe Val  Val Ala Thr Leu Glu  Ala Leu Ser Trp His  Leu Ile His
    2255                 2260                 2265

Glu Gln  Ile Pro Leu Ser Leu  Asp Leu Gln Ala Gly  Leu Asp Cys
    2270                 2275                 2280

Cys Cys  Leu Ala Leu Gln Leu  Pro Gly Leu Trp Ser  Val Val Ser
    2285                 2290                 2295

Ser Thr  Glu Phe Val Thr His  Ala Cys Ser Leu Ile  Tyr Cys Val
    2300                 2305                 2310

His Phe  Ile Leu Glu Ala Val  Ala Val Gln Pro Gly  Glu Gln Leu
    2315                 2320                 2325

Leu Ser  Pro Glu Arg Arg Thr  Asn Thr Pro Lys Ala  Ile Ser Glu
    2330                 2335                 2340

Glu Glu  Glu Glu Val Asp Pro  Asn Thr Gln Asn Pro  Lys Tyr Ile
    2345                 2350                 2355

Thr Ala  Ala Cys Glu Met Val  Ala Glu Met Val Glu  Ser Leu Gln
    2360                 2365                 2370

Ser Val  Leu Ala Leu Gly His  Lys Arg Asn Ser Gly  Val Pro Ala
    2375                 2380                 2385

Phe Leu  Thr Pro Leu Leu Arg  Asn Ile Ile Ile Ser  Leu Ala Arg
    2390                 2395                 2400

Leu Pro  Leu Val Asn Ser Tyr  Thr Arg Val Pro Pro  Leu Val Trp
    2405                 2410                 2415

Lys Leu  Gly Trp Ser Pro Lys  Pro Gly Gly Asp Phe  Gly Thr Ala
    2420                 2425                 2430

Phe Pro  Glu Ile Pro Val Glu  Phe Leu Gln Glu Lys  Glu Val Phe
    2435                 2440                 2445

Lys Glu  Phe Ile Tyr Arg Ile  Asn Thr Leu Gly Trp  Thr Ser Arg
    2450                 2455                 2460

Thr Gln  Phe Glu Glu Thr Trp  Ala Thr Leu Leu Gly  Val Leu Val
    2465                 2470                 2475

Thr Gln  Pro Leu Val Met Glu  Gln Glu Glu Ser Pro  Pro Glu Glu
    2480                 2485                 2490

Asp Thr  Glu Arg Thr Gln Ile  Asn Val Leu Ala Val  Gln Ala Ile
    2495                 2500                 2505

Thr Ser  Leu Val Leu Ser Ala  Met Thr Val Pro Val  Ala Gly Asn
    2510                 2515                 2520

Pro Ala  Val Ser Cys Leu Glu  Gln Gln Pro Arg Asn  Lys Pro Leu
    2525                 2530                 2535

Lys Ala  Leu Asp Thr Arg Phe  Gly Arg Lys Leu Ser  Ile Ile Arg
    2540                 2545                 2550

Gly Ile  Val Glu Gln Glu Ile  Gln Ala Met Val Ser  Lys Arg Glu
    2555                 2560                 2565

Asn Ile  Ala Thr His His Leu  Tyr Gln Ala Trp Asp  Pro Val Pro
    2570                 2575                 2580

Ser Leu  Ser Pro Ala Thr Thr  Gly Ala Leu Ile Ser  His Glu Lys
    2585                 2590                 2595

Leu Leu  Leu Gln Ile Asn Pro  Glu Arg Glu Leu Gly  Ser Met Ser
    2600                 2605                 2610
```

```
Tyr Lys  Leu Gly Gln Val Ser  Ile His Ser Val Trp  Leu Gly Asn
    2615                 2620                 2625

Ser Ile  Thr Pro Leu Arg Glu  Glu Glu Trp Asp Glu  Glu Glu Glu
    2630                 2635                 2640

Glu Glu  Ala Asp Ala Pro Ala  Pro Ser Ser Pro Pro  Thr Ser Pro
    2645                 2650                 2655

Val Asn  Ser Arg Lys His Arg  Ala Gly Val Asp Ile  His Ser Cys
    2660                 2665                 2670

Ser Gln  Phe Leu Leu Glu Leu  Tyr Ser Arg Trp Ile  Leu Pro Ser
    2675                 2680                 2685

Ser Ser  Ala Arg Arg Thr Pro  Ala Ile Leu Ile Ser  Glu Val Val
    2690                 2695                 2700

Arg Ser  Leu Leu Val Val Ser  Asp Leu Phe Thr Glu  Arg Asn Gln
    2705                 2710                 2715

Phe Glu  Leu Met Tyr Val Thr  Leu Thr Glu Leu Arg  Arg Val His
    2720                 2725                 2730

Pro Ser  Glu Asp Glu Ile Leu  Ala Gln Tyr Leu Val  Pro Ala Thr
    2735                 2740                 2745

Cys Lys  Ala Ala Ala Val Leu  Gly Met Asp Lys Ala  Val Ala Glu
    2750                 2755                 2760

Pro Val  Ser Arg Leu Leu Glu  Ser Thr Leu Arg Ser  Ser His Leu
    2765                 2770                 2775

Pro Ser  Arg Val Gly Ala Leu  His Gly Val Leu Tyr  Val Leu Glu
    2780                 2785                 2790

Cys Asp  Leu Leu Asp Asp Thr  Ala Lys Gln Leu Ile  Pro Val Ile
    2795                 2800                 2805

Ser Asp  Tyr Leu Leu Ser Asn  Leu Lys Gly Ile Ala  His Cys Val
    2810                 2815                 2820

Asn Ile  His Ser Gln Gln His  Val Leu Val Met Cys  Ala Thr Ala
    2825                 2830                 2835

Phe Tyr  Leu Ile Glu Asn Tyr  Pro Leu Asp Val Gly  Pro Glu Phe
    2840                 2845                 2850

Ser Ala  Ser Ile Ile Gln Met  Cys Gly Val Met Leu  Ser Gly Ser
    2855                 2860                 2865

Glu Glu  Ser Thr Pro Ser Ile  Ile Tyr His Cys Ala  Leu Arg Gly
    2870                 2875                 2880

Leu Glu  Arg Leu Leu Leu Ser  Glu Gln Leu Ser Arg  Leu Asp Ala
    2885                 2890                 2895

Glu Ser  Leu Val Lys Leu Ser  Val Asp Arg Val Asn  Val His Ser
    2900                 2905                 2910

Pro His  Arg Ala Met Ala Ala  Leu Gly Leu Met Leu  Thr Cys Met
    2915                 2920                 2925

Tyr Thr  Gly Lys Glu Lys Val  Ser Pro Gly Arg Thr  Ser Asp Pro
    2930                 2935                 2940

Asn Pro  Ala Ala Pro Asp Ser  Glu Ser Val Ile Val  Ala Met Glu
    2945                 2950                 2955

Arg Val  Ser Val Leu Phe Asp  Arg Ile Arg Lys Gly  Phe Pro Cys
    2960                 2965                 2970

Glu Ala  Arg Val Val Ala Arg  Ile Leu Pro Gln Phe  Leu Asp Asp
    2975                 2980                 2985

Phe Phe  Pro Pro Gln Asp Ile  Met Asn Lys Val Ile  Gly Glu Phe
    2990                 2995                 3000

Leu Ser  Asn Gln Gln Pro Tyr  Pro Gln Phe Met Ala  Thr Val Val
```

```
    3005                3010                3015

Tyr Lys  Val Phe Gln Thr Leu  His Ser Thr Gly Gln  Ser Ser Met
    3020                3025                3030

Val Arg  Asp Trp Val Met Leu  Ser Leu Ser Asn Phe  Thr Gln Arg
    3035                3040                3045

Ala Pro  Val Ala Met Ala Thr  Trp Ser Leu Ser Cys  Phe Phe Val
    3050                3055                3060

Ser Ala  Ser Thr Ser Pro Trp  Val Ala Ala Ile Leu  Pro His Val
    3065                3070                3075

Ile Ser  Arg Met Gly Lys Leu  Glu Gln Val Asp Val  Asn Leu Phe
    3080                3085                3090

Cys Leu  Val Ala Thr Asp Phe  Tyr Arg His Gln Ile  Glu Glu Glu
    3095                3100                3105

Leu Asp  Arg Arg Ala Phe Gln  Ser Val Leu Glu Val  Val Ala Ala
    3110                3115                3120

Pro Gly  Ser Pro Tyr His Arg  Leu Leu Thr Cys Leu  Arg Asn Val
    3125                3130                3135

His Lys  Val Thr Thr Cys
    3140


<210> SEQ ID NO 58
<211> LENGTH: 3307
<212> TYPE: DNA
<213> ORGANISM: Homo Sapiens

<400> SEQUENCE: 58

caccttctgc actgctcatc tgggcagagg aagcttcaga aagctgccaa ggcaccatct     60

ccaggaactc ccagcacgca gaatccatct gagaatatgc tgccacaaat accctttttg    120

ctgctagtat ccttgaactt ggttcatgga gtgttttacg ctgaacgata ccaaatgccc    180

acaggcataa aaggcccact acccaacacc aagacacagt tcttcattcc ctacaccata    240

aagagtaaag gtatagcagt aagaggagag caaggtactc ctggtccacc aggccctgct    300

ggacctcgag ggcacccagg tccttctgga ccaccaggaa aaccaggcta cggaagtcct    360

ggactccaag gagagccagg gttgccagga ccaccgggac catcagctgt agggaaacca    420

ggtgtgccag gactcccagg aaaaccagga gagagaggac catatggacc aaaaggagat    480

gttggaccag ctggcctacc aggaccccgg ggcccaccag gaccacctgg aatccctgga    540

ccggctggaa tttctgtgcc aggaaaacct ggacaacagg gacccacagg agccccagga    600

cccaggggct ttcctggaga aaagggtgca ccaggagtcc ctggtatgaa tggacagaaa    660

ggggaaatgg gatatggtgc tcctggtcgt ccaggtgaga ggggtcttcc aggccctcag    720

ggtcccacag gaccatctgg ccctcctgga gtgggaaaaa gaggtgaaaa tggggttcca    780

ggacagccag gcatcaaagg tgatagaggt tttccgggag aaatgggacc aattggccca    840

ccaggtcccc aaggccctcc tggggaacga gggccagaag gcattggaaa gccaggagct    900

gctggagccc caggccagcc agggattcca ggaacaaaag gtctccctgg ggctccagga    960

atagctgggc ccccagggcc tcctggcttt gggaaaccag gcttgccagg cctgaaggga   1020

gaaagaggac ctgctggcct tcctgggggt ccaggtgcca aaggggaaca agggccagca   1080

ggtcttcctg ggaagccagg tctgactgga ccccctggga atatgggacc ccaaggacca   1140

aaaggcatcc cgggtagcca tggtctccca ggccctaaag gtgagacagg gccagctggg   1200

cctgcaggat accctggggc taagggtgaa aggggttccc ctgggtcaga tggaaaacca   1260

gggtacccag gaaaaccagg tctcgatggt cctaagggta acccagggtt accaggtcca   1320
```

```
aaaggtgatc ctggagttgg aggacctcct ggtctcccag gccctgtggg cccagcagga   1380
gcaaagggaa tgcccggaca caatggagag gctggcccaa gaggtgcccc tggaatacca   1440
ggtactagag gccctattgg gccaccaggc attccaggat tccctgggtc taaaggggat   1500
ccaggaagtc ccggtcctcc tggcccagct ggcatagcaa ctaagggcct caatggaccc   1560
accgggccac cagggcctcc aggtccaaga ggccactctg gagagcctgg tcttccaggg   1620
ccccctgggc ctccaggccc accaggtcaa gcagtcatgc ctgagggttt tataaaggca   1680
ggccaaaggc ccagtctttc tggggacccct cttgttagtg ccaaccaggg ggtaacagga   1740
atgcctgtgt ctgcttttac tgttattctc tccaaagctt acccagcaat aggaactccc   1800
ataccatttg ataaaatttt gtataacagg caacagcatt atgacccaag gactggaatc   1860
tttacttgtc agataccagg aatatactat ttttcatacc acgtgcatgt gaaagggact   1920
catgtttggg taggcctgta taagaatggc acccctgtaa tgtacaccta tgatgaatac   1980
accaaaggct acctggatca ggcttcaggg agtgccatca tcgatctcac agaaaatgac   2040
caggtgtggc tccagcttcc caatgccgag tcaaatggcc tatactcctc tgagtatgtc   2100
cactcctctt tctcaggatt cctagtggct ccaatgtgag tacacacaga gctaatctaa   2160
atcttgtgct agaaaaagca ttctctaact ctaccccacc ctacaaaatg catatggagg   2220
taggctgaaa agaatgtaat tttattttc tgaaatacag atttgagcta tcagaccaac   2280
aaaccttccc cctgaaaagt gagcagcaac gtaaaaacgt atgtgaagcc tctcttgaat   2340
ttctagttag caatcttaag gctctttaag gttttctcca atattaaaaa atatcaccaa   2400
agaagtcctg ctatgttaaa aacaaacaac aaaaaacaaa caacaaaaaa aaaattaaaa   2460
aaaaaaacag aaatagagct ctaagttatg tgaaatttga tttgagaaac tcggcatttc   2520
ctttttaaaa aagcctgttt ctaactatga atatgagaac ttctaggaaa catccaggag   2580
gtatcatata actttgtaga acttaaatac ttgaatattc aaatttaaaa gacactgtat   2640
cccctaaaat atttctgatg gtgcactact ctgaggcctg tatggcccct ttcatcaata   2700
tctattcaaa tatacaggtg catatatact tgttaaagct cttatataaa aaagccccaa   2760
aatattgaag ttcatctgaa atgcaaggtg ctttcatcaa tgaacctttt caaacttttc   2820
tatgattgca gagaagcttt ttatataccc agcataactt ggaaacaggt atctgaccta   2880
ttcttattta gttaacacaa gtgtgattaa tttgatttct ttaattcctt attgaatctt   2940
atgtgatatg attttctgga tttacagaac attagcacat gtaccttgtg cctcccattc   3000
aagtgaagtt ataatttaca ctgagggttt caaaattcga ctagaagtgg agatatatta   3060
tttatttatg cactgtactg tatttttata ttgctgttta aaacttttaa gctgtgcctc   3120
acttattaaa gcacaaaatg ttttacctac tccttattta cgacgcaata aaataacatc   3180
aatagatttt taggctgaat taatttgaaa gcagcaattt gctgttctca accattcttt   3240
caaggctttt cattgttcaa agttaataaa aaagtaggac aataaagtga aaaaaaaaaa   3300
aaaaaaa                                                             3307
```

<210> SEQ ID NO 59
<211> LENGTH: 680
<212> TYPE: PRT
<213> ORGANISM: Homo Sapiens

<400> SEQUENCE: 59

```
Met Leu Pro Gln Ile Pro Phe Leu Leu Leu Val Ser Leu Asn Leu Val
1               5                   10                  15
```

-continued

```
His Gly Val Phe Tyr Ala Glu Arg Tyr Gln Met Pro Thr Gly Ile Lys
            20                  25                  30

Gly Pro Leu Pro Asn Thr Lys Thr Gln Phe Phe Ile Pro Tyr Thr Ile
        35                  40                  45

Lys Ser Lys Gly Ile Ala Val Arg Gly Glu Gln Gly Thr Pro Gly Pro
    50                  55                  60

Pro Gly Pro Ala Gly Pro Arg Gly His Pro Gly Pro Ser Gly Pro Pro
65                  70                  75                  80

Gly Lys Pro Gly Tyr Gly Ser Pro Gly Leu Gln Gly Glu Pro Gly Leu
                85                  90                  95

Pro Gly Pro Pro Gly Pro Ser Ala Val Gly Lys Pro Gly Val Pro Gly
            100                 105                 110

Leu Pro Gly Lys Pro Gly Glu Arg Gly Pro Tyr Gly Pro Lys Gly Asp
        115                 120                 125

Val Gly Pro Ala Gly Leu Pro Gly Pro Arg Gly Pro Pro Gly Pro Pro
    130                 135                 140

Gly Ile Pro Gly Pro Ala Gly Ile Ser Val Pro Gly Lys Pro Gly Gln
145                 150                 155                 160

Gln Gly Pro Thr Gly Ala Pro Gly Pro Arg Gly Phe Pro Gly Glu Lys
                165                 170                 175

Gly Ala Pro Gly Val Pro Gly Met Asn Gly Gln Lys Gly Glu Met Gly
            180                 185                 190

Tyr Gly Ala Pro Gly Arg Pro Gly Glu Arg Gly Leu Pro Gly Pro Gln
        195                 200                 205

Gly Pro Thr Gly Pro Ser Gly Pro Pro Gly Val Gly Lys Arg Gly Glu
    210                 215                 220

Asn Gly Val Pro Gly Gln Pro Gly Ile Lys Gly Asp Arg Gly Phe Pro
225                 230                 235                 240

Gly Glu Met Gly Pro Ile Gly Pro Pro Gly Pro Gln Gly Pro Pro Gly
                245                 250                 255

Glu Arg Gly Pro Glu Gly Ile Gly Lys Pro Gly Ala Ala Gly Ala Pro
            260                 265                 270

Gly Gln Pro Gly Ile Pro Gly Thr Lys Gly Leu Pro Gly Ala Pro Gly
        275                 280                 285

Ile Ala Gly Pro Pro Gly Pro Pro Gly Phe Gly Lys Pro Gly Leu Pro
    290                 295                 300

Gly Leu Lys Gly Glu Arg Gly Pro Ala Gly Leu Pro Gly Gly Pro Gly
305                 310                 315                 320

Ala Lys Gly Glu Gln Gly Pro Ala Gly Leu Pro Gly Lys Pro Gly Leu
                325                 330                 335

Thr Gly Pro Pro Gly Asn Met Gly Pro Gln Gly Pro Lys Gly Ile Pro
            340                 345                 350

Gly Ser His Gly Leu Pro Gly Pro Lys Gly Glu Thr Gly Pro Ala Gly
        355                 360                 365

Pro Ala Gly Tyr Pro Gly Ala Lys Gly Glu Arg Gly Ser Pro Gly Ser
    370                 375                 380

Asp Gly Lys Pro Gly Tyr Pro Gly Lys Pro Gly Leu Asp Gly Pro Lys
385                 390                 395                 400

Gly Asn Pro Gly Leu Pro Gly Pro Lys Gly Asp Pro Gly Val Gly Gly
                405                 410                 415

Pro Pro Gly Leu Pro Gly Pro Val Gly Pro Ala Gly Ala Lys Gly Met
            420                 425                 430

Pro Gly His Asn Gly Glu Ala Gly Pro Arg Gly Ala Pro Gly Ile Pro
        435                 440                 445
```

```
Gly Thr Arg Gly Pro Ile Gly Pro Pro Gly Ile Pro Gly Phe Pro Gly
    450                 455                 460

Ser Lys Gly Asp Pro Gly Ser Pro Gly Pro Pro Gly Pro Ala Gly Ile
465                 470                 475                 480

Ala Thr Lys Gly Leu Asn Gly Pro Thr Gly Pro Pro Gly Pro Pro Gly
                485                 490                 495

Pro Arg Gly His Ser Gly Glu Pro Gly Leu Pro Gly Pro Pro Gly Pro
            500                 505                 510

Pro Gly Pro Pro Gly Gln Ala Val Met Pro Glu Gly Phe Ile Lys Ala
        515                 520                 525

Gly Gln Arg Pro Ser Leu Ser Gly Thr Pro Leu Val Ser Ala Asn Gln
    530                 535                 540

Gly Val Thr Gly Met Pro Val Ser Ala Phe Thr Val Ile Leu Ser Lys
545                 550                 555                 560

Ala Tyr Pro Ala Ile Gly Thr Pro Ile Pro Phe Asp Lys Ile Leu Tyr
                565                 570                 575

Asn Arg Gln Gln His Tyr Asp Pro Arg Thr Gly Ile Phe Thr Cys Gln
            580                 585                 590

Ile Pro Gly Ile Tyr Tyr Phe Ser Tyr His Val His Val Lys Gly Thr
        595                 600                 605

His Val Trp Val Gly Leu Tyr Lys Asn Gly Thr Pro Val Met Tyr Thr
    610                 615                 620

Tyr Asp Glu Tyr Thr Lys Gly Tyr Leu Asp Gln Ala Ser Gly Ser Ala
625                 630                 635                 640

Ile Ile Asp Leu Thr Glu Asn Asp Gln Val Trp Leu Gln Leu Pro Asn
                645                 650                 655

Ala Glu Ser Asn Gly Leu Tyr Ser Ser Glu Tyr Val His Ser Ser Phe
            660                 665                 670

Ser Gly Phe Leu Val Ala Pro Met
        675                 680


<210> SEQ ID NO 60
<211> LENGTH: 2125
<212> TYPE: DNA
<213> ORGANISM: Porcine

<400> SEQUENCE: 60

accttctgca ttgctcccct gggcacagag gaggacacag tgagctggta ggacaccaac      60

tccaggagct cccaacatcc agaatccatc tgcaaacatg ctgccacaaa cagccctttt     120

gctgctgcta ttgtccttga acttggttca tggagtgttt tatactgagc aataccaaac     180

acctacaggc ataaaaggcc caccatccaa caccaaggca cagttcttca tcccctacgc     240

cataaagagt aaaggtatat cactaagagg agagcaaggt attcccggtc caccaggccc     300

cgctggacca cgagggcacc caggtccatc tggaccccca ggaaaaccag gcttcggaag     360

ccctggaccc caaggacagc cagggctgcc aggaccacca ggaccatcag ccactgggaa     420

gccaggtttg ccaggacccc aaggaaaacc aggggagaga ggaccatatg gaccaaaagg     480

agatatggga ccggctggtt taccaggacc acggggccca ccagggccac ctggtatccc     540

cggcccggct ggaatttctg ttacaggaaa acctggacaa cagggacctg caggagcccc     600

aggacccagg ggctttcctg gagaaaaggg tgcaccagga gtccctggta tcaatggaca     660

gaaaggggaa acgggatatg gtgctcctgg ccgcccaggt gacaggggcc ttccaggccc     720

ccagggccca atgggaccac ctggccctcc tggagtggga aagagagggg aaaatgggtt     780
```

```
tcccggacaa ccaggcatca aaggtgatcg ggctttcca ggagaaagtg gaccggctgg    840

tccaccaggc ccccaaggtc ctcctgggga acaaggacga gaaggcattg gaaagccagg    900

agctcctgga gccgcaggcc agccagggct tccagggaca aaaggtcacc ccggggctcc    960

aggaatggct gggcctccag gggctcctgg ctttgggaaa ccaggcttgc caggcctgaa   1020

gggacaaaga ggtcctatag gccttccagg ggctccaggt gccaaagggg aacaaggccc   1080

ggcaggtcat cctggggaac caggtctgac tggacccccct ggaagtaggg gaccccaagg   1140

accaaaaggc atcccaggca ataacggggt cccaggccct aagggtgaga tagggctggc   1200

tgggcctgca ggattccctg ggctaaggg agaaaggggc cctccgggt tagatggaaa   1260

accagggtac ccaggagaac caggtctcaa tggtcccaag ggtaacccag ggttacccgg   1320

cccaaaaggt gaccctggaa ttggaggacc tcctggtctc ccaggccctg tgggcccagc   1380

aggagctaag ggagtgcctg gacacaatgg tgaggctggg ccaagaggtg cccctggaat   1440

accaggtacc agaggtccca tcgggccacc aggcattcca ggattccctg gctctaaagg   1500

ggatccagga aatccaggtc ctcctggtcc agctggcata gcaactaagg gcctcaatgg   1560

acccactggg ccaccagggc ctccaggacc aaaaggtcat gctggagagc ctggcctccc   1620

agggccccca gggcccccag gccctccagg ccaagcggtc ccacccgaag gctttgtaaa   1680

ggaaggacag agggcttttg ttagtgccaa ccagggagta acaggaatgc ctgtatctgc   1740

cttcactgtg attctctcca aagcttaccc agctataggt gctcccatcc cctttgataa   1800

gattttatat aacgggcaac agcactatga cccaaaaact ggaatcttta cctgcaggat   1860

acctggaatc tattacttct cctaccacat tcacgtgaag gggacccatg cttgggtggg   1920

cctgtataaa aatggcaccc ctgtcatgta cacctatgat gaatatgtca aaggctacct   1980

ggatcaggct tcagggagtg ccatccttga tctcacagat aatgaccagg tatggctcca   2040

gctgcccaac gctgggtcga acgggctgta ctcctctgag tacgtccact cctctttctc   2100

aggattccta gtggctccaa tgtga                                          2125
```

<210> SEQ ID NO 61
<211> LENGTH: 675
<212> TYPE: PRT
<213> ORGANISM: Porcine

<400> SEQUENCE: 61

```
Met Leu Pro Gln Thr Ala Leu Leu Leu Leu Leu Leu Ser Leu Asn Leu
1               5                   10                  15

Val His Gly Val Phe Tyr Thr Glu Gln Tyr Gln Thr Pro Thr Gly Ile
            20                  25                  30

Lys Gly Pro Pro Ser Asn Thr Lys Ala Gln Phe Phe Ile Pro Tyr Ala
        35                  40                  45

Ile Lys Ser Lys Gly Ile Ser Leu Arg Gly Glu Gln Gly Ile Pro Gly
    50                  55                  60

Pro Pro Gly Pro Ala Gly Pro Arg Gly His Pro Gly Pro Ser Gly Pro
65                  70                  75                  80

Pro Gly Lys Pro Gly Phe Gly Ser Pro Gly Pro Gln Gly Gln Pro Gly
                85                  90                  95

Leu Pro Gly Pro Pro Gly Pro Ser Ala Thr Gly Lys Pro Gly Leu Pro
            100                 105                 110

Gly Pro Gln Gly Lys Pro Gly Glu Arg Gly Pro Tyr Gly Pro Lys Gly
        115                 120                 125

Asp Met Gly Pro Ala Gly Leu Pro Gly Pro Arg Gly Pro Pro Gly Pro
    130                 135                 140
```

-continued

```
Pro Gly Ile Pro Gly Pro Ala Gly Ile Ser Val Thr Gly Lys Pro Gly
145                 150                 155                 160

Gln Gln Gly Pro Ala Gly Ala Pro Gly Pro Arg Gly Phe Pro Gly Glu
                165                 170                 175

Lys Gly Ala Pro Gly Val Pro Gly Ile Asn Gly Gln Lys Gly Glu Thr
            180                 185                 190

Gly Tyr Gly Ala Pro Gly Arg Pro Gly Asp Arg Gly Leu Pro Gly Pro
        195                 200                 205

Gln Gly Pro Met Gly Pro Pro Gly Pro Pro Gly Val Gly Lys Arg Gly
    210                 215                 220

Glu Asn Gly Phe Pro Gly Gln Pro Gly Ile Lys Gly Asp Arg Gly Phe
225                 230                 235                 240

Pro Gly Glu Ser Gly Pro Ala Gly Pro Pro Gly Pro Gln Gly Pro Pro
                245                 250                 255

Gly Glu Gln Gly Arg Glu Gly Ile Gly Lys Pro Gly Ala Pro Gly Ala
            260                 265                 270

Ala Gly Gln Pro Gly Leu Pro Gly Thr Lys Gly His Pro Gly Ala Pro
        275                 280                 285

Gly Met Ala Gly Pro Pro Gly Ala Pro Gly Phe Gly Lys Pro Gly Leu
    290                 295                 300

Pro Gly Leu Lys Gly Gln Arg Gly Pro Ile Gly Leu Pro Gly Ala Pro
305                 310                 315                 320

Gly Ala Lys Gly Glu Gln Gly Pro Ala Gly His Pro Gly Glu Pro Gly
                325                 330                 335

Leu Thr Gly Pro Pro Gly Ser Arg Gly Pro Gln Gly Pro Lys Gly Ile
            340                 345                 350

Pro Gly Asn Asn Gly Val Pro Gly Pro Lys Gly Glu Ile Gly Leu Ala
        355                 360                 365

Gly Pro Ala Gly Phe Pro Gly Ala Lys Gly Glu Arg Gly Pro Ser Gly
    370                 375                 380

Leu Asp Gly Lys Pro Gly Tyr Pro Gly Glu Pro Gly Leu Asn Gly Pro
385                 390                 395                 400

Lys Gly Asn Pro Gly Leu Pro Gly Pro Lys Gly Asp Pro Gly Ile Gly
                405                 410                 415

Gly Pro Pro Gly Leu Pro Gly Pro Val Gly Pro Ala Gly Ala Lys Gly
            420                 425                 430

Val Pro Gly His Asn Gly Glu Ala Gly Pro Arg Gly Ala Pro Gly Ile
        435                 440                 445

Pro Gly Thr Arg Gly Pro Ile Gly Pro Pro Gly Ile Pro Gly Phe Pro
    450                 455                 460

Gly Ser Lys Gly Asp Pro Gly Asn Pro Gly Pro Pro Gly Pro Ala Gly
465                 470                 475                 480

Ile Ala Thr Lys Gly Leu Asn Gly Pro Thr Gly Pro Pro Gly Pro Pro
                485                 490                 495

Gly Pro Lys Gly His Ala Gly Glu Pro Gly Leu Pro Gly Pro Pro Gly
            500                 505                 510

Pro Pro Gly Pro Pro Gly Gln Ala Val Pro Pro Glu Gly Phe Val Lys
        515                 520                 525

Glu Gly Gln Arg Ala Phe Val Ser Ala Asn Gln Gly Val Thr Gly Met
    530                 535                 540

Pro Val Ser Ala Phe Thr Val Ile Leu Ser Lys Ala Tyr Pro Ala Ile
545                 550                 555                 560

Gly Ala Pro Ile Pro Phe Asp Lys Ile Leu Tyr Asn Gly Gln Gln His
```

565 570 575

Tyr Asp Pro Lys Thr Gly Ile Phe Thr Cys Arg Ile Pro Gly Ile Tyr
580 585 590

Tyr Phe Ser Tyr His Ile His Val Lys Gly Thr His Ala Trp Val Gly
595 600 605

Leu Tyr Lys Asn Gly Thr Pro Val Met Tyr Thr Tyr Asp Glu Tyr Val
610 615 620

Lys Gly Tyr Leu Asp Gln Ala Ser Gly Ser Ala Ile Leu Asp Leu Thr
625 630 635 640

Asp Asn Asp Gln Val Trp Leu Gln Leu Pro Asn Ala Gly Ser Asn Gly
645 650 655

Leu Tyr Ser Ser Glu Tyr Val His Ser Ser Phe Ser Gly Phe Leu Val
660 665 670

Ala Pro Met
675

<210> SEQ ID NO 62
<211> LENGTH: 19
<212> TYPE: DNA
<213> ORGANISM: Artificial
<220> FEATURE:
<223> OTHER INFORMATION: Primer

<400> SEQUENCE: 62
atggcgacga aggccgtgt 19

<210> SEQ ID NO 63
<211> LENGTH: 26
<212> TYPE: DNA
<213> ORGANISM: Artificial
<220> FEATURE:
<223> OTHER INFORMATION: Primer

<400> SEQUENCE: 63
ttactgggtg atcccaatta caccac 26

<210> SEQ ID NO 64
<211> LENGTH: 37
<212> TYPE: DNA
<213> ORGANISM: Artificial
<220> FEATURE:
<223> OTHER INFORMATION: Primer

<400> SEQUENCE: 64
gactgctggc aaagatcgtg tggccactgt gtacatc 37

<210> SEQ ID NO 65
<211> LENGTH: 37
<212> TYPE: DNA
<213> ORGANISM: Artificial
<220> FEATURE:
<223> OTHER INFORMATION: Primer

<400> SEQUENCE: 65
gatgtacaca gtggccacac gatctttgcc agcagtc 37

<210> SEQ ID NO 66
<211> LENGTH: 25
<212> TYPE: DNA
<213> ORGANISM: Artificial
<220> FEATURE:
<223> OTHER INFORMATION: Primer

<400> SEQUENCE: 66
gtcggaacag gagagcgcac gaggg 25

<210> SEQ ID NO 67
<211> LENGTH: 23
<212> TYPE: DNA
<213> ORGANISM: Artificial
<220> FEATURE:
<223> OTHER INFORMATION: Primer

<400> SEQUENCE: 67
gggtgatggt tcacgtagtg ggc 23

<210> SEQ ID NO 68
<211> LENGTH: 20
<212> TYPE: DNA
<213> ORGANISM: Artificial
<220> FEATURE:
<223> OTHER INFORMATION: Primer

<400> SEQUENCE: 68
gtctccaccc cattgacgtc 20

<210> SEQ ID NO 69
<211> LENGTH: 20
<212> TYPE: DNA
<213> ORGANISM: Artificial
<220> FEATURE:
<223> OTHER INFORMATION: Primer

<400> SEQUENCE: 69
ggatcggtcc cggtgtcttc 20

<210> SEQ ID NO 70
<211> LENGTH: 21
<212> TYPE: DNA
<213> ORGANISM: Artificial
<220> FEATURE:
<223> OTHER INFORMATION: Primer

<400> SEQUENCE: 70
gctgtaccag tgcaggtcct c 21

<210> SEQ ID NO 71
<211> LENGTH: 20
<212> TYPE: DNA
<213> ORGANISM: Artificial
<220> FEATURE:
<223> OTHER INFORMATION: Primer

<400> SEQUENCE: 71
ccattgtgcg gccaatgatg 20

<210> SEQ ID NO 72
<211> LENGTH: 21
<212> TYPE: DNA
<213> ORGANISM: Artificial
<220> FEATURE:
<223> OTHER INFORMATION: Primer

<400> SEQUENCE: 72
ggatcaagag aggcacgttg g 21

<210> SEQ ID NO 73
<211> LENGTH: 22
<212> TYPE: DNA
<213> ORGANISM: Artificial

<220> FEATURE:
<223> OTHER INFORMATION: Primer

<400> SEQUENCE: 73
ggcgatcaca gaatcttcga tg 22

<210> SEQ ID NO 74
<211> LENGTH: 18
<212> TYPE: DNA
<213> ORGANISM: Artificial
<220> FEATURE:
<223> OTHER INFORMATION: Primer

<400> SEQUENCE: 74
caaagatggt gtggccac 18

<210> SEQ ID NO 75
<211> LENGTH: 18
<212> TYPE: DNA
<213> ORGANISM: Artificial
<220> FEATURE:
<223> OTHER INFORMATION: Primer

<400> SEQUENCE: 75
caaagatcgt gtggccac 18

<210> SEQ ID NO 76
<211> LENGTH: 20
<212> TYPE: DNA
<213> ORGANISM: Artificial
<220> FEATURE:
<223> OTHER INFORMATION: Primer

<400> SEQUENCE: 76
cgctccacca actaagaacg 20

<210> SEQ ID NO 77
<211> LENGTH: 20
<212> TYPE: DNA
<213> ORGANISM: Artificial
<220> FEATURE:
<223> OTHER INFORMATION: Primer

<400> SEQUENCE: 77
ctcaacacgg gaaacctcac 20

<210> SEQ ID NO 78
<211> LENGTH: 8
<212> TYPE: DNA
<213> ORGANISM: Artificial
<220> FEATURE:
<223> OTHER INFORMATION: Probe

<400> SEQUENCE: 78 ggtggtgg 8

<210> SEQ ID NO 79
<211> LENGTH: 30
<212> TYPE: DNA
<213> ORGANISM: Artificial
<220> FEATURE:
<223> OTHER INFORMATION: Primer

<400> SEQUENCE: 79
ccatggatgt attcatgaaa ggactttcaa 30

<210> SEQ ID NO 80
<211> LENGTH: 25
<212> TYPE: DNA
<213> ORGANISM: Artificial
<220> FEATURE:
<223> OTHER INFORMATION: Primer

<400> SEQUENCE: 80
cttccggctc atagtcctga taccc 25

<210> SEQ ID NO 81
<211> LENGTH: 39
<212> TYPE: DNA
<213> ORGANISM: Artificial
<220> FEATURE:
<223> OTHER INFORMATION: Primer

<400> SEQUENCE: 81
gaccacgcgt atcgatgtcg actttttttt ttttttttv 39

<210> SEQ ID NO 82
<211> LENGTH: 23
<212> TYPE: DNA
<213> ORGANISM: Artificial
<220> FEATURE:
<223> OTHER INFORMATION: Primer

<400> SEQUENCE: 82
gaaaacgcgt atcgatgttc gac 23

<210> SEQ ID NO 83
<211> LENGTH: 30
<212> TYPE: DNA
<213> ORGANISM: Artificial
<220> FEATURE:
<223> OTHER INFORMATION: Primer

<400> SEQUENCE: 83
ccatggatgt attcatgaaa ggactttcaa 30

<210> SEQ ID NO 84
<211> LENGTH: 24
<212> TYPE: DNA
<213> ORGANISM: Artificial
<220> FEATURE:
<223> OTHER INFORMATION: Primer

<400> SEQUENCE: 84
ggatcctaca tagagcacac cctc 24

<210> SEQ ID NO 85
<211> LENGTH: 23
<212> TYPE: DNA
<213> ORGANISM: Artificial
<220> FEATURE:
<223> OTHER INFORMATION: Primer

<400> SEQUENCE: 85
gaaaacgcgt atcgatgttc gac 23

<210> SEQ ID NO 86
<211> LENGTH: 24
<212> TYPE: DNA
<213> ORGANISM: Artificial
<220> FEATURE:
<223> OTHER INFORMATION: Primer

<400> SEQUENCE: 86
tcccgctgct tctgccacac cctg 24

<210> SEQ ID NO 87
<211> LENGTH: 27
<212> TYPE: DNA
<213> ORGANISM: Artificial
<220> FEATURE:
<223> OTHER INFORMATION: Primer

<400> SEQUENCE: 87
agtctgttag ggggaggagc ttatttc 27

<210> SEQ ID NO 88
<211> LENGTH: 29
<212> TYPE: DNA
<213> ORGANISM: Artificial
<220> FEATURE:
<223> OTHER INFORMATION: Primer

<400> SEQUENCE: 88
atagttaata tttataggtg catagttcc 29

<210> SEQ ID NO 89
<211> LENGTH: 34
<212> TYPE: DNA
<213> ORGANISM: Artificial
<220> FEATURE:
<223> OTHER INFORMATION: Primer

<400> SEQUENCE: 89
gggtgtggca gaagcaccgg gaaagacaaa agag 34

<210> SEQ ID NO 90
<211> LENGTH: 34
<212> TYPE: DNA
<213> ORGANISM: Artificial
<220> FEATURE:
<223> OTHER INFORMATION: Primer

<400> SEQUENCE: 90
ctcttttgtc tttcccggtg cttctgccac accc 34

<210> SEQ ID NO 91
<211> LENGTH: 25
<212> TYPE: DNA
<213> ORGANISM: Artificial
<220> FEATURE:
<223> OTHER INFORMATION: Primer

<400> SEQUENCE: 91
gtcggaacag gagagcgcac gaggg 25

<210> SEQ ID NO 92
<211> LENGTH: 23
<212> TYPE: DNA
<213> ORGANISM: Artificial
<220> FEATURE:
<223> OTHER INFORMATION: Primer

<400> SEQUENCE: 92
gggtgatggt tcacgtagtg ggc 23

<210> SEQ ID NO 93
<211> LENGTH: 20
<212> TYPE: DNA
<213> ORGANISM: Artificial

<220> FEATURE:
<223> OTHER INFORMATION: Primer

<400> SEQUENCE: 93
gattccccgt gccaagagtg 20

<210> SEQ ID NO 94
<211> LENGTH: 27
<212> TYPE: DNA
<213> ORGANISM: Artificial
<220> FEATURE:
<223> OTHER INFORMATION: Primer

<400> SEQUENCE: 94
ttgcccagct gatccttttt gccaaag 27

<210> SEQ ID NO 95
<211> LENGTH: 24
<212> TYPE: DNA
<213> ORGANISM: Artificial
<220> FEATURE:
<223> OTHER INFORMATION: Primer

<400> SEQUENCE: 95
tggaggagaa cacatgaaag aaag 24

<210> SEQ ID NO 96
<211> LENGTH: 33
<212> TYPE: DNA
<213> ORGANISM: Artificial
<220> FEATURE:
<223> OTHER INFORMATION: Primer

<400> SEQUENCE: 96
ggggaattct ggaggagaac acatgaaaga aag 33

<210> SEQ ID NO 97
<211> LENGTH: 33
<212> TYPE: DNA
<213> ORGANISM: Artificial
<220> FEATURE:
<223> OTHER INFORMATION: Primer

<400> SEQUENCE: 97
ggggaattcc ctgactttgt tagatgtgga cac 33

<210> SEQ ID NO 98
<211> LENGTH: 20
<212> TYPE: DNA
<213> ORGANISM: Artificial
<220> FEATURE:
<223> OTHER INFORMATION: Primer

<400> SEQUENCE: 98
gccatgctca ctttcatggc 20

<210> SEQ ID NO 99
<211> LENGTH: 20
<212> TYPE: DNA
<213> ORGANISM: Artificial
<220> FEATURE:
<223> OTHER INFORMATION: Primer

<400> SEQUENCE: 99
cacgactgcg tccagtgacc 20

<210> SEQ ID NO 100
<211> LENGTH: 20
<212> TYPE: DNA
<213> ORGANISM: Artificial
<220> FEATURE:
<223> OTHER INFORMATION: Primer

<400> SEQUENCE: 100
ggaggtggta atgtggttgg 20

<210> SEQ ID NO 101
<211> LENGTH: 21
<212> TYPE: DNA
<213> ORGANISM: Artificial
<220> FEATURE:
<223> OTHER INFORMATION: Primer

<400> SEQUENCE: 101
ccaaccataa gaagaactgg g 21

<210> SEQ ID NO 102
<211> LENGTH: 23
<212> TYPE: DNA
<213> ORGANISM: Artificial
<220> FEATURE:
<223> OTHER INFORMATION: Primer

<400> SEQUENCE: 102
cctataacgt tgccatggat tac 23

<210> SEQ ID NO 103
<211> LENGTH: 19
<212> TYPE: DNA
<213> ORGANISM: Artificial
<220> FEATURE:
<223> OTHER INFORMATION: Primer

<400> SEQUENCE: 103
cacagccaag atgagccac 19

<210> SEQ ID NO 104
<211> LENGTH: 22
<212> TYPE: DNA
<213> ORGANISM: Artificial
<220> FEATURE:
<223> OTHER INFORMATION: Primer

<400> SEQUENCE: 104
gctggttgaa acagctcagg ag 22

<210> SEQ ID NO 105
<211> LENGTH: 24
<212> TYPE: DNA
<213> ORGANISM: Artificial
<220> FEATURE:
<223> OTHER INFORMATION: Primer

<400> SEQUENCE: 105
ccagcaaacg aagtgggcca tttg 24

<210> SEQ ID NO 106
<211> LENGTH: 20
<212> TYPE: DNA
<213> ORGANISM: Artificial
<220> FEATURE:
<223> OTHER INFORMATION: Primer

<400> SEQUENCE: 106
caacaatggt gtggttggtg 20

<210> SEQ ID NO 107
<211> LENGTH: 21
<212> TYPE: DNA
<213> ORGANISM: Artificial
<220> FEATURE:
<223> OTHER INFORMATION: Primer

<400> SEQUENCE: 107
ggataccttc ctttgggctt c 21

<210> SEQ ID NO 108
<211> LENGTH: 22
<212> TYPE: DNA
<213> ORGANISM: Artificial
<220> FEATURE:
<223> OTHER INFORMATION: Primer

<400> SEQUENCE: 108
gacacttacc tggggctttg tg 22

<210> SEQ ID NO 109
<211> LENGTH: 25
<212> TYPE: DNA
<213> ORGANISM: Artificial
<220> FEATURE:
<223> OTHER INFORMATION: Primer

<400> SEQUENCE: 109
ccaagtaagg tgagacagga aaacc 25

<210> SEQ ID NO 110
<211> LENGTH: 25
<212> TYPE: DNA
<213> ORGANISM: Artificial
<220> FEATURE:
<223> OTHER INFORMATION: Primer

<400> SEQUENCE: 110
gctacgagta tgaaggtggg atatg 25

<210> SEQ ID NO 111
<211> LENGTH: 20
<212> TYPE: DNA
<213> ORGANISM: Artificial
<220> FEATURE:
<223> OTHER INFORMATION: Primer

<400> SEQUENCE: 111
ccaggagtca agataactgg 20

<210> SEQ ID NO 112
<211> LENGTH: 21
<212> TYPE: DNA
<213> ORGANISM: Artificial
<220> FEATURE:
<223> OTHER INFORMATION: Primer

<400> SEQUENCE: 112
ccaccatctg tttacctgct a 21

<210> SEQ ID NO 113
<211> LENGTH: 21
<212> TYPE: DNA
<213> ORGANISM: Artificial

<220> FEATURE:
<223> OTHER INFORMATION: Primer

<400> SEQUENCE: 113
ggccatcatt acatgtgttt g 21

<210> SEQ ID NO 114
<211> LENGTH: 27
<212> TYPE: DNA
<213> ORGANISM: Artificial
<220> FEATURE:
<223> OTHER INFORMATION: Primer

<400> SEQUENCE: 114
ggtgacatta agaagtttgg tgacttg 27

<210> SEQ ID NO 115
<211> LENGTH: 21
<212> TYPE: DNA
<213> ORGANISM: Artificial
<220> FEATURE:
<223> OTHER INFORMATION: Primer

<400> SEQUENCE: 115
gggtgttacc acagcttgga g 21

<210> SEQ ID NO 116
<211> LENGTH: 28
<212> TYPE: DNA
<213> ORGANISM: Artificial
<220> FEATURE:
<223> OTHER INFORMATION: Primer

<400> SEQUENCE: 116
gtgatttcag tatacgattt agtggctg 28

<210> SEQ ID NO 117
<211> LENGTH: 22
<212> TYPE: DNA
<213> ORGANISM: Artificial
<220> FEATURE:
<223> OTHER INFORMATION: Primer

<400> SEQUENCE: 117
caccaaccac accattgttg ac 22

<210> SEQ ID NO 118
<211> LENGTH: 15
<212> TYPE: DNA
<213> ORGANISM: Artificial
<220> FEATURE:
<223> OTHER INFORMATION: Probe

<400> SEQUENCE: 118
ttgtgtccaa atggc 15

<210> SEQ ID NO 119
<211> LENGTH: 19
<212> TYPE: DNA
<213> ORGANISM: Artificial
<220> FEATURE:
<223> OTHER INFORMATION: Primer

<400> SEQUENCE: 119
ggaggaaagg ggcgtgaag 19

<210> SEQ ID NO 120
<211> LENGTH: 20
<212> TYPE: DNA
<213> ORGANISM: Artificial
<220> FEATURE:
<223> OTHER INFORMATION: Primer

<400> SEQUENCE: 120
cacaaaccga tgaggatggc 20

<210> SEQ ID NO 121
<211> LENGTH: 17
<212> TYPE: DNA
<213> ORGANISM: Artificial
<220> FEATURE:
<223> OTHER INFORMATION: Probe

<400> SEQUENCE: 121
ctggaacacc acgctgg 17

<210> SEQ ID NO 122
<211> LENGTH: 21
<212> TYPE: DNA
<213> ORGANISM: Artificial
<220> FEATURE:
<223> OTHER INFORMATION: Primer

<400> SEQUENCE: 122
gactcatgac cacggtccat g 21

<210> SEQ ID NO 123
<211> LENGTH: 21
<212> TYPE: DNA
<213> ORGANISM: Artificial
<220> FEATURE:
<223> OTHER INFORMATION: Primer

<400> SEQUENCE: 123
gtcagatcca caaccgacac g 21

<210> SEQ ID NO 124
<211> LENGTH: 17
<212> TYPE: DNA
<213> ORGANISM: Artificial
<220> FEATURE:
<223> OTHER INFORMATION: Probe

<400> SEQUENCE: 124
catcactgcc acccaga 17

<210> SEQ ID NO 125
<211> LENGTH: 24
<212> TYPE: DNA
<213> ORGANISM: Artificial
<220> FEATURE:
<223> OTHER INFORMATION: Primer

<400> SEQUENCE: 125
gtttgtgtct gaccctcctg ctgc 24

<210> SEQ ID NO 126
<211> LENGTH: 23
<212> TYPE: DNA
<213> ORGANISM: Artificial
<220> FEATURE:
<223> OTHER INFORMATION: Primer

<400> SEQUENCE: 126
cagatgtaga gctggtgggg agg 23

<210> SEQ ID NO 127
<211> LENGTH: 19
<212> TYPE: DNA
<213> ORGANISM: Artificial
<220> FEATURE:
<223> OTHER INFORMATION: Primer

<400> SEQUENCE: 127
cagcgctccc agctggagg 19

<210> SEQ ID NO 128
<211> LENGTH: 20
<212> TYPE: DNA
<213> ORGANISM: Artificial
<220> FEATURE:
<223> OTHER INFORMATION: Primer

<400> SEQUENCE: 128
ggaygtactg gttctgctgg 20

<210> SEQ ID NO 129
<211> LENGTH: 22
<212> TYPE: DNA
<213> ORGANISM: Artificial
<220> FEATURE:
<223> OTHER INFORMATION: Primer

<400> SEQUENCE: 129
gccaccgtag aggaggagga ag 22

<210> SEQ ID NO 130
<211> LENGTH: 19
<212> TYPE: DNA
<213> ORGANISM: Artificial
<220> FEATURE:
<223> OTHER INFORMATION: Primer

<400> SEQUENCE: 130
ctcaccatgt cgctgaagc 19

<210> SEQ ID NO 131
<211> LENGTH: 23
<212> TYPE: DNA
<213> ORGANISM: Artificial
<220> FEATURE:
<223> OTHER INFORMATION: Primer

<400> SEQUENCE: 131
ccatgggaat agtttttctc atg 23

<210> SEQ ID NO 132
<211> LENGTH: 23
<212> TYPE: DNA
<213> ORGANISM: Artificial
<220> FEATURE:
<223> OTHER INFORMATION: Primer

<400> SEQUENCE: 132
ggttggcttt tcacatggat gtg 23

<210> SEQ ID NO 133
<211> LENGTH: 20
<212> TYPE: DNA
<213> ORGANISM: Artificial

<220> FEATURE:
<223> OTHER INFORMATION: Primer

<400> SEQUENCE: 133
cggccacacg tgtcctattc 20

<210> SEQ ID NO 134
<211> LENGTH: 19
<212> TYPE: DNA
<213> ORGANISM: Artificial
<220> FEATURE:
<223> OTHER INFORMATION: Primer

<400> SEQUENCE: 134
ggccgctggg ggccgctcg 19

<210> SEQ ID NO 135
<211> LENGTH: 21
<212> TYPE: DNA
<213> ORGANISM: Artificial
<220> FEATURE:
<223> OTHER INFORMATION: Primer

<400> SEQUENCE: 135
ggagcggaaa gaatgtcgga g 21

<210> SEQ ID NO 136
<211> LENGTH: 21
<212> TYPE: DNA
<213> ORGANISM: Artificial
<220> FEATURE:
<223> OTHER INFORMATION: Primer

<400> SEQUENCE: 136
cccacagatt ccacgactgt c 21

<210> SEQ ID NO 137
<211> LENGTH: 19
<212> TYPE: DNA
<213> ORGANISM: Artificial
<220> FEATURE:
<223> OTHER INFORMATION: Primer

<400> SEQUENCE: 137
gaagagctgt ggagtctgg 19

<210> SEQ ID NO 138
<211> LENGTH: 21
<212> TYPE: DNA
<213> ORGANISM: Artificial
<220> FEATURE:
<223> OTHER INFORMATION: Primer

<400> SEQUENCE: 138
ctatccattt tggaggagca g 21

<210> SEQ ID NO 139
<211> LENGTH: 21
<212> TYPE: DNA
<213> ORGANISM: Artificial
<220> FEATURE:
<223> OTHER INFORMATION: Primer

<400> SEQUENCE: 139
ggaggccagt ccactgctca c 21

<210> SEQ ID NO 140
<211> LENGTH: 21
<212> TYPE: DNA
<213> ORGANISM: Artificial
<220> FEATURE:
<223> OTHER INFORMATION: Primer

<400> SEQUENCE: 140
ccgccatggc gaccctggaa a 21

<210> SEQ ID NO 141
<211> LENGTH: 20
<212> TYPE: DNA
<213> ORGANISM: Artificial
<220> FEATURE:
<223> OTHER INFORMATION: Primer

<400> SEQUENCE: 141
ggtggcggct gaggaggctg 20

<210> SEQ ID NO 142
<211> LENGTH: 22
<212> TYPE: DNA
<213> ORGANISM: Artificial
<220> FEATURE:
<223> OTHER INFORMATION: Primer

<400> SEQUENCE: 142
cgtttcggtt tcacttccgg tg 22

<210> SEQ ID NO 143
<211> LENGTH: 21
<212> TYPE: DNA
<213> ORGANISM: Artificial
<220> FEATURE:
<223> OTHER INFORMATION: Primer

<400> SEQUENCE: 143
ccgcacttcc accaccagct c 21

<210> SEQ ID NO 144
<211> LENGTH: 21
<212> TYPE: DNA
<213> ORGANISM: Artificial
<220> FEATURE:
<223> OTHER INFORMATION: Primer

<400> SEQUENCE: 144
tgcggcggca gcagccgcta c 21

<210> SEQ ID NO 145
<211> LENGTH: 22
<212> TYPE: DNA
<213> ORGANISM: Artificial
<220> FEATURE:
<223> OTHER INFORMATION: Primer

<400> SEQUENCE: 145
cccctgtgag tgtgtaagtg tg 22

<210> SEQ ID NO 146
<211> LENGTH: 22
<212> TYPE: DNA
<213> ORGANISM: Artificial
<220> FEATURE:
<223> OTHER INFORMATION: Primer

<400> SEQUENCE: 146
gggaggagcc tcgcctttaa tg 22

<210> SEQ ID NO 147
<211> LENGTH: 21
<212> TYPE: DNA
<213> ORGANISM: Artificial
<220> FEATURE:
<223> OTHER INFORMATION: Primer

<400> SEQUENCE: 147
cgcgacaaaa tggtgccttt c 21

<210> SEQ ID NO 148
<211> LENGTH: 22
<212> TYPE: DNA
<213> ORGANISM: Artificial
<220> FEATURE:
<223> OTHER INFORMATION: Primer

<400> SEQUENCE: 148
gccctgctgc cttctctagg tc 22

<210> SEQ ID NO 149
<211> LENGTH: 22
<212> TYPE: DNA
<213> ORGANISM: Artificial
<220> FEATURE:
<223> OTHER INFORMATION: Primer

<400> SEQUENCE: 149
ccccagctct agccctgtga tc 22

<210> SEQ ID NO 150
<211> LENGTH: 21
<212> TYPE: DNA
<213> ORGANISM: Artificial
<220> FEATURE:
<223> OTHER INFORMATION: Primer

<400> SEQUENCE: 150
ccgccatggc gaccctggaa a 21

<210> SEQ ID NO 151
<211> LENGTH: 20
<212> TYPE: DNA
<213> ORGANISM: Artificial
<220> FEATURE:
<223> OTHER INFORMATION: Primer

<400> SEQUENCE: 151
ggtggcggct gaggaggctg 20

<210> SEQ ID NO 152
<211> LENGTH: 35
<212> TYPE: DNA
<213> ORGANISM: Artificial
<220> FEATURE:
<223> OTHER INFORMATION: Primer

<400> SEQUENCE: 152
aacagatcta tgctgccaca aacagccctt ttgct 35

<210> SEQ ID NO 153
<211> LENGTH: 34
<212> TYPE: DNA
<213> ORGANISM: Artificial

<220> FEATURE:
<223> OTHER INFORMATION: Primer

<400> SEQUENCE: 153
gcagaattct cacattggag ccactaggaa tcct 34

<210> SEQ ID NO 154
<211> LENGTH: 25
<212> TYPE: DNA
<213> ORGANISM: Artificial
<220> FEATURE:
<223> OTHER INFORMATION: Primer

<400> SEQUENCE: 154
gtcggaacag gagagcgcac gaggg 25

<210> SEQ ID NO 155
<211> LENGTH: 23
<212> TYPE: DNA
<213> ORGANISM: Artificial
<220> FEATURE:
<223> OTHER INFORMATION: Primer

<400> SEQUENCE: 155
gggtgatggt tcacgtagtg ggc 23

<210> SEQ ID NO 156
<211> LENGTH: 20
<212> TYPE: DNA
<213> ORGANISM: Artificial
<220> FEATURE:
<223> OTHER INFORMATION: Primer

<400> SEQUENCE: 156
gtctccaccc cattgacgtc 20

<210> SEQ ID NO 157
<211> LENGTH: 20
<212> TYPE: DNA
<213> ORGANISM: Artificial
<220> FEATURE:
<223> OTHER INFORMATION: Primer

<400> SEQUENCE: 157
ggatcggtcc cggtgtcttc 20

<210> SEQ ID NO 158
<211> LENGTH: 27
<212> TYPE: DNA
<213> ORGANISM: Artificial
<220> FEATURE:
<223> OTHER INFORMATION: Primer

<400> SEQUENCE: 158
gctctagagg tcccacccac ccgaagg 27

<210> SEQ ID NO 159
<211> LENGTH: 29
<212> TYPE: DNA
<213> ORGANISM: Artificial
<220> FEATURE:
<223> OTHER INFORMATION: Primer

<400> SEQUENCE: 159
tctctagatc acattggagc cactacgaa 29

TRANSGENIC PIG MODEL FOR A HEREDITARY NEURODEGENERATIVE AUTOSOMAL DOMINANT DISEASE

This application is a §371 national phase filing of PCT/DK2007/000204, filed Apr. 30, 2007, and claims priority to Danish Application No. PA 2006 00616, filed May 1, 2006, U.S. Provisional Application No. 60/796,196, filed May 1, 2006, and Danish Application No. PA 2007 00429, filed Mar. 20, 2007.

All patent and non-patent references cited in the application are hereby incorporated by reference in their entirety.

FIELD OF INVENTION

The present invention relates to a non-human animal model, such as a porcine animal model, and methods for producing a non-human animal model by sperm-mediated gene transfer (SMGT). When a genetic determinant involved in a hereditary disease is used for SMGT, i.e. a genetic determinant which confers a dominant phenotype for said hereditary disease, the non-human animal model can be used for studying such hereditary diseases, such as autosomal dominant hereditary diseases, for example protein conformation diseases, such as Amyotrophic Lateral Sclerosis (ALS), Alzheimer's disease, Parkinson's disease, diseases related to trinucleotide repeats, Huntington's disease but also dyschondroplasia.

BACKGROUND OF INVENTION

Transgenic, non-human animals can be used to understand the action of a single gene in the context of the whole animal and the interrelated phenomena of gene activation, expression, and interaction. The technology has also led to the production of models for various diseases in humans and other animals which contributes significantly to an increased understanding of genetic mechanisms and of genes associated with specific diseases.

While smaller animals, such as mice, have proved to be suitable models for certain diseases, their value as animal models for many human diseases is quite limited. Larger transgenic animals are much more suitable than mice for the study of many of the effects and treatments of most human diseases because of their greater similarity to humans in many aspects.

For the past two decades, pigs have been used in biomedical research with increasing frequency as replacements for dog and primates. This is due to the anatomical and physiological similarity to humans. Pigs and human share anatomical and physiological characteristics such as heart size, cardiac output, and coronary blood supply which have made pigs widely used in cardiac surgery, pacemaker studies and heart transplantions. Similarly, pig and humans share features in digestive physiology and pigs are therefore widely used in nutritional studies and subjects in relations to this including lipid metabolism, gastric ulceration, diabetes and alcoholism, Furthermore, porcine models are used for the study of disorders of the skin. Organs of porcine origin are also used in organ transplantation research. However, the pig constitutes an evolutionary clade in relation to humans and rodents.

Many human diseases are hereditary. The inheritance of genetic disorders, abnormalities, or traits is a function of both the type of chromosome on which the abnormal gene resides (autosomal or sex chromosome), and of the trait itself, i.e. whether the trait is dominant or recessive. The trait can be due to a single defective gene from one parent (dominant inheritance) or the trait can arise when two copies of the gene (one from each parent) are defective (recessive inheritance).

Dominant inheritance occurs when an abnormal gene from one parent is capable of causing disease even though the matching gene from the other parent is normal. Accordingly, the abnormal gene dominates the outcome of the gene pair and one copy of the mutant gene is sufficient for expression of the abnormal phenotype.

Several distinct characteristics of autosomal dominant inheritance include: Every affected individual has an affected parent (except in cases of new mutations or incomplete penetrance); males and females are equally likely to inherit the allele and be affected (as the genes are located on autosomes, of which each male and female has two copies); and recurrence risk (the probability that a genetic disorder that is present in a patient will recur in another member of the family) for each child of an affected parent is ½ (as only one copy of a gene is necessary for development of the disease). If one parent is a heterozygote for a particular gene, their offspring will either inherit the gene or they will not, with each outcome equally likely. Accordingly, if an affected individual's siblings are not affected, they do not carry the mutation and cannot therefore pass it on to their own offspring.

As many of these autosomal dominant diseases are deleterious, one would expect that over time they would disappear from the population due to natural selection. However, there are several phenomena, cf. below, that can lead to maintenance of these alleles in the population.

Variable expressivity: the variable severity of a genetic trait. Different individuals with the same mutation will develop different degrees of the disorder due to difference in environment and the modifying effects of other genes. Because of this, a mutation that leads to a relatively mild form of the disease in one individual stands a good chance of being passed on and maintained in the population. The same mutation in another individual may lead to such a severe manifestation that the affected individual is unable to propagate the mutation to the next generation. This demonstrates very well the fact that genetic disease results as combination of genetic and environmental influences.

Late onset: when a disease has an onset later in life, affected individuals may have passed the gene to their offspring before they even knew they carried it themselves. One example of this is Huntington's disease, a late onset neurodegenerative disorder. It is now possible to receive genetic testing for this disorder, a practice that leads to many complex issues for the family undergoing the testing.

High recurrent mutation rate: 85% of cases of achondroplasia, a major cause of dwarfism, are the result of new mutations. Some segments of the genome are subject to higher than normal rates of mutation, which can lead to the maintenance of the disease in the population even if both parents were normal. This is particularly true of diseases that affect fertility. If the disease is invariably lethal at a young age, before reproduction is possible, the only source of the disease would be new mutations.

Incomplete penetrance: phenomena where a portion of individuals with a disease-associated genotype do not develop a disease. If only 30 people out of 50 who have a disease-associated mutation actually develop the disease, it is incompletely penetrant. A disease that is 75% penetrant is one in which 75% of those who carry the disease-associated mutation eventually develop the disease. The rest do not.

Transgenic animals carrying a dominant disease gene which is expressed in the animal makes it possible to study the phenotype associated with said dominant disease gene if the gene when expressed in the animal actually leads to the same disease as in humans. Transgenic animals have traditionally been used for the improvement of livestock, and for the large scale production of biologically active pharmaceuticals. Historically, transgenic animals have been produced almost exclusively by microinjection of the fertilized egg. The pronuclei of fertilized eggs are microinjected in vitro with foreign, i.e., xenogeneic or allogeneic DNA or hybrid DNA molecules. The microinjected fertilized eggs can then be transferred to the genital tract of a pseudopregnant female.

Only a few examples of success with sperm-mediated gene transfer methods in monkeys and mice have been reported (reviewed e.g. by Vodicka (2005): Ann. N.Y. Acad. Sci.; 1049: 161-171; Chan (2004): Reprod. Biol. Endocrinol.; 2:39; and by Wall (2002): Theriogenology; 57: 189-201).

As noted by Wall (ibid), only few studies convincingly demonstrate transgene expression. Wall (ibid) concludes that the body of evidence is still not sufficient to warrant elevating sperm-mediated gene transfer to the status of other available state of the art methods.

Smith (2004): Int. J. Med. Sci.; 1(2):76-91; notes that sperm-mediated gene transfer has not yet become established as a reliable form of genetic modification and that concerted attempts to utilise sperm-mediated gene transfer often have produced negative results.

WO 2005/038001 is directed to a method for producing transgenic animals.

US 2005/0053910 pertains to cell culture media for sperm-mediated gene transfer methods.

JP 2000-316420 is related to transgene pigs obtained by methods involving micro-injection and not sperm-mediated gene transfer. The pig may carry a gene causing an autosomal, dominant disease.

However, as pigs constitute a distinct evolutionary clade in comparison with humans the introduction of mutations known as disease causing mutations in specific genes in humans cannot be expected to yield a desired phenotype in the pig model.

There is a need for improved animal models for human diseases in order to gain more information of the onset, progression and treatment regimes of hereditary diseases in humans.

SUMMARY OF INVENTION

Until now it has been believed that the phenotypic display of an autosomal dominant disease is caused by the continuous expression of an inherited mutated gene. However, the present invention discloses that a phenotype of an autosomal dominant disease is caused by a sufficiently high expression of the mutated gene in a transient manner. Thus, the present invention discloses that the expression of a gene involved in the development of autosomal dominant diseases primarily has to be expressed in sufficiently high amounts at a specific time point during the development of the embryo of a non-human animal model. The fact that the expression of particular genes associated with autosomal dominant genes is transient also allows for the production of non-human animal models by the addition of gene products to for example embryos or other target cells (seeding effect).

In a first aspect the present invention relates to non-human animal model for a hereditary autosomal dominant disease, wherein the non-human animal model expresses at least one phenotype associated with said hereditary autosomal dominant disease obtained by a genetic determinant.

In a second aspect a non-human animal model for a hereditary autosomal dominant disease, wherein the non-human animal model expresses at least one phenotype associated with said hereditary autosomal dominant disease obtained by sperm-mediated gene transfer.

A third aspect of the present invention pertains to a pig model for a hereditary autosomal dominant disease obtained by a genetic determinant, wherein the pig model expresses at least one phenotype associated with said hereditary autosomal disease.

A fourth aspect relates to a pig model for a hereditary autosomal dominant disease obtained by a genetic determinant, wherein said disease is a protein conformation disease.

A fifth aspect concerns a pig model for a hereditary neurodegenerative autosomal dominant disease obtained by a genetic determinant.

In further aspects of the invention is disclosed a pig model for amyotrophic lateral sclerosis, Alzheimer's Disease, Parkinson's Disease, diseases related to Trinucleotide Repeats, Huntington's chorea or dyschondroplasia obtained by a genetic determinant, wherein the pig model expresses at least one phenotype associated with Amyotrophic Lateral Sclerosis, Alzheimer's Disease, Parkinson's Disease, diseases related to Trinucleotide Repeats, Huntington's chorea or dyschondroplasia, respectively.

The present invention also relates to a method for producing the model according to the present invention, said method comprising the steps of i) providing semen from a male, non-human animal, ii) providing at least one genetic determinant capable of establishing said at least one phenotype associated with said hereditary disease when the at least one genetic determinant is expressed in said non-human animal model, iii) contacting said semen and said at least one genetic determinant, iv) fertilising an oocyte from a female, non-human animal with the semen and the genetic material, and v) incubating said fertilised oocyte under conditions allowing said fertilised oocyte to develop into said non-human animal model.

Furthermore, a method for evaluating the response of a therapeutical treatment of a hereditary disease, said method comprising the steps of a. providing the non-human animal model according to the present invention, b. treating said non-human animal with at least one pharmaceutical composition exerting an effect on said at least one phenotype, and c. evaluating the effect observed, is disclosed.

Yet other aspects concern a non-human sperm cell comprising at least one genetic determinant exerting at least one dominant phenotype for at least one hereditary disease when expressed in a non-human animal host organism, and a method for producing the non-human sperm cell, said method comprising the steps of a. providing a non-human sperm cell, b. providing at least one genetic determinant exerting a dominant phenotype for a hereditary disease when expressed in a non-human animal host organism, c. contacting said non-human sperm cell and said at least one genetic determinant, wherein said contacting results in the uptake of the genetic determinant into the non-human sperm cell.

Moreover, the present invention also relates to a composition comprising a non-human sperm cell in combination with at least one genetic determinant exerting at least one dominant phenotype for at least one hereditary disease when expressed in a non-human animal host organism.

In further aspects the invention pertains to a method for fertilising an oocyte by sperm-mediated gene transfer, said method comprising the steps of providing the non-human sperm cell or the composition as defined above and introducing said non-human sperm cell into the oocyte to be fertilised.

The present invention also relates to an embryo obtained by fertilising an oocyte with the non-human sperm cell or with the composition as defined herein.

Yet a further aspect relates to a method for the cultivation and development of the embryo as described herein, said method comprising the step of cultivating said embryo under conditions allowing the embryo to develop into a non-human animal offspring expressing said genetic determinant and exerting a dominant phenotype for a hereditary disease.

In a final aspect is disclosed a method for screening the efficacy of a pharmaceutical composition, said method comprising the steps of a. providing the non-human animal model of the present invention, b. expressing in said animal model said at least one genetic determinant and exerting said dominant phenotype for said hereditary disease, c. administering to said non-human animal the pharmaceutical composition the efficacy of which is to be evaluated, and d. evaluating the effect, if any, of the pharmaceutical composition on the phenotype exerted by the genetic determinant when expressed in the non-human model.

DESCRIPTION OF FIGURES

FIG. 1: Sequence of porcine SOD1 cDNA.

FIG. 2: Sequence of the mutated porcine SOD1 cDNA.

FIG. 3: Comparison of the deduced amino acid sequence of porcine SOD1 (*S. scrofa*), with human (*H. sapiens*), mouse (*M. musculus*) and rat (*R. norvegicus*). Asterisks indicate amino acid residues that are conserved among the sequences. Dots indicate that the residues are non-conservative among the sequences, and semicolons indicate residues which are conservative. Dashes indicate gaps that have been introduced to optimize the alignment. The amino acid (G) which has shifted is marked in bold.

FIG. 16: The porcine SNCA cDNA sequence.

FIG. 17: Alignment of the porcine α-synuclein protein with α-synucleins from other species. Human mutants: A30P, E46K and A53T are indicated by bold and underlined letters. Differences between the human and the porcine sequences are indicated by old blue letters. Asterisks indicate amino acid residues that are conserved among the sequences. The amino acid Ala30 substituted by a Pro in the mutated SNCA sequence is marked by an arrow.

FIG. 19: The mutated porcine SNCA cDNA sequence. The substituted nucleotide is shown as a bold underlined letter.

FIG. 25: TH staining of thin-layer sections from substantia nigra of boar #4363 (A) and a minipig control (B). The number of dopaminergic cells are reduced in 4363. Remaining dopaminergic cells and neuropil appear more rough and unordered (lower panels).

FIG. 26: GFAB staining of thin-layer sections from substantia nigra of boar #4363. Intense GFAB staining is seen in the mesencephalon. Numerous astrocytes are present indicative of active inflammation and reactive gliosis.

FIG. 28: Multiple amino acid sequence alignment of PSEN1. The alignment was performed using Clustal W. The sequences are *Sus scrofa* (DQ853416), *Bos Taurus* (NM 174721), *Homo sapiens* (NM 000021), and *Mus musculus* (NM 008943). Asterisk (*) indicates amino acids conserved among the sequences; Above the sequence alignments are by (+) indicated the position of pathogenic missense mutations identified in human PSEN1. Also the position of human missense SNPs are indicated above the sequence alignments with the alternative amino acids in bold.

FIG. 29: Multiple amino acid sequence alignment of PSEN2. The alignment was performed using Clustal W. The sequences are *Sus scrofa* (DQ853415), *Bos Taurus* (NM 174440), *Homo sapiens* (NM 000447), and *Mus musculus* (NM 011183). Asterisk (*) indicates conserved amino acids among the sequences. Above the sequence alignments are by (+) indicated the position of pathogenic missense mutations identified in human PSEN2. Also the position of a human missense SNP is indicated above the sequence alignments with the alternative amino acid in bold.

FIG. 32: Sequence alignment of non-coding TNRs from human, pig, and mouse. For the human sequences the most common identified alleles are shown with the variable number of TNRs indicated. Within brackets the most common occurring number of TNRs is shown. Note that human and chimpanzee alleles are highly polymorphic and only one representative sequence is shown. For the porcine sequences the allele frequencies are shown in brackets, furthermore, the identified alleles are revealed. N.P. indicates that a corresponding genomic sequence not was extractable from NCBI. En indicates the number of repeats present minimal in disease causing human alleles.

FIG. 33: Sequence alignment of poly-glutamine encoding TNRs in pig, human, chimpanzee (chimp), dog, opossum, rat, and mouse. For the human sequences the most common alleles are shown with the variable number of TNRs indicated. The most common number of TNRs are shown in brackets. Note that human and chimpanzee alleles are highly polymorphic and only one representative sequence is shown. For the porcine sequences the different alleles are shown and the number in brackets indicates the frequency of each allele. Q indicates the number of glutamines, H the number of histidines, and P the number of prolines. For the Huntingtin gene additional alleles with potential to encode 14 or 15 polyglutamines were identified in a larger Yorkshire and Landrace sample cohort (see table 1). N.P. indicates that a corresponding genomic sequence not was extractable from NCBI. En indicates the number of repeats present minimal in disease causing human alleles.

DETAILED DESCRIPTION OF THE INVENTION

Definitions

Figure 4:
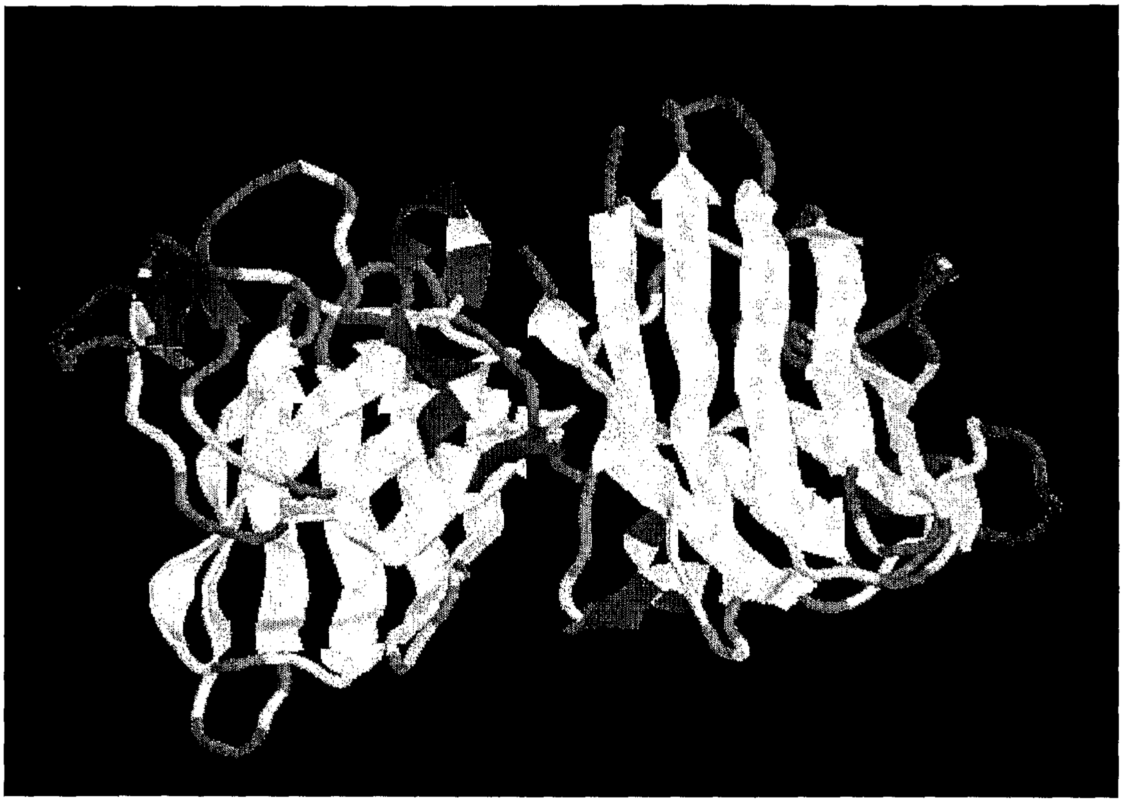
FIG. 4: Projection of mutations in SOD1 onto the crystal structure of the human SOD1 dimer. The Protein is shown in cartoon mode where helices are red, strands are yellow, and loops are blue. Grey areas represent regions which have been mutated in humans with ALS. The mutations are distributed all over the protein, illustrating that the majority or all of the residues in the protein are important for correct function of the enzyme.

For purposes of the present invention, the following terms are defined below.

The term "sperm" is used to refer to a male gamete cell and includes, without limitation, spermatogonia, primary and secondary permatocytes, spermatids, differentiating spermatids, round spermatids, and spermatozoa.

The term "oocyte" is used to refer to a female gamete cell, and includes primary oocytes, secondary oocytes, and mature, unfertilized ovum.

In some cases the term "embryo" is used to describe a fertilized oocyte after implantation in the uterus until 8 weeks after fertilization at which stage it becomes a foetus. According to this definition the fertilized oocyte is often called a pre-embryo until implantation occurs. However, throughout this patent application we will use a broader definition of the term embryo, which includes the pre-embryo phase. It thus encompasses all developmental stages from the fertilization of the oocyte through morula, blastocyst stages hatching and implantation. An embryo is approximately spherical and is composed of one or more cells (blastomeres) surrounded by a gelatine-like shell, the acellular matrix known as the zona pellucida. The zona pellucida performs a variety of functions until the embryo hatches, and is a good landmark for embryo evaluation. An embryo is formed when an oocyte is fertilized by fusion or injection of a sperm cell (spermatozoa). The feritilised oocyte is traditionally called an embryo for the first 8 weeks. After that (i.e. after eight weeks and when all major organs have been formed) it is called a foetus. However the distinction between embryo and foetus is not generally well defined. During embryonic development, blastomere numbers increase geometrically (1-2-4-8-16-etc.). Synchronous cell division is generally maintained to the 16-cell stage in embryos. After that, cell division becomes asynchronous and finally individual cells possess their own cell cycle. At about the 32-cell stage (morula stage), embryos undergo compaction, as inter-cell adhesion occur when adhesion proteins are expressed.

Accordingly, the term embryo is used in the following to denote each of the stages fertilized oocyte, zygote, 2-cell, 4-cell, 8-cell, 16-cell, morula, blastocyst, expanded blastocyst and hatched blastocyst, as well as all stages in between (e.g. 3-cell or 5-cell).

The term "non-human animal" can be a non-human primate, e.g., an ape or a monkey; and a farm animal, such as an animal selected from the group consisting of cattle, swine; sheep; goats; horses; and donkeys. Accordingly, the non-human animal can e.g. be a cow, a bull, a bison, a buffalo, a pig, a big-horn sheep, a pony, a mule, a deer, an elk, a lama, and an alpaca. Similarly the non-human animal can be a rodent, such as a mouse or rat.

The term "non-human animal model" refers to any non-human animal in which one or more cells comprise genetic determinants. The non-human animal comprising genetic determinants may for example be the result of introduction of the genetic determinant by sperm-mediated gene transfer. However, the genetic determinant may also be introduced for example by injection into cells or tissues desired.

The term "genetic determinant" of the present invention refers to genes or parts thereof, transcriptional products or parts thereof and/or translational products or part thereof that confer the display of one or more features of phenotypes of autosomal dominant hereditary diseases. Thus, in some embodiments the term "genetic determinant" is used herein to refer to a single-stranded or double-stranded "polynucleotide molecule" or "nucleic acid" comprising a structural gene of interest. The "genetic determinant" encodes a protein not ordinarily made in appreciable amounts in the target cells.

The term genetic determinant is also used to refer to a single-stranded or double stranded ribonucleic acid, RNA expressed from a gene of interest. Thus, "genetic determinants" include nucleic acids which are not ordinarily found in the genome of the target cell. "Genetic determinants" also include nucleic acids which are ordinarily found within the genome of the target cell, but is in a form which allows for the expression of proteins which are not ordinarily expressed in the target cells in appreciable amounts. Alternatively, "genetic determinants" may encode a variant or mutant form of a naturally-occurring protein.

The term genetic determinant is also used herein to refer to a protein or part thereof or a RNA molecule or part thereof of a gene of interest, wherein the gene or polynucleotide encoding said protein or RNA is not present in the target cell. Throughout the description and claims either the three letter code or the one letter code for natural amino acids are used. Where the L or D form has not been specified it is to be understood that the amino acid in question has the natural L form, cf. Pure & Appl. Chem. Vol. (56(5) pp 595-624 (1984) or the D form, so that the peptides formed may be constituted of amino acids of L form, D form, or a sequence of mixed L forms and D forms.

Where nothing is specified it is to be understood that the C-terminal amino acid of a peptide for use according to the invention exists as the free carboxylic acid, this may also be specified as "—OH". However, the C-terminal amino acid of a peptide for use according to the invention may be the amidated derivative, which is indicated as "—$NH_2$". Where nothing else is stated the N-terminal amino acid of a polypeptide comprises a free amino-group, this may also be specified as "H-".

A peptide, fragment, homologue or variant for use according to the invention can also comprise one or several unnatural amino acids.

Conservative amino acid substitutions: Substitutions within the groups of amino acids, shown below, are considered conservative amino acid substitutions. Substitutions between the different groups of amino acids are considered non-conservative amino acid substitutions.

P, A, G, S, T (neutral, weakly hydrophobic)
Q, N, E, D, B, Z (hydrophilic, acid amine)
H, K, R (hydrophilic, basic)
F, Y, W (hydrophobic, aromatic)
L, I, V, M (hydrophobic)
C (cross-link forming)

In one embodiment the genetic determinant is in the form of microRNAs (miRNA) that are single-stranded RNA molecules of about 21-23 nucleotides in length. miRNAs are typically encoded by genes that are transcribed from DNA but not translated into protein (non-coding RNA); instead they are processed from primary transcripts known as pri-miRNA to short stem-loop structures called pre-miRNA and finally to functional miRNA. Mature miRNA molecules are partially complementary to one or more messenger RNA. Thus, protein or RNA may be produced outside the target cell and introduced into a target cell by any method known to the skilled person. For example the genetic determinant is provided from extracts of brains from diseased subjects, such as humans or animals of the present invention. Subsequently, said brain tissue is introduced into a target cell of the present invention.

The target cell may be a sperm cell, an oocyte, a fertilized oocyte, an embryo, which includes the pre-embryo phase encompassing all developmental stages from the fertilization of the oocyte through morula, blastocyst stages hatching and implantation, a fetus, or a cell derived from tissue of the developing fetus. In one embodiment of the present invention the target cell is an adult animal or tissue thereof.

The genetic determinant may be introduced to the target cell by for example injection, virus-mediated transfer or similar methods known to the skilled person.

The genetic determinant may in the form of RNA or protein be introduced into the target cell to yield a non-human animal model for autosomal dominant diseases, such as neurodegenerative diseases as described elsewhere herein, for example protein conformation disorders. In preferred embodiments the genetic determinant is introduced into the target cell to produce a pig model expressing at least one phenotype associated with ALS, Alzheimer's disease, Parkinson's disease, Huntington's chorea, diseases related to trinucleotide repeats. Similarly, in one particular embodiment a pig model is produced expressing at least one phenotype associated with dyschondroplasia.

The genetic determinant may in particular embodiments be introduced by sperm-mediated gene transfer to produce a pig model for autosomal dominant diseases, such as neurodegenerative diseases as described elsewhere herein, for example protein conformation disorders. In preferred embodiments the genetic determinant is introduced by sperm mediated gene transfer to produce a pig model expressing at least one phenotype associated with ALS, Alzheimer's disease, Parkinson's disease, Huntington's chorea, diseases related to trinucleotide repeats. Similarly, in one particular embodiment a pig model is produced expressing at least one phenotype associated with dyschondroplasia.

The genetic determinant when present as a gene or DNA construct need not be integrated into the genome of the target cell, fertilised oocyte, embryo, fetus or tissue. In such an example the gene or DNA construct needs to be expressed in an amount sufficient for triggering a cascade that eventually results in the onset and progression of the disease in question. This is in particular the case for autosomal diseases of the neurodegenerative kind, such as protein conformation diseases. Thus, the genetic determinant involved in ALS, Alzheimer's Disease, Parkinson's disease, diseases related to trinucleotide repeats and Huntington's chorea need not to be integrated in the genome of the pig model. The expression of the gene of interest or DNA construct need not be continuous but has to take place during the development of the embryo to fetus. Similarly, when the genetic determinant is present in the form of protein where the protein is involved in the development of protein conformation diseases the protein need to be present in the embryo or fetus but need not be present continuously in the pig model.

The genetic determinant when present in the form of DNA or cDNA may further comprise regulatory sequences to direct expression of the DNA or cDNA. Such regulatory sequences may be promoters or enhancers. The term promoter will be used here to refer to a group of transcriptional control modules that are clustered around the initiation site for RNA polymerase II. Promoters are composed of discrete functional modules, each consisting of approximately 7-20 bp of DNA, and containing one or more recognition sites for transcriptional activator proteins. At least one module in each promoter functions to position the start site for RNA synthesis. The best known example of this is the TATA box.

Additional promoter elements regulate the frequency of transcriptional initiation. Typically, these are located in the region 30-110 bp upstream of the start site, although a number of promoters have recently been shown to contain functional elements downstream of the start site as well. The spacing between elements is flexible, so that promoter function is preserved when elements are inverted or moved relative to one another. Enhancers were originally detected as genetic elements that increased transcription from a promoter located at a distant position on the same molecule of DNA. The basic distinction between enhancers and promoters is operational. An enhancer region as a whole must be able to stimulate transcription at a distance; this need not be true of a promoter region or its component elements. On the other hand, a promoter must have one or more elements that direct initiation of RNA synthesis at a particular site and in a particular orientation, whereas enhancers lack these specificities. Aside from this operational distinction, enhancers and promoters are very similar entities. They have the same general function of activating transcription in the cell. They are often overlapping and contiguous, often seeming to have a very similar modular organization.

The terms "polynucleotide" and "nucleic acid" are used interchangeably, and, when used in singular or plural, generally refers to any polyribonucleotide or polydeoxyribonucleotide, which may be unmodified RNA or DNA or modified RNA or DNA. Thus, for instance, polynucleotides as defined herein include, without limitation, single- and double-stranded DNA, DNA including single- and double-stranded regions, single- and double-stranded RNA, and RNA including single- and double-stranded regions, hybrid molecules comprising DNA and RNA that may be single-stranded or, more typically, double-stranded or include single- and double-stranded regions. In addition, the term "polynucleotide" as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide. The term "polynucleotide" specifically includes cDNAs. The term includes DNAs (including cDNAs) and RNAs that contain one or more modified bases. Thus, DNAs or RNAs with backbones modified for stability or for other reasons are "polynucleotides" as that term is intended herein. Moreover, DNAs or RNAs comprising unusual bases, such as inosine, or modified bases, such as tritiated bases, are included within the term "polynucleotides" as defined herein. In general, the term "polynucleotide" embraces all chemically, enzymatically and/or metabolically modified forms of unmodified polynucleotides, as well as the chemical forms of DNA and RNA characteristic of viruses and cells, including simple and complex cells.

"Sperm mediated gene transfer" as used herein refers to any method wherein a non-human animal sperm cell is mixed with a genetic determinant (gene) under conditions resulting in the genetic determinant being 1) taken up by the sperm cell, 2) occurring as extrachromosomal DNA or as stably integrated into the genetic material (genome) harboured by the sperm cell, and 3) optionally expressed in said sperm cell. Once taken up by the sperm cell, the genetic material (gene) can be transferred to a non-human animal model which allows one to study the expression of the genetic determinant in the chosen genetic background.

"Autosomal diseases" are used herein to refer to diseases which are inherited through the non-sex chromosomes (pairs 1 through 22). The term "autosomal dominant" is used herein to refer to a single, abnormal gene on one of the autosomal chromosomes (one of the first 22 "non-sex" chromosomes) from either parent which can cause certain diseases. One of the parents will usually have the disease (as the gene is dominant) in this mode of inheritance. Only one parent must have an abnormal gene in order for the offspring to inherit the disease.

The present invention relates to animal models for hereditary autosomal dominant diseases. The models of the present invention can be used as model for hereditary autosomal dominant diseases as known from humans. Animal models for human diseases and especially those diseases such as the autosomal dominant diseases which develop over a long period of time, having a late onset in life are very useful in order to gain information on the onset, progression and treatment regime of individuals suffering from such type of diseases. It is appreciated that the animal models are non-human animals. In one aspect of the invention the non-human animal model for a hereditary autosomal dominant disease is a model wherein the non-human animal model expresses at least one phenotype associated with said hereditary autosomal dominant disease obtained by at least one genetic determinant. In another aspect of the invention the non-human animal model for a hereditary autosomal dominant disease is a model wherein the non-human animal model expresses at least one phenotype associated with said hereditary autosomal dominant disease obtained by sperm-mediated gene transfer.

It is appreciated that the non-human animal model may be obtained by the use of at least one, two, three, four, five, six, seven, eight, nine or ten genetic determinants. The genetic determinants of a given autosomal dominant disease whether in the form of DNA, RNA or protein as described herein may be combined in one animal model in order to obtain a strong phenotype of an autosomal dominant disease.

Autosomal dominant diseases are as described elsewhere herein diseases that are normally inherited through the non-sex chromosomes from one of the parents. Autosomal dominant diseases comprise diseases known as protein conformation diseases, neurodegenerative diseases such as amyotrophic lateral sclerosis (ALS), Alzheimer's disease, Parkinson's disease, diseases related to Trinucleotide Repeats for example huntington's chorea, but also conditions related to dyschondroplasia.

Protein conformation diseases are one type of neurodegenerative diseases in which protein folding disorders occur. The protein misfolding of specific proteins can be observed in affected neuronal tissue. Protein conformation diseases according to the present invention are ALS, Alzheimer's disease, Parkinson's disease, diseases associated with trinucleotide repeats and Huntington's chorea.

ALS

In one embodiment the non-human animal model expresses at least one phenotype associated with ALS. In a particular aspect the non-human animal model is a pig model expressing at least one phenotype associated with ALS.

"Amyotroph lateral sclerosis (ALS)" is used herein to refer to any neurodegenerative disease that usually attacks both upper and lower motor neurons and causes degeneration throughout the brain and spinal cord.

Physicians have limited choices for treating ALS. At this time, Riluzole® is the only drug that has been approved by the FDA for treatment of ALS. In clinical trials, Riluzole® has shown a slight benefit in modestly increasing survival time of patients suffering from ALS.

Amyotrophic lateral Sclerosis (ALS) is the most common motor neurodegenerative disease characterised by a progressive loss of motor neurons in the spinal cord, brain stem, and motor cortex, causing weakness, muscular wasting and paresis, ultimately leading to death. Symptoms of the disease constitute weakness, stiffness, abnormal reflexes, fasciculations, cramps and atrophy. However, especially in the early phases of the disease, ALS can be difficult to diagnose since all symptoms are rarely present at that stage [1].

A common first symptom is a painless weakness in a hand, foot, arm or leg, which occurs in more than half of all cases. Other early symptoms include swallowing or walking difficulty. The biological mechanisms that cause ALS are only partially understood. One known cause of ALS is a mutation of a specific human gene: The SOD1 gene. This mutation is believed to make a defective protein that is toxic to motor nerve cells. The SOD1 mutation, however, accounts for only 1 or 2 percent of ALS cases, or 20 percent of the familial (inherited) cases. Familial ALS represents between five to 10 percent of all cases—the remaining cases seemingly arise spontaneously and attacks previously healthy adults.

The present invention relates to the production of a non-human animal model for ALS. The below Table 1 shows mutations which are associated with ALS in humans. According to the present invention any of the in table 1 listed mutations and substitutions as known from humans are embodiments of the present invention. Thus, the mutated forms of the porcine homolog of the human SOD1 and/or human SOD1 genes/cDNA, RNA and/or protein or parts thereof may comprise any of the listed mutations in order to produce an non-human animal model for ALS and in particular a pig model for ALS. It is appreciated that at least one or more mutations may be introduced into the porcine homolog of the human SOD1 and/or human SOD1 genes/cDNA, RNA and/or protein or parts thereof. Any number of the listed mutations may be used in combination.

TABLE 1

| Location | Codon | Mutation | Mutation | Mutation | Mutation | Mutation | Mutation |
|---|---|---|---|---|---|---|---|
| exon 1 | 4 | Ala4Ser | Ala4Thr | Ala4Val | | | |
| exon 1 | 6 | Cys6Phe | Cys6Gly | | | | |
| exon 1 | 7 | Val7Glu | | | | | |
| exon 1 | 8 | Leu8Val | Leu8Gln | | | | |
| exon 1 | 10 | Gly10Val | | | | | |
| exon 1 | 12 | Gly12Arg | | | | | |
| exon 1 | 14 | Val14Met | Val14Gly | | | | |
| exon 1 | 16 | Gly16Ser | Gly16Ala | | | | |
| exon 1 | 19 | Asn19Ser | | | | | |
| exon 1 | 20 | Phe20Cys | | | | | |
| exon 1 | 21 | Glu21Lys | Glu21Gly | | | | |
| exon 1 | 22 | Gln22Leu | | | | | |
| intron 1 | | 319t > a | | | | | |
| exon 2 | 37 | Gly37Arg | | | | | |
| exon 2 | 38 | Leu38Val | Leu38Arg | | | | |
| exon 2 | 40 | Glu40Gly | | | | | |
| exon 2 | 41 | Gly41Ser | Gly41Asp | | | | |
| exon 2 | 43 | His43Arg | | | | | |
| exon 2 | 45 | Phe45Cys | | | | | |
| exon 2 | 46 | His46Arg | | | | | |
| exon 2 | 47 | Val47Phe | | | | | |
| exon 2 | 48 | His48Arg | His48Gln | | | | |
| exon 2 | 49 | Glu49Lys | | | | | |
| exon 2 | 54 | Thr54Arg | | | | | |
| exon 3 | 57 | Cys57Arg | | | | | |
| exon 3 | 59 | Ser59Ile | | | | | |
| exon 3 | 65 | Asn65Ser | | | | | |
| exon 3 | 67 | Leu67Arg | | | | | |
| exon 3 | 72 | Gly72Cys | Gly72Ser | | | | |
| exon 3 | 76 | Asp76Tyr | Asp76Val | | | | |
| exon 4 | 80 | His80Arg | | | | | |
| exon 4 | 84 | Leu84Val | Leu84Phe | | | | |
| exon 4 | 85 | Gly85Arg | | | | | |
| exon 4 | 86 | Asn86Asp | Asn86Ser | | | | |
| exon 4 | 87 | Val87Met | Val87Ala | | | | |
| exon 4 | 89 | Ala89Thr | Ala89Val | | | | |
| exon 4 | 90 | Asp90Ala | Asp90Val | | | | |
| exon 4 | 93 | Gly93Cys | Gly93Arg | Gly93Ser | Gly93Asp | Gly93Ala | Gly93Val |
| exon 4 | 95 | Ala95Thr | | | | | |
| exon 4 | 96 | Asp96Asn | | | | | |
| exon 4 | 97 | Val97Met | | | | | |
| exon 4 | 100 | Glu100Lys | Glu100Gly | | | | |
| exon 4 | 101 | Asp101His | Asp101Asn | Asp101Gly | | | |
| exon 4 | 104 | Ile104Phe | | | | | |
| exon 4 | 105 | Ser105Leu | | | | | |
| exon 4 | 106 | Leu106Val | | | | | |
| exon 4 | 108 | Gly108Val | | | | | |
| exon 4 | 112 | Ile112Thr | Ile112Met | | | | |
| exon 4 | 113 | Ile113Phe | Ile113Thr | | | | |
| exon 4 | 114 | Gly114Ala | | | | | |
| exon 4 | 115 | Arg115Gly | | | | | |
| exon 4 | 116 | Thr116Arg | | | | | |
| exon 4 | 118 | Val118Leu GTG to TTG) | Val118Leu (GTG to CTG) | | | | |
| intron 4 | | 1415t > g | | | | | |
| exon 5 | 124 | Asp124Val | Asp124Gly | | | | |
| exon 5 | 125 | Asp125His | | | | | |
| exon 5 | 126 | Leu126STOP | Leu126Ser | | | | |
| exon 5 | 134 | Ser134Asn | | | | | |
| exon 5 | 139 | Asn139His | Asn139Lys | | | | |
| exon 5 | 140 | Ala140Gly | | | | | |
| exon 5 | 141 | Gly141STOP | Gly141Glu | | | | |
| exon 5 | 144 | Leu144Ser | Leu144Phe (TTG to TTC) | Leu144Phe (TTG to TTT) | | | |
| exon 5 | 145 | Ala145Thr | Ala145Gly | | | | |
| exon 5 | 146 | Cys146Arg | | | | | |
| exon 5 | 147 | Gly147Arg | | | | | |
| exon 5 | 148 | Val148Ile | Val148Gly | | | | |
| exon 5 | 149 | Ile149Thr | | | | | |
| exon 5 | 151 | Ile151Thr | Ile151Ser | | | | |

Furthermore two mutations in ALS 2 (Ala46delA and Leu623delCT) and three mutations in ALS4, SETX, (Thr3Ile, Leu389Ser, and Arg2136His) are associated with ALS.

Thus, in one aspect of the present invention the non-human animal model expressing at least one phenotype associated with ALS due to the introduction of at least one genetic determinant, wherein the at least one genetic determinant is a gene or DNA or fragment thereof, and/or RNA or fragment thereof and/or protein or part thereof of the human SOD1 gene, mRNA and/or protein (see SEQ ID NO:1, SEQ ID NO:2) comprises at least one mutation yielding the acid mutations as described in table 1, or as described above for ALS 2 (Ala46delA and Leu623delCT) and three mutations in ALS4, SETX, (Thr3Ile, Leu389Ser, and Arg2136His), all associated with ALS.

Similarly, in one embodiment the non-human animal model expressing at least one phenotype associated with ALS due to the introduction of at least one genetic determinant, wherein the genetic determinant is a gene or DNA or fragment thereof, and/or RNA or fragment thereof and/or protein or part thereof of the porcine SOD1 gene, mRNA and/or protein (see SEQ ID NO:3, SEQ ID NO:4 or fragments or parts thereof) comprising at least one mutation yielding the amino acid mutations as described in table 1 or as described above for ALS 2 (Ala46delA and Leu623delCT) and three mutations in ALS4, SETX, (Thr3Ile, Leu389Ser, and Arg2136His), all associated with ALS. It is appreciated that the at least one mutation is present in the gene fragment or DNA fragment, RNA fragment or protein part. In particular the mutated porcine SOD1 cDNA with SEQ ID NO: 5 is used to produce a pig model for ALS.

The non-human animal model for ALS may be generated by introduction of said at least one genetic determinant into a target cell by any method available to the skilled person, for example by injection into the target cell, or by virus-mediated transfer or any method suitable as known by the skilled person.

In one particular embodiment the non-human animal model for ALS is generated by sperm mediated gene transfer.

The present invention discloses a pig model for ALS which in one embodiment is produced by sperm mediated gene transfer of the mutated porcine SOD1 (SEQ ID NO:5) as described elsewhere herein. However, the pig model for ALS may also be produced by introducing the mutated procine SOD1 (SEQ ID NO: 5) or protein expressed (SEQ ID NO:6) thereof into a target cell.

It is appreciated that at least one mutation yielding the amino acid mutation of SOD1 in the human SOD1 as listed in table 1 or as described above for ALS 2 (Ala46delA and Leu623delCT) and three mutations in ALS4, SETX, (Thr3Ile, Leu389Ser, and Arg2136His), all associated with ALS are comprised in the human or porcine SOD1 gene or DNA, RNA or proteins of the present invention, such as for example at least two mutations, at least three mutations, at least four mutations, at least five mutations, at least six mutations, at least seven mutations, at least eight mutations, at least ten mutations, at least fifteen mutations yielding the amino acid mutation of SOD1 of table 1 or as described above for ALS 2 (Ala46delA and Leu623delCT) and three mutations in ALS4, SETX, (Thr3Ile, Leu389Ser, and Arg2136His), all associated with ALS.

The non-human animal model for ALS, in particular the pig model for ALS, will typically develop at least one of the symptoms described above such as weakness, stiffness, abnormal reflexes, fasciculations, cramps and atrophy. A common first symptom is a painless weakness in a leg, which occurs in more than half of all cases. Other early symptoms include swallowing or walking difficulty. Furthermore, histopathology performed on a biopsy as described in the examples, herein can be used to diagnose the animal model with ALS. The analysis of the motor neurons for the presence aggregates, or even loss of the motor neurons are also characteristics of ALS.

Alzheimer's Disease

In another aspect of the present invention the non-human animal model expresses at least one phenotype associated with Alzheimer's disease. In a particular aspect the non-human animal model is a pig model expressing at least one phenotype associated with Alzheimer's disease.

Alzheimer's disease" is used herein to refer to any neurodegenerative brain disorder characterized by progressive memory loss and severe dementia in advanced cases. Alzheimer's disease is associated with certain abnormalities in brain tissue, involving a particular protein, beta-amyloid. Memory impairment is a necessary feature for the diagnosis of this type of dementia. Change in one of the following areas must also be present: language, decision-making ability, judgment, attention, and other areas of mental function and personality.

The rate of progression is different for each person. If Alzheimer's disease develops rapidly, it is likely to continue to progress rapidly. If it has been slow to progress, it will likely continue on a slow course. There are two types of Alzheimer's disease—early onset and late onset. In early onset Alzheimer's disease, symptoms first appear before age 60. Early onset Alzheimer's disease is much less common, accounting for only 5-10% of cases. However, it tends to progress rapidly.

Early onset disease can run in families and involves autosomal dominant, inherited mutations that may be the cause of the disease. So far, three early onset genes have been identified. Late onset Alzheimer's disease, the most common form of the disease, develops in people 60 and older and is thought to be less likely to occur in families. Late onset Alzheimer's disease may run in some families, but the role of genes is less direct and definitive. These genes may not cause the problem itself, but simply increase the likelihood of formation of plaques and tangles or other Alzheimer's disease-related pathologies in the brain.

The cause of Alzheimer's disease is not entirely known but is thought to include both genetic and environmental factors. A diagnosis of Alzheimer's disease is made based on characteristic symptoms and by excluding other causes of dementia. The only way to validate a case of Alzheimer's disease is by microscopic examination of a sample of brain tissue after death.

The brain tissue shows "neurofibrillary tangles" (twisted fragments of protein within nerve cells that clog up the cell), "neuritic plaques" (abnormal clusters of dead and dying nerve cells, other brain cells, and protein), and "senile plaques" (areas where products of dying nerve cells have accumulated around protein). Although these changes occur to some extent in all brains with age, there are many more of them in the brains of people with Alzheimer's disease.

The destruction of nerve cells (neurons) leads to a decrease in neurotransmitters (substances secreted by a neuron to send a message to another neuron). The correct balance of neurotransmitters is critical to the brain. By causing both structural and chemical problems in the brain, Alzheimer's disease appears to disconnect areas of the brain that normally work together.

The following human genes are linked to Alzheimer's disease:

Presenilin 1 (PSEN1, NM_000021),

Presenilin 2 (PSEN2, NM_000447),

Amyloid beta precursor protein (APP, NM_000484)

The below indicated substitutions are believed to be relevant regarding transgenic porcine models for Alzheimer's disease.

TABLE 2

Mutations causing Alzheimer's disease in APP (NM_000484)

| Mutation # | Mutation |
|---|---|
| 1 | Duplication of APP |
| 2 | LysMet670/671AsnLeu |
| 3 | Ala673Thr |
| 4 | Asp678Asn |
| 5 | Ala692Gly |
| 6 | Glu693Lys |
| 7 | Glu693Gln |
| 8 | Glu693Gly |
| 9 | Asp694Asn |
| 10 | Leu705Val |
| 11 | Ala713Thr |
| 12 | Ala713val |
| 13 | Thr714Ala |
| 14 | Thr714Ile |
| 15 | Val715Ala |
| 16 | Ile716Thr |
| 17 | Val717Ile |
| 18 | Val717Leu |
| 19 | Val717Phe |
| 20 | Val717Gly |
| 21 | Leu723Pro |

TABLE 3

Mutations causing Alzheimer's disease in PSEN2 (NM_000447)

| Mutation # | Mutation |
|---|---|
| 1 | Arg62His |
| 2 | Thr122Pro |
| 3 | Ser130Leu |
| 4 | Asn141Ile |
| 5 | Val148Ile |
| 6 | Gln228Leu |
| 7 | Met239Ile |
| 8 | Met239Val |
| 9 | Thr430Met |
| 10 | Asp439Ala |

TABLE 4

Mutations causing Alzheimer's disease in PSEN1 (NM_000021)

| Mutation # | Mutation |
|---|---|
| 1 | Ala79Val |
| 2 | Val82Leu |
| 3 | delIle83/Met84 |
| 4 | Leu85Pro |
| 5 | Val89Leu |
| 6 | Cys92Ser |
| 7 | Val94Met |
| 8 | Val96Phe |
| 9 | Phe105Ile |
| 10 | Phe105Leu |
| 11 | Leu113Gln |
| 12 | Leu113Pro |
| 13 | Intron4; InsTAC |
| 14 | Tyr115Asp |
| 15 | Tyr115Cys |

TABLE 4-continued

Mutations causing Alzheimer's disease in PSEN1 (NM_000021)

| Mutation # | Mutation |
|---|---|
| 16 | Tyr115Asp |
| 17 | Thr116Asn |
| 18 | Thr116Ile |
| 19 | Pro117Ser |
| 20 | Pro117Arg |
| 21 | Pro117Leu |
| 22 | Glu120Lys |
| 23 | Glu120Asp |
| 24 | Glu123Lys |
| 25 | Asn135Asp |
| 26 | Asn135Ser |
| 27 | Met139Val |
| 28 | Met139Lys |
| 29 | Met139Thr |
| 30 | Met139Ile |
| 31 | Ile143Phe |
| 32 | Ile143Asn |
| 33 | Ile143The |
| 34 | Ile143Met |
| 35 | Met146Leu |
| 36 | Met146Val |
| 37 | Met146Leu |
| 38 | Met146Ile |
| 39 | Thr147Ile |
| 40 | Leu153Val |
| 41 | Tyr154Asn |
| 42 | Tyr154Cys |
| 43 | InsPhe/Ile |
| 44 | His163Tyr |
| 45 | His163Arg |
| 46 | Trp165Gly |
| 47 | Trp165Cys |
| 48 | Leu166Pro |
| 49 | Leu166Arg |
| 50 | Del_Ile197 |
| 51 | Ser169Pro |
| 52 | Ser170Phe |
| 53 | Leu171Pro |
| 54 | Leu173Trp |
| 55 | Leu174Met |
| 56 | Leu174Arg |
| 57 | Phe177Leu |
| 58 | Phe177Ser |
| 59 | Ser178Pro |
| 60 | Gly183Val |
| 61 | Glu184Asp |
| 62 | Gly206Ser |
| 63 | Gly206Asp |
| 64 | Gly206Ala |
| 65 | Gly206Val |
| 66 | Gly209Val |
| 67 | Gly209Arg |
| 68 | Gly209Glu |
| 69 | Ile213Leu |
| 70 | Ile213Phe |
| 71 | Ile213Thr |
| 72 | His214Tyr |
| 73 | Gly217Asp |
| 74 | Leu219Phe |
| 75 | Leu219Pro |
| 76 | Gln222Arg |
| 77 | Gln222His |
| 78 | Leu226Arg |
| 79 | Ile229Phe |
| 80 | Ala231Thr |
| 81 | Ala231Val |
| 82 | Met233Leu |
| 83 | Met233Val |
| 84 | Met233Thr |
| 85 | Leu235Val |
| 86 | Leu235Pro |
| 87 | Phe237Leu |
| 88 | Ala246Glu |
| 89 | Leu250Val |
| 90 | Leu250Ser |
| 91 | Tyr256Ser |

TABLE 4-continued

| Mutations causing Alzheimer's disease in PSEN1 (NM_000021) | |
|---|---|
| Mutation # | Mutation |
| 92 | Ala260Val |
| 93 | Val261Phe |
| 94 | Leu262Phe |
| 95 | Cys263Arg |
| 96 | Cys263Phe |
| 97 | Pro264Leu |
| 98 | Pro267Ser |
| 99 | Pro267Leu |
| 100 | Arg269Gly |
| 101 | Arg269His |
| 102 | Leu271Val |
| 103 | Val272Ala |
| 104 | Glu273Ala |
| 105 | Thr274Arg |
| 106 | Arg278Lys |
| 107 | Arg278Thr |
| 108 | Glu280Ala |
| 109 | Glu280Gly |
| 110 | Leu282Val |
| 111 | Leu282Arg |
| 112 | Pro284Leu |
| 113 | Ala285Val |
| 114 | Leu286Val |
| 115 | Deletions in intron 8 |
| 116 | InsArg(g63786_63787) |
| 117 | Thr354Ile |
| 118 | Arg358Gln |
| 119 | Ser365Tyr |
| 120 | Arg377Met |
| 121 | Gly378Glu |
| 122 | Gly378Val |
| 123 | Leu381Val |
| 124 | Gly384Ala |
| 125 | Phe386Ser |
| 126 | Ser390Ile |
| 127 | Val391Phe |
| 128 | Leu392Val |
| 129 | Leu392Pro |
| 130 | Gly394Val |
| 131 | Asn405Ser |
| 132 | Ala409The |
| 133 | Cys410Tyr |
| 134 | Leu418Phe |
| 135 | Leu424His |
| 136 | Leu424Arg |
| 137 | Ala426Pro |
| 138 | Ala431Glu |
| 139 | Ala431Val |
| 140 | Ala434Cys |
| 141 | Leu435Phe |
| 142 | Pro436Ser |
| 143 | Pro436Gln |
| 144 | Ile439Val |
| 145 | DelThr440 |

Thus, in one embodiment the non-human animal model expressing at least one phenotype associated with Alzheimer's disease due to the introduction of at least one genetic determinant, wherein the at least one genetic determinant is a gene or DNA or fragment thereof, and/or RNA or fragment thereof and/or protein or part thereof of the human PSEN1 gene, mRNA and/or protein (see SEQ ID NO:7, SEQ ID NO:8), comprises at least one mutation yielding the amino acid mutations as described in table 4.

Similarly, in one embodiment the non-human animal model expressing at least one phenotype associated with Alzheimer's disease due to the introduction of at least one genetic determinant, wherein the genetic determinant is a gene or DNA or fragment thereof, and/or RNA or fragment thereof and/or protein or part thereof of the porcine PSEN1 gene, mRNA and/or protein (see SEQ ID NO:9, SEQ ID NO:10) or fragments or parts thereof, respectively) comprising at least one mutation yielding the amino acid mutations as described in table 4 It is appreciated that the at least one mutation is present in the gene fragment or DNA fragment, RNA fragment or protein part. In particular the mutated porcine PSEN1 protein with SEQ ID NO: 11 is used to produce a pig model for Alzheimer's disease.

The non-human animal model for ALS may be generated by introduction of said at least one genetic determinant into a target cell by any method available to the skilled person, for example by injection into the target cell, or by virus-mediated transfer or any method suitable as known by the skilled person.

In one particular embodiment the non-human animal model for Alzheimer's disease is generated by sperm mediated gene transfer.

According to the present invention a pig model for Alzheimer's disease is in one embodiment produced by sperm mediated gene transfer of the mutated porcine PSEN1 as described elsewhere herein. However, the pig model for Alzheimer's disease may also be produced by introducing the mutated PSEN1 or protein expressed thereof ((SEQ ID NO: 11) into a target cell.

Moreover, in one embodiment the non-human animal model expressing at least one phenotype associated with Alzheimer's disease due to the introduction of at least one genetic determinant, wherein the genetic determinant is a gene or DNA or fragment thereof, and/or RNA or fragment thereof and/or protein or part thereof of the human PSEN2 gene, mRNA and/or protein (see SEQ ID NO:12, SEQ ID NO:13) comprises at least one mutation yielding the amino acid mutations as described in table 3.

Similarly, in one embodiment the non-human animal model expressing at least one phenotype associated with Alzheimer's disease due to the introduction of at least one genetic determinant, wherein the genetic determinant is a gene or DNA or fragment thereof, and/or RNA or fragment thereof and/or protein or part thereof of the porcine PSEN2 gene, mRNA and/or protein corresponding to SEQ ID NO:14, SEQ ID NO:15, or fragments or parts thereof, respectively) fitted with at least one mutation yielding the amino acid mutations as described in table 3. It is appreciated that the at least one mutation is present in the gene fragment or DNA fragment, RNA fragment or protein part. In particular the mutated porcine PSEN2 DNA with SEQ ID NO: 16 is used to produce a pig model for Alzheimer's disease.

The non-human animal model for ALS may be generated by introduction of said at least one genetic determinant into a target cell by any method available to the skilled person, for example by injection into the target cell, or by virus-mediated transfer or any method suitable as known by the skilled person.

In one particular embodiment the non-human animal model for Alzheimer's disease is generated by sperm mediated gene transfer.

According to the present invention a pig model for Alzheimer's disease is in one embodiment produced by sperm mediated gene transfer of the mutated porcine PSEN1 as described elsewhere herein. However, the pig model for Alzheimer's disease may also be produced by introducing the mutated PSEN1 or protein expressed thereof into a target cell (SEQ ID NO: 16).

Furthermore, in yet another embodiment the non-human animal model expressing at least one phenotype associated with Alzheimer's disease due to the introduction of at least one genetic determinant, wherein the genetic determinant is a gene or DNA or fragment thereof, and/or RNA or fragment thereof and/or protein or part thereof of the human APP gene, mRNA and/or protein (SEQ ID NO:17, SEQ ID NO:18) comprises at least one mutation yielding the amino acid mutations as described in table 2. Similarly, in one embodiment the non-human animal model expressing at least one phenotype associated with Alzheimer's disease due to the introduction of at least one genetic determinant, wherein the genetic determinant is a gene or DNA or fragment thereof, and/or RNA or fragment thereof and/or protein or part thereof of the porcine APP gene, mRNA and/or protein corresponding to SEQ ID NO:19, SEQ ID NO:20, or fragments or parts thereof, comprising at least one mutation yielding the amino acid mutations as described in table 2. It is appreciated that the at least one mutation is present in the gene fragment or cDNA fragment, RNA fragment or protein part. In particular the mutated porcine APP DNA is used to produce a pig model for Alzheimer's disease.

The non-human animal model for Alzheimer's disease may be generated by introduction of said genetic determinant into a target cell by any method available to the skilled person, for example by injection into the target cell.

In one particular embodiment the non-human animal model for Alzheimer's disease is generated by sperm mediated gene transfer.

According to the present invention a pig model for Alzheimer's disease is in one embodiment produced by sperm mediated gene transfer of the mutated porcine APP as described elsewhere herein. However, the pig model for Alzheimer's disease may also be produced by introducing the mutated APP or protein expressed thereof into a target cell (SEQ ID NO: 21).

It is within the scope of the present invention that at least one mutation yielding the amino acid mutation homologous to the human PSEN1, PSEN2 and/or APP as listed in table 4, 3, and/or 2 is comprised in the human or porcine PSEN1, PSEN2 and/or APP gene or DNA, RNA or proteins of the present invention, such as for example at least two mutations, at least three mutations, at least four mutations, at least five mutations, at least six mutations, at least seven mutations, at least eight mutations, at least ten mutations, at least fifteen mutations yielding the amino acid mutation homologous to the human PSEN1, PSEN2 and/or APP as listed in table 4, 3, and/or 2. It is appreciated that one or more of the genes and mutations thereof may be combined in an animal model for example a pig model for Alzheimer's disease.

The non-human animal model for Alzheimer's disease, in particular the pig model for Alzheimer's disease, will typically develop at least one of the symptoms described above such as progressive memory loss and severe dementia in advanced cases which can be monitored by behavioural studies. Evidence also exists for the impairment of olfactoric sense which can be monitored by behavioural changes. Furthermore, scannings of the brain of the animal models by magnetic resonance and/or positron emission tomography can also be employed to determine whether the animal model is indicative for Alzheimer's disease.

Parkinson's Disease

In one embodiment of the present invention the non-human animal model expresses at least one phenotype associated with Parkinson's disease. In a particular aspect the non-human animal model is a pig model expressing at least one phenotype associated with Parkinson's disease.

"Parkinson's disease" is used herein to refer to an inherited condition usually associated with the following symptoms—all of which result from the loss of dopamine-producing brain cells: tremor or trembling of the arms, jaw, legs, and face; stiffness or rigidity of the limbs and trunk; bradykinesia—slowness of movement; postural instability, or impaired balance and coordination.

Parkinson's disease (PD) is a common progressive neurodegenerative disease affecting 1-2% of the population over 60 years of age. The number of PD affected individuals reaches a maximum value between 70 and 79 years of age with a mean age of onset between 60 and 65 years (1). The cardinal clinical symptoms of PD are resting tremor, bradykinesia, rigidity and postural instability. The pathological manifestations of PD are characterized by degeneration of dopaminergic neurons in the substantia nigra pars compacta and the presence of so called Lewy bodies in degenerating neurons. Lewy bodies are cytoplasmic protein inclusions and the main constituent is the protein α-synuclein. Lewy bodies are required for a pathological diagnosis of PD but can also be observed in other neurodegenerative diseases. Degeneration of dopaminergic neurons results in decreased production of dopamine and the lack of this signal substance is responsible for bradykinesia and rigidity. The etiology of PD is largely unknown but is probably due to both genetic and environmental factors. Impaired mitochondrial function, changes in protein sorting by the ubiquitin-proteasome pathway and facilitated apoptosis may all represent factors associated with development of PD (2). Environmental factors suggested are exposure to pesticides and heavy metals (3).

Most cases of PD are sporadic but 5-10% of cases are caused by genetic mutations.

Several transgenic animal models of PD have been established including nematodes (*C. elegans*), *Drosophila*, mice and rats and different PD associated genes. Several limitations to the mice models have been observed, including the absence of loss of nigrostriatal dopaminergic neurons in some of the models suggesting that a better animal model would be of advantage regarding the study of the factors involved in PD pathology and underlying mechanisms.

The following genes are linked to Parkinson's disease:

Alpha synuclein (SNCA, NM_000345),

Ubiquitin C-terminal hydrolase (UCHL1, NM_004181),

Leucine rich repeat kinase (LRRK2, NM_198578).

The below indicated substitutions are believed to be relevant regarding transgenic porcine models for Parkinsons's disease.

TABLE 5

Mutations causing Parkinson's disease in SNCA (NM_000345)

| Mutation # | Mutation |
|---|---|
| 1 | Ala30Pro |
| 2 | Glu46Lys |
| 3 | Ala53Thr |

TABLE 6

Mutations causing Parkinson's disease in UCHL1 (NM_004181)

| Mutation # | Mutation |
|---|---|
| 1 | Ser18Tyr |
| 2 | Ile93Met |

TABLE 7

Putative pathogenic mutations causing Parkinson's disease in LRRK2 (NM_198578)

| Mutation # | Mutation |
|---|---|
| 1 | Arg793Met |
| 2 | Gln930Arg |
| 3 | Arg1067Gln |
| 4 | Ser1096Cys |
| 5 | Ser1228Thr |
| 6 | Ile1371Val |
| 7 | Arg1441His |
| 8 | Arg11514Gln |
| 9 | Met1869Thr |
| 10 | Arg1941His |
| 11 | Thr2356Ile |
| 12 | Gly2385Arg |

One aspect of the present invention thus relates to a non-human animal model expressing at least one phenotype associated with Parkinson's disease due to the introduction of at least one genetic determinant, wherein the genetic determinant is a gene or DNA or fragment thereof, and/or RNA or fragment thereof and/or protein or part thereof of the human SNCA gene, mRNA and/or protein (SEQ ID NO:22, SEQ ID NO:23) comprises at least one mutation yielding the amino acid mutations as described in table 5.

Similarly, in one embodiment the non-human animal model expressing at least one phenotype associated with Parkinson's disease due to the introduction of at least one genetic determinant, wherein the genetic determinant is a gene or DNA or fragment thereof, and/or RNA or fragment thereof and/or protein or part thereof of the porcine SNCA gene, mRNA and/or protein corresponding to SEQ ID NO:24, SEQ ID NO:25 or fragments or parts thereof, respectively) comprising at least one mutation yielding the amino acid mutations as described in table 5. It is appreciated that the at least one mutation is present in the gene fragment or DNA fragment, RNA fragment or protein part. In particular the mutated porcine SNCA cDNA with SEQ ID NO: 26 is used to produce a pig model for Parkinson's disease.

The non-human animal model for ALS may be generated by introduction of said at least one genetic determinant into a target cell by any method available to the skilled person, for example by injection into the target cell, or by virus-mediated transfer or any method suitable as known by the skilled person.

In one particular embodiment the non-human animal model for Parkinson's disease is generated by sperm mediated gene transfer.

According to the present invention a pig model for Parkinson's disease is in one embodiment produced by sperm mediated gene transfer of the mutated porcine SNCA (SEQ ID NO:26) as described elsewhere herein. However, the pig model for Parkinson's disease may also be produced by introducing the mutated SNCA DNA (SEQ ID NO: 26) or protein expressed thereof into a target cell SEQ ID NO: 27).

Moreover, in one embodiment the non-human animal model expressing at least one phenotype associated with Parkinson's disease due to the introduction of at least one genetic determinant, wherein the genetic determinant is a gene or DNA or fragment thereof, and/or RNA or fragment thereof and/or protein or part thereof of the human UCHL1 gene, mRNA and/or protein (SEQ ID NO:28, SEQ ID NO:29) comprises at least one mutation yielding the amino acid mutations as described in table 6.

Similarly, in one embodiment the non-human animal model expressing at least one phenotype associated with Parkinson's disease due to the introduction of at least one genetic determinant, wherein the genetic determinant is a gene or DNA or fragment thereof, and/or RNA or fragment thereof and/or protein or part thereof of the porcine UCHL1 gene, mRNA and/or protein or fragments or parts thereof comprising at least one mutation yielding the amino acid mutations as described in table 6. It is appreciated that the at least one mutation is present in the gene fragment or DNA fragment, RNA fragment or protein part. In particular the mutated porcine UCHL1 DNA is used to produce a pig model for Parkinson's disease.

The non-human animal model for Parkinson's disease may be generated by introduction of said genetic determinant into a target cell by any method available to the skilled person, for example by injection into the target cell.

In one particular embodiment the non-human animal model for Parkinson's disease is generated by sperm mediated gene transfer.

According to the present invention a pig model for Parkinson's disease is in one embodiment produced by sperm mediated gene transfer of the mutated porcine UCHL1 as described elsewhere herein. However, the pig model for Parkinson's disease may also be produced by introducing the mutated UCHL1 or protein expressed thereof into a target cell.

Furthermore, in yet another embodiment the non-human animal model expressing at least one phenotype associated with Parkinson's disease due to the introduction of at least one genetic determinant, wherein the genetic determinant is a gene or DNA or fragment thereof, and/or RNA or fragment thereof and/or protein or part thereof of the human LRRK2 gene, mRNA and/or protein (SEQ ID NO:30, SEQ ID NO:31) comprises at least one mutation yielding the amino acid mutations as described in table 7.

Similarly, in one embodiment the non-human animal model expressing at least one phenotype associated with Parkinson's disease due to the introduction of at least one genetic determinant, wherein the genetic determinant is a gene or DNA or fragment thereof, and/or RNA or fragment thereof and/or protein or part thereof of the porcine LRRK2 gene, mRNA and/or protein or fragments or parts thereof, respectively) fitted with at least one mutation yielding the amino acid mutations as described in table 7. It is appreciated that the at least one mutation is present in the gene fragment or DNA fragment, RNA fragment or protein part. In particular the mutated porcine LRRK2 DNA is used to produce a pig model for Parkinson's disease.

The non-human animal model for Parkinson's disease may be generated by introduction of said genetic determinant into a target cell by any method available to the skilled person, for example by injection into the target cell.

In one particular embodiment the non-human animal model for Parkinson's disease is generated by sperm mediated gene transfer.

According to the present invention a pig model for Parkinson's disease is in one embodiment produced by sperm mediated gene transfer of the mutated porcine LRRK2 as described elsewhere herein. However, the pig model for Alzheimer's disease may also be produced by introducing the mutated LRRK2 or protein expressed thereof into a target cell.

It is within the scope of the present invention that at least one mutation yielding the amino acid mutation homologous to the human SNCA, UCHL1 and/or LRRK2 as listed in table 5, 6 and/or 7 is comprised in the human or porcine SNCA, UCHL1 and/or LRRK2 gene or DNA, RNA or proteins of the present invention, such as for example at mutations, at least six mutations, at least seven mutations, at least eight mutations, at least ten mutations, at least fifteen mutations yielding the amino acid mutation homologous to the human SNCA, UCHL1 and/or LRRK2 as listed in table 5, 6 and/or 7. It is appreciated that one or more of the genes and mutations thereof may be combined in an animal model for example a pig model for Parkinson's disease.

The non-human animal model for Parkinson's disease, in particular the pig model for Parkinson's disease, will typically develop at least one of the symptoms described above such as symptoms—all of which result from the loss of dopamine-producing brain cells: tremor or trembling of the jaw, legs, and face, stiffness or rigidity of the limbs and trunk, bradykinesia—slowness of movement; postural instability, or impaired balance and coordination.

Trinucleotide Repeat (TNR) Disorders

In one embodiment of the present invention the non-human animal model expresses at least one phenotype associated with diseases related to trinucleotide repeat disorders. In a particular aspect the non-human animal model is a pig model expressing at least one phenotype associated with diseases related to trinucleotide repeat disorders.

Trinucleotide repeat disorders or expansion disorders are caused by stretches of DNA in a gene that contain the same trinucleotide sequence repeated many times. Unstable microsatellite repeats are found throughout all genomic sequences and TNRs constitute a subset of such unstable repeats.

Nucleotide repeat instability is associated with more than 40 inherited neurodegenerative, neuromuscular, and mental retardation disorders in humans [2,3]. The nucleotide repeat instability process is a dynamic process, where mutations continue to recur during meiosis and in mitotic tissue [3]. Long stretches of repeats are more likely to expand than short stretches of repeats and the length is correlated with age of onset and the severity of disease, a phenomena called anticipitation [3]. Diseases caused by trinucleotide repeat (TNR) instability can be divided into two groups. In the first group the TNRs reside in the untranslated part of the affected genes. The untranslated TNR expansions, constituting either CTGs, CAGs, GAAs, or CGGs, result in an RNA gain-of-function that may alter the gene expression control of the affected genes or have cis and trans effects on splicing and gene regulation at the chromatin level [4-7]. Expanded noncoding TNRs have been identified as causative mutations in disorders including Friedreich ataxia, spinocerebellar ataxia 8 (SCA-8), SCA-12, myotonic dystrophy, and fragile-X syndromes [3].

In the second group the TNRs are located in the coding region of the transcript. This type of TNRs are translated in frame of the coding region and expansions include GAC encoding poly-aspargine, GCG encoding poly-alanine, and the most commonly identified CAG TNRs encoding polyglutamine [3]. Expanded CAG TNRs, are identified as causative mutations in disorders, including SCA-1, SCA-2, SCA-3, SCA-6, SCA-7, SCA17, Huntington's disease, spinal and bulbar muscular atrophy (SBMA), and dentatorubral pallidoluysian atrophy (DRPLA). In these disorders cytoskeletal and vesicular functions are affected as well as the regulation of cellular gene expression due to the sequestering of transcriptional regulatory proteins.

The molecular mechanisms responsible for TNR instability are not completely elucidated. The degree of tissue-specific and inherited TNR instability is determined by both the specific cis-sequences within the affected genes and trans-functioning metabolic proteins as for example DNA repair proteins [3]. TNR instability probably involves the formation of specific DNA structures during DNA replication, repair and recombination [8]. Slippage during DNA replication is the best characterized mechanism. The direction of DNA replication through the TNR tract also affects the stability [9-11]. In addition to the TNR itself, the sequence environment of the repeat contributes to the mechanism of instability, and, for example, similar CAG tract lengths show different stability depending on the genomic context [3, 12]. In the human population the length of TNR repeat tracts is polymorphic but stably transmitted [13]. Beyond a certain TNR length, which appears to be gene specific, the TNR tract becomes unstable [3]. An unstable TNR tract that has not yet expanded to a size sufficient for the full disease phenotype is called a premutation [2]. However, TNR expansions of the premutation size in for example FMR1 have been shown to result in a specific disease phenotype of late onset. The genetic instability of TNRs is related to the repeat tract length and expanded tracts have increased risk of being affected by a subsequent expanding mutation than the original tract [2, 3, 14]. Also TNR interruptions, as for example CAA triplets in CAG TNRs, play an important role conferring TNR stability and their absence predisposes alleles towards instability and pathological expansions [15]. A large level of somatic and transmitted instability is observed for premutation and fully expanded TNR tracts [2,3]. The fully expanded and disease causing TNR tracts can be composed of approximately twenty TNRs as observed in SCA-6 to several thousands as observed in for example myotonic dystrophy [2,3]. Interestingly, it was recently shown that an induced level of transcription promotes contraction of TNR tracts in human cells [16]. Furthermore, transgenic animal models of TNR instability also points out the importance for specific TNR flanking sequences to create TNR instability [9, 17, 18].

One embodiment of the present invention relates to a non-human animal model expressing at least one phenotype associated with myotonic dystrophy. In a particular aspect the non-human animal model is a pig model expressing at least one phenotype associated with myotonic dystrophy.

Myotonic dystrophy is caused by TNR in the 3'-UTR of the human myotonic dystrophy protein kinase gene, DMPK, where a CTG TNR is located [19-23]. The normal size of this TNR varies between 5 and 37. Expansions from above 50 to several thousand CTG repeats result in myotonic dystrophy.

One aspect of the present invention thus relates to a non-human animal model expressing at least one phenotype associated with myotonic dystrophy due to the introduction of at least one genetic determinant, wherein the genetic determinant is a gene or DNA or fragment thereof, and/or RNA or fragment thereof and/or protein or part thereof of the human myotonic dystrophy protein kinase gene, DMPK gene, mRNA and/or protein (SEQ ID NO:32, SEQ ID NO:33), wherein the number of CTG repeats is at least 40, 45, 50 or at least 60.

Similarly, in one embodiment the non-human animal model expressing at least one phenotype associated with myotonic dystrophy due to the introduction of a genetic determinant, wherein the genetic determinant is a gene or DNA or fragment thereof, and/or RNA or fragment thereof and/or protein or part thereof of the porcine homolog of the human DMPK gene, mRNA and/or protein or fragments or parts thereof, respectively), wherein the number of CTG repeats in the DNA is at least 40, 45, 50 or at least 60.

The non-human animal model for myotonic dystrophy may be generated by introduction of said genetic determinant into a target cell by any method available to the skilled person, for example by injection into the target cell, or by virus-mediated transfer or any method suitable as known by the skilled person.

In one particular embodiment the non-human animal model for myotonic dystrophy is generated by sperm mediated gene transfer.

According to the present invention a pig model for myotonic dystrophy is in one embodiment produced by sperm mediated gene transfer of the human or porcine DMPK gene, mRNA and/or protein, wherein the number of CTG repeats in the DNA is at least 40, 45, 50 or at least 60. However, the pig model for myotonic dystrophy may also be produced by introducing the human or porcine DMPK gene, mRNA and/or protein, wherein the number of CTG repeats in the DNA is at least 40, 45, 50 or at least 60, or protein expressed thereof into a target cell.

The non-human animal model for myotonic dystrophy, in particular the pig model for myotonic dystrophy, will typically develop at least one of the symptoms such as generalized weakness and muscular wasting that affects the face and neck; difficulty with the feet that spreads to the legs, shoulders and hips. Other symptoms include a wasting of the muscles (muscular dystrophy), opacity of the lens of the eyes (cataracts), heart conduction defects and myotonia (difficulty in relaxing muscles).

Fragile X Syndrome

One embodiment of the present invention relates to a non-human animal model expressing at least one phenotype associated with fragile X syndrome. In a particular aspect the non-human animal model is a pig model expressing at least one phenotype associated with fragile X syndrome.

Fragile X syndrome is caused by repeats in the promoter region of the human FMR1 gene, 6 to 52 CGG repeats are normally present [24, 25]. Expansions in the range of 55 to 200 repeats result in the pre-mutation while the full mutation ranges from 200 to several thousand repeats resulting in fragile X syndrome. Fragile X syndrome may also be by caused by CCG repeats in the TNR of the 5' end of the human FMR2 gene, wherein the number of repeats varies from 6 to 35 [26]. Expansions containing from 61 to 200 repeats result in the pre-mutation and expansions above 200 repeats result in the full mutation and the fragile X syndrome.

One aspect of the present invention thus relates to a non-human animal model expressing at least one phenotype associated with Fragile X syndrome due to the introduction of at least one genetic determinant, wherein the at least one genetic determinant is a gene or DNA or fragment thereof, and/or RNA or fragment thereof and/or protein or part thereof of the human FMR1 gene/cDNA, mRNA and/or protein (SEQ ID NO:34, SEQ ID NO:35) wherein the number of CGG repeats is at least 55, 60, 70 or at least 200, and/or of the human FMR2 gene/cDNA, mRNA and/or protein (SEQ ID NO:36, SEQ ID NO:37) wherein the number of CCG repeats is at least 61, 65, 70, 80 or at least 200, Similarly, one embodiment relates to the non-human animal model expressing at least one phenotype associated with fragile X syndrome due to the introduction of at least one genetic determinant, wherein the at least one genetic determinant is a gene or DNA or fragment thereof, and/or RNA or fragment thereof and/or protein or part thereof of the porcine homolog of the human FMR1 gene/cDNA, mRNA and/or protein, wherein the number of CGG repeats is at least 55, 60, 70 or at least 200, and/or of the porcine homolog of the human FMR2 gene/cDNA, mRNA and/or protein, wherein the number of CCG repeats is at least 61, 65, 70, 80 or at least 200, The non-human animal model for fragile X syndrome may be generated by introduction of said genetic determinant into a target cell by any method available to the skilled person, for example by injection into the target cell.

In one particular embodiment the non-human animal model for fragile X syndrome is generated by sperm mediated gene transfer.

According to the present invention a pig model for fragile X syndrome is in one embodiment produced by sperm mediated gene transfer of the human or the porcine homolog of the human FMR1 gene/cDNA, mRNA and/or protein, fragments or part thereof, wherein the number of CGG repeats is at least 55, 60, 70 or at least 200, and/or the human or the porcine homolog of the human FMR2 gene/cDNA, mRNA and/or protein, fragment or part thereof, wherein the number of CCG repeats is at least 61, 65, 70, 80 or at least 200, However, the pig model for myotonic dystrophy may also be produced by introducing the human or porcine FMR1 gene/cDNA, mRNA and/or protein, fragments or part thereof, wherein the number of CGG repeats is at least 55, 60, 70 or at least 200, and/or the human or the porcine homolog of the human FMR2 gene/cDNA, mRNA and/or protein, fragment or part thereof, wherein the number of CCG repeats is at least 61, 65, 70, 80 or at least 200, or protein expressed thereof into a target cell.

The non-human animal model for fragile X syndrome, in particular the pig model for fragile X syndrome, will typically develop at least one of the symptoms associated with autism. Non-limiting examples of symptoms of autism is for example repetitive behaviour and impairment in social interaction.

Spinocerebellar Ataxia

One embodiment of the present invention relates to a non-human animal model expressing at least one phenotype associated with spinocerebellar ataxia. In a particular aspect the non-human animal model is a pig model expressing at least one phenotype associated with spinocerebellar ataxia.

Spinocerebellar ataxia (SCA12) is caused by repeats in the within the 5'-UTR of the human PPP2R2B gene and the number of CAG repeats normally varies in size from 7 to 28 and in the expanded form from above 65 to 78 TNRs [27].

Spinocerebellar ataxia (SCA 1) is caused by CAG repeats in the ATX1 protein. The human SCA1 TNR region is characterized by the presence of 12 CAG repeats followed by two CAT repeats flanking a CAG triplet [28]. The CAG TNR prone to expand is normally composed of between 6 and 39 repeats and the expanded version consists of 41 to 81 repeats.

Spinocerebellar ataxia (SCA 2) is caused by TNR expansions affecting the ATX2 protein. This TNR normally consists of 15 to 30 CAG repeats and the expanded form ranges from 35 to 59 triplets [29].

Spinocerebellar ataxia (SCA 3) is caused by a CAG TNR expansion in the human ataxin-3 gene, wherein the presence of above 54 repeats results in ataxia whereas the normal number of CAG repeats varies between 12 and 36 [30-32].

Spinocerebellar ataxia (SCA6) is caused by TNR expansion in the CACNA1A voltage dependent calcium channel results in ataxia [33]. The normal number of TNRs is between 4 and 18 and expansions from 21 to 27 TNRs are disease causative.

Spinocerebellar ataxia (SCA7) is caused by TNR of the human SCA7 locus in the N-terminal end of the ataxin-7 protein, which is normally composed of 7 to 35 CAG repeats [34]. Disease causing expansions range from 37 to 200 repeats.

Spinocerebellar ataxia (SCA17) is caused by a CAG expansion in the TATA box binding protein (TBP) gene and results in the SCA17 phenotype resulting in ataxia [35]. The human TNR region is composed of two groups of CAG repeats separated by multiple CAA and CAG triplets. Expansions normally progress from the larger of the two CAG groups. The normal stretch of encoded poly-glutamines varies between 29 and 42 whereas poly-glutamine stretches from 47 to 55 have been identified in SCA17 patients.

One aspect of the present invention thus relates to a non-human animal model expressing at least one phenotype associated with Spinocerebellar ataxia due to the introduction of at least one genetic determinant, wherein the at least one genetic determinant is a gene or DNA or fragment thereof, and/or RNA or fragment thereof and/or protein or part thereof of the human PPP2R2B gene/cDNA, mRNA and/or protein (SEQ ID NO:38, SEQ ID NO:39), wherein the number of CAG repeats is at least 65, 70 or at least 75, and/or of the human ATX1 gene/cDNA, mRNA and/or protein (SEQ ID NO:40 SEQ ID NO:41), wherein the number of 12 CAG repeats followed by two CAT repeats flanking a CAG triplet is at least 41, 45, 50, 60, 70 or at least 80. The at least one genetic determinant may also be a gene or DNA or fragment thereof, and/or RNA or fragment thereof and/or protein or part thereof of the human ATX2 gene/cDNA, mRNA and/or protein (SEQ ID NO:42, SEQ ID NO:43), wherein the number of CAG repeats is at least 35, 40, 45, 50 or at least 55, and/or the at least one genetic determinant is a gene or DNA or fragment thereof, and/or RNA or fragment thereof and/or protein or part thereof of the human ataxin-3 gene/cDNA, mRNA and/or protein (SEQ ID NO:44, SEQ ID NO:45), wherein the number of CAG repeats is at least 54 and/or the at least one genetic determinant is a gene or DNA or fragment thereof, and/or RNA or fragment thereof and/or protein or part thereof of the human CACNA1A gene/cDNA, mRNA and/or protein (SEQ ID NO:46, SEQ ID NO:47), wherein the number of TNR expansions is at least 21, 22, 23, 24, 25, 26 or at least 27, or in the range of 21 to 27 repeats; and/or the at least one genetic determinant is a gene or DNA or fragment thereof, and/or RNA or fragment thereof and/or protein or part thereof of the human N-terminal end of the ataxin-7 protein encoding gene/cDNA, mRNA and/or protein (SEQ ID NO:48, SEQ ID NO:49), wherein the number of CAG expansions is at least 37, 45, 55, 65, or at least 100; and/or the at least one genetic determinant is a gene or DNA or fragment thereof, and/or RNA or fragment thereof and/or protein or part thereof of the human TATA box binding protein (TBP) gene/cDNA, mRNA and/or protein (SEQ ID NO:50, SEQ ID NO:51), wherein the number of poly-glutamine stretches as defined above is in the range of from 47 to 55 repeats.

Similarly, one embodiment relates to the non-human animal model expressing at least one phenotype associated with spinocerebellar ataxia due to the introduction of at least one genetic determinant, wherein the at least one genetic determinant is a gene or DNA or fragment thereof, and/or RNA or fragment thereof and/or protein or part thereof of the porcine homolog of the human PPP2R2B gene/cDNA, mRNA and/or protein, wherein the number of CAG repeats is at least 65, 70 or at least 75, and/or of the porcine homolog of the human ATX1 gene/cDNA, mRNA and/or protein, wherein the number of 12 CAG repeats followed by two CAT repeats flanking a CAG triplet is at least 41, 45, 50, 60, 70 or at least 80. The at least one genetic determinant may also be a gene or DNA or fragment thereof, and/or RNA or fragment thereof and/or protein or part thereof of the porcine homolog of the human ATX2 gene/cDNA, mRNA and/or protein, wherein the number of CAG repeats is at least 35, 40, 45, 50 or at least 55, and/or the at least one genetic determinant is a gene or DNA or fragment thereof, and/or RNA or fragment thereof and/or protein or part thereof of the porcine homolog of the human ataxin-3 gene/cDNA, mRNA and/or protein, wherein the number of CAG repeats is at least 54 and/or the at least one genetic determinant is a gene or DNA or fragment thereof, and/or RNA or fragment thereof and/or protein or part thereof of the porcine homolog of the human CACNA1A gene/cDNA, mRNA and/or protein, wherein the number of TNR expansions is at least 21, 22, 23, 24, 25, 26 or at least 27, or in the range of 21 to 27 repeats; and/or the at least one genetic determinant is a gene or DNA or fragment thereof, and/or RNA or fragment thereof and/or protein or part thereof of the porcine homolog of the human N-terminal end of the ataxin-7 protein encoding gene/cDNA, mRNA and/or protein, wherein the number of CAG expansions is at least 37, 45, 55, 65, or at least 100; and/or the at least one genetic determinant is a gene or DNA or fragment thereof, and/or RNA or fragment thereof and/or protein or part thereof of the porcine homolog of the human TATA box binding protein (TBP) gene/cDNA, mRNA and/or protein, wherein the number of poly-glutamine stretches as defined above is in the range of from 47 to 55 repeats.

The non-human animal model for spinocerebellar ataxia may be generated by introduction of said genetic determinant into a target cell by any method available to the skilled person, for example by injection into the target cell, or by virus-mediated transfer or any method suitable as known by the skilled person.

In one particular embodiment the non-human animal model for spinocerebellar ataxia is generated by sperm mediated gene transfer.

According to the present invention a pig model for spinocerebellar ataxia is in one embodiment produced by sperm mediated gene transfer of the human or the porcine homolog of the human PPP2R2B gene/cDNA, mRNA and/or protein, wherein the number of CAG repeats is at least 65, 70 or at least 75, and/or the porcine homolog of the human or the human ATX1 gene/cDNA, mRNA and/or protein, wherein the number of 12 CAG repeats followed by two CAT repeats flanking a CAG triplet is at least 41, 45, 50, 60, 70 or at least 80, and/or the human or the porcine homolog of the human ATX2 gene/cDNA, mRNA and/or protein, wherein the number of CAG repeats is at least 35, 40, 45, 50 or at least 55, and/or the human or the porcine homolog of the human ataxin-3 gene/cDNA, mRNA and/or protein, wherein the number of CAG repeats is at least 54 and/or the human or the porcine homolog of the human CACNA1A gene/cDNA, mRNA and/or protein, wherein the number of TNR expansions is at least 21, 22, 23, 24, 25, 26 or at least 27, or in the range of 21 to 27 repeats; and/or the human or the porcine homolog of the human N-terminal end of the ataxin-7 protein encoding gene/cDNA, mRNA and/or protein, wherein the number of CAG expansions is at least 37, 45, 55, 65, or at least 100; and/or the human or porcine homolog of the human TATA box binding protein (TBP) gene/cDNA, mRNA and/or), wherein the number of poly-glutamine stretches as defined above is in the range of from 47 to 55 repeats.

However, the pig model for spinocerebellar ataxia may also be produced by introducing the human or porcine homolog of PPP2R2B, ATX1, ATX2, ataxin-3, CACNA1A, ataxin-7 and/or TATA box binding protein (TBP) in any combination.

The non-human animal model for spinocerebellar ataxia, in particular the pig model for spinocerebellar ataxia, will typically develop at least one of the symptoms such as atrophy of the cerebellum which can be seen by magnetic resonance imaging and/or poor coordination of movement.

Dentatorubral-Pallidoluysian Atrophy (DRPLA)

One embodiment of the present invention relates to a non-human animal model expressing at least one phenotype associated with DRPLA. In a particular aspect the non-human animal model is a pig model expressing at least one phenotype associated with DRPLA.

DRPLA is caused by CAG expansions within the human atrophin-1 gene results in dentatorubral-pallidoluysian atrophy (DRPLA) [36]. The normal range of repetitive CAG repeats is from 3 to 25, and in patients with DRPLA allele sizes have expanded to 49 to 88 CAG repeats. The most common natural occurring human allele encodes a stretch of 17 poly-glutamines.

Thus, one aspect of the present invention thus relates to a non-human animal model expressing at least one phenotype associated with DRPLA due to the introduction of at least one genetic determinant, wherein the at least one genetic determinant is a gene or DNA or fragment thereof, and/or RNA or fragment thereof and/or protein or part thereof of the human atrophin-1/cDNA, mRNA and/or protein (SEQ ID NO:52, SEQ ID NO:53), wherein the number of CAG repeats is at least 49, 55, 60, 70 or at least 80 repeats.

Similarly, one embodiment relates to the non-human animal model expressing at least one phenotype associated with DRPLA due to the introduction of at least one genetic determinant, wherein the at least one genetic determinant is a gene or DNA or fragment thereof, and/or RNA or fragment thereof and/or protein or part thereof of the porcine homolog of the human atrophin-1 gene/cDNA, mRNA and/or protein, wherein the number of CAG repeats is at least 49, 55, 60, 70 or at least 80 repeats.

The non-human animal model for DRPLA may be generated by introduction of said genetic determinant into a target cell by any method available to the skilled person, for example by injection into the target cell, or by virus-mediated transfer or any method suitable as known by the skilled person.

In one particular embodiment the non-human animal model for DRPLA is generated by sperm mediated gene transfer.

According to the present invention a pig model for DRPLA is in one embodiment produced by sperm mediated gene transfer of the human or the porcine homolog of the human atrophin-1 gene/cDNA, mRNA and/or protein, fragments or part thereof), wherein the number of CAG repeats is at least 49, 55, 60, 70 or at least 80 repeats.

However, the pig model for DRPLA may also be produced by introducing the human or porcine homolog of the human atrophin-1 gene/cDNA, mRNA and/or protein, fragments or part thereof, wherein the number of CAG repeats is at least 49, 55, 60, 70 or at least 80 repeats, or protein expressed thereof into a target cell.

The non-human animal model for DRPLA, in particular the pig model for ALS, will typically develop at least one of the symptoms epileptic seizures, myoclonus, ataxia, and dementia.

Spinal and Bulbar Muscular Atrophy (SBMA)

One embodiment of the present invention relates to a non-human animal model expressing at least one phenotype associated with SBMA. In a particular aspect the non-human animal model is a pig model expressing at least one phenotype associated with SBMA.

SBMA is caused by CAG repeat expansions in exon 1 of the androgen receptor (AR) gene on the X-chromosome results in spinal and bulbar muscular atrophy (Kennedy's disease) [37]. The normal length of the human CAG TNR is between 11 and 33 CAG copies and in diseased individuals the expansion ranges from 38 to 62.

Thus, one aspect of the present invention thus relates to a non-human animal model expressing at least one phenotype associated with SBMA due to the introduction of at least one genetic determinant, wherein the at least one genetic determinant is a gene or DNA or fragment thereof, and/or RNA or fragment thereof and/or protein or part thereof of the human AR gene/cDNA, mRNA and/or protein (SEQ ID NO:54, SEQ ID NO:55), wherein the number of CAG repeats is at least 38, 45, 50, 55 or at least 60, or in the range of 38 to 62 repeats.

Similarly, one embodiment relates to the non-human animal model expressing at least one phenotype associated with SBMA due to the introduction of at least one genetic determinant, wherein the at least one genetic determinant is a gene or DNA or fragment thereof, and/or RNA or fragment thereof and/or protein or part thereof of the porcine homolog of the human AR gene/cDNA, mRNA and/or protein, wherein the number of CAG repeats is at least 38, 45, 50, 55 or at least 60, or in the range of 38 to 62 repeats.

The non-human animal model for SBMA may be generated by introduction of said genetic determinant into a target cell by any method available to the skilled person, for example by injection into the target cell, or by virus-mediated transfer or any method suitable as known by the skilled person.

In one particular embodiment the non-human animal model for SBMA is generated by sperm mediated gene transfer.

According to the present invention a pig model for SBMA is in one embodiment produced by sperm mediated gene transfer of the human or the porcine homolog of the human AR gene/cDNA, mRNA and/or protein, wherein the number of CAG repeats is at least 38, 45, 50, 55 or at least 60, or in the range of 38 to 62 repeats.

However, the pig model for SBMA may also be produced by introducing the human or porcine homolog of the human AR gene/cDNA, mRNA and/or, wherein the number of CAG repeats is at least 38, 45, 50, 55 or at least 60, or in the range of 38 to 62 repeats, or protein expressed thereof into a target cell.

The non-human animal model for SBMA, in particular the pig model for SBMA, will typically develop at least one of the symptoms: uncontrollable twitching (fasciculations) followed by weakness and wasting of the muscles becomes apparent sometime after the age of fifteen. The muscles of the face, lips, tongue, mouth, throat, vocal chords, trunk and limbs may be affected.

Huntington's Disease (HD)

One embodiment of the present invention relates to a non-human animal model expressing at least one phenotype associated with HD. In a particular aspect the non-human animal model is a pig model expressing at least one phenotype associated with HD.

"Huntington's disease" (also known as Huntington chorea) is used herein to refer to any inherited condition characterized by abnormal and/or uncontrolled body movements, mental and emotional problems, and loss of thinking ability (cognition).

Adult-onset Huntington disease, the most common form of this disorder, usually begins in middle age. Signs and symptoms can include irritability, depression, small involuntary movements, poor coordination, and trouble learning new information or making decisions. As the disease progresses, involuntary jerking movements (chorea) become more pronounced. Affected individuals may have trouble walking, speaking, and swallowing. People with the disorder also typically experience changes in personality and a decline in thinking and reasoning abilities. Individuals with this form of Huntington disease generally survive about 15 to 25 years after onset.

There is also an early-onset form of Huntington disease that begins in childhood or adolescence. Some of the clinical features of this disease differ from those of the adult-onset form. Signs and symptoms can include slowness, clumsiness, rigidity, loss of developmental milestones (such as motor skills), slow speech, and drooling. Seizures occur in 30 percent to 50 percent of individuals with this condition. The course of early-onset Huntington disease may be shorter than adult-onset Huntington disease; affected individuals generally survive 10 to 15 years after onset.

Huntington's disease in humans is linked to the Huntingtin gene (HD gene, accession number: NM_002111). The function of the corresponding protein is not yet known, but it likely plays an important role in nerve cells. The disease causing mutation in Huntington's disease is an extension of a CAG repeat, to a length above 35 CAG units. The number of repeats can to a certain extent be correlated with disease onset.

The expanded repeat leads to the production of a huntingtin protein that contains a long stretch of the amino acid glutamine. The elongated protein disrupts the normal function of nerve cells in certain parts of the brain, and ultimately leads to the death of those cells. The dysfunction and loss of nerve cells cause the signs and symptoms of Huntington disease.

Thus, one aspect of the present invention thus relates to a non-human animal model expressing at least one phenotype associated with HD due to the introduction of at least one genetic determinant, wherein the at least one genetic determinant is a gene or DNA or fragment thereof, and/or RNA or fragment thereof and/or protein or part thereof of the human Huntingtin gene/cDNA, mRNA and/or protein (SEQ ID NO:56, SEQ ID NO:57), wherein the number of CAG repeats is at least 35, 45, 50, 55 or at least 60.

Similarly, one embodiment relates to the non-human animal model expressing at least one phenotype associated with HD due to the introduction of at least one genetic determinant, wherein the at least one genetic determinant is a gene or DNA or fragment thereof, and/or RNA or fragment thereof and/or protein or part thereof of the porcine homolog of the human Huntingtin gene/cDNA, mRNA and/or protein, wherein the number of CAG repeats is at least 35, 45, 50, 55 or at least 60.

The non-human animal model for HD may be generated by introduction of said genetic determinant into a target cell by any method available to the skilled person, for example by injection into the target cell, or by virus-mediated transfer or any method suitable as known by the skilled person.

In one particular embodiment the non-human animal model for HD is generated by sperm mediated gene transfer.

According to the present invention a pig model for HD is in one embodiment produced by sperm mediated gene transfer of the human or the porcine homolog of the human Huntingtin gene/cDNA, mRNA and/or protein, wherein the number of CAG repeats is at least 35, 45, 50, 55 or at least 60.

However, the pig model for HD may also be produced by introducing the human or porcine homolog of the human huntingtin gene/cDNA, mRNA and/or, wherein the number of CAG repeats is at least 35, 45, 50, 55 or at least 60; or protein expressed thereof into a target cell.

The non-human animal model for HD, in particular the pig model for HD, will typically develop at least one of the symptoms described above such as slowness, clumsiness, rigidity, loss of developmental milestones (such as motor skills), slow speech, and drooling or seizures.

Dyschondroplasia (Collagen X Type)

In one embodiment of the present invention the non-human animal model expresses at least one phenotype associated with dyschondroplasia. In a particular aspect the non-human animal model is a pig model expressing at least one phenotype associated with dyschondroplasia.

Chondrodysplasias are a group of disorders affecting the skeleton and are often associated with proteins of the collagen superfamily constituting at least 19 different types of collagen, these being major components of cartilages throughout the mammalian organism implicating roles in the processes of calcification and ossification [38]. One third of the collagens (types I, II, III, V, and IX) are denoted fibrillar collagens due to their tissual status as long, highly organised fibers. The remaining two thirds of the collagens are nonfibrillar and are further divided into two groups; the fibril associated with interrupted helices and the network forming collagens [39]. Collagen X belongs to the group of network forming collagens and has been reported to be expressed mainly in the hypertrophic region of growth plate cartilage [40], and has only rarely been detected in calcifying region of articular cartilage [41].

Type X collagen has been suggested to be structurally important in the extracellular matrix by offering the molecular milieu essential for endochondral bone formation [40]. Furthermore, it has been shown that type X collagen exists in ostechondrotic and osteoarthritic porcine articular cartilage and it may be a product of the cell population trying to repair the breakdown [41]. However, in osteochondrosis the endochondral ossification is impaired regardless of the unaltered collagen X levels in the growth plate and the increase of said collagen in articular cartilage. This could indicate that type X collagen alone is not able to cause ossification of cartilage [41]. Moreover, it has previously been shown, in a naturally occurring porcine model, that a mutation in the porcine non-collagenous domain 1 (NC1) of collagen X causes a phenotype similar to the human dwarfism Schmid metaphyseal chondrodysplasia (SCMD) [42]. Said cartilage disorder is an autosomal dominant disease which characteristics are short stature, coxa vara, and a waddling gait, and histopathological examinations show an extremely irregular organisation of the growth plate in long bones [43,44].

Transgenic animals are important tools as model organisms in basic research as well as in applied scientific areas and they have now been used for several years to study for instance gene function and human diseases. In relation to transgenesis, collagen X offers a unique opportunity regarding the detection of transgene expression, since wild type collagen X is almost selectively expressed in chondrocytes, making the detection of transgene expression in other tissues uncomplicated and hence easy to ascribe to the transgenic procedure.

One aspect of the present invention thus relates to a non-human animal model expressing at least one phenotype associated with dyschondroplasia due to the introduction of at least one genetic determinant, wherein the genetic determinant is a gene or DNA or fragment thereof, and/or RNA or fragment thereof and/or protein or part thereof of the human COL10 A1 gene, mRNA and/or protein (SEQ ID NO:58, SEQ ID NO:59) being present in at least a transient manner.

Similarly, in one embodiment the non-human animal model expressing at least one phenotype associated with dyschondroplasia due to the introduction of a genetic determinant, wherein the genetic determinant is a gene or DNA or fragment thereof, and/or RNA or fragment thereof and/or protein or part thereof of the porcine COL10A1 gene, mRNA and/or protein corresponding to SEQ ID NO:60, SEQ ID NO:61 or fragments or parts thereof, being present in at least a transient manner.

The non-human animal model for dyschondroplasia may be generated by introduction of said genetic determinant into a target cell by any method available to the skilled person, for example by injection into the target cell, or by virus-mediated transfer or any method suitable as known by the skilled person.

In one particular embodiment the non-human animal model for dyschondroplasia is generated by sperm mediated gene transfer.

According to the present invention a pig model for dyschondroplasia is in one embodiment produced by sperm mediated gene transfer of the constitutively expressed porcine COL10A1 of porcine or human origin as described elsewhere herein. However, the pig model for dyschondroplasia may also be produced by introducing the COL10A1 DNA or protein expressed thereof into a target cell.

The non-human animal model for dyschondroplasia, in particular the pig model for dyschondroplasia, will typically develop at least one of the symptoms described above such as disorders involving tubular bones, and characterized by a neoplasmlike proliferation of cartilage in the metaphyses that cause distorted growth in length or pathological fractures.

Non-Human Animals

The present invention relates to a non-human animal serving as a disease model for autosomal dominant disorders, for example neurodegenerative diseases such as protein conformation diseases such as listed elsewhere herein.

In one embodiment the non-human animal model may be any model with the proviso that the animal is not a rodent such as rat, mouse or hamster. The non-human animal is selected from the group consisting of ape, monkey, cattle, pig, sheep, goat, horse, donkey.

In a special embodiment of the present invention the non-human animal model is a pig.

In one embodiment the pig presenting the pig model is a wild pig. In another embodiment the pig is the domestic pig, *Sus scrofa*, such as *S. domesticus*. In yet another embodiment the invention relates to mini pigs, as well as to inbred pigs. The pig can be selected e.g. from the group consisting of Landrace, Yorkshire, Hampshire, Duroc, Chinese Meishan, Berkshire and Pietrain, such as the group consisting of Landrace, Yorkshire, Hampshire and Duroc, for example the group consisting of Landrace, Duroc and Chinese Meishan, such as the group consisting of Berkshire, Pietrain, Landrace and Chinese Meishan, for example the group consisting of Landrace and Chinese Meishan. In one embodiment, the pig is not a mini-pig.

In another embodiment of the present invention the pig is a mini-pig and the mini-pig is preferably selected from the group consisting of Goettingen, Yucatan, Bama Xiang Zhu, Wuzhishan and Xi Shuang Banna.

One aspect of the present invention relates to a non-human animal model produced by sperm-mediated gene transfer. The method of sperm mediated gene transfer of the present invention for the production of a non-human animal model for studying a hereditary autosomal dominant disease and/or for the production of a pig model for studying amyotrophic lateral sclerosis, Alzheimer's disease, Parkinson's disease, diseases associated with trinucleotide repeats, Huntington's chorea and/or dyschondroplasia comprises the steps of i) providing semen from a male, non-human animal ii) providing a genetic determinant capable of establishing said hereditary disease when the genetic determinant is expressed in said non-human animal model iii) contacting said semen and said genetic determinant iv) fertilising an oocyte from a female, non-human animal with the semen and the genetic determinant and v) incubating said fertilised oocyte under conditions allowing said fertilised oocyte to develop into said non-human animal model.

The semen for the method is provided from a male, non-human animal, in particular a boar. The selection of the sperm donor boars is crucial for the outcome of the procedure. The boars of choice are selected so that the initial sperm motility is >90%. Preferably the semen is fresh and collected in sterile 10 mL tubes and transported undiluted at a temperature not below 15° C. as this will cause damage to the sperm cells. The quality of the sperm cell and thus the efficiency of the sperm-mediated gene transfer procedure is affected by numerous factors such as season of year, collection frequency, breed and age of the donor. In order to choose the correct donor cells, the sperm cells from the different boars are examined under a light microscope. The sperm cells originating from the boar having the highest sperm cell motility after the washing procedure are chosen. Next, the sperm cells from the boar of choice are counted. It is important for the present invention that the sperm cell motility is maintained following the removal of seminal fluid.

In one embodiment the boar has abstained for 1 to 10 days, 2-8 days, 1-2 days or in a particular embodiment of the invention the donor boar has abstained for 2 days prior to collecting the semen to be employed in the procedure.

The mechanism of internalization of foreign DNA involves specific proteins capable of binding DNA in a CD4-like manner to sperm heads. The proteins of 30-35 kDa have been identified in a variety of species such as mice, cattle, pig and humans. However, under normal conditions the seminal fluid strongly protects the sperm cells from foreign DNA by antagonizing the binding of the DNA to be internalized. The main antagonist is inhibitory factor 1 (IF-1). Accordingly, the antagonist has to be removed or neutralised before the sperm is used in sperm-mediated gene transfer procedures. Therefore, in one embodiment of the present invention the seminal fluid is removed from the spermatozoa for example by washing.

Ejaculated spermatozoa will under normal conditions capacitate which means that the spermatozoa undergo physiological changes rendering the cells able to fertilise. Therefore, in one embodiment of the present invention the sperm-mediated gene transfer method the initiation of the sperm-DNA interaction should be started shortly after removal of the seminal fluid (for example during the washing step of the procedure). In another embodiment, in order to facilitate capacitation and correct sperm-DNA incubation time, the applied buffer is calcium free as calcium under normal conditions promotes capacitation. Additionally, the absence of calcium prevents endonucleases from acting on the foreign DNA. Thus, in a particular embodiment of the invention the sperm is washed in a buffer devoid of calcium. In a further particular embodiment the washing buffer comprises the following components are 56.1 g Glucose, 3.5 g EDTA ($2H_20$), 3.5 g Sodium citrate, 1.1 g Sodium bicarbonate (for 1 liter of buffer) dissolved in water and the solution is sterilized through a filter. Before the buffer is added to the sperm cells, 6 mg/ml BSA (Bovine Serum Albumine, Fraction V, Sigma) is added.

One preferred washing procedure according to the present invention is accomplished as fast as possible as follows: 5 mL sperm is transferred to a 50 mL tube and 5 mL washing buffer preheated to 37° C. is added, mix by inverting the tubes. The solution is incubated for 5 min at room temperature (approximately 22° C.) and 40 mL buffer (room temperature) is added. Upon centrifugation at 800 g, for 10 min at 25° C. the supernatant is removed and the pellet resuspended in 50 mL buffer (room temperature). The mixture is subjected to centrifugation at 800 g, for 10 min at 17° C. and the supernatant is removed. The pellet is carefully resuspended in the remaining buffer in the tube.

When the genetic determinant has been provided the semen is contacted with the genetic determinant. Sperm cells are diluted in buffer as described above for the washing of sperm cells. In one embodiment the buffer temperature is in the range of 15° C. to 25° C., and in particular the temperature is 17° C. The genetic determinant in the form of DNA is added to the diluted sperm cells. The concentration of the genetic determinant is in the range of 0.1 μg to 1 μg per $10^6$ sperm cells. In a particular embodiment the genetic determinant is linearised DNA added in a concentration of 0.4 μg linearised DNA/$10^6$ sperm cells.

In one particular embodiment the following procedure is used:

$10^9$ sperm cells are diluted into 120 mL 17° C. buffer 0.4 μg linearised DNA/106 sperm cells is added (that is, a total of 400 μg linearised DNA)

Incubate 100 min at 17° C.

To avoid sedimentation of the cells, invert the tube every 20 min

Transfer the tube to room temperature, and transport it (at room temperature) to animal houses or stable facilities (approx. 10 minutes.)

The incubated sperm cells are now ready to be applied in artificial insemination methods.

The non-human animal model and in particular the pig models of the present invention may be produced by methods other than sperm mediated gene transfer, for example by pronuclear microinjection, somatic cell nuclear transfer, or retrovirus mediated gene transfer.

A further aspect of the present invention pertains to a non-human sperm cell comprising at least one genetic determinant exerting at least one dominant phenotype for at least one hereditary disease when expressed in a non-human animal host organism. The non-human sperm cell may originate from any of the animals listed elsewhere herein. As described in detail elsewhere herein the genetic determinant is of mammalian origin, for example of human and/or porcine origin. The non-human sperm cell may be a non-human sperm cell exerting an autosomal dominant phenotype for a hereditary disease such as any of the diseases according to the present invention. The non-human host organism is any of the animals presented herein, and in particular a pig.

The non-human sperm cell according to the present invention may be produced by a method comprising the steps of a) providing a non-human sperm cell, b) providing at least one genetic determinant exerting a dominant phenotype for a hereditary disease when expressed in a non-human animal host organism, c) contacting said non-human sperm cell and said at least one genetic determinant, wherein said contacting results in the uptake of the genetic determinant into the non-human sperm cell.

A further aspect of the invention relates to a composition comprising a non-human sperm cell in combination with at least one genetic determinant exerting at least one dominant phenotype for at least one hereditary disease when expressed in a non-human animal host organism. In preferred embodiments the genetic determinant is of human and/or porcine origin.

The present invention also discloses a method for fertilising an oocyte by sperm-mediated gene transfer. The method comprises the steps of providing the non-human sperm cell as carrying the at least one genetic determinant for a phenotype associated with autosomal dominant diseases as defined herein and introducing the non-human sperm cell into the oocyte to be fertilised. Consequently, another aspect of the invention relates to a method for fertilising an oocyte by sperm-mediated gene transfer, wherein the method comprises the steps of providing the composition as described herein and introducing the composition into the oocyte to be fertilised.

Therefore, the present invention also pertains to an embryo obtained by fertilising an oocyte with the non-human sperm cell comprising at least one genetic determinant exerting at least one dominant phenotype for at least one hereditary disease of the present invention when expressed in a non-human animal host organism. Similarly an embryo obtained by fertilising an oocyte with the composition as disclosed herein is within the scope of the present invention. Furthermore, as an embryo has been established the present invention offers a method for the cultivation and development of the embryo comprising the step of cultivating the embryo under conditions allowing the embryo to develop into a non-human animal offspring expressing said genetic determinant and exerting a dominant phenotype for a hereditary disease.

The presence of a non-human animal model of autosomal dominant diseases provides the opportunity of evaluating whether a given pharmaceutical composition, compound, treatment and/or drug has an effect on the phenotype of the given non-human animal. Therefore, it is within the scope of the present invention to provide for a method for evaluating the response of a therapeutical treatment of a hereditary disease, said method comprising the steps of a) providing the non-human animal model according to the invention b) treating said non-human animal with at least one pharmaceutical composition exerting an effect on said at least one phenotype, and c) evaluating the effect observed. Additionally, the method also allows for a further step of advising on medical treatment of for example a human being suffering from an autosomal dominant disease such as a neurodegenarative diseases, protein conformation diseases such as ALS, Alzheimer's disease, HD, PD, trinucleotide repeat-associated diseases but also dyschondroplasia based on the effects observed during the method of evaluation.

In addition the availability of a non-human animal model expressing a particular phenotype associated with autosomal dominant diseases offers the ability of providing a method for screening the efficacy of a pharmaceutical composition, wherein the method comprises the steps of a) providing the non-human animal model of the present invention, b) expressing in said animal model said at least one genetic determinant and exerting said dominant phenotype for said hereditary disease, c) administering to said non-human animal the pharmaceutical composition the efficacy of which is to be evaluated, and d) evaluating the effect, if any, of the pharmaceutical composition on the phenotype exerted by the genetic determinant when expressed in the non-human model.

Furthermore, the present invention also relates to a method for treatment of a human being suffering from an autosomal dominant disease, wherein the method comprises the initial steps of a) providing the non-human animal model of the present invention, b) expressing in said animal model said genetic determinant and exerting said dominant phenotype for said hereditary disease, c) treating said non-human animal with a pharmaceutical composition exerting an effect on said phenotype, d) evaluating the effect observed, and e) treating said human being suffering from said hereditary disease based on the effects observed in the non-human animal model.

Moreover, a method for linking a genetic determinant with the occurrence of a hereditary disease in a human being is also disclosed, said method comprising the steps of a) cultivating and developing an embryo obtained by fertilising an oocyte with a non-human sperm cell and a genetic determinant potentially constituting an autosomal dominant disease gene, for example a porcine gene exerting a dominant phenotype for a disease, such as a neurodegenerative disease when expressed in a non-human animal host organism, wherein said cultivation and development result in the generation of an non-human animal offspring, and b) observing whether said genetic determinant confers said autosomal dominant disease in said non-human animal offspring.

EXAMPLES

Example 1

Transgenic Porcine Model of Amyotrophic Lateral Sclerosis (ALS)

In order to establish transgenic pigs which could serve as potential animal models for the human neurodegenerative disease ALS, a mutation, Gly93Arg, was introduced into the gene encoding porcine SOD1 by means of site directed mutagenesis. The choice of mutation was based on protein structural speculations, since the crystal structure of human SOD1 reveals an extremely condensed structure, showing that a substitution of the small relatively flexible glycine at position with the large charged arginine is likely to cause severe alteration in the protein. Furthermore, several different substitutions at this position cause ALS in humans including the G93R mutation [45,46]. In order to impede possible truncation of important elements in the DNA construct following the SMGT procedure the DNA fragment containing the porcine SOD1 cDNA contains additional nucleotides 5'- and 3'-prime to the CMV promoter and SVpolyA fragment. Totally, as shown in FIG. 1, the fragment used to make transgenic animals constitutes approximately 2100 bp.

RNA Isolation and cDNA Synthesis

Various porcine tissues were dissected from slaughtered pigs (Duroc boars and Landrace-Yorkshire sows (D×LY) and immediately frozen in liquid nitrogen and stored at −80° C. 100 mg of the tissue of choice was used for RNA isolation. RNA was isolated using the Nucleospin, Midi Kit from Macherey-Nagel.

cDNA synthesis was accomplished by mixing 1 μg of total RNA with 1 μL of oligo (dT) 12-18 (500 μg/mL), and DEPC treated H20 to a final volume of 12 μL. The mixture was incubated at 70° C. for 10 min, after which 4 μL of 5× first-strand buffer, 2 μL of 0.1 mM DTT, 1 μL of 10 mM dNTP mix and 1 μL (200 U/μL) of Superscript II (Invitrogen) was added and the sample was further incubated at 42° C. for 1 hour followed by an inactivation step at 70° C. for 15 min.

Sequencing Genes of Interest, Including Porcine SOD1

Based on homology search between the human SOD1 gene and an "in house" porcine EST database, 2 primers (SOD1_CDF and SOD1_CDR) were designed for amplification of the cDNA for the porcine SOD1 gene. The PCR reaction was performed in a total volume of 25 μL consisting of 2.5 μL of 10× reaction buffer, 4 μL of dNTP (2.5 mM), 1 μL of both forward and reverse primer (10 pmol each), 1 μL 1 U/μL Dynazyme polymerase (Finnzymes), 2 μL cDNA template, and 13.5 μL H20.

The touchdown PCR reaction was performed in a GeneAmp® PCR System 9700 (Applied Biosystems) under the following conditions: Initial denaturation at 95° C. for 3 min, denaturation at 95° C. for 30 sec, touchdown from 63° C. to 58° C. with a decrement of 0.5° C. for 30° C., followed by 1 min of elongation at 72° C. per cycle. Furthermore 35 cycles of 30 sec denaturation at 95° C., 30 sec of annealing at 58° C., and 1 min of elongation at 72° C. was included together with a final elongation step at 72° C. for 7 min.

The primers used to amplify the SOD1 cDNA were:

```
                                    (SEQ ID NO: 62)
SOD1_CDF: 5'-ATGGCGACGAAGGCCGTGT-3'

                                    (SEQ ID NO: 63)
SOD1_CDR: 5'-TTACTGGGTGATCCCAATTACACCAC-3'
```

The PCR product was purified using QIAEX® II Gel Extraction Kit (Qiagen) from a 1% Seakem agarose gel.

Amplicons were cloned into the pCR®2.1-TOPO vector (Invitrogen, CA) using manufactures recommendations and, applying standard procedures, clones were subsequently sequenced to ensure that they contained the SOD1 amplicon.

The porcine SOD1 cDNA sequence is shown in FIG. 1

Cycle sequencing reactions were accomplished in a GeneAmp® PCR System 9700 (Applied Biosystems) where an initial denaturation step at 95° C. for 2 min, 99 cycles of 10 sec denaturation and 4 min elongation at 60° C., was applied to the sample mixture consisting of: 1.5 μL of Big Dye Terminator mix version 3.1, 1 μL of primer (5 pmol), 2 μL of a 5× reaction buffer, 2 μL of the purified PCR product and 3.5 μL H20. Sequencing product were precipitated with 2.5 volumes of ethanol and 1/10 volume of 3 M NaAc, air dried and resuspended in 10 μL formamide (sequencing grade). The samples were run on a 3730xl DNA Analyzer (Applied Biosystems).

Site Directed Mutagenesis of Porcine SOD1

In order to introduce the Gly93Arg mutation into SOD1 site directed mutagenesis was performed using the QuickChange® XL Site-Directed Mutagenesis Kit (Stratagene) and accomplished in accordance with the manufacturer's recommendations as described herein. The PCR reaction was performed in a total volume of 50 μL consisting of 5 μL of 10× reaction buffer, 2 μL of both forward and reverse primer (10 pmol each), 1 μL dNTP mix, 3 μL QuickSolution, 1 μL PfuTurbo® DNA polymerase (2.5 U/μL), 1 μL TOPO-SOD1 template (10 ng), and 35 μL H20.

Forward and reverse primers used for the above PCR procedure were:

```
SOD1G93R_F:
                                    (SEQ ID NO: 64)
5'-GACTGCTGGCAAAGATCGTGTGGCCACTGTGTACATC-3'

SOD1G93R_R:
                                    (SEQ ID NO: 65)
5'-GATGTACACAGTGGCCACACGATCTTTGCCAGCAGTC-3'
```

The PCR reaction was accomplished in a GeneAmp® PCR System 9700 (Applied Biosystems) under the following conditions: Initial denaturation at 95° C. for 1 min, 18 cycles of 50 sec denaturation at 95° C., 50 sec of annealing at 60° C., and 6 min of elongation at 68° C. and a final elongation step at 68° C. for 7 min.

Subsequently 1 μL of Dpn I (10 U/μL) was added to the sample mixture in order to digest the nonmutated parental DNA template. The reaction was incubated for 1 hour at 37° C. After digestion of the parental DNA template XL10-Gold® Ultracompetent Cells (Invitrogen, CA) were transformed with the Dpn I treated DNA in the following manner: XL10-Gold® Ultracompetent Cells were thawn on ice and 45 μL were aliquoted to a prechilled Eppendorf tube and 2 μL of β-mercaptoethanol was added followed by a gentle swirling of the tube. The tube was now left on ice for 10 min. After incubation, 2 μL of the Dpn I treated DNA was added, the sample was swirled and incubated on ice for another 30 min and then exposed to a heat pulse of 42° C. for 30 sec. Subsequently, the sample was put on ice for 2 min followed by an addition of 0.5 mL 42° C. NZY+broth. The mix was plated onto LB-amp plates and incubated overnight at 37° C. To ensure that the mutation of interest was integrated in the porcine SOD1 gene, 16 colonies were picked and grown overnight in liquid LB-Amp media and plasmids were purified using the QIAprep® Spin Miniprep kit (Qiagen) according to manufactures recommendations. Cycle sequencing reactions were accomplished in a GeneAmp® PCR System 9700 (Applied Biosystems) where an initial denaturation step at 95° C. for 2 min, 99 cycles of 10 sec denaturation and 4 min elongation at 60° C., was applied to the sample mixture consisting of: 1.5 μL of Big Dye Terminator mix version 3.1, 1 μL of either T7 or SP6 primer (5 pmol), 2 μL of a 5× reaction buffer, 1 μL of the purified plasmid and 4.5 μL H20. Sequencing product were precipitated with 2.5 volumes of ethanol and 1/10 volume of 3 M NaAc, air dried and resuspended in 10 μL formamide (sequencing grade). The samples were run on a 3730xl DNA Analyzer (Applied Biosystems). Sequences were checked and a plasmid containing the mutation was chosen as template for the subsequent procedures. The sequence of the mutated porcine SOD1 cDNA is shown in FIG. 2.

Cloning of Gene(s) of Interest—SOD1 into the Expression Vector, phCMV1

To facilitate a continuous high expression of the transgene of interest, the gene was cloned into the phCMV1 vector (Gene Therapy Systems). For release of the mutated SOD1 DNA 6 μL plasmid DNA was digested with 1.5 μL EcoRI (20 U/μL) in a total volume of 30 μL in addition of 3 μL EcoRI 10× reaction buffer. The reaction was incubated at 37° C. for 90 min and run on a 1% Seakem GTG agarose gel. The correctly sized band was isolated from the agarose gel employing a QIAEX® II Gel Extraction Kit (Qiagen) and dissolved in 30 μL $H_2O$. Likewise, phCMV1 was EcoRI digested and isolated from a 0.8% Seakem GTG agarose gel and dissolved in 30 μL $H_2O$. Furthermore, in order to avoid self-ligation of the vector, 6 μL of the digested phCMV1 vector was dephosphorylated in a total volume of 25 μL applying 1.5 μL CIP (10 U/μL) and 2.5 μL 10×CIP reaction buffer. The sample was incubated 60 min at 37° C. Enzyme inactivation occurred at 80° C. for 15 min.

Ligation of mutagenised SOD1 into the EcoRI digested and dephosphorylated phCMV1 was performed in a total volume of 15 μL in the addition of 3 μL dephosphorylated phCMV1, 8 μL EcoRI linked mutagenised SOD1, 1.5 μL T4 DNA ligase (400 U/μL), 1.5 μL 10×T4 DNA ligase buffer, and 1 μL $H_2O$. The reaction was incubated at 16° C. overnight. XL10-Gold® Ultracompetent Cells were thawn on ice and 45 μL were aliquoted to a prechilled ependorf tube and 2 μL of β-mercaptoethanol was added followed by a gentle swirling of the tube. The sample was now left on ice for 10 min. After incubation, 3 μL of the ligation mix was added, the sample was swirled and incubated on ice for another 30 min and then exposed to a heat pulse of 42° C. for 30 sec. Subsequently, the sample was put on ice for 2 min followed by an addition of 0.5 mL 42° C. NZY+broth. The mix was plated onto LB-amp plates and incubated overnight at 37° C.

To ensure that the insert had integrated correctly into the phCMV1 vector 16 colonies were picked and grown overnight in liquid LB-Amp media and plasmids were purified using the QIAprep® Spin Miniprep kit (Qiagen) in accordance with manufactures recommendations. Cycle sequencing reactions were accomplished in a GeneAmp® PCR System 9700 (Applied Biosystems) where an initial denaturation step at 95° C. for 2 min, 99 cycles of 10 sec denaturation and 4 min elongation at 60° C., was applied to the sample mixture consisting of: 1.5 μL of Big Dye Terminator mix version 3.1, 1 μL of either T7 or SP6 primer (5 pmol), 2 μL of a 5× reaction buffer, 1 μL of the purified plasmid and 4.5 μL $H_2O$, Sequencing product was precipitated with 2.5 volumes of ethanol and 1/10 volume of 3 M NaAc, air dried and resuspended in 10 μL formamide (sequencing grade). The samples were run on a 3730xl DNA Analyzer (Applied Biosystems). Sequences were checked and a plasmid containing the SOD1 construct in the correct direction was chosen.

Large Scale Preparation of DNA

In order to create DNA for incubation of sperm cells both PCR and large scale plasmid preparations have been employed.

The PCR reaction was performed in a GeneAmp® PCR System 9700 (Applied Biosystems) in a final volume of 25 μL consisting of 5 μL 5× Phusion HF buffer, 2 μL dNTP (2.5 mM each) 0.63 μL forward and reverse primer 5 pmol, 0.1 μL Phusion DNA Polymerase (2 U/μL), 1 μL SOD1-phCMV1 template, and 15.6 μL $H_2O$. The PCR reaction consisted of an initial denaturation at 98° C. for 30 sec followed by 30 cycles of denaturation for 10 sec at 98° C., annealing at 74° C. for 30 sec and elongation for 95 sec at 72° C. followed by a final elongation step at 72° C. for 7 min.

The following primers were used to amplify the mutagenised SOD1 construct plus the flanking (før var termen matching) CMV promoter, intron sequence, and SVpolyA, generating a fragment of 1643 bp+the mutagenised SOD1 fragment, generating a fragment of approximately 2100 bp:

```
                                        (SEQ ID NO: 66)
phCMVF: 5'-GTCGGAACAGGAGAGCGCACGAGGG-3'

                                        (SEQ ID NO: 67)
phCMVR: 5'-GGGTGATGGTTCACGTAGTGGGC-3'
```

In order to purify the generated PCR product a “High Pure PCR Product Purification Kit” (Roche) was applied. The suppliers' instructions were followed throughout the purification procedure. The PCR purified fragments were sequenced to check for errors in the sequence as described below.

Large scale plasmid preparation was accomplished from ½ liter *E. coli* cell cultures. Purification of plasmids was performed using a Plasmid Mega Kit (Qiagen). In order to linearise and release the desired fragment from the vector, the vector was digested with BssS I and Dra III in the following way: 1.5 μL BssSI (4 U/μL), 1.5 μL DraIII (20 U/μL), 3 μL 10×BSA, 3 μL 10×Ne buffer 3, and 2 μL plasmid DNA was added to 19 μL $H_2O$ to yield a total volume of 30 μL and was left overnight at 37° C. The digested fragments were separated on a 0.8% GTG Seakem agarose gel and the correctly sized band were isolated and extracted from the gel using QIAquick Gel Extraction Kit Protocol (Qiagen), according to manufactures recommendations.

Both the PCR purified fragments and the plasmid prepared fragments were sequenced to check for errors in the sequence. Cycle sequencing reactions were accomplished in a GeneAmp® PCR System 9700 (Applied Biosystems) where an initial denaturation step at 95° C. for 2 min, 99 cycles of 10 sec denaturation and 4 min elongation at 60° C., was applied to the sample mixture consisting of: 1.5 μL of Big Dye Terminator mix version 3.1, 1 μL of either T7 or SP6 primer (5 pmol), 2 μL of a 5× reaction buffer, 1 μL of the purified plasmid and 4.5 μL $H_2O$. Sequencing product were precipitated with 2.5 volumes of ethanol and 1/10 volume of 3 M NaAc, air dried and resuspended in 10 μL formamide (sequencing grade). The samples were run on a 3730xl DNA Analyzer (Applied Biosystems).

FIG. 3 illustrates a comparison of the deduced amino acid sequence of porcine SOD1 with human, mouse and rat. The amino acid (G) which is mutated is marked in bold.

FIG. 4 shows projection of mutations in SOD1 onto the crystal structure of the human SOD1 dimer. The mutations are distributed all over the protein, illustrating that all residues of the protein are important for correct function of the enzyme.

Preparation of Sperm and DNA Uptake

Selection of Sperm Donor Boars

The selection of the sperm donor boars are crucial for the outcome of the procedure. A boar station (Hatting KS Viborg), have therefore been contacted and the boars of choice are selected so that the initial sperm motility is >90%. The sperm is collected in sterile 10 mL tubes and transported undiluted at a temperature not below 15° C. as this will cause damage to the sperm cells.

First and second semen ejaculate, were collected from 8 different boars yielding 16 semen fractions in total. All fractions of spermatozoa had an initial motility of 90 prior to the washing procedure. Seminal fluid was quickly removed by centrifugation and washing the sperm in Fertilization Buffer (FB) consisting of 56.1 g Glucose, 3.5 g EDTA ($2H_2O$), 3.5 g Sodium Citrate ($2H_2O$), and 1.1 g sodium bicarbonate dissolved in 1 liter of sterilized water. Furthermore 6 mg/ml BSA (Fraction V, Sigma) was added. Briefly, 5 mL of FB/BSA prewarmed to 37° C. was added to 5 mL of undiluted semen, mixed by inverting the tube, and left for 5 minutes at room temperature (approximately 22° C.). Next, FB/BSA at room temperature was added to 50 ml and centrifuged for 10 minutes at room temperature at 500 g, or alternatively at 800 g for 10 min at 25° C. The supernatant was removed and semen was resuspended in 50 mL FB/BSA at room temperature and further centrifuged at 500 g at 17° C., after which, the supernatant was removed again and the spermatozoa was resuspended in 15 mL of FB/BSA. Next, in order to choose the optimal donor cells, the spermatozoa from the different boars and the two separate ejaculates were quickly examined under a light microscope. The sperm cells originating from the two boars having the highest sperm cell motility after the washing procedure were chosen as vehicles for the subsequent transgenic procedures. Furthermore, the spermatozoa were counted.

Figure 5:
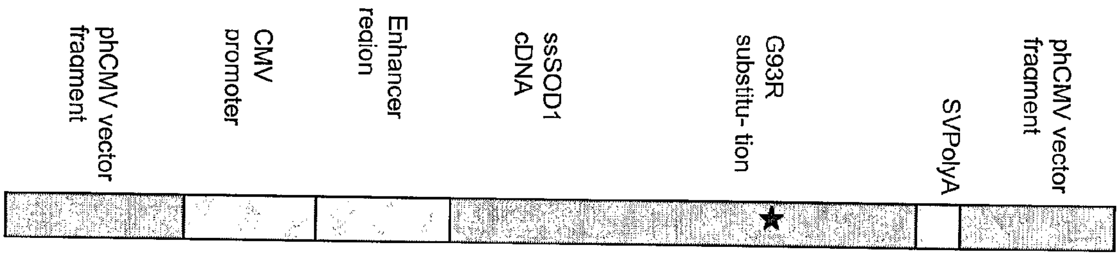
FIG. 5: SOD1 linearised construct used to create transgenic pigs by means of SMGT. The fragment constitutes approximately 2100 bp and includes a CMV promoter, en enhancer region, the porcine SOD1 cDNA, and the SVPolyA (simian virus 40 poly A) fragment. Furthermore, the 5'- and 3'-prime end of the DNA fragment include additional bases derived from the phCMV vector to protect crucial element from being truncated following SMGT.

Generation of Transgene Pigs $1\times10^9$ sperm cells washed spermatozoa from each of the two chosen donor boars were incubated for 100 minutes at 17° C. with the linearized SOD1 DNA fragment (FIG. 5) in a concentration of 0.4 μg DNA/106 spermatozoa in a suspension of 120 mL FB/BSA. Containers were inverted every 20 minutes to prevent sedimentation of spermatozoa. Finally, the mixture was incubated 10 minutes at room temperature and employed in artificial insemination of two sows in natural heat.

Animals

Two recipient sows (Danish Landrace×Yorkshire) at approximately 140 kg were selected due to their natural heating period and used for artificial insemination ($1\times10^9$ DNA treated sperm (spermatozoa)/sow) meeting standard insemination procedures. Insemination was accomplished in the local stable areas at DIAS. Semen was collected from trained Danish Landrace boars that have abstained for 2 days. Semen was treated according to aforementioned procedures. Both sows were examined for pregnancy 24 and 42 days after insemination, showing that only one of the sows was pregnant. After ended gestation period, 2 boars and 5 sow piglets were born naturally. Animal care and experimental procedures met local, national and European Union Guidelines.

Analysis of Piglets

Test for the Transgene

After 115 days (20 Jun. 2005) 7 normal looking piglets were born, 2 of these were boar piglets and 5 were sow piglets. Blood samples were collected from the piglets in 6 mL EDTA blood collection tubes. Furthermore, blood from a wild type animal was collected as well and handled together with the 7 aforementioned animals. DNA was purified according to standard blood purification procedures in special clean laboratories, in order to avoid any possible contamination.

The PCR reaction was performed in a total volume of 10 μL consisting of 1 μL 10×MgCl2 free reaction buffer, 0.4 μL 50 mM MgCl2, 1 μL of both forward and reverse primer (10 pmol each), 0.5 μL dNTP mix, 0.5 μL DyNazyme EXT DNA polymerase (1 U/μL), 0.5 μL DNA template (50 ng), and 5.1 μL $H_2O$.

Forward and reverse primer used for the above PCR procedure:

```
                                    (SEQ ID NO: 68)
PhCMV_430F: 5'-GTCTCCACCCCATTGACGTC-3'

                                    (SEQ ID NO: 69)
PhCMV_646R: 5'-GGATCGGTCCCGGTGTCTTC-3'
```

The touchdown PCR reaction was accomplished in a GeneAmp® PCR System 9700 (Applied Biosystems) under the following conditions: Initial denaturation at 95° C. for 3 min, denaturation at 95° C. for 30 sec, touchdown from 62° C. to 57° C. with a decrement of 0.5° C. for 20 sec, followed by 1 min of elongation at 72° C. pr cycle. Furthermore 35 cycles of 30 sec denaturation at 95° C., 20 sec of annealing at 57° C., and 1 min of elongation at 72° C. was included together with a final elongation step at 72° C. for 7 min.

Figure 6:
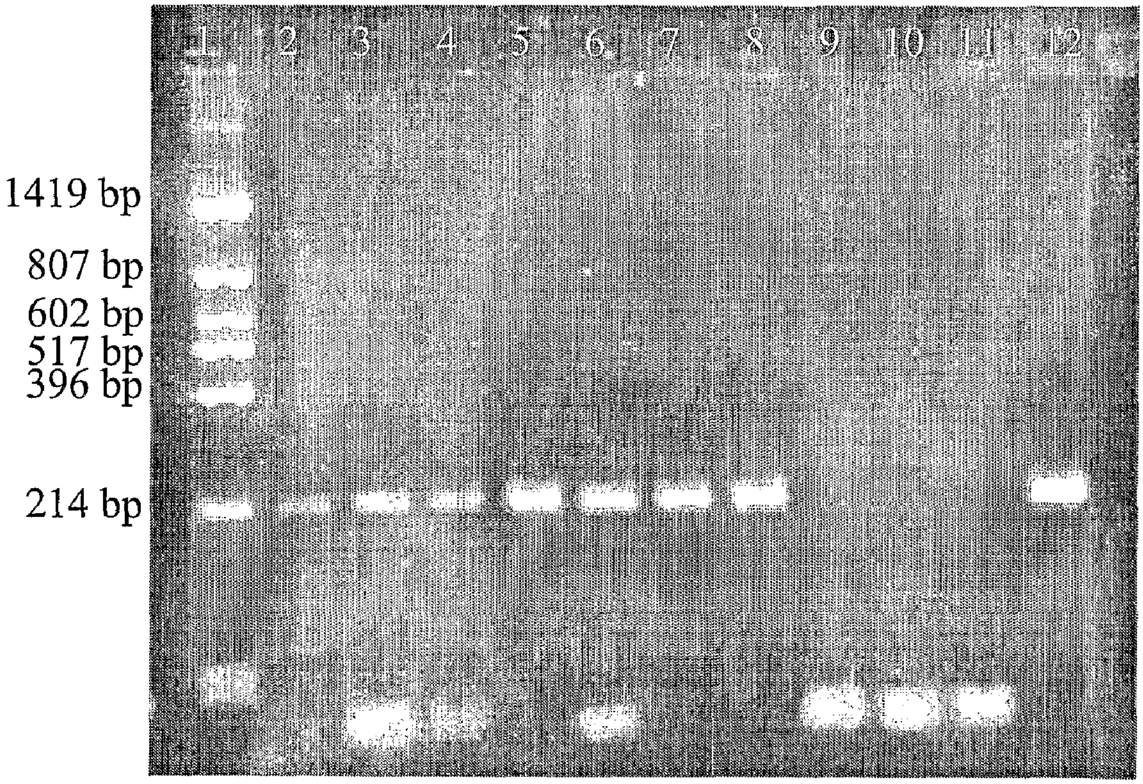
FIG. 6: PCR evaluation of transgenic offspring. Lane 1: PUC 19 marker, lane 2: piglet 4905, lane 3: piglet 4906, lane 4: piglet 4907, lane 5: piglet 4908, lane 6: piglet 4909, lane 7: piglet 4910, lane 8: piglet 4911, lane 9: minus DNA, lane 10: minus DNA, lane 11: negative control, and lane 12: positive control. All the tested piglets (animal 4905-4911) from the litter are positive regarding the transgenic fragment.

This created PCR fragments of 218 bp and the result is shown in FIG. 6.

FIG. 6 shows that all animals (4905-4911) are positive regarding the transgenic DNA fragment. However, mosaicsm can not be ruled out neither the possibility of the various animals having different copy numbers. Therefore 2 animals were sacrificed (pig 4906 and pig 4909) and various tissues were sampled and snap frozen in liquid nitrogen and subsequently stored at −80° C. DNA was purified from the different tissues and the same PCR as above was performed, the only difference being that the amount of DNA was not normalized.

Figure 7:
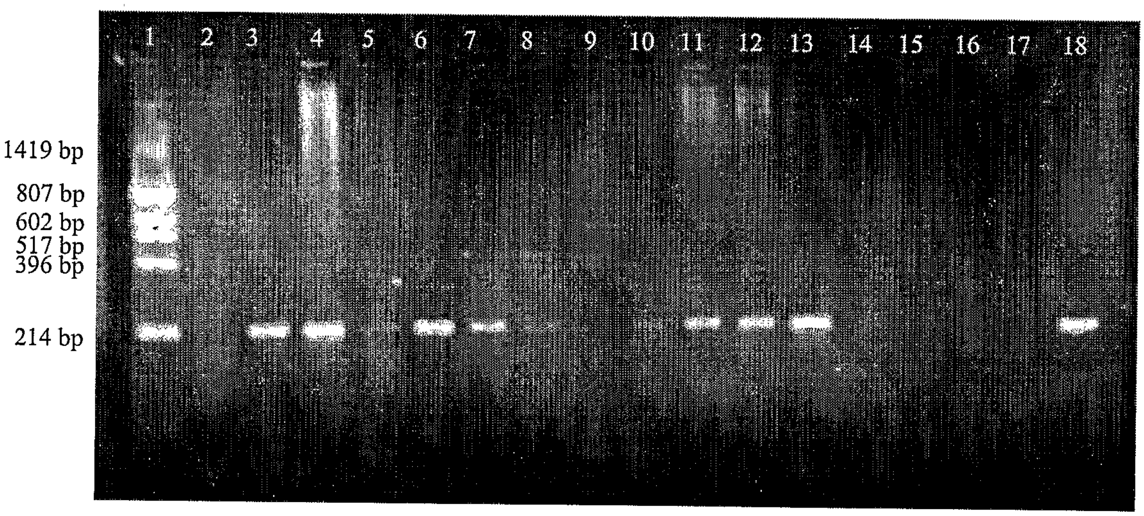
FIG. 7: PCR evaluation of DNA from different tissues from animal 4906. Lane 1: PUC 19 marker, lane 2: empty, lane 3: liver, lane 4: lung, lane 5: kidney, lane 6: heart, left ventricle, lane 7: jaw muscle, lane 8: top round, lane 9: shoulder muscle, lane 10: diaphragms, lane 11: cerebellum, lane 12: hippocampus, lane 13: frontal cortex, lane 14: cervical medulla spinallis from 4909, lane 15: minus DNA, lane 16 minus DNA, lane 17 negative control, lane 18: positive control.
Figure 8:
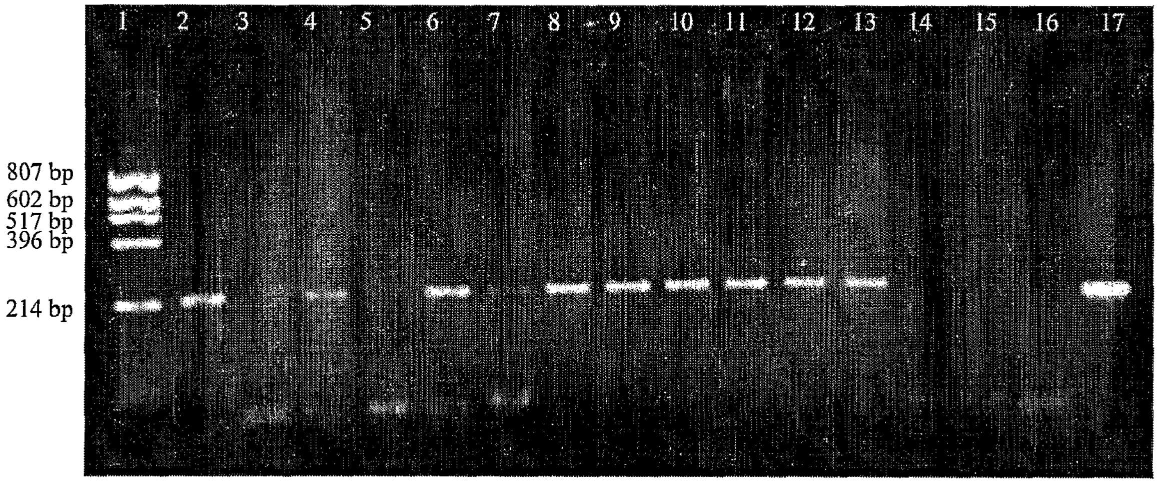
FIG. 8. PCR evaluation of DNA from different tissues from animal 4909. Lane 1: PUC 19 marker, lane 2: left shoulder muscle, lane 3: right Spinacea oleracea, lane 4: musculus gloteus, lane 5: musculus pectoralis major, lane 6: facial muscle, lane 7: diaphragms, lane 8: heart, left ventricle, lane 9: lung, upper right part, lane 10 kidney, lane 11: liver, lane 12: hippocampus, lane 13: frontal cortex, lane 14: minus DNA, lane 15: minus DNA, lane 16: negative control, and lane 17: positive control.

The result of the PCR for animal 4906 and 4909 is shown in FIGS. 7 and 8, respectively.

FIGS. 7 and 8 show that nearly all tissues applied in the PCR control harbor the transgenic fragment. Furthermore, it should be noted that the genomic template DNA is not normalized regarding concentration. Still, the lack of DNA fragments in lane 9 in FIG. 6 and in lanes 3 and 5 in FIG. 8 could well be explained by a mosaic nature of the animals regarding the transgene. However, for pigs 4906 and 4909 the transgene is present in a large variety of tissues.

Transgene in the Germ Cells

In order to transfer the transgene to next generation it is important to ensure that the transgene is present in the germ cells. Therefore, DNA has been extracted from sperm cells from the two boars (4905 and 4908). The purification of DNA was accomplished using two different procedures, standard purification procedure and miniprep purification procedure:

Standard Purification Procedure

300 μL of semen was washed in 1 mL 0.9% NaCl, followed by centrifugation for 5 min at 3000 rpm where after the supernatant was discarded. This step was repeated twice and 20 μL Pronase (20 mg/mL), 20 μL 1 M DTT, and 300 μL buffer S was added to each sample, where after these were left to incubate at room temperature overnight. Subsequently, 180 μL 6 M NaCl was added to each sample and shaken vigorously for approximately 20 seconds. The samples were now centrifuged for 15 min. at 10000 rpm and the supernatant was then carefully transferred to a new eppendorf tube where the DNA was precipitated adding twice the volume of supernatant and centrifuged at 10000 rpm for 10 min. Subsequently the ethanol was removed and the DNA was air dried and resuspended in 300 μL of nuclease free water.

Miniprep Purification Procedure

300 μL of semen was washed in 1 mL 0.9% NaCl, followed by centrifugation for 5 min at 3000 rpm where after the supernatant was discarded. This step was repeated twice and 20 μL Pronase (20 mg/mL), 20 μL 1 M DTT, and 300 μL buffer S was added to each sample, where after these were left to incubate at room temperature overnight. In order to enrich each sample regarding low molecular DNA and obtain a more pure DNA product the miniprep procedure from Qiagen was applied. The DNA was eluted in 200 μL of nuclease free water.

Buffer S composition: 10 mM Tris HCl (pH 8.0); 100 mM NaCl; 10 mM EDTA (pH 8.0); 0.5% SDS; $H_2O$.

Figure 9:
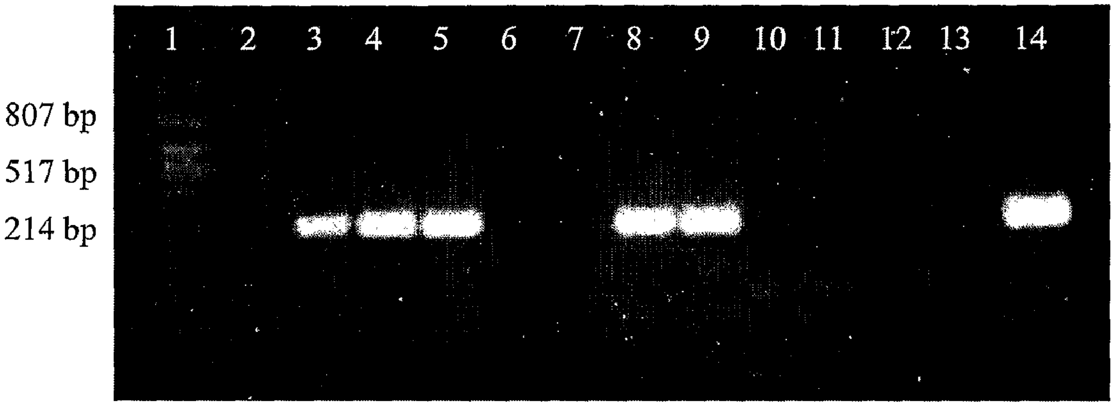
FIG. 9: PCR evaluation of DNA purified from sperm cells from boar 4905 and 4908. The DNA is purified both by means of a standard purification procedure and the miniprep purification procedure. Lane 1: marker, lane 2: 4905, standard purification procedure, lane 3: 4905, standard purification procedure, lane 4: 4905, miniprep purification procedure, lane 5: 4905, miniprep purification procedure, lane 6: 4908, standard purification procedure, lane 7: 4908, standard purification procedure, lane 8: 4908, miniprep purification procedure, lane 9: 4908, miniprep purification procedure, lane 10: minus DNA, lane 11: minus DNA, lane 12: negative control, lane 13: empty, lane 14: positive control.

DNA from both procedures was employed in the same PCR test as already mentioned and the result is shown in FIG. 9.

FIG. 9 shows that the transgene is present in the sperm cells, however DNA purified with the miniprep purification procedure clearly shows much more distinct bands that the DNA purified with the standard procedure. This is probably due either the DNA being more pure or to the DNA being present as extra chromosomal fragments. Still, as the two boars harbor the transgene, these will used in the production of the next transgene SOD1 generation.

Veterinary Declaration

Extracts from Veterinary Declarations dated 9th of Feb. 2006 and 9th of Mar. 2006, respectively, concerning transgenic animals are disclosed below.

"The boar 4905 has a bent back and very straight hocks. It raises and lays down with difficulty and stands with uneasiness in the back portion, seems slightly ataxic. A significant deterioration has occurred as compared to last month. No direct signs of soreness in the limbs.

It is unclear if the cause is in the big joints at the back and pelvis region or the nerve system. Neurological symptoms of ataxia in the back portion of pigs are normally assumed to be caused by damages in the bone marrow and not the brain. Ataxia can be due to a lacking propioception, i.e. feeling of the positioning of the limbs.

The remaining pigs in the experiment move freely around."

The above section is a translation of an extract of a Veterinary Declaration dated 9th of Feb. 2006.

"White 4905: Boar in normal condition and without signs of external damages. It stands on both front and rear legs, but is a little insecure when having to move and if pushed. This is clear from slight ataxic movements: Crosses front legs and have cocked angles from time to time and stands with rear legs widely to the side. Strong itching reflex can be released by touching the backside. Eats and drinks normally. No signs of limping.

White 4908: Boar in normal condition and without signs of external damages. It stands with underpositioned ("understillede") rear legs. It is slightly ataxic when turning and pushes from the side. No signs of limping.

White 4907, 4911, 4910: 3 sows move freely. They show some signs of slight ataxic movements which can be provoked when pushing them around."

The above section is a translation of an extract of a Veterinary Declaration dated 9th of Mar. 2006.

Analysis of Transgenic Piglets

Biological Samples

Blood samples were withdrawn 3 days after birth and when the piglets reached 115 days blood samples were withdrawn every third week in 6 mL EDTA tubes and 6 mL serum tubes. Two sows were sacrificed at the age of 5 month, and before any phenotypic changes could be observed. One 1 boar, 4908 was sacrificed at the age of 14 month and another boar, 4905, was sacrificed at the age of 15 month. Both boars had severe phenotypic changes. For all sacrificed animals various tissues have been snap frozen in liquid nitrogen and subsequently stored at −80° C. Furthermore, various tissues, including porcine brains have been fixed in formalin.

DNA and RNA Studies of Transgenic Pigs

DNA was prepared from EDTA stabilized blood samples and from snap frozen tails.

RNA was prepared from snap frozen tissues from heart, kidney, liver, lung, spleen, medulla spinalis (M. spinalis), frontal cortex (FCO), parietal cortex (PCO), musculus longissimus dorsi (M. L. dorsi), musculus semitendinosus, left side (M.semit. l.), musculus semitendinosus, right side (M.semit. r.), musculus semibranosus, left side (M.semb. l.), and musculus semibranosus. All DNA and RNA samples were extracted in special clean laboratory facilities under highly stringent experimental conditions using standard protocols.

PCR Evaluation 50 ng of genomic DNA isolated from blood samples from each of the seven pigs were amplified using the following primers: SOD1 Exon3F: 5'-GCTGTACCAGTGCAGGTC-CTC-3' (SEQ ID NO:70) and SOD1 Exon4R: 5'-CCATTGT-GCGGCCAATGATG-3' (SEQ ID NO:71) yielding a fragment of approximately 800 bp when amplifying the endogenous genomic SOD1 and approximately 200 bp when amplifying the exon 3 to exon 4 cDNA fragment. The following sample mix was employed 1 μL 10×MgCl2 free reaction buffer, 0.4 μL 50 mM MgCl2, 10 pmol of each primer, 5 mM dNTP-mix, and 0.5 U Dynazyme Ext DNA polymerase. The reaction was performed in a total volume of 10 μL and accomplished as a touchdown PCR in a GeneAmp® PCR system 9700 (Applied Biosystems) under the following conditions: Initial denaturation at 95° C. for 3 min, denaturation at 95° C. for 30 sec, touchdown from 62° C. to 57° C. with a decrement of 0.5° C. for sec, followed by 1 min of elongation at 72° C. pr cycle. Furthermore, 35 cycles of 30 sec denaturation at 95° C., 20 sec of annealing at 57° C., and 1 min of elongation at 72° C. was included together with a final elongation step at 72° C. for 7 min.

Expression Analysis

Of the total RNA, 2 μg was reverse transcribed from the various tissues, employing a SuperScript III kit (Invitrogen, USA) according to manufactures recommendation using random hexamer primers. RT-PCR experiments were conducted in triplicate. The risk of amplifying genomic DNA was apart from primer designed to span exon-exon junctions ruled out by running the PCR prior to reverse transcription. Quantitative real time PCR was performed using the TaqMan® assay and PCR amplification in an ABI-PE prism 7900 sequence detection system (PE Applied Biosystems). Primers, ssSOD1_EX4F 5'-GGATCAAGAGAGGCACGTTGG-3' (SEQ ID NO:72) and ssSOD1_EX4R 5'-GGCGATCACA-GAATCTTCGATG-3' (SEQ ID NO:73), and MGB probes were designed using the Primer Express Software 2.0 (PE Applied Biosystems), and the MGB probes, designed to match the endogenous and mutated porcine SOD1, were designed with VIC and FAM as reporter dyes (SS_SOD1_WT: VIC-5'-CAAAGATGGTGTGGCCAC-3' (SEQ ID NO:74) and SS_SOD1_Mut: FAM-5'-CAAA-GATCGTGTGGCCAC-3') (SEQ ID NO:75). Furthermore the 18S ribosomal RNA gene was chosen as the endogenous control using the following primers and probes: 18S-F: 5'-CGCTCCACCAACTAAGAACG-3' (SEQ ID NO:76), 18S-R: 5'-CTCAACACGGGAAACCTCAC-3' (SEQ ID NO:77), and 18S-probe: SYBR-5'-GGTGGTGG-3' (SEQ ID NO:78). Separate mixtures for mutated SOD1, wild type SOD1, and 18S were prepared and consisted of 5 μL 2× TaqMan® Universal PCR Master Mix, 0.3 μL of each primer (10 μM), 0.25 μL probe (5 μM), 2 μL of a 10 fold diluted cDNA template, or in the case of 18s, 2 μL of a 10,000 fold diluted cDNA template, and $H_2O$ to a final volume of 10 μL. Real-time PCR was accomplished under the following conditions: 2 min at 50° C., 10 min at 95° C., 40 cycles of 95° C. for 15 sec and 60° C. for 1 min. All PCRs were performed in triplicate. The cycle threshold (Ct) values corresponding to the PCR cycle number at which fluorescence emission in real time reaches a threshold above baseline emission were determined in the software SDS 2.2 (PE Applied Biosystems). To compare expression levels of wild type SOD1 in the various tissues relative mRNA template concentrations were calculated using the standard curve method.

Southern Blot Analysis

Transgene integration was determined by Southern blot analysis of DNA from musculus longissimus dorsi from the two affected boars. 15 μg of genomic DNA, undigested, Pvu II-digested, and double digested with Pvu II and Bam HI were separated on a 0.9% agarose gel, blotted to a nylon membrane and probed with [32P]-labelled SOD1 cDNA fragment constituting approximately 450 bp spanning the entire porcine SOD1 coding region derived from PCR amplification followed by nick translation. Genomic DNA from a healthy wild type pig was subjected to the same treatment as DNA from the two boars and has been included as control. Hybridization was accomplished in a hybridization buffer containing 5×Denhardt's solution and 6×SSC at 68° C. for 16 hours.

SOD Analysis

The SOD activity was determined with the Superoxide Dismutase assay kit (Cayman Chemicals, Ann Arbor, Mich.), based on the ability of SOD1 to inhibit the reduction of tetrazolium salt induced by xanthine-xanthine oxidase as described [47], and was accomplished according to manufactures recommendations using serum from the two diseased pigs and one control. One unit of SOD is defined as the amount of enzyme needed to exhibit 50% dismutation of the superoxide radical, O2.—, and a solution of bovine erythrocyte SOD (Cu/Zn was used as standard. Serum samples have been extracted on regular basis for 9 month yielding a total 19 samples from boar 4905, 17 from 4908, and 19 from the control pig, which all were included in the assay. The absorbance was read at 450 nm using a plate reader. The serum protein content was determined with a standard protein assay based on bicinchoninic acid (BCA) using manufactures recommendations (Pierce, Rockford, Ill.) employing bovine serum albumin as a reference and measuring the absorbance at 562 nm.

Histopathology

For examination of muscle tissue samples were taken from the center of longissimus dorsi above the curvature of the last rib from the two affected boars (4905 and 4908) and two wild type controls (147 and 3713). The size of the sample was app. 5×5×1 cm. At excision the samples were frozen in isopentane cooled in liquid nitrogen to minimize internal freeze artefacts. Transverse serial sections (10 μm) were cut in a cryostat at −20° C. and collected on lysine coated cover slips. The sections were immunohistochemically stained for slow myosin heavy chain (MHC) isoform (Catalogue no. CRL-2043, American Type Culture Collection) to identify type I fibres. A description of the methods used for the immunohistochemical stainings is given in Pedersen et al. (2001) [48]. The architecture of fibre types in pig muscles is unique as type I and IIA fibres are located in clusters. For the analysis we have counted the number of fibres within clusters as this is less affected by growth or differences in size of animals and compared the distributional characteristics of fibres within clusters. In the analysis clusters of type I fibres have been included.

For histopathological investigation of medulla spinalis both affected boars, 4905 and 4908, as well as two wild type boars, 147 and 3713, at approximately the same age were employed. After immersion fixation of cervical medulla spinalis in 4% paraformaldehyde, the tissues were embedded in paraffin was and sectioned into slices of 5 μm. Sections were stained with 7 anti-SOD1 peptide antibodies. However, only the 100-115 anti SOD1 peptide antibody were specific for the porcine SOD1, and is therefore, the one used in this work. The immunohistochemistry was performed using the Ventana immunohistochemistry system.

Statistics

Variation in number of type I muscle fibers in musculus longissimus dorsi between the two affected boars (4905 and 4908) and controls (3713 and 147) were tested with respect to statistical significance employing students t-test considering unequal variances ($\alpha=0.05$), since data approaches the underlying assumption of normality.

Description of the Porcine Phenotype

Initially, the first signs of phenotypic alterations were appearing in one of the boars, 4905, at the age of seven months. The boar was slightly ataxic and showed reduced propioception and it preferred to lie down. The symptoms became gradually worse and at the age of ten months the boar showed fasciculation when getting up and laying down. Furthermore, the boar had pronounced, abnormal itching reflexes and at the age of 15 months the boar was sacrificed since it was nearly unable to get up without help. The other boar, 4908 got slightly symptomatic at the age of approximately 8 months, where it like the other boar, was slightly ataxic and showed reduced propioception. One month later it showed fasciculations, which turned gradually worse and at the age of 12 month, these fasciculations was very severe and continuously present when the boar was standing in an upright position. Furthermore, this boar showed abnormal tongue movements. At the age of 14 months the boar was sacrificed. Both of the boars were all the time able to accomplish basic necessities of life such as eating, drinking, and urinating without any help.

Southern Blot Analysis

Figure 10:
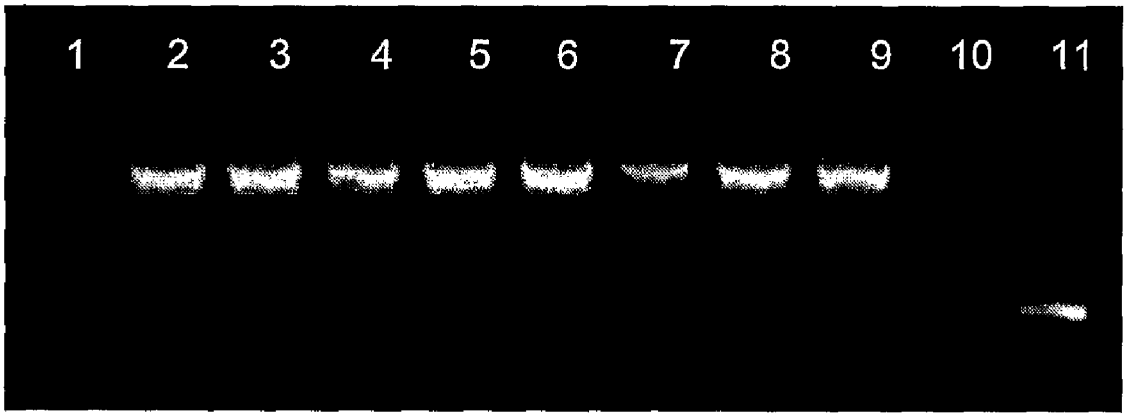
FIG. 10: PCR evaluation of transgenic offspring. Lane 1: DNA ladder, lane 2: pig 4905, lane 3: piglet 4908, lane 4: pig 4909, lane 5: pig 4906, lane 6: pig 4907, lane 7: pig 4911, lane 8: pig 4910, lane 9: wild type animal, lane 10: minus DNA, and lane 11: positive control.

To establish whether integration of the transgene had occurred Southern blot analysis was performed on tissue from musculus logissimus dorsi from the two affected boars and on wild type control. The used probe spans the entire SOD1 coding region, constituting approximately 450 bp. However, no detectable bands can be seen in any of the samples constituting undigested, Pvu II digested and Pvu II and BAM HI double digested DNA from boar 4905 and 4908 and the wild type pig showing that genomic integration has not occurred. Furthermore, under the same conditions the ~five copy fragment control harboring the SOD1 cDNA, were clearly detected (lane 11 and 12, in FIG. 10), suggesting that the SOD1 cDNA is markedly underrepresented in the genome (<1 copy per genome).

PCR Analysis

Figure 11:
FIG. 11: Southern blot. Lane 1-3: genomic DNA from boar 4905, 4908, and wt-pig digested with Pvu II, lane 4-6: genomic DNA from boar 4905, 4908, and wt-pig digested with Pvu II and BAM HI, lane 7-9: undigested genomic DNA from boar 4905, 4908, and wt-pig lane 10: SOD1 fragment used in SMGT digested with Pvu II (1-5 copies), lane 11: SOD1 fragment used in SMGT digested with Pvu II and Bam HI (1-5 copies).

To further establish if the transgene could be present, for instance as an extrachromosomal entity, which has been demonstrated in a recent study [49], both the two affected boars and the five littermates were checked for the presence of transgene using DNA purified from blood as a template. Primers enabling both the amplification of the wild type genomic SOD1 fragment spanning exon 3 to exon 4, yielding approximately 800 bp, and the mutated SOD1 DNA fragment, yielding approximately 200 bp were employed. FIG. 11 shows that apart from the positive control only the 800 bp DNA fragment arising from the endogenous SOD1 was amplified. This indicates that none of the seven animals harbour the fragment used during the SMGT procedure. Furthermore, also DNA extracted from the tails of the seven animals has been subjected to PCR analysis, yielding also negative results regarding the occurrence of the mutated SOD1.

Still, it can not be ruled out that a minor fraction of the cells harbours the construct, applied in the SMGT procedure, possibly stored as an extrachromosomal fragment; however this is beyond our detection limit. Furthermore, the presence of transgene in other tissues in a minor fraction of the cells ruled out either; however since PCR amplification in various tissues of the sacrificed pigs did not give rise to any consistent amplification of the DNA fragment used in the SMGT procedure only a minor fraction of the total number of cells include said fragment.

SOD1 Expression Analysis

Figure 12:
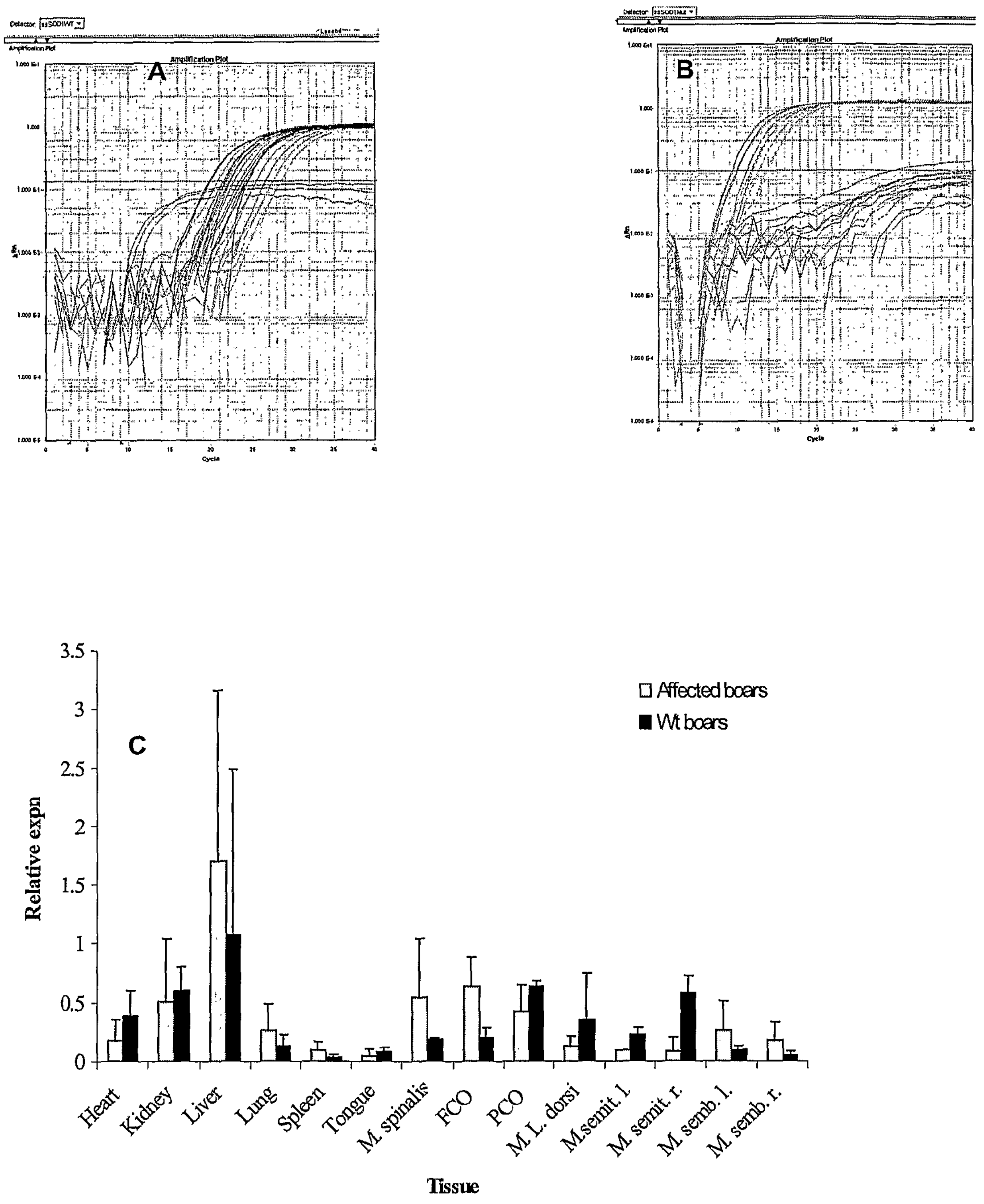
FIG. 12: Analysis of porcine WT SOD1 expression levels in various porcine tissues by quantitative real-time RT-PCR. A) Detection of porcine endogenous SOD1, showing both SOD1 standard dilution and samples from the two affected boars and wild type controls, showing no difference. B) Detection of mutated porcine SOD1. Pink and yellow curves represent amplification of the mutated SOD1 fragment in various dilutions. Blue and green curves shows the lack of amplification of mutated SOD1 in both wild type and affected boars. C) SOD1 endogenous expression analysis. Each sample was conducted in triplicate. The expression analysis was performed on samples from heart, kidney, liver, lung, spleen, medulla spinalis (M. spinalis), frontal cortex (FCO), parietal cortex (PCO), musculus longissimus dorsi (M. L. dorsi), musculus semitendinosus, left side (M.semit. l.), musculus semitendinosus, right side (M.semit. r.), musculus semibranosus, left side (M.semb. l.), and musculus semibranosus, left side (M.semb. r.) from the two affected boars (4905 and 4908) and two wild type control boars (147 and 3713). SOD1 expression levels were normalized against the 18S ribosomal gene.

Expression of the SOD1 construct harbouring the Gly93Arg substitution was accomplished by quantitative RT-PCR using TaqMan probes spanning the DNA region harbouring the substitution, and hence separate RT-PCR's were conducted regarding the wild type SOD1 mRNA and the mutagenised SOD1 mRNA from heart, kidney, liver, lung, spleen, medulla spinalis, frontal cortex, parietal cortex, musculus longissimus dorsi, musculus semitendinosus left side, musculus semitendinosus right side, musculus semibranosus left side, and musculus semibranosus from the two affected boars and from the two wild type controls and assayed for the presence of the mutagenised SOD1 transcript or alternatively altered endogenous SOD1 levels. Furthermore, the mutagenised SOD1 fragment was included in the expression analysis to ensure that the SOD1 probe matching the mutagenised fragment was perfectly suited to detect any transcript. FIG. 12B shows amplification of the mutagenised fragment in various concentrations emphasizing, that the probe is suitable for detection of mutagenised transcripts. However, since no difference is seen between the amplification curves, representing of the affected boars and the controls in any of the 12 tissues it is concluded that mutagenised transcripts are not present in the affected boars, FIG. 12. Although a wide variety of tissues have been included, it can not be ruled out that expression of the transgene could possibly be present in other tissues or at very low levels which could not be detected in this assay.

FIG. 12A shows the amplification curves using the probe detecting the SOD1 wild type transcript. This reveals that the SOD1 probe detects the SOD1 transcript, even though some background amplification would be present in case of possible SOD1 mutant transcript, since an amplification curve is present using the SOD1 mutagenised fragment (pink curve in FIG. 12A). However, since no mutagenised transcript could be detected, this is not considered in the real time analysis in FIG. 12C. The real time analysis reveals no differences in the endogenous SOD1 expression levels between the two wild type boars and the two affected boars in any of the analysed tissues. However, large inter tissue variations are present, which is also the case between tissues. The highest expression levels are seen in liver and kidney, which is also in agreement with studies performed on human tissues [50].

SOD Analysis in Serum

Figure 13:
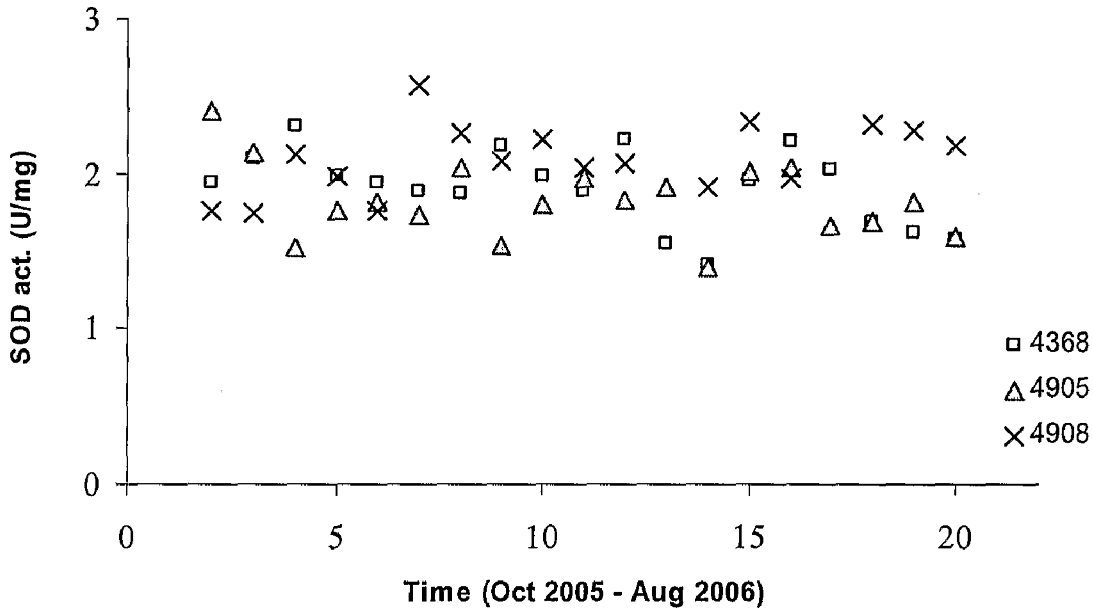
FIG. 13: SOD activity in serum from symptomatic animals (4905 and 4908) and a healthy control (4368).

SOD1 activity was detected spectrophotometrically in serum as a measurement for the SOD1 to inhibit the reduction of tetrazolium salt induced by xanthine-xanthine oxidase [47] and was not corrected for Mn-SOD, meaning that the activities in FIG. 13 represent the total SOD activity in serum. However, since Mn-SOD accounts for a minor fraction of the total SOD activity in serum [51] it is not likely that it would mask possible differences between affected boars and the control. The SOD activity levels in serum of the two transgenic affected boars was approximately at the same level as the control boar during the time course recorded, and no significant variation across time (from October 2005-August 2006) has been revealed, FIG. 13.

Furthermore, proteome analysis employing protein extracts from liver and musculus longissimus dorsi failed to detect any mutagenised SOD1 protein in the two transgenic boars (data not shown).

Histopathological Investigations

Figure 14:
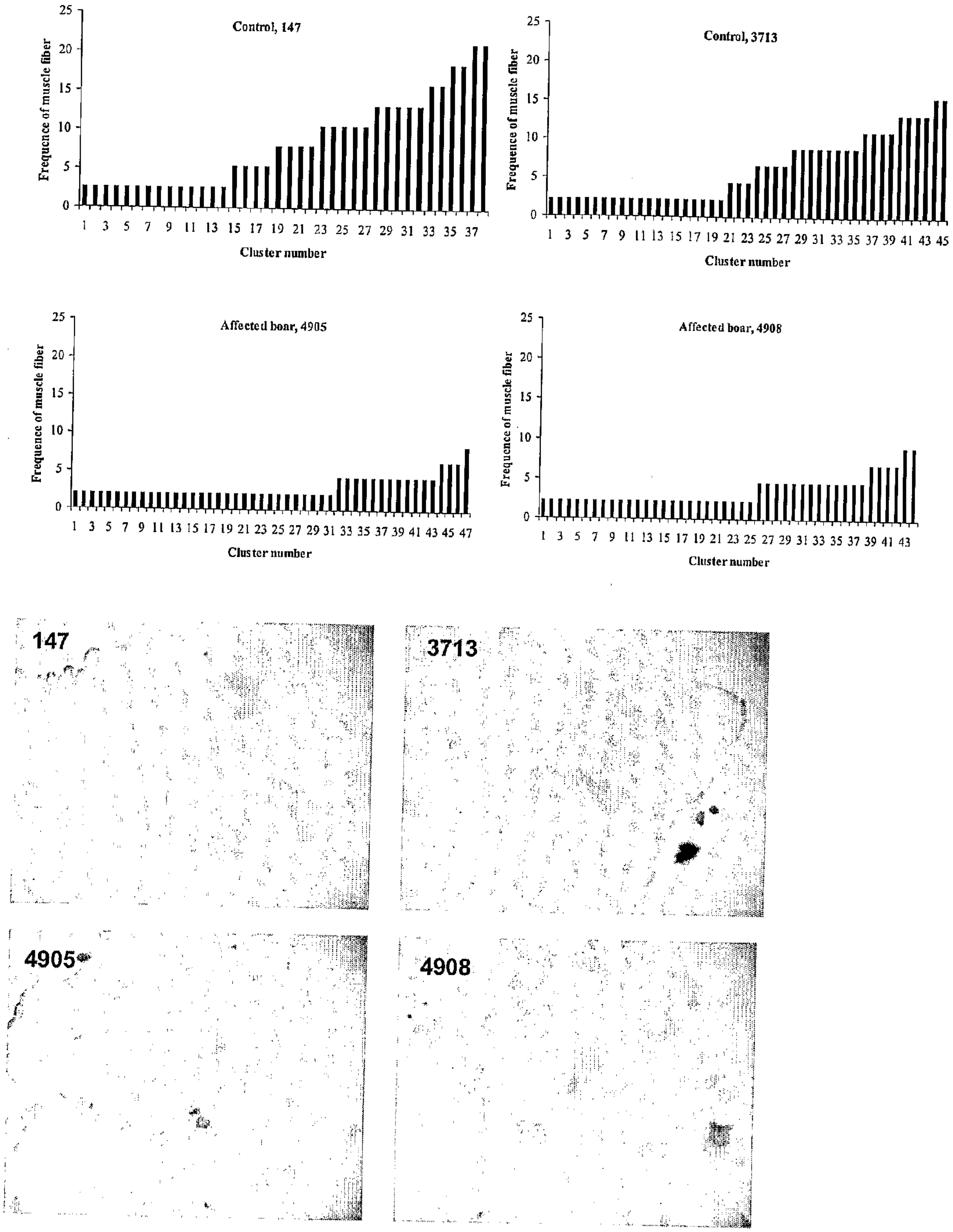
FIG. 14: Investigation of muscle fibers, type 1, in affected boars (4905 and 4908) and healthy wild type controls (3713 and 147). The number of type I muscle fibers in each muscle cluster was counted in musculus longissimus dorsi, and the frequency of muscle fibers in each cluster for the four boars are shown in the histograms. The stainings represents typical type I muscle fibers from musculus longissimus dorsi from the four boars.

Since the nature of muscle fibers may be used to assess disease progression of ALS the clusters including type I muscle fibers in musculus logissimus dorsi were examined regarding the number of fibers in each cluster. This investigation revealed that the frequencies of type I fibers in the two affected boars are significantly decreased in comparison to controls, FIG. 14. Statistical evaluation reveals P-values of $3\times10^{-6}$ and $2\times10^{-5}$ for 4905 and 4908, with respect to the control boar, 147, emphasizing highly significant differences. Furthermore a P-value of 0.08 reveals that the two controls are not statistically different, which is also the case for the two affected boars, P=0.11. The stainings, FIG. 14, further highlights the large differences in number of type I fibers, both regarding the size of the clusters and the absolute number, which is also reduced in the two transgenic boars.

Figure 15:
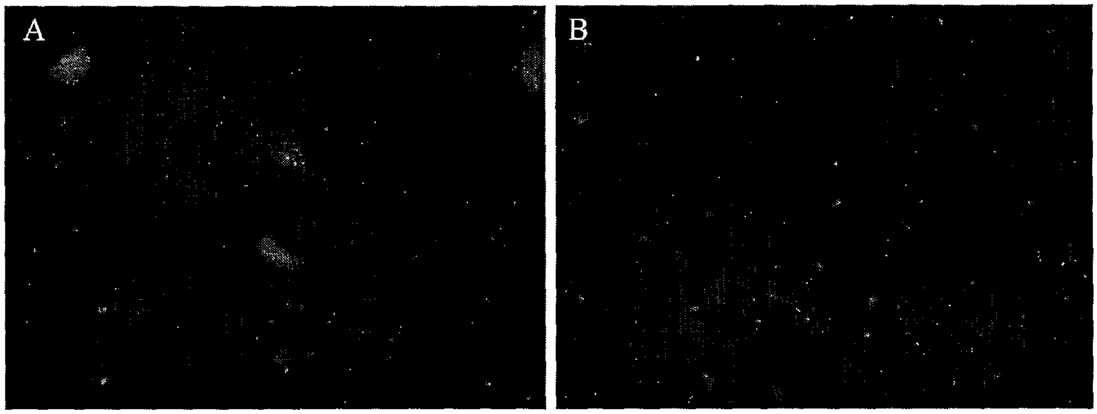
FIG. 15: Photomicrographs of immunohistochemistry sections from cervical spinal cord showing motorneuron from A) the affected boar (4908) and B) an unaffected wild type control (147) stained with the 100-115 anti-SOD1 peptide antibody.

Sections from cervical spinal cord of the two the two affected boars and two age matched wild type boars were stained with various peptide antibodies raised against human SOD1. However, only the 100-115 anti-SOD1 peptide antibody proved to be specific with respect to porcine SOD1. FIG. 15 shows a motorneuron from the spinal cord of both an affected boar (4908) and the age matched control boar (147). In FIG. 15A) showing a motor neuron from the affected boar, SOD1 stainings are seen in the motor axon, most likely arising from SOD1 inclusions. In comparison no stainings are seen in the axon of the control. Furthermore, in FIG. 15A large fluorescent compartments are seen in the neuropil which are not present in the control either.

Example 2

A Transgenic Pig Model for Parkinson's Disease

Cloning of the Porcine SNCA cDNA

The full-length porcine α-synuclein (SNCA) cDNA was isolated from cerebellum by a combination of RT-PCR and RACE. Initially, blast searches using the human SNCA cDNA sequence were carried out with GenBank (http://www.ncbi.nlm.nih.gov/Genbank/index.html) and with the porcine EST data bank at The Danish Institute of Agricultural Sciences (DIAS). Sequence similarity search was performed with gapped alignment using NCBI Blastall with options blastn, minimum value 10-8. The porcine cDNAs thus identified were used to derive oligonucleotide primers for cloning and as queries for further searches in the local genomic DIAS sequence database.

The pig cerebellum tissue used for RT-PCR cloning of porcine SNCA was obtained from an adult pig. After removal, tissue was dissected and pulverized in liquid nitrogen. Total RNA was isolated by the RNeasy method (Qiagen). The integrity of the RNA samples was verified by ethidium bromide staining of the ribosomal RNA on 1% agarose gels.

The porcine SNCA cDNA presented here was isolated using an RT-PCR cloning approach. Synthesis of cDNA was conducted with 5 μg of total RNA isolated from pig cerebellum using SuperScript II RNase H-reverse transcriptase (Invitrogen). The cDNA synthesis was initiated by heating of total RNA, oligo(dT) 12-18 primer, dNTP at 65° C. for 5 min followed by addition of 200 units reverse transcriptase and then incubation at 42° C. for 50 min followed by 70° C. for 15 min.

The RT-PCR reaction mix contained: 2.5 μl cDNA, 1.5 mM MgCl2, 0.2 mM dNTP, 0.5 μM of each primer SNCA-F: 5'-CCATGGATGTATTCATGAAAGGACTTTCAA-3' (SEQ ID NO:79) and SNCA-R: 5'-CTTCCGGCTCATAGTCCTGATACCC-3' (SEQ ID NO:80), and 1 U Phusion DNA polymerase (Finnzymes), in a total volume of 25 μl. PCR amplification was carried out in the total volume using the following program: Denaturation at 94° C. for 2 min., 10 cycles of 94° C. for 15 s, 55° C. for 30 s, 72° C. for 40 s, followed by 25 cycles of 94° C. for 15 s, 60° C. for 30 s, 72° C. for 40 s. The PCR program was concluded by an extension at 72° C. for 7 min. Twentyfive microlitres of the amplification product was applied to a 1% agarose gel and visualized after electrophoresis by ethidium bromide staining. A fluorescent band of approx. 400 bp was cut out and eluted using the Qiaquick Gel Extraction kit from Qiagen. The eluted PCR product was cloned directly into the pCR TOPO 2.1 vector (Invitrogen) and sequenced in both directions.

To obtain a full-length coding SNCA cDNA, sense and antisense primers derived from the isolated SNCA fragment were used in 5' and 3' RACE (rapid amplification of cDNA ends) experiments. A sense SNCA specific primer was used in combination with a kit anchor primer (Roche Molecular Biochemicals). In brief, for 3'-RACE, an oligodT reverse transcription oligonucleotide primer, 5'-GACCACGCGTATCGATGTCGACTTTTTTTTTTTTTTTTV-3' (V=A, C or G) (SEQ ID NO: 81) was used in a reverse transcription reaction. The resultant SNCA cDNA was used as a template for PCR amplification employing the proof-reading DNA polymerase Phusion (Finnzymes), in combination with a kit PCR anchor primer: 5'-GAAAACGCGTATCGATGTTCGAC-3' (SEQ ID NO:82) and a gene-specific primer SNCA-F: 5'-CCATGGATGTATTCATGAAAGGACTTTCAA-3' (SEQ ID NO:83). PCR products were recovered as described above, cloned into the pCR TOPO2.1 vector and sequenced. one PCR amplicon of approx. 800 bp contained a DNA fragment that showed homology to SNCA and which also matched the sequence of the partial SNCA cDNA where the sequences overlapped. For 5'-RACE a reverse transcription oligonucleotide primer, SNCA5-it1: 5'-GGATCCTACATAGAGCACACCCTC-3' (SEQ ID NO:84) was used in a reverse transcription reaction. The synthesized SNCA cDNA was used as a template for PCR amplification employing Phusion DNA polymerase (Finnzymes), in combination with a kit PCR anchor primer: 5'-GAAAACGCGTATCGATGTTCGAC-3' (SEQ ID NO:85) and a gene-specific primer, SNCA5-it2: 5'-TCCCGCTGCTTCTGCCACACCCTG-3' (SEQ ID NO:86). PCR products were recovered as described above, cloned into the pCR TOPO2.1 vector and sequenced. one PCR product contained a DNA fragment that showed homology to SNCA and also matched the sequence of the partial SNCA cDNA where the sequences overlapped.

The interconnectedness between the original cDNA clone and the 5'- and 3'RACE sequences was confirmed by PCR with the primers SNCA5-F: 5'-CAGTCTGTTAGGGGGAGGAGCTTATTTC-3' (SEQ ID NO:87) and SNCA-it3: 5'-CTATAGTTAATATTTATAGGTGCATAGTTCC-3' (SEQ ID NO:88). PCR amplification was carried out in the total volume using the following program: Denaturation at 95° C. for 2 min., 10 cycles of touchdown (−0.5° C. per cycle) 95° C. for 20 s, 60° C. for 30 s, 72° C. for 45 s, followed by 25 cycles of 95° C. for 20 s, 55° C. for 30 s, 72° C. for 45 s. The PCR program was concluded by an extension at 72° C. for 5 min.

DNA sequencing was performed employing the dideoxy chain termination method using BigDye terminator cycle sequencing kit with AmpliTaq DNA polymerase FS (PE Applied Biosystems). The sequencing analysis was performed on an automated DNA sequencer (ABI PRISM™ Genetic Analyzer Model 3730xl, PE Applied Biosystems). Traces were aligned and visualized using the SEQUENCHER version 4.0.5 for Windows (Gene Codes Corporation).

Characterization of the Porcine SNCA cDNA

The SNCA cDNA was amplified by the reverse transcriptase polymerase chain reaction (RT-PCR) using oligonucleotide primers derived from in silico sequences. Partial porcine SNCA EST sequences identified in the DIAS EST library were used to derive primers for RT-PCR amplification of the SNCA cDNA. A 420 bp fragment was obtained which showed a high level of homology to published SNCA sequences. Sense and antisense primers were designed from this sequence and used for 5' and 3'-RACE experiments. With one round of PCR a SNCA cDNA covering the coding and 3'UTR sequence was obtained. Similarly, one round of PCR generated the missing 5'UTR sequence. To confirm that the obtained porcine SNCA fragments were interconnected, a PCR reaction using primers covering the near full-length coding sequence of was performed. This resulted in the 982 bp cDNA sequence shown in FIG. 16.

The identity of the porcine SNCA cDNA was established by comparing the deduced polypeptide sequence with other isolated alpha-synuclein proteins. The porcine SNCA cDNA (GenBank Access. No. DQ073395) is 982 bp in length with the translational start site at nucleotide 104 and the TAA stop codon at nucleotide 524. The open reading frame (ORF) of SsSNCA has a G+C content of 50% and it encodes a polypeptide of 140 amino acids with an estimated molecular mass of 14.5 kDa and a μl of 4.6. The encoded porcine □-synuclein protein contains the characteristic motifs of other □-synuclein proteins: five imperfect repeats with a core consensus sequence KTKEGV distributed from the amino terminus to the central part of the protein. As for other □-synucleins eleven central hydrophobic amino acids are missing compared to the homologous β-synuclein and γ-synuclein.

Amino acid sequence similarity between porcine α-synuclein and other published mammalian α-synuclein proteins was determined by the Clustal method. Multiple alignment of α-synuclein amino acids sequences from pig, human, mouse and rat, cow, chicken and *Xenopus* (FIG. 17) revealed a very high overall homology. Interestingly, it was found that the amino acid in position 53 which is an alanine in human is a threonine residue in all other species. This particular alanine residue is found substituted to a threonine (Ala53Thr) in familial Parkinsonism.

Figure 18:
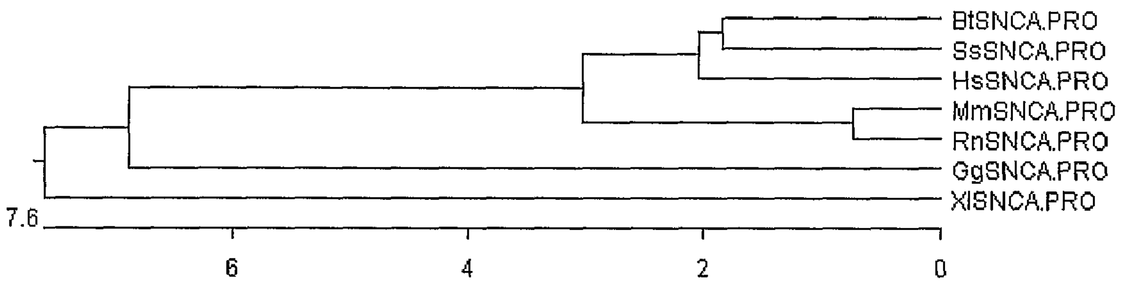
FIG. 18: Phylogenetic tree (unrooted) of porcine alpha-synuclein, and other alpha-synuclein proteins. The tree was constructed using the using the clustal method of DNASTAR Megalign (DNASTAR Inc., Madison, Wis.) based on amino acid similarities of the full sequences. The length of each pair of branches represents the distance between sequence pairs, while the units at the bottom of the tree indicate the number of substitution events. The following abbreviations for species acronyms are used along with: Ss=*Sus scrofa*; Hs=*Homo sapiens*; Bt=*Bos taurus*; Mm=*Mus musculus*; Rn=*Rattus norvegicus*; Gg=*Gallus gallus*; Xl=*Xenopus laevis*. The Accession numbers of the sequences used for construction of the phylogenetic tree are: SsSNCA (AY049786); HsSNCA (NM_001037145); BtSNCA (NM_001034041); MmSNCA (AF44672); RnSNCA (NM_019169); GgSNCA (NM_204673); XlSNCA (BC054200).

A very high degree of identity between porcine α-synuclein and most other alpha-synuclein proteins was found. The encoded pig α-synuclein polypeptide exhibits significant sequence identity to human α-synuclein (98%), cow α-synuclein (96%) and mouse and rat α-synuclein (both 94%). The lowest amino acid identity between pig α-synuclein and other α-synuclein proteins was observed with the chicken α-synuclein (84%) and the *Xenopus* sequence (80%). See FIG. 18 for a phylogenetic tree. The Prosite Web site (http://www.expasy.ch/prosite/) was used to analyze the 140 amino acid porcine α-synuclein protein sequence and predicted a molecular weight of 14.5 kDa and identified potential post translational modifications. These include one casein kinase II phosphorylation site, one tyrosine kinase phosphorylation site and five putative myristoylation sites.

Site Directed Mutagenesis of Porcine SNCA

In order to introduce the Ala30Pro mutation into the porcine SCNA, site directed mutagenesis was performed employing the QuickChange® XL Site-Directed Mutagenesis Kit (Stratagene) and accomplished in accordance with manufactures recommendation applying the following primers:

```
SNCA-A30P-F:
                                    (SEQ ID NO: 89)
5'-GGGTGTGGCAGAAGCACCGGGAAAGACAAAAGAG-3'

SNCA-A30P-R:
                                    (SEQ ID NO: 90)
5'-CTCTTTTGTCTTTCCCGGTGCTTCTGCCACACCC-3'.
```

The PCR conditions were: Denaturation at 95° C. for 1 min., 18 cycles of 95° C. for 50 s, 60° C. for 50 s and 68° C. for 6 min. The PCR program was concluded by an extension at 68° C. for 7 min.

To ensure that the mutation of interest was integrated in the porcine SNCA gene, several colonies were picked and grown overnight and plasmids were harvested and sequenced according to standard procedures. A plasmid containing the mutation was chosen as template for the subsequent procedures. Next, the plasmid containing the mutated SNCA cDNA was digested with KpnI and EcoRV releasing the SNCA fragment, which was now cloned into the KpnI and SmaI digested phCMV1 expression vector using standard protocols. XL10-Gold® Ultracompetent Cells (Invitrogen, CA) were transformed with the phCMV1 vector preparation and to ensure that the SNCA insert had integrated correctly into the phCMV1 vector colonies were grown in liquid LB-Amp and plasmids were purified and sequenced according to standard procedures.

Vector constructs containing correctly integrated mutagenized SNCA fragments were selected for following procedures.

Large-Scale SNCA DNA Preparation

In order to create DNA for incubation of sperm cells large scale PCR reactions were performed. The PCR reactions were carried out in a GeneAmp® PCR System 9700 (Applied Biosystems) in a final volume of 25 μL consisting of 5 μL 5× Phusion HF buffer, 2 μL dNTP (2.5 mM each) 0.63 μL forward and reverse primer 5 pmol, 0.1 μL Phusion DNA Polymerase (2 U/μL), 1 μL SNCA-phCMV1 template, and 15.6 μL $H_2O$. The PCR reaction consisted of an initial denaturation at 98° C. for 30 sec followed by 30 cycles of denaturation for 10 sec at 98° C., annealing at 74° C. for 30 sec and elongation for 95 sec at 72° C. followed by a final elongation step at 72° C. for 7 min. The following primers were used to amplify the mutagenized SOD1 construct plus the flanking CMV promoter, intron sequence, and SV polyA, generating a fragment of approximately 2100 bp.

```
                                    (SEQ ID NO: 91)
phCMVF: 5'-GTCGGAACAGGAGAGCGCACGAGGG-3'

                                    (SEQ ID NO: 92)
phCMVR: 5'-GGGTGATGGTTCACGTAGTGGGC-3'
```

Figure 20:
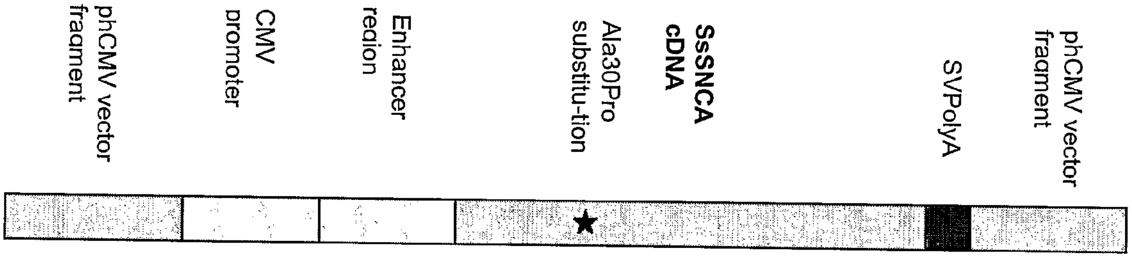
FIG. 20: SNCA-phCMV1 linearized construct used to create transgenic pigs by means of SMGT. The fragment constitutes approximately 2100 bp and includes a CMV promoter, en enhancer region, the mutated (A30P) porcine SNCA cDNA, and the SVPolyA (simian virus 40 poly(A) fragment. Furthermore, the 5'- and 3'-prime end of the DNA fragment include additional bases derived from the phCMV vector to protect crucial element from being truncated following SMGT.

In order to purify the generated PCR product a "High Pure PCR Product Purification Kit" (Roche) was applied. The suppliers' instructions were followed throughout the purification procedure. The PCR purified fragments were sequenced to check for errors in the sequence. See FIGS. 19 and 20.

Sperm Mediated Gene Transfer SMGT

Sperm Mediated Gene Transfer, Buffer:

In order to wash the porcine sperm cells and hence remove the sperm liquid, the following optimized buffer is applied:

| For 1 liter: | |
|---|---|
| 56.1 g | Glucose |
| 3.5 g | EDTA (2 $H_2O$) |
| 3.5 g | Sodium citrate |
| 1.1 g | Sodium bicarbonate |

The components are dissolved in water and the solution is sterilized through a filter. Before the buffer is added to the sperm cells, 6 mg/ml BSA (Bovine Serum Albumine, Fraction V, Sigma) is added.

Selection of Sperm Donor Boars:

The selection of the sperm donor boars are crucial for the outcome of the procedure. A boar station (Hatting KS Viborg), have therefore been contacted and the boars of choice are selected so that the initial sperm motility is >90%. The sperm is collected in sterile 10 mL tubes and transported undiluted at a temperature not below 15° C. as this will cause damage to the sperm cells.

Washing Procedure:

The following procedure is accomplished as fast as possible (buffer is as indicated above):

5 mL sperm is transferred to a 50 mL Falcon tube 5 mL buffer preheated to 37° C. is added Mix by inverting the tubes The solution is incubated for 5 min at room temperature (~22° C.)

40 mL buffer (room temperature) is added

Centrifuge at 800 g, for 10 min at 25° C.

Remove the supernatant

Resuspend the pellet in 50 mL buffer (room temperature)

Centrifuge at 800 g, for 10 min at 17° C.

Remove the supernatant

Carefully resuspend the pellet in the remaining buffer in the bottom of the Falcon tube.

Examination of the Sperm Cells:

In order to choose the correct donor cells, the sperm cells from the different boars are examined under a light microscope. The sperm cells originating from the boar having the highest sperm cell motility after the washing procedure are chosen. Next, the sperm cells from the boar of choice are counted.

DNA Uptake/Incubation:

$10^9$ sperm cells are diluted into 120 mL 17° C. buffer 0.4 μg linearized DNA/$10^6$ sperm cells is added (that is, a total of 400 μg linearized DNA)

Incubate 100 min at 17° C.

To avoid sedimentation of the cells, invert the tube every 20 min

Transfer the tube to room temperature, and transport it, still at room temperature to stable facilities. This takes approx. 10 min. The incubated sperm cells are now ready to be applied in artificial insemination.

Animals:

Two recipient sows (Danish Landrace×Yorkshire) at approximately 140 kg were selected due to their natural heating period and used for artificial insemination ($1\times10^9$ DNA treated sperm/sow) meeting standard insemination procedures. Insemination was accomplished in the local stable areas at DIAS. Semen was collected from trained Landrace boars that have abstained for 2 days. Semen was treated according to aforementioned procedures. Both sows were examined for pregnancy 24 and 42 days after insemination, showing that only one of the sows was pregnant. Animal care and experimental procedures met local, national and European Union Guidelines.

Test for Presence of the Transgene:

After 115 days (17 Jun. 2005) 10 normal looking piglets were born, 5 of these were boar piglets and 5 were sow piglets. One of the boar piglets died the following day (17 Jun. 2005). Blood samples were collected from the piglets in 6 mL EDTA blood collection tubes. Furthermore, blood from a wild type animal was collected as well and handled together with the 9 aforementioned animals. At a later stage semen was collected from selected animals and genomic DNA was isolated. DNA was purified according to standard blood purification procedures in special clean laboratories, in order to avoid any possible contamination.

The PCR reaction was performed in a total volume of 10 μL consisting of 1 μL 10×MgCl2 free reaction buffer, 0.4 μL 50 mM MgCl2, 1 μL of both forward and reverse primer (10 pmol each), 0.5 μL dNTP mix, 0.5 μL DyNazyme EXT DNA polymerase (1 U/μL), 0.5 μL DNA template (50 ng), and 5.1 μL $H_2O$.

Forward and reverse primer used for the above PCR procedure:

```
                                    (SEQ ID NO: 93)
PHCMV_682F:   5'-GATTCCCCGTGCCAAGAGTG-3'

                                    (SEQ ID NO: 94)
SNCA-4R:      5'-TTGCCCAGCTGATCCTTTTTGCCAAAG-3'
```

The touchdown PCR reaction was accomplished in a GeneAmp® PCR System 9700 (Applied Biosystems) under the following conditions: Initial denaturation at 95° C. for 3 min, denaturation at 95° C. for 30 sec, touchdown from 62° C. to 57° C. with a decrement of 0.5° C. for 20 sec, followed by 1 min of elongation at 72° C. pr cycle. Furthermore, 35 cycles of 30 sec denaturation at 95° C., 20 sec of annealing at 57° C., and 1 min of elongation at 72° C. was included together with a final elongation step at 72° C. for 7 min.

Figure 21:
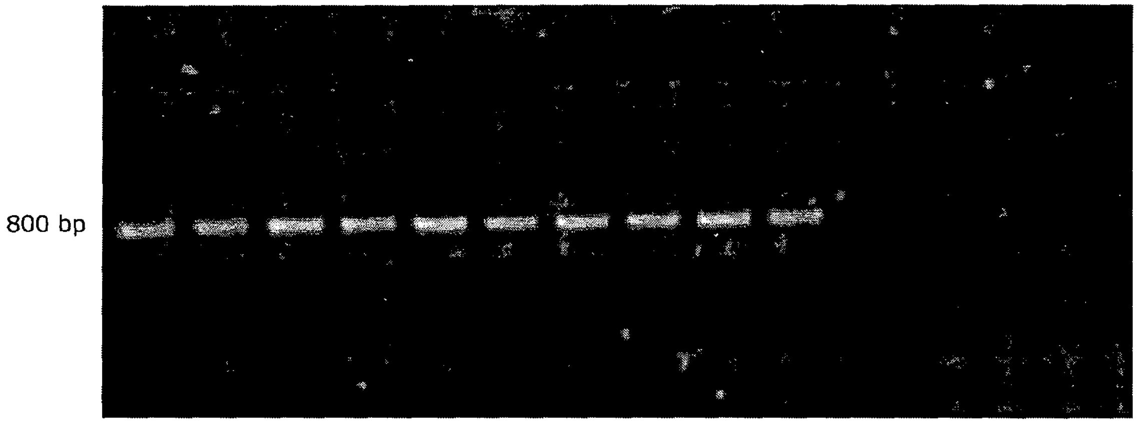
FIG. 21: PCR evaluation of transgenic offspring. Lane 1: piglet 4363, lane 2: piglet 4364, lane 3: piglet 4365, lane 4: piglet 4366, lane 5: piglet 4367, lane 6: piglet 4368, lane 7: piglet 4369, lane 8: piglet 4370, lane 9: piglet 4371, lanes 10 and 11: positive control, lanes 12 and 13: minus DNA, lane 14: untransformed control. All the tested piglets (animal 4363-4371) from the litter are positive regarding the transgenic fragment.

Blood samples were withdrawn form potentially transgenic piglets and PCR reactions were carried out on purified DNA as described above. FIG. 21 shows that all animals (4363-4371) are positive regarding the transgenic DNA fragment of 800 bp. However, mosaicsm can not be ruled neither the possibility of the various animals having different copy numbers.

Transgene in the Germ Cells:

In order to transfer the transgene to next generation it is important to ensure that the transgene is present in the germ cells. Therefore, DNA has been extracted from sperm cells from the two boars (4905 and 4908). The purification of DNA was accomplished using a standard purification procedure:

Standard Purification Procedure:

300 μL of semen was washed in 1 mL 0.9% NaCl, followed by centrifugation for 5 min at 3000 rpm where after the supernatant was discarded. This step was repeated twice and 20 μL Pronase (20 mg/mL), 20 μL1 M DTT, and 300 μL buffer S was added to each sample, where after these were left to incubate at room temperature overnight. Subsequently, 180 μL 6 M NaCl was added to each sample and shaken vigorously for approximately 20 seconds. The samples were now centrifuged for 15 min. at 10000 rpm and the supernatant was then carefully transferred to a new Eppendorf tube where the DNA was precipitated adding twice the volume of supernatant and centrifuged at 10000 rpm for 10 min. Subsequently the ethanol was removed and the DNA was air dried and resuspended in 300 μL of nuclease free water.

Buffer S composition: 10 mM Tris HCl (pH 8.0); 100 mM NaCl; 10 mM EDTA (pH 8.0); 0.5% SDS; $H_2O$.

Figure 22:
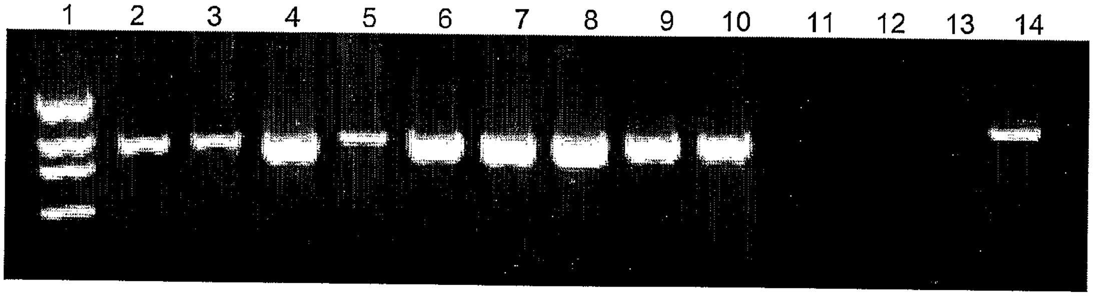
FIG. 22: PCR evaluation of DNA purified from sperm cells from boars 4363-4371. The DNA is purified both by means of a standard purification procedure. Lane 1: DNA marker, lane 2: 4363, lane 3: 4364, lane 4: 4365, lane 5: 4366, lane 6: 4367, lane 7: 4368, lane 8: 4369, lane 9: 4370 lane 10: 4371, lane 11: minus DNA, lanes 12 and 13: negative control, lane 14: positive control.

Presence of the modified SNCA transgene was examined in DNA purified from sperm cells from boars 4363-4371. As shown in FIG. 22 all boars harbored the transgene in the sperm cells. A PCR of the expected size of 800 bp can be observed in for all animals although at differential amounts.

Phenotypic Characterization of Boar #4363

First symptoms were observed in three boars at the age of 17 months. The pigs were examined by Knud Larsen and veterinarian Keld Dahl Winter (Danish Meat). One boar #4363) had the most pronounced symptoms. When standing the boar showed a strongly upward curved (convex) back. Loss of muscle tissue was observed in musculus longissimus dorsi left side while the right side was unaffected. During activity permanent tremor of the tail was observed. More pronounced tremor was seen in the neck especially when the head was raised. Tremor was also visible in the tail and in ear tips. The tremor was intermittent and disappeared partly when the boar was at rest. The tremor in head and neck was worsened when the boar was surprised by visitors and by rising of the head. The boar appeared with a rigid body posture, moved very slowly and did not turn around when people were circling around it. This is not a normal behaviour. The coordination of the limbs was fully normal. However, the movements were very slow. The general state of health was largely unaffected and the boar did not show any signs of pain.

One month later boar #4363 was examined. Tremor of head, neck and tail had increased significantly and were now present partly as resting tremor. The pronounced tremor symptoms have not been observed in any earlier described syndromes in pigs (pers. comm. Keld Dahl Winter). The boar's movements were very slow and considered inhibitory as no turning towards people approaching at the tail was seen. A normal healthy pig would immediately turn towards an arriving person. Since the latest examination one month earlier the muscular atrophy had increased and spread to both sides of the back. The backline had become more visible and the neural spines were more protruding.

Sixteen days later the boar #4363 was sacrificed and dissected for further analyses.

Pathological Examination of Boar #4363

Figure 23:
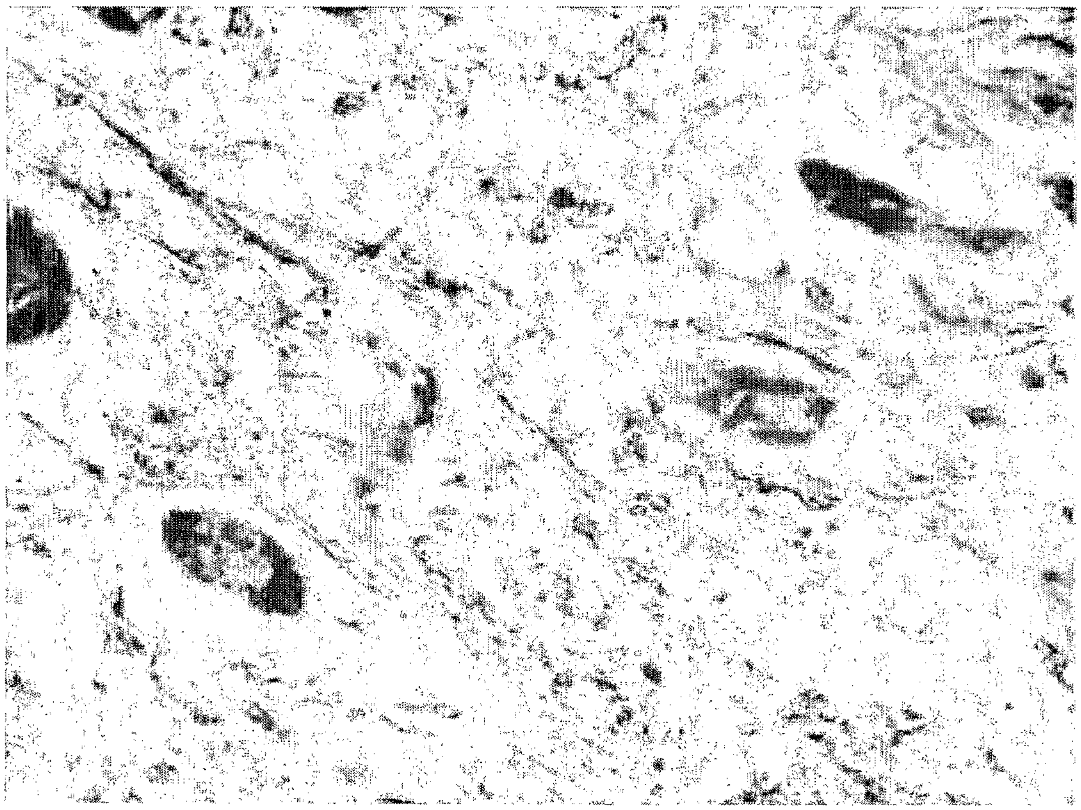
FIG. 23: Nissl AMG staining of thin-layer sections from substantia nigra of boar #4363. Neurons in substantia nigra abnormal; presence of cytoplasmatic vacuoles and shrinking of cells. Lewy bodies are not visible and this staining.
Figure 24:
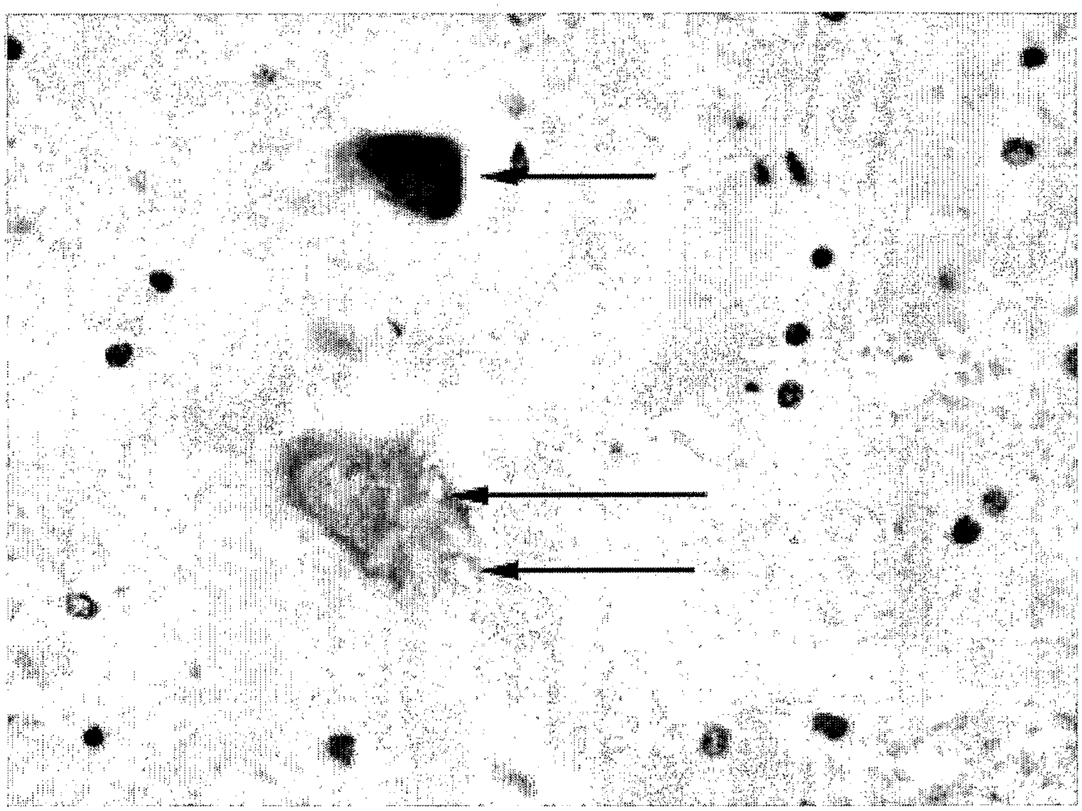
FIG. 24: HE staining of thin-layer sections from substantia nigra of boar #4363. Neurons are shrunken and with numerous lacunae.

Boar #4363 was sacrificed and dissected. Samples from different organs such as heart, liver, kidney, lung, spleen were collected together with samples from testis and selected muscles (musculus longissimus dorsi). Also the brain was taken out and divides into to halves, both were dissected into discrete regions and either snap-frozen or fixed in formaldehyde. After three weeks fixation different brain samples were embedded in paraffin, sliced with a microtome and subjected to different stainings. Nissl AMG-staining of thin-layer sections from substantia nigra revealed presence of neurons but most of the neurons were shrunken with lacunae and no clear segregation between the nucleus, nucleolus and cytoplasm (FIG. 23). Similarly, as shown in FIG. 24, HE-staining also demonstrated shrunken neurons with numerous lacunae (holes) which is a clear indication of neural degeneration.

A staining procedure for tyrosine hydrolase (TH) was also carried out on the thin layer sections. The results showed as illustrated in FIG. 25, that 1) The number of dopaminergic cells seemed to be reduced and 2) The remaining dopaminergic cells and neuropil seemed to be more rough and unordered.

For comparison a brain sample from a mini-pig was also examined for TH staining. Numerous dopaminergic cells were observed.

Figure 27:
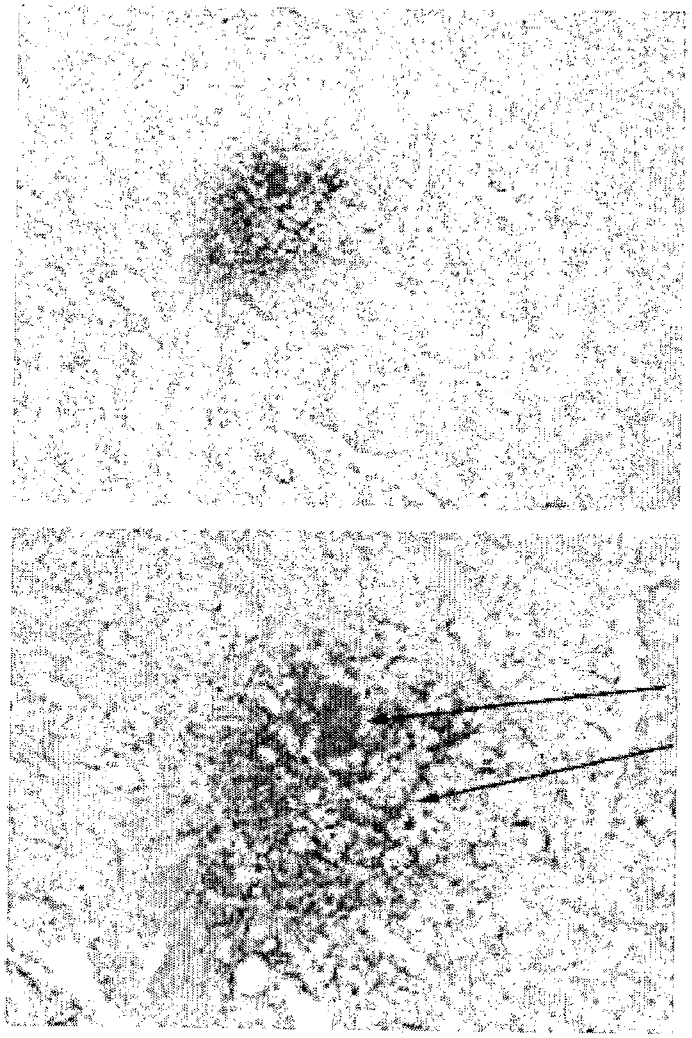
FIG. 27: α-synuclein Ab staining of thin-layer sections from substantia nigra of boar #4363.

A GFAB staining revealed an intense staining in the mesencephalon of boar #4363, an indication of pronounced inflammation and gliosis (FIG. 26). Numerous astrocytes are noted indicative of active inflammation and reactive gliosis. Very interestingly, a specific antibody staining for α-synuclein, using Ab raised against human α-synuclein, revealed patches of large □-synuclein aggregates throughout the mesencephalon (FIG. 27). α-synuclein s located in the cell bodies and extracellular surroundings In conclusion, all pathological examinations of boar #4363 are clearly indicative for PD. However, no classical Lewy bodies are observed. Lewy bodies are a cardinal symptom of PD and presence of Lb is needed to recapitulate the development and progression of PD. The explanation for the missing LBs could easily be that boar #4363 was sacrificed too early in the progression of disease. As the boar was at the age of 18 months and showing a large row of the clinical symptoms of PD but without complete resting tremor it was what could be expected at this particular stage.

FIG. 23 shows a Nissl staining of substantia nigra isolated from boar #4363. The figures clearly demonstrate that there are fewer cells present than expected from a normal healthy individual. Furthermore, neurons in substantia nigra look abnormal and also presence of cytoplasmatic vacuoles and shrinking of cells is indicative of an abnormal condition. Lewy bodies are not visible in this staining.

Example 3

A Transgenic Pig Model Animal of Alzheimer's Disease

PSEN1 and PSEN2 Isolation and Sequencing

Pig brain, lymphocyte, and liver RNA was isolated with the TRI-reagent (Sigma). For RT-PCR of PSEN1 the following primers were used (PSEN1forward, 5'-TGGAGGAGAACACATGAAAGAAAG-3' (SEQ ID NO: 95); PSEN1-forward-EcoR1 5'-GGGGAATTCTGGAGGAGAACACATGAAAGAAAG-3' (SEQ ID NO:96); PSEN1reverseEcoR1, 5'-GGGGAATTCCCTGACTTTGTTAGATGTGGACAC-3' (SEQ ID NO:97). The RT-PCR reaction was incubated at 50° C. for 60 min with the reverse primer followed by PCR with the PSEN1forward-EcoR1 and PSEN1 reverse-EcoR1 primers at conditions (94° C. for 3 min, 35 cycles of; 94° C., 45 sec; 62° C., 30 sec; 68° C., 2 min, followed by a final elongation step at 68° C. for 7 min). Amplified DNA fragments were purified from agarose gels and either directly sequenced or EcoR1 cloned into pCDNA3 followed by DNA purification and sequencing. For RT-PCR of PSEN2 the following primers were used (PSEN2-forward, 5'-GCCATGCTCACTTTCATGGC-3'; PSEN2-reverse (SEQ ID NO: 98), 5'-CACGACTGCGTCCAGTGACC-3' (SEQ ID NO: 99). The reverse transcription reaction was accomplished using the Invitrogen reverse transcription system (Invitrogen) and 5 μg of total-RNA according to the manufacturer's instructions. Subsequently, the PCR reaction was carried out at the following conditions: (94° C. for 3 min, 35 cycles of; 94° C., 45 sec; 60° C., 30 sec; 68° C., 2 min, followed by a final elongation step at 68° C. for 7 min). Amplified DNA fragments were purified from agarose gels and either directly sequenced or cloned into pCR® 2.1-TOPO® Vector (Invitrogen) followed by DNA purification and sequencing. The porcine pSEN1 and pSEN2 cDNA sequences were submitted to GenBank (Accession numbers DQ853416, and DQ853415, respectively)

BAC-Hybridisation

Radioactive probes were generated employing the nick translation kit from Invitrogen which incorporated [α-32P] dCTP into the PCR generated PSEN1-exon8 fragment. High-density colony BAC filters (a generous gift from Dr. P. D. Jong) of the porcine genome were screened with the PSEN1-exon8 probe. The filters were pre-hybridized, hybridized, washed and autoradiographed according to standard methods. Positive spots were localised and BAC DNA of positive clones was isolated using the alkaline lysis method described by Zhang et al. (1996). BAC clone 388G9 contained the PSEN1 genomic sequence and was used for intronic sequence generation.

Generation of Intron Sequence Information

The BAC clone 388G9 was sequenced with primers located in exons 5, 7, 8 and 9 and pointing towards the intronic sequences. Table 8 shows the applied primers. All exon and flanking intronic sequences were deposited as a gapped submission to GenBank (Accession number DQ86246).

TABLE 8

Sequences of primers and real time PCR probes

| Primer and probes | Sequence | SEQ ID NO: | Application |
|---|---|---|---|
| PS1 Exon 5 forward primer1 | 5'-GGAGGTGGTAATGTGGTTGG-3' | 100 | BAC sequencing |
| PS1 Exon 5 reverse primer1 | 5'-CCAACCATAAGAAGAACTGGG-3' | 101 | BAC sequencing |
| PS1 Exon 7 forward primer1 | 5'-CCTATAACGTTGCCATGGATTAC-3' | 102 | BAC sequencing |
| PS1 exon 7 reverse primer1 | 5'-CACAGCCAAGATGAGCCAC-3' | 103 | BAC sequencing |

TABLE 8-continued

| Sequences of primers and real time PCR probes | | | |
|---|---|---|---|
| Primer and probes | Sequence | SEQ ID NO: | Application |
| PS1 Exon 8 forward primer1 | 5'-GCTGGTTGAAACAGCTCAGGAG-3' | 104 | BAC sequencing |
| PS1 Exon 8 reverse primer1 | 5'-CCAGCAAACGAAGTGGGCCATTTG-3' | 105 | BAC sequencing |
| PS1 Exon 9 forward primer1 | 5'-CAACAATGGTGTGGTTGGTG-3' | 106 | BAC sequencing |
| PS1 Exon 9 reverse primer1 | 5'-GGATACCTTCCTTTGGGCTTC-3' | 107 | BAC sequencing |
| PS1 Exon 5 forward primer2 | 5'-GAGACTTAGCTGGGGGTTTGTG-3' | 108 | SNP screening |
| PS1 Exon 5 reverse primer2 | 5'-CCAAGTAAGGTGAGACAGGAAAACC-3' | 109 | SNP screening |
| PS1 Exon 7 forward primer2 | 5'-GCTACGAGTATGAAGGTGGGATATG-3' | 110 | SNP screening |
| PS1 exon 7 reverse primer2 | 5'-CCAGGAGTCAAGATAACTGG-3' | 111 | SNP screening |
| PS1 Exon 8 forward primer2 | 5'-CCACCATCTGTTTACCTGCTA-3' | 112 | SNP screening |
| PS1 Exon 8 reverse primer2 | 5'-GGCCATCATTACATGTGTTTG-3' | 113 | SNP screening |
| PS1 Exon 9 forward primer2 | 5'-GGTGACATTAAGAAGTTTGGTGACTTG-3' | 114 | SNP screening |
| PS1 Exon 9 reverse primer2 | 5'-GGGTGTTACCACAGCTTGGAG-3' | 115 | SNP screening |
| PS1 forward primer | 5'-GTGATTTCAGTATACGATTTAGTGGCTG-3' | 116 | Real Time PCR |
| PS1 reverse primer | 5'-CACCAACCACACCATTGTTGAC-3' | 117 | Real Time PCR |
| PS1 MGB probe | 5'-VIC-TTGTGTCCAAATGGC-3' | 118 | Real Time PCR |
| PS2 forward primer | 5'-GGAGGAAAGGGGCGTGAAG-3' | 119 | Real Time PCR |
| PS2 reverse primer | 5'-CACAAACCGATGAGGATGGC-3' | 120 | Real Time PCR |
| PS2 MGB probe | 5'-VIC-CTGGAACACCACGCTGG-3' | 121 | Real Time PCR |
| GAPDH forward primer | 5'-GACTCATGACCACGGTCCATG-3' | 122 | Real Time PCR |
| GAPDH reverse primer | 5'-GTCAGATCCACAACCGACACG-3' | 123 | Real Time PCR |
| GAPDH MGB probe | 5'-VIC-CATCACTGCCACCCAGA-3' | 124 | Real Time PCR |

SNP Screening

Exons 5, 7, 8 and 9 and flanking intron sequences were amplified by PCR (primers listed in table 8 under SNP-screening application). Exon 5 and flanking intron sequences were amplified at conditions 50 ng DNA; 94° C. for 3 min and 35 cycles; 94° C., 30 sec; 60° C., 20 sec; 72° C., 1 min. Exon 7 and flanking intron sequences were amplified at conditions 50 ng DNA; 94° C. for 3 min and 35 cycles; 94° C., 20 sec; 58° C., 20 sec; 72° C., 1 min. Exon 8 and flanking intron sequences were amplified at conditions 50 ng DNA; 94° C. for 3 min and 35 cycles; 94° C., 45 sec; 64° C., 30 sec; 72° C., 1 min. Exon 9 and the flanking intron sequences were amplified at conditions 50 ng DNA; 94° C. for 3 min and 35 cycles; 94° C., 20 sec; 58° C., 20 sec; 72° C., 1 min. All PCR products were incubated with exozap at 37° C. for 1 hour and sequenced with the forward amplification primer. The sequences were analyzed using PolyBace and checked manually in Consed.

Hybrid Cell Mapping

A porcine-rodent somatic cell hybrid panel was used for physical mapping (Yerle et al., 1996) of both PSEN1 and PSEN2. For PSEN1 the exon 9 forward and reverse primers 2 were used for amplification of the probe fragment. For PSEN2 the PCR primers (PSEN2exon12F; 5'-GTTTGTGTCTGACCCTCCTGCTGC-3' (SEQ ID NO: 125) and PSEN2exon12R; 5'-CAGATGTAGAGCTGGTGGGGAGG-3' (SEQ ID NO: 126)) were used for amplification of the probe fragment. PCR's were performed in a total volume of 10 μL containing 10 ng DNA, 1×PCR buffer, 2.5 mM of each dNTP, 5 pmol of each primer, and 0.5 U of Taq polymerase (Bioline) under the following conditions: 94° C. for 3 min; 35 cycles of 94° C. for 20 s, 65° C. for 20 s and 72° C. for 20 s, and a final elongation step for 5 min at 72° C.

Immunohistochemistry

Fetal pig brains were immersion fixed in formalin and paraffin-embedded tissue blocks were produced from various brain regions. 10 micrometer coronal sections were then obtained on coated glass slides. The sections were deparaffinized and pretreated with proteinase K for 6 min. The slides were blocked with BSA (1 mg/ml) for 10 min. Immunohistochemical demonstration of PSEN1 and PSEN2 was performed using the EnVision+ System-HRP-DAB (DAKO). The anti-PSEN1 antibody was a rabbit polyclonal antiserum 520 (a generous gift from Dr. Poul Fraser, Toronto, Canada) used in 1:100 dilution with incubation time 2 hours. The anti-PSEN2 antibody was the mouse monoclonal antibody, APS 26, used in 1:33 dilution with incubation time 2 hours (abcam). Nuclei were counterstained in haematoxylen solution. The slides were finally coverslipped with Faramount Aqueous Mounting Medium (DAKO).

Real-Time Quantitative PCR Assay

Total RNA was isolated from cerebellum, frontal cortex, hippocampus, brainstem, and basal ganglia from 60, 80, 100, and 115 days old porcine fetuses using the TRI Reagent™ (Sigma) in compliance with the manufacturer's instructions. Three separate tissues were applied for each type of tissue and time in gestation, yielding a total of 60 samples. The reverse transcription reaction was accomplished using an Invitrogen reverse transcription system (Invitrogen) and 5 μg of RNA according to the manufacturer's instructions. Quantitative real time PCR was performed using the TaqMan® assay and PCR amplification in an ABI-PE prism 7900 sequence detection system (PE Applied Biosystems). Primers and MGB probes were designed using the Primer Express Software 2.0 (PE Applied Biosystems), so that both forward and reverse primer spanned an exon-exon junction. The MGB probe was synthesized with VIC as a reporter dye. After an initial screening with different control genes GAPDH was chosen as the endogenous control and the MGB-probe was synthesized with VIC as a reporter dye. The primers and probes are detailed in table 8. Separate mixtures for PSEN1, PSEN2, and GAPDH were prepared and consisted of 5 μL 2× TaqMan® Universal PCR Master Mix, 0.3 μL of each primer (10 μM), 0.25 μL probe (5 μM), 2 μL of a 5-fold diluted cDNA template, and $H_2O$ to a final volume of 10 μL. Real-time PCR was done under the following conditions: 2 min at 50° C., 10 min at 95° C., 40 cycles of 95° C. for 15 sec and 60° C. for 1 min. For both PSEN1, PSEN2, and GAPDH PCRs were performed in triplicate. The cycle threshold (Ct) values corresponding to the PCR cycle number at which fluorescence emission in real time reaches a threshold above baseline emission were determined in SDS 2.2 (PE Applied Biosystems). To compare expression patterns in the various brain tissues at different developmental stages mRNA template concentrations for GAPDH, PSEN1, and PSEN2 were calculated using the standard curve method. Standard curves were constructed using 8 fold dilution of day 115 frontal cortex cDNA (4, 2, 1, 0.5, 0.25, 0.125, and 0.0625 μL). The mRNA quantity of each amplicon was calculated for each standard and experimental sample.

Statistical Analysis

The equality of PSEN1 and PSEN2 expression levels between different time of gestation within the 5 sampled tissues were tested for statistical significance using the standalone software REST© [52]. The statistical model applied was the Pair Wise Fixed Reallocation Randomisation Test. The assumption regarding normal distribution of the data was avoided, and differences in expression between groups were assessed using the means for statistical significance by randomization. The level of probability was set at $P<0.05$ as statistically significant and 50000 randomization steps were implemented in each comparison.

Results

PSEN1 and PSEN2 cDNA and Protein Sequence

To determine the cDNA sequence of porcine PSEN1 we designed a set of primers based on the conserved 5' and 3' untranslated regions between the rodent, bovine, and human PSEN1. Using RT-PCR, the cDNA representing the entire pig PSEN1 open reading frame was amplified, cloned and sequenced. The porcine cDNA was throughout the sequence homologous to human PSEN1 (90%) but only homologous to human PSEN2 in short dispersed regions. The porcine PSEN1 protein has a length of 467 amino acids, which compares well with the 467 amino acids of the human and mouse counterparts (FIG. 28). Multiple amino acid sequence alignment of PSEN1 revealed a 92% sequence identity between pig and human (FIG. 28). Furthermore, 34 changes were observed between the two sequences, 11 of these being conservative. Comparison of pig and mouse revealed a sequence identity of 89% and 16 of 50 amino acid changes were conservative. The cow PSEN1 has a length of 478 amino acids and a sequence identity of 94% to porcine, 12 of 28 changes being conservative, and hence, cow PSEN1 is the PSEN1 variant that shows the highest degree of identity to the porcine counterpart. Mutations in human PSEN1 can be cause Alzheimer's disease and it is noteworthy that none of the amino acid changes between pig and human are located in positions known to cause Alzheimer's disease. (FIG. 28) (www.molgen.ua.ac.be/ADMutations). By contrast, at position 318 where human PSEN1 contains a non-pathogenic polymorphism, E318G, a Q residue is present at the equivalent position in pig, cow, and mouse PSEN1 [53]. Two other non-pathogenic polymorphisms R35Q and F175S present in human PSEN1 are in the porcine PSEN1 R and F, respectively (FIG. 28) [54,55].

The human PSEN2 cDNA sequence was used to blast NCBI porcine databases as well as an in house porcine database allowing the design of primers corresponding to the 5'-end of the coding region and the 3'-non-coding region of the putative porcine PSEN2. The primers amplified a porcine cDNA fragment of approximately 1.4 kb and sequence analysis revealed high sequence homology with human PSEN2 (92%) but only homologous to human PSEN1 cDNA in small dispersed regions, demonstrating that the porcine orthologous of PSEN2 was identified. Analysis of the porcine PSEN2 open reading frame showed that the porcine PSEN2 protein consisted of 448 amino acid residues, as do the human and mouse orthologous (FIG. 29). Multiple amino acid sequence alignment of PSEN2 revealed 97.8% sequence identity between pig and human, and 1 of the observed 10 changes was conservative (FIG. 29). Comparison of pig and mouse showed a sequence identity of 95%, 8 of the 20 changes being conservative. The cow PSEN2 has a length of 449 amino acids and a sequence identity of 98.2%, where 4 of the 8 changes are of conservative. Thus, as observed for PSEN1, also the bovine PSEN2 protein shows the highest degree of identity to the porcine counterpart. Moreover, it should be noted that none of the observed changes between the sequences of the different species are located in PSEN2 positions identified to be mutated in Alzheimer's disease patients (FIG. 29) (www.molgen.ua.ac.be/ADMutations). At position 334 a non-pathogenic polymorphism, P334R, has been identified in human PSEN2 [54,56], and the proline residue was conserved in the porcine cDNA.

The amino acid sequence for porcine PSEN1 shows 64% identity to porcine PSEN2 and particularly amino acids in the transmembrane domains and the C-terminus are conserved (data not shown). Also the two aspartic acid residues located in transmembrane domain 6 (D257 in PSEN1 and D263 in PSEN2) and transmembrane domain 7 (D385 in PSEN1 and D363 in PSEN2), and the "PAL" sequence, (P433, A434, L435 in PSEN1 and P414, A415, L416 in PSEN2) are conserved in both porcine PSEN1 and PSEN2, consistent with the essential role of these residues for the protease catalytic function of the presenilins [54,57,58].

Mapping of Porcine PSEN1 and PSEN2

A porcine-rodent somatic cell hybrid panel was used for the chromosomal mapping of porcine PSEN1 and PSEN2 genes (data not shown) [59]. Statistical evaluation applying the "Interpreting PCR data" program (http://www.toulouse.inra.fr/lgc/pig/pcr/pcr.htm) showed a chromosomal localization for the PSEN1 gene to chromosome 7q12-q26 with a probability of 0.4494 and a correlation of 1, and for the PSEN2 gene to chromosome 10p11-p16 with a probability of 0.9959 and a correlation of 0.7255. The specified regions of porcine chromosomes 7 and 10 have synteny with human chromosomes 14 and 1, respectively. This is in agreement with mapping of the human PSEN1 gene to 14q24.3 and the human PSEN2 gene to 1q31-q42.

Single Nucleotide Polymorphism Screening of Porcine PSEN1

To examine for genetic variation in porcine PSEN1, we resequenced exons 5, 7, 8, and 9 in a large animal material consisting of 900 Landrace/Yorkshire crossbreed sows and a pig breed panel consisting of 55 Landrace, Duroc, Yorkshire and Hampshire breeds. These exons were chosen for sequence analysis because they constitute "hotspots" for mutations in familiar Alzheimer's disease. However, no SNP's were identified in the 4 exonic regions (data not shown). Next, we extended the polymorphism analysis to include intronic sequences, which identified a C/T SNP at position 58 in intron 8 (position 1163 in the sequence deposited in DQ86246) as well as two C/T polymorphisms at positions 52 and 92 and a G/A polymorphism at position 117 in intron 10 (positions 1535, 1575, and 1600 in the DQ86246). The genotyping data are summarized in table 9 and 10. All breeds except Hampshire were polymorphic in intron 8 and at positions 52 and 92 in intron 10, whereas only the Yorkshire breed was polymorphic at position 117 in intron 10. Genotype frequencies were in accordance with Hardy-Weinberg equilibrium, indicating that no selective disadvantage is associated with the SNPs.

PSEN Expression in the Developing Porcine Brain

PSEN1 and PSEN2 have been shown to be widely expressed during embryonic development and especially the expression profile in the CNS is well characterized [60-62]. Here, we measured the mRNA expression levels of PSEN1 and PSEN2 in hippocampus, cerebellum, frontal cortex, basal ganglia, and brain stem from dissected porcine foetus brains at days 60, 80, 100 and 115 of gestation using three biological samples for each of the time points. Day E115 corresponds to the normal day of birth. The PCR analyses were performed in triplicates. The requirement for a proper internal control gene was met by normalization to the GAPDH expression level to compensate for inter-PCR variation with respect to RNA integrity and sample loading. Although housekeeping gene expression has been reported to vary considerably within different tissues or treatments, we did not find any significant differential expression of GAPDH within the 5 different porcine brain tissues at the various developmental stages. The standard curve for the control GAPDH ($R^2$=0.98), PSEN1 ($R^2$=0.98), and PSEN2 ($R^2$=0.98) were generated by plotting Ct values versus log μL of cDNA. The slope of the regression line was used to calculate the amount of cDNA and thus mRNA in each sample. All GAPDH cDNA's generated almost identical Ct values within each type of tissue (data not shown) and accordingly the mRNA expression levels of PSEN1 and PSEN2 were normalized to the GAPDH expression level. Ethidium bromide-staining after real time PCR confirmed specific amplification of the relevant PCR products (data not shown).

Figure 30:
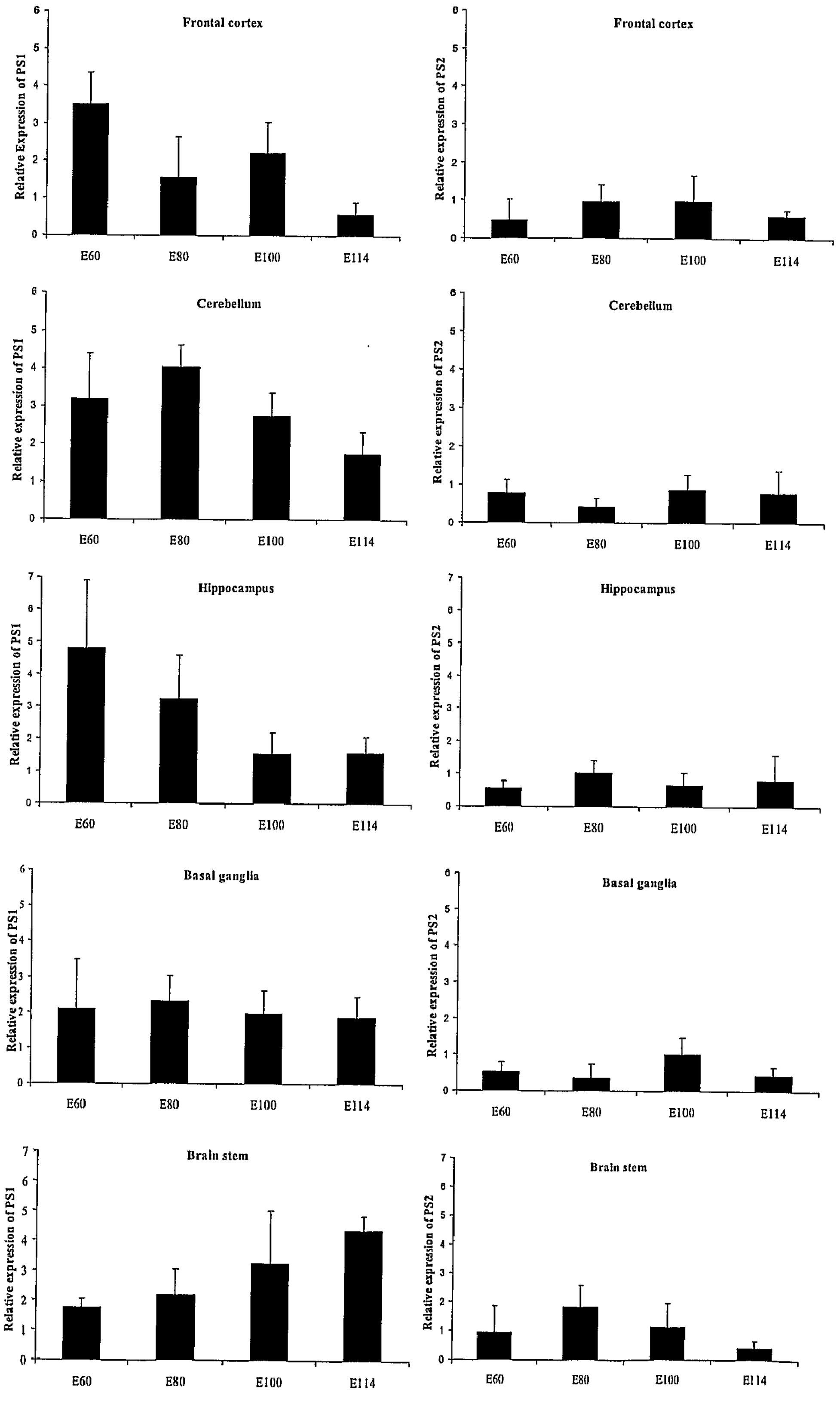
FIG. 30: Analysis of porcine PSEN1 and PSEN2 expression levels in the developing pig brain by quantitative real-time RT-PCR. Quantitative results are presented as normalized mean (±SD). For quantification and statistical analysis see materials and methods section. Each sample was run both in three biological and three technical triplicates. The expression analysis was performed on samples from frontal cortex, cerebellum, hippocampus, basal ganglia, and brain stem derived from embryonic days 60, 80, 100, and 115 (E60, E80, E100, and E115).

PSEN1 and PSEN2 were expressed in all 5 tissues at the 4 time points evaluated. However, it should be noted, that for both PSEN1 and PSEN2 the mean standard deviation is considerable, reflecting a high heterogeneity among animals. In basal ganglia the PSEN1 expression levels did not vary significantly between the different times of gestation (FIG. 30). In frontal cortex, cerebellum, and hippocampus the PSEN1 expression level was significantly lower at day 115 of gestation compared to day 60 (P=0.001, P=0.036, and P=0.003, respectively), yielding a reduction of 5, 2, and 3 times for the said tissues (FIG. 30). Furthermore, the reduction in PSEN1 expression in frontal cortex is also significant at day 80 compared to day 60 (P=0.003). Similarly, PSEN1 expression is gradually reduced in hippocampus during the time period of gestation (FIG. 30). Moreover, the same tendency is seen in cerebellum, however the reduction in expression levels is only significant between day 100 and 115 (P=0.015) and day 60 and 115 (P=0.036).

For PSEN2 no differential expression was observed in frontal cortex. In hippocampus the only significant variation was seen as an increase in expression level between day 60 and 80 of gestation (P=0.015) (FIG. 30). Also in the brain stem, PSEN2 is upregulated between day 60 and 80 of gestation (P=0.032) (FIG. 30). In cerebellum and basal ganglia the expression levels of PSEN2 are up-regulated between day 80 and 100 (P=0.003, and P=0.03) (FIG. 30). When comparing the overall expression levels of PSEN1 and PSEN2, an approximately three fold lower PSEN2 expression level is observed. In conclusion, the real time PCR analysis showed significant, albeit small, alterations in the expression levels of PSEN1 and PSEN2 mRNA in different brain compartments during embryonic brain development, which likely reflect biological importance.

Figure 31:
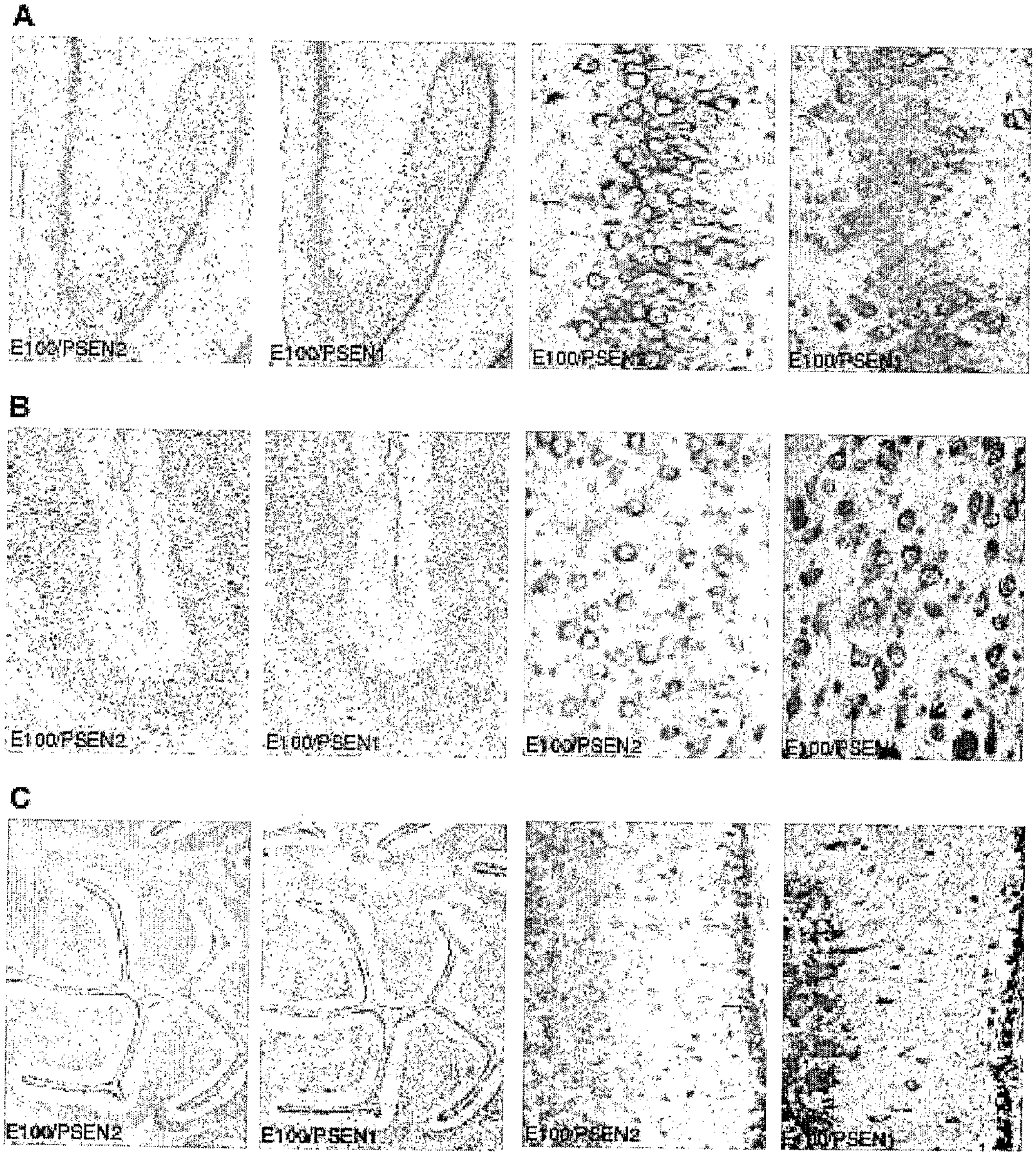
FIG. 31: Immunohistochemical analysis of PSEN1 and PSEN2 expression in embryonic E100 porcine brains. Brain sections were immunohistochemical stained for PSEN1 or PSEN2 and nuclei counterstained by haematoxylin. Sections illustrating PSEN1 and PSEN2 staining patterns in hippocampus (A), cortex (B), and cerebellum (C) are shown for embryonic day E100. Higher magnitude illustrations of neurons representative for each of the three regions are shown in the right part of each panel.

To examine the localization of the PSEN1 and PSEN2 proteins in situ we utilized immunohistochemical stainings at embryonic day 100 brain slides with antibodies for PSEN1 and PSEN2. PSEN1 staining was more intense and diffusible outside cell bodies than observed for the PSEN2 staining (FIG. 31). We note that all PSEN2 stained regions also were positive for PSEN1 staining (FIG. 31). No clear alterations in localization or intensity of PSEN1 and PSEN2 staining were detected in analysis of other embryonic time points or brain regions (data not shown). Intracellular immunostaining was confined to the cytoplasm with a distinct sparing of the nuclei. The immunostaining was observed in all parts of the CNS, especially in neurons but also to some extend in astrocytes (FIG. 31 and data not shown). In cortex both pyramidal and nonpyramidal cells were stained (FIG. 31). Also all hippocampus CA subfields and the granule cells were PSEN positive (FIG. 31). The immunohistochemical analysis supports that the PSEN proteins are located in the majority, if not all, of the neurons. Moreover, all PSEN2 stained cell types were also positive for PSEN1 staining in accordance with the observed redundancies in PSEN1 and PSEN2 functions [63,64].

TABLE 9

Genotype-frequencies of a C/T SNP in position 1163 (DQ86246) in PSEN1 intron 8 in a pig breed-panel.

| | No. of | Genotype frequencies SNP position 1163 | | |
|---|---|---|---|---|
| Breed | animals | C/C | T/T | C/T |
| Landrace | 14 | 0 | 0.71 | 0.29 |
| Duroc | 15 | 0 | 0.60 | 0.40 |
| Hampshire | 17 | 1 | 0 | 0 |
| Yorkshire | 14 | 0 | 0.62 | 0.38 |

TABLE 10

Genotype-frequencies for three SNPs in PSEN1 intron 10 (DQ86246) in a pig breed-panel.

| | | Genotype frequencies | | | | | |
|---|---|---|---|---|---|---|---|
| | No. of | SNP position 1535/1575 | | | SNP position 1600 | | |
| Breed | animals | C/C | T/T | C/T | G/G | A/A | G/A |
| Landrace | 14 | 0.71 | 0 | 0.29 | 1 | 0 | 0 |
| Duroc | 14 | 0.57 | 0.07 | 0.36 | 1 | 0 | 0 |
| Hampshire | 11 | 0 | 1 | 0 | 1 | 0 | 0 |
| Yorkshire | 16 | 0.63 | 0 | 0.37 | 0.69 | 0 | 0.31 |

Example 4

Model Animal of Diseases Related to Trinucleotide Repeat Sequences

Human TNR disease causing regions are in most cases also identifiable in the primate and rodent genomes [65-67]. However, in rodents the TNR regions in general are composed of significantly fewer TNR units and are less polymorphic. As TNR sequences are rapidly evolving and may functionally influence the affected genes, changes in such regions have the potential to participate in functional diversification [65, 68]. To analyse how the disease causing TNR regions identified in humans have evolved in the porcine genome, we analysed porcine TNRs. We here describe that in terms of TNR tract lengths the porcine TNRs in general represent an intermediate between rodent and humans and that several of the TNRs are polymorphic in the pig. In addition, the length of TNRs was in several of the porcine loci comparable to the lengths normally identified in primates.

Genomic Samples

Genomic DNA was prepared from unrelated (no common parents and grandparents) Duroc, Landrace, Hampshire, Yorkshire, and Goettingen minipig males according to standard procedures. The DNA was isolated from EDTA stabilized blood using a salting out procedure [69].

PCR and Sequencing of Genomic DNA

To sequence porcine genomic TNR regions flanking sequences conserved between mouse and humans were identified and corresponding PCR primers designed. 50 ng of Duroc pig genomic DNA was used in PCR with conditions 95° C. 30", 58° C. 30", 72° C. 1', cycles. Standard taq polymerase PCR conditions were used except for the inclusion of 1 M Betaine and 5% DMSO. After agarose gel electrophoresis analysis DNA of expected size was purified and sequenced. If the intensity of bands or the sequencing result was evaluated inadequate for further analysis new PCR primers were designed either based on the evolutionary approach or nested according to determined sequences. By this scheme the following optimized primer sets were used to amplify genomic TNR regions (all PCR reactions run for 35 cycles with 50 ng genomic DNA as input): SCA1: SCA1+, CAGCGCTCCCAGCTGGAGG (SEQ ID NO: 127); SCA1−, GGAYGTACTGGTTCTGCTGG (SEQ ID NO:128); 95° C. 30", 58° C. 30", 72° C. 1' with betaine and DMSO. SCA2: SCA2NyTRI−, GCCACCGTAGAGGAGGAGGAAG (SEQ ID NO:129); SCA2TRI(+), CTCACCATGTCGCTGAAGC (SEQ ID NO:130); 95° C. 30", 58° C. 30", 72° C. 1' with betaine and DMSO. SCA3: SCA3-I7+, CCATGGGAATAGTTTTTCTCATG (SEQ ID NO:131); SCA3exon10(−), GGTTGGCTTTTCACATGGATGTG (SEQ ID NO:132); 95° C. 30", 58° C. 30", 72° C. 1' with betaine and DMSO. SCA6: SCA6nyTRI+, CGGCCACACGTGTCCTATTC (SEQ ID NO:133); SCA6NYTRI−, GGCCGCTGGGGGCCGCTCG (SEQ ID NO:134); 95° C. 30", 58° C. 30", 72° C. 1' with betaine and DMSo. SCA7: SCA7Tri(+), GGAGCGGAAAGAATGTCGGAG (SEQ ID NO:135); SCA7Tri(−), CCCACAGATTCCACGACTGTC (SEQ ID NO:136); 95° C. 30", 58° C. 30", 72° C. 1' with betaine and DMSO. SCA17: pTBP−, GAAGAGCTGTGGAGTCTGG (SEQ ID NO:137); pTBP+, CTATCCATTTTGGAGGAGCAG (SEQ ID NO:138); 95° C. 30", 58° C. 30", 72° C. 1' with betaine and DMSo. DRPLA: Drpla-Ny+, GGAGGCCAGTCCACTGCTCAC (SEQ ID NO:139); Drpla-Ny−, GGGAGACATGGCATAAGGGTG (SEQ ID NO:79); 95° C. 30", 58° C. 30", 72° C. 1' with betaine and DMSO. SMBA: ARTri+, X; ARTri−, X, 94° C. 45", 58° C. 30", 72° C. 2'. HD: pHUNNYRE+, CCGCCATGGCGACCCTGGAAA (SEQ ID NO:140); pHUNNYRE−, GGTGGCGGCTGAGGAGGCTG (SEQ ID NO:141); 95° C. 30", 65° C. 30", 72° C. 1' with betaine and DMSO. FMR1: FMR1(Ny+1), CGTTTCGGTTTCACTTCCGGTG (SEQ ID NO:142); FMR1Zoo−, CCGCACTTCCACCACCAGCTC (SEQ ID NO:143); 95° C. 30", 60° C. 30", 72° C. 1' with betaine and DMSO. FMR2: FMR2-Ny−, TGCGGCGGCAGCAGCCGCTAC (SEQ ID NO:1444); FMR2(Ny+2), CCCCTGTGAGTGTGTAAGTGTG (SEQ ID NO:145); 95° C. 30", 58° C. 30", 72° C. 1' with betaine and DMSo. SCA12: SCA12TRI(+), GGGAGGAGCCTCGCCTTTAATG (SEQ ID NO:146); SCA12Tri(−), CGCGACAAAATGGTGCCTTTC (SEQ ID NO:147), 95° C. 30", 58° C., 30", 72° C. 1' with betaine and DMSO. DMPK: gDMPKpoly+, GCCCTGCTGCCTTCTCTAGGTC (SEQ ID NO:148); gDMPKpoly−, CCCCAGCTCTAGCCCTGTGATC (SEQ ID NO:149), 94° C. 30", 64° C. 30", 72° C. 2'. DNA fragments were purified from agarose gels using GFX columns (Amersham Biosciences) and sequenced according to standard procedures. DNA fragments were amplified from Duroc, Landrace, Hampshire, Yorkshire, and Goettingen minipig male genomic DNA.

Sequence information for TNRs in *Homo sapiens* (human), Pan troglodytes (chimpanzee), *Canis familiaris* (dog), *Rattus norvegicus* (rat), *Mus musculus* (mouse), and *Monodelphis domestica* (opossum) was extracted from genome browsers at NCBI (www.ncbi.nlm.nih.gov/Genomes).

Microsatellite Analysis on Sows and Offspring Originating from Boars with Extended TNRs Genotyping of different Huntingtin allele lengths was performed by microsatellite analysis in a porcine material consisting of 14 Duroc boars, 611 Landrace and Landrace×Yorkshire crossbred sows and 349 offspring originating from 4 of the Duroc boars and the aforementioned sows. The following primers were used; Fw: FAM-CCGCCATGGCGACCCTGGAAA (SEQ ID NO:150), Rw: GGTGGCGGCTGAGGAG- GCTG (SEQ ID NO:151). The amplicon was amplified in a total volume of 10 μL in a mixture consisting of: 50 ng of genomic DNA, 5 pmol of each primer, 2.5 mM dNTPs, 1 μL of 10× reaction buffer, 0.5 μL DMSO, 2.5 μL 4 M Betaine, and 5 U Taq DNA polymerase (Applied Biosystems, USA). PCR amplification was as follows: initial denaturation for 4 min at 95° C., and 35 cycles at 95° C. for 30 sec, 64° C. for 30 sec, 72° C. for 1 min. An extension step of 72° C. for 5 min was added after the final cycle. PCR products were denatured with formamide and electrophoresis was carried out on a 3730 DNA Analyzer (Applied Biosystems, USA) using the recommended protocol. Size analyses of DNA fragments were accomplished with the GeneMapper® Software Ver 3.0 (Applied Biosystems, USA). The internal size standard GeneScan-LIZ 500 (Applied Biosystems, USA) was employed for allele sizing.

Accession numbers

The determined porcine TNR regions and flanking sequences were submitted to genebank and have been assigned the following accession numbers: SCA1 (DQ915251, DQ915252), SCA2 (DQ915254), SCA3 (DQ915255, DQ915256), SCA6 (DQ915259, DQ915260, DQ915261), SCA7 (DQ915262), SCA17 (DQ915258), DRPLA (DQ915263, DQ915264), SMBA (DQ915257), HD (DQ915274, DQ915275, DQ915276, DQ915277, DQ915278, DQ915279, DQ915280, DQ915281, DQ915282), FMR1 (DQ915269, DQ915270, DQ915271, DQ915272, DQ915273), FMR2 (DQ915268), SCA12 (DQ915265, DQ915266, DQ915267), DMPK (DQ915253).

Results

To sequence porcine genomic regions homologous to human disease causing TNRs we first identified flanking sequences showing highly conserved regions between mouse and humans. Employing this PCR approach 12 porcine genomic loci corresponding to human disease causing TNRs were amplified. The identified TNRs were located in coding regions and 5'-UTRs. The DMPK 3'-UTR TNR was amplified using primers based on EST sequences available in Genbank. To search for TNR polymorphisms in different porcine breeds we included Duroc, Landrace, Hampshire, Yorkshire and Goettingen minipig. For each of the pig breeds a number of animals were analysed assuring the detection of common alleles (allele frequency >10%).

Porcine genomic sequences homologous to human non-coding TNR expansion regions. We first addressed porcine genomic sequences homologous to human non-coding TNRs.

DMPK: In the 3'-UTR of the human myotonic dystrophy protein kinase gene, DMPK, a CTG TNR is located [19-23]. The normal size of this TNR varies between 5 and 37. Expansions from above 50 to several thousand CTG repeats result in myotonic dystrophy. A CTG TNR consisting of 4 CTG repeats in all the pig breeds studied (Duroc, Landrace, Yorkshire, Hampshire, and minipigs) (FIG. 32) was identified at the same localization in the porcine DMPK. No length variation in the DMPK TNR was identified (FIG. 32). The repeat number found is below the minimum number of CTG repeats (5 CTGs) observed in humans. In the mouse the TNR sequence of DMPK is composed of 2 CAG repeats flanked by single CTG repeats (FIG. 32). In dog and rat a single CTG is present flanked by other types of TNRs (FIG. 32).

SCA12: The SCA12 CAG TNR within the 5'-UTR of the human PPP2R2B gene normally varies in size from 7 to 28 repeats and in the expanded form from above 65 to 78 TNRs [27]. Three alleles consisting of 8, 9, and 10 CAG repeats were identified in the porcine breeds (FIG. 32). The most abundant allele in Duroc contained 8 CAG repeats, whereas the most abundant allele in Hampshire contained 10 CAG repeats (FIG. 32). An allele containing 9 CAG repeats was the only allele observed in Landrace, Yorkshire and Minipigs (FIG. 32). The presence of long uninterrupted CAG TNRs in the porcine SCA12 locus is distinct from the mouse and rat SCA12 locus which is composed of CAG TNRs interrupted with CAC and GAG triplets (FIG. 32). Notably, the lengths of the porcine SCA12 alleles are comparable and even higher than SCA12 allele lengths identified in some humans (FIG. 32).

FMR1/FRAXA: In the promoter region of the human FMR1 gene, 6 to 52 CGG repeats are normally present [24, 25]. Expansions in the range of 55 to 200 repeats result in the pre-mutation while the full mutation ranges from 200 to several thousand repeats resulting in fragile X syndrome. The sequence of the FMR1 TNR region in Duroc showed the presence of two alleles: a 14 CGG repeat allele with a frequency of 90% and a 13 CGG repeat allele with a frequency of 10% (FIG. 32). Sequence analysis of the FMR1 TNR in the other porcine breeds showed a high degree of FMR1 TNR length polymorphisms. A 15 CGG repeat allele was identified in Duroc, Hampshire and Yorkshire (FIG. 32). This allele was the most common in Yorkshire, whereas a 9 CAG repeat allele was also identified in Hampshire and a 12 CAG repeat allele in Duroc and Minipigs. No allele polymorphism was observed in Landrace. All the porcine FMR1 alleles were longer than the homologous mouse TNR sequence which is composed of 6 CGG repeats and 2 CGG repeats separated by a CGA (FIG. 32). The dog FMR1TNR has a size similar to the pig TNR (FIG. 32). In the most common type of human FMR1 TNR allele two groups of CGG repeats are separated by an AGG triplet (FIG. 32). Also the chimpanzee FMR1TNR is highly polymorphic and includes AGG triplet interruptions [70]. Interestingly, the porcine FMR1TNR length exceeds the minimal length present in the human FMR1CGG TNR prone to expand.

FMR2/FRAXE: The number of CCG repeats in the TNR of the 5' end of the human FMR2 gene varies from 6 to 35 [26]. Expansions containing from 61 to 200 repeats result in the pre-mutation and expansions above 200 repeats result in the full mutation and the fragile X syndrome. The homologous region in the porcine FMR2 gene was found to contain 7 CCG repeats in all breeds analysed (FIG. 32). The porcine TNR length exceeds the length of the homologous mouse TNR which is composed of 4 CCG repeats (FIG. 32). Furthermore, the length of the porcine CCG TNR is longer than the minimal CCG allele length identified in humans (FIG. 32).

Porcine Genomic Sequences Homologous to Human Poly-Glutamine Coding TNR Expansion Regions.

Next we addressed the sequence of poly-glutamine coding TNR sequences of nine porcine loci. SCA1: In the human SCA1 locus CAG TNR expansions in the ATX1 protein causes spinocerebellar ataxia [71, 73]. The human SCA1 TNR region is characterized by the presence of 12 CAG repeats followed by two CAT repeats flanking a CAG triplet [28]. The CAG TNR prone to expand is normally composed of between 6 and 39 repeats and the expanded version consists of 41 to 81 repeats. The porcine SCA1 TNR is composed of two CAG repeats separated by eight proline encoding triplets (FIG. 33). However, in Minipigs a variant was detected; the most common allele having a CAG TNR duplication (FIG. 33). The dog SCA1 region includes 6 CAG repeats (FIG. 33). The mouse and rat homologous region is composed of two CAG repeats and three proline coding triplets (FIG. 33). Thus, in terms of CAG repeat numbers the porcine and rodent SCA1 TNRs are similar but distinct from the homologous human TNR (FIG. 33). However, due to the presence of numerous proline codons (CCX) the porcine SCA1 TNR have increased complexity compared to the TNR in rodents.

SCA2: The SCA2 TNR expansion, affecting the ATX2 protein, results in spinocerebellar ataxia [73]. This TNR normally consists of 15 to 30 CAG repeats and the expanded form ranges from 35 to 59 triplets [29]. The porcine locus is composed of 7 CAG repeats separated by two CAA triplets (FIG. 33). Accordingly, the region encodes a stretch of nine poly-glutamines. No polymorphism whatsoever was observed in the porcine SCA2 TNR region. The dog SCA2 TNR had proline interruptions in the poly-glutamine stretch (FIG. 33). The homologous rodent SCA2 TNR is composed of CAG repeats separated by a proline encoding triplet (FIG. 33).

SCA3: In the human SCA3 locus a CAG TNR expansion in the ataxin-3 gene above 54 repeats results in ataxia whereas the normal number of CAG repeats varies between 12 and 36 [30-32]. In pigs a five CAG TNR allele was identified in Duroc, Hampshire, and Landrace whereas five and six CAG TNR alleles were identified in Yorkshire and Minipigs (FIG. 33). In terms of the number of encoded poly-glutamines the porcine SCA3 TNR region is homologous to the mouse SCA3 TNR region (FIG. 33) and well below the critical number in the human counterpart. The dog SCA3 TNR encodes 12 glutamines but includes several CAA interrupting triplets (FIG. 33).

SCA6: The SCA6 TNR expansion in the CACNA1A voltage dependent calcium channel results in ataxia [33]. The normal number of TNRs is between 4 and 18 and expansions from 21 to 27 TNRs are disease causative. In pigs a SCA6 allele was identified composed of 5 and 4 CAG repeats separated by a CAA triplet thereby encoding a poly-glutamine stretch of 10 (FIG. 33). In Minipigs longer SCA6 alleles composed of 7 or 9 CAG repeats followed by the CAA triplet and 4 CAG repeats (FIG. 33) were identified. These alleles encode stretches of 12 and 14 poly-glutamines, respectively. The poly-glutamine stretches encoded by the porcine SCA6 TNR region were comparable in length to the normal range encoded by the human SCA6 sequence, and the 14 poly-glutamine stretch identified in Minipigs matches the upper range of the more common human alleles (FIG. 33). In dog a 10 CAG SCA6 TNR was present (FIG. 33). We note the absence of a SCA6 TNR in rodents and a high degree of divergence in the CACNA1A sequence between rodents and pig, dog, and primates at the particular genomic position.

SCA7: The TNR of the human SCA7 locus in the N-terminal end of the ataxin-7 protein is normally composed of 7 to 35 CAG repeats [54]. Disease causing expansions range from 37 to 200 repeats. The TNR of the porcine SCA7 locus contains 5 CAG repeats and no polymorphisms were observed in the breeds (FIG. 33). Similarly, the TNR of the mouse SCA7 locus contains 5 CAG repeats (FIG. 33). Interestingly, a SCA7 allele with 5 CAG repeats has also been identified in humans. Note that the SCA7 CAG repeats are flanked by a poly-alanine stretch and a glutamine and proline rich stretch highly variable between the examined mammalian genomes (data not shown).

DRPLA: CAG expansions within the human atrophin-1 gene results in dentatorubral-pallidoluysian atrophy (DRPLA) [36]. The normal range of repetitive CAG repeats is from 3 to 25, and in patients with DRPLA allele sizes have expanded to 49 to 88 CAG repeats. The most common natural occurring human allele encodes a stretch of 17 poly-glutamines. In the porcine atrophin-1 TNR, six CAG repeats flanked by multiple CAG and CAA triplets resulting in an allele encoding 14 poly-glutamines (FIG. 33) was identified. Moreover, in Minipigs an allele with seven CAGs resulting in a 15 poly-glutamine encoding allele was observed (FIG. 33). This means that the length of the porcine atrophin-1 poly-glutamine stretches is above the minimal length observed in humans. The TNR of the mouse atrophin-1 gene encodes six glutamines with an interrupting proline and from the rat gene is encoded 11 glutamines highly interrupted by proline residues (FIG. 33). The dog atrophin-1 TNR encodes a stretch of 12 poly-glutamines (FIG. 33). In mammalians the atrophin-1 TNR is flanked by histidine rich stretches polymorphic between the examined mammalian genomes (data not shown).

SCA17: A CAG expansion in the TATA box binding protein (TBP) gene is causative of the SCA17 phenotype resulting in ataxia [35]. The human TNR region is composed of two groups of CAG repeats separated by multiple CAA and CAG triplets. Expansions normally progress from the larger of the two CAG groups. The normal stretch of encoded poly-glutamines varies between 29 and 42 whereas poly-glutamine stretches from 47 to 55 have been identified in SCA17 patients. The porcine SCA17 TNR region encodes 26 poly-glutamines and thus is the largest poly-glutamine encoding TNR identified in pigs (FIG. 33). The pig SCA17 sequence is composed of four groups of CAG TNRs intervened by CAA triplets (FIG. 33). The longest CAG group consists of 10 CAGs. No allele polymorphism was identified in porcine SCA17. In comparison, mouse SCA17 TNR encodes 13 poly-glutamines and a maximum of three CAG triplets in one stretch (FIG. 33). The dog SCA17 TNR encodes 22 glutamines but includes several alanine interruptions (FIG. 33).

SBMA: CAG repeat expansions in exon 1 of the androgen receptor (AR) gene on the X-chromosome results in spinal and bulbar muscular atrophy (Kennedy's disease) [37]. The normal length of the human CAG TNR is between 11 and 33 CAG copies and in diseased individuals the expansion ranges from 38 to 62. In the pig an AR allele encoding 7 poly-glutamines interrupted by a single CTG leucine triplet was identified (FIG. 33). No TNR variation was observed between the different porcine breeds. In mouse and rat the AR TNR sequence encodes 3 glutamines interrupted by a single AGG arginine triplet or CGG arginine triplet, respectively (FIG. 33). The dog AR TNR is composed of a 10 CAG repeats (FIG. 33). Note, in mammalians the TNR is flanked by a proline and glutamine rich stretch highly polymorphic between the examined mammalian genomes (data not shown).

HD: The CAG TNR in the Huntingtin gene is located in the 5'-end of the coding region. Normally, the gene contains from 6 to 35 CAG repeats and in Huntington's disease patients more than 35 CAG repeats are present [74]. A large degree of variation was observed in the pig Huntingtin TNR region (FIG. 33). This difference was due both to a variable number of CAG repeats but also due to the absence or presence of a CAA triplet which separates the continuous CAG theme into two groups (FIG. 33). Alleles with sizes encoding 13 to 24 poly-glutamines from were identified. Highly interesting, in Duroc, an allele composed of a stretch of 21 uninterrupted CAGs, a CAA triplet, and two CAGs resulting in the encoding of a total of 24 poly-glutamines (FIG. 33) was identified. This allele represents the largest number of uninterrupted CAGs identified in the analysis of porcine TNRs. The long allele was specifically identified in Duroc and has an allele frequency of 20%. The Minipig Huntingtin gene and polymorphisms therein were described previously [75]. The numbers of poly-glutamines encoded by porcine Huntingtin TNRs are indeed comparable to the human repeat and are for the 24 poly-glutamine allele even above the number of poly-glutamines most frequently found in human Huntingtin alleles. In contrast the mouse Huntingtin TNR region encodes seven poly-glutamines intervened by a CAA triplet and the dog TNR region 10 poly-glutamines (FIG. 33). The Huntingtin TNR is flanked by a proline and glutamine rich stretch polymorphic between the examined mammalian genomes (data not shown).

The porcine Huntingtin TNR length is meiotic stable

Since a long uninterrupted CAG TNR sequence was present in the Huntingtin gene of Duroc pigs, we next examined if this sequence was stably inherited or prone to retractions or expansions. For this purpose we used a porcine material consisting of Duroc boars crossed with Landrace and Landrace/Yorkshire crossbread sows. The genotyping of different Huntingtin allele lengths was performed by microsatellite analysis. From the boar cohort, four heterozygous boars were identified having both a 161 bp fragment and a 140 bp fragment corresponding to 24 and 17 glutamines, respectively. The genotyping result of the 4 heterozygous boars was verified by DNA sequencing. The genotyping data from the cohort of the 611 sows used in the breeding scheme resulted in the identification of the alleles also present in the pure Landrace and Yorkshire breeds. Furthermore, two new Huntingtin alleles encoding 14 and 15 glutamines not present in the pure breeds were identified in the sow cohort (table 11). Also the 24 poly-glutamine encoding allele was present in the sow population, however only at a low frequency (0.3%, table 11). Interestingly, no alleles were identified with a size less than 13 poly-glutamines or a polyglutamine number of 19, 20, 21, 22, or 23 (table 1 and data not shown). However, since the population of sows was not completely unrelated, the allele frequency calculations are only indicative. The group of genotyped offspring consisted of 349 pigs. All these 349 animals had a genotype in accordance with the inheritance of a maternal and paternal Huntingtin allele without any TNR retractions or expansions (table 12). Thus, we could not identify any evidence for transmission instability of Huntingtin TNRs.

such as trachea, in comparison to growth plate cartilages. We isolated the full length cDNA encoding collagen X from porcine trachea illustrating that collagen X is not solely present in hypotrophic chondrocytes of calcifying matrix typically present in long bones. However, in humans collagen X have, previously been shown in trachea especially in elderly individuals where ossification occur in the tracheal cartilage as a result of the progressing age. Furthermore, in developing rat tracheal cartilage, collagen X was confined to the peripheral uncalcified region of the cartilage [76] indicating that collagen X might play a role beside providing the molecular structural environment in relation to endochondral ossification, however this is not confirmed in humans [77].

Materials and Methods

RNA Isolation

The pig trachea tissue used for RT-PCR cloning of COLA was obtained from an adult pig. Tissue was dissected and pulverized in liquid nitrogen after removal. Total RNA was isolated by RNeasy method (Qiagen). The integrity of RNA samples was verified by ethidium bromide staining of the ribosomal RNA on 1.5% agarose gels.

DNA Constructs

Generation of a porcine COL10A1 clone was accomplished in the following way: RNA derived from adult porcine trachea was employed in a cDNA synthesis using conditions where 5 µg of total RNA was mixed with 1 µL of oligo (dT) 12-18 (500 µg/mL), and DEPC treated $H_2O$ to a final volume of 12 µL. The mixture was incubated at 70° C. for 10 min, after which 4 µL of 5× first-strand buffer, 2 µL of 0.1 mM DTT, 1 µL of 10 mM dNTP mix and 1 µL (200 U/µL) of Superscript II (Invitrogen) was added and the sample was further incubated at 42° C. for 1 hour followed by an inactivation step at 70° C. for 15 min. oligonucleotides used for RT-PCR cloning were derived from the genomic COL10A1 sequence (Accession number: AF222861) and also contained linkers (Bgl II in the sense primer and Eco RI in the antisense primer) for subsequent cloning. The RT-PCR reaction mix contained 2.5 µL cDNA, 1.5 mM MgCl2, 0.2 mM dNTP, 10 pmol of each primer (COL-F: 5'-AACAGATCTATGCTGC-CACAAACAGCCCTTTTGCT-3' (SEQ ID NO:152) and COL-R: 5'-GCAGAATTCTCACATTGGAGCCACTAG-GAATCCT-3' (SEQ ID NO:153), and 1.0 U Phusion Fidelity DNA polymerase (Finnzymes), in a total volume of 25 µL using the following conditions: denaturation at 98° C. for 2 min., followed by 30 cycles of 98° C. for 10 s., 60° C. for 30 s., and 72° C. for 1 min. The PCR program was concluded by a final extension step at 72° C. for 5 min. The PCR was accomplished in a GeneAmp® PCR System 9700 (Applied Biosystems). The amplification product was applied to a 1% ethidium bromide stained agarose gel and a fluorescent band

TABLE 11

Meiotic stability of porcine Huntingtin (CAG)24 and (CAG)17 alleles.

| | | Female haplotypes | | | | | | |
|---|---|---|---|---|---|---|---|---|
| | | Q = 13<br>L = 128<br>F = 0.18 | Q = 14<br>L = 131<br>F = 0.02 | Q = 15<br>L = 134<br>F = 0.05 | Q = 16<br>L = 137<br>F = 0.025 | Q = 17<br>L = 140<br>F = 0.51 | Q = 18<br>L = 143<br>F = 0.21 | Q = 24<br>L = 161<br>F = 0.003 |
| Male haplotypes | Q = 17<br>L = 140 | Q = 13, 17<br>L = 128, 140<br>N = 24 | Q = 14, 17<br>L = 131, 140<br>N = 0 | Q = 15, 17<br>L = 134, 140<br>N = 11 | Q = 16, 17<br>L = 137, 140<br>N = 2 | Q = 17, 17<br>L = 140, 140<br>N = 88 | Q = 18, 17<br>L = 143, 140<br>N = 49 | Q = 24, 17<br>L = 161, 140<br>N = 0 |
| | Q = 24<br>L = 161 | Q = 13, 24<br>L = 128, 161<br>N = 18 | Q = 14, 24<br>L = 131/,161<br>N = 0 | Q = 15, 24<br>L = 134, 161<br>N = 10 | Q = 16, 24<br>L = 137, 161<br>N = 1 | Q = 17, 24<br>L = 140, 161<br>N = 115 | Q = 18, 24<br>L = 143, 161<br>N = 31 | Q = 24, 24<br>L = 161, 161<br>N = 0 |

The paternal genotype was 140/161. The sow haplotypes are indicated together with the frequency (F) within the breeding cohort. For all offspring a genotype could be assigned in accordance with transmission of both paternal and maternal alleles not subjected to expansions or retractions. A total of 349 offspring were genotyped. The genotypes are visualized according to the length (L) of the analysed fragments. Q indicates the number of glutamines encoded from the TNR alleles. N indicates the number of offspring with the indicated genotype.

Example 5

Animal Model of Chondrodysplasia

Only a very limited amount of knowledge is available regarding the presence of collagen X in permanent cartilages, of approximately 2000 bp was isolated using standard procedures and cloned into the pCR®2.1-TOPO vector (Invitrogen, CA) and sequenced in both forward and reverse direction applying standard procedures to ensure that they harboured the COL10A1 amplicon. The COL10A1 plasmid DNA was digested with Eco RI and ligated into a phCMV1 (Gene Therapy Systems Inc.) expression vector pre-digested with Eco RI. The successful cloning of COL10A1 into the phCMV1 vector was confirmed by sequencing.

In order to create DNA for incubation of sperm cells, large scale PCR reactions were performed. The PCR reactions were carried out in a GeneAmp® PCR System 9700 (Applied Biosystems) in a final volume of 25 μL consisting of 5 μL 5× Phusion HF buffer, 2 μL dNTP (2.5 mM each) 0.63 μL forward and reverse primer 5 pmol, 0.1 μL Phusion DNA Polymerase (2 U/μL), 1 μL COL10A1-CMV1 template, and 15.6 μL $H_2O$. The PCR reaction consisted of an initial denaturation at 98° C. for 30 sec followed by 30 cycles of denaturation for 10 sec at 98° C., annealing at 74° C. for 30 sec and elongation for 95 sec at 72° C. followed by a final elongation step at 72° C. for 7 min. The following primers were used to amplify the COL10A1 construct plus the flanking CMV promoter, intron/enhancer sequence, and SVpolyA, generating a fragment of approximately 3600 bp.

```
                                   (SEQ ID NO: 154)
phCMVF: 5'-GTCGGAACAGGAGAGCGCACGAGGG-3'

                                   (SEQ ID NO: 155)
phCMVR: 5'-GGGTGATGGTTCACGTAGTGGGC-3'
```

In order to purify the generated PCR product a "High Pure PCR Product Purification Kit" (Roche) was applied. The suppliers' instructions were followed throughout the purification procedure. The PCR purified fragments were sequenced to check for errors in the sequence.

Preparation of Sperm and DNA Uptake

First and second semen ejaculate, were collected from 8 different boars yielding 16 semen fractions in total. All fractions of spermatozoa had an initial motility of 90 prior to the washing procedure. Seminal fluid was quickly removed by washing the sperm in Fertilization Buffer (FB) consisting of 56.1 g Glucose, 3.5 g EDTA ($2H_2O$), 3.5 g Sodium Citrate ($2H_2O$), and 1.1 g sodium bicarbonate dissolved in 1 liter of sterilized water. Furthermore 6 mg/ml BSA (Fraction V, Sigma) was added. Briefly, 5 mL of FB/BSA prewarmed to 37° C. was added to 5 mL of undiluted semen and left for 5 minutes at room temperature. Next, FB/BSA at room temperature was added to 50 ml and centrifuged for 10 minutes at room temperature at 500 g. The supernatant was removed and semen was resuspended in 50 mL FB/BSA at room temperature and further centrifuged at 500 g at 17° C., after which, the supernatant was removed again and the spermatozoa was resuspended in 15 mL of FB/BSA. Next, in order to select the optimal donor cells, the spermatozoa from the different boars were quickly examined under a light microscope. The sperm cells originating from the boar having the highest sperm cell motility after the washing procedure were chosen as vehicles for the subsequent transgenic procedures. Furthermore, the atozoa were counted.

$1\times10^9$ sperm cells from the chosen donor boar were incubated for 100 minutes at 17° C. with the linear COL10A1 DNA fragment in a concentration of 0.4 μg DNA/$10^6$ spermatozoa in a suspension of 120 mL FB/BSA. The container was inverted every 20 minutes to prevent sedimentation of spermatozoa. Finally, the mixture was incubated 10 minutes at room temperature and employed in artificial insemination of a sow in natural heat.

Animals

Semen was collected from trained Danish Landrace boars that had abstained for 2 days. one recipient sow (Danish Landrace×Yorkshire) at approximately 140 kg were selected due to its natural heating period and used for artificial insemination ($1\times10^9$ DNA treated spermatozoa/sow) meeting standard insemination procedures. Insemination was accomplished in the local stable areas at DIAS. The sow was examined for pregnancy 24 and 42 days after insemination, showing that was successfully pregnant. After ended gestation period 6 boar and 6 sow piglets were naturally born and blood samples were withdrawn from the piglets three days after birth in EDTA and serum tubes. Due to economical reasons, 9 animals were sacrificed and hence 2 boars and 1 sow piglet were kept for later investigation. The sow was sacrificed at the age of 7 month since severe phenotypic alterations were present. Animal care and experimental procedures met local, national and European Union Guidelines.

DNA and RNA Studies

DNA was prepared from EDTA stabilized blood samples from the 12 piglets. RNA was prepared from snap frozen tissues from the sacrificed sow (heart, kidney, liver, lung, skin, ovary, musculus longissimus dorsi, musculus semimembranosus, and musculus triceps brachii). To avoid any contamination, all DNA and RNA samples were extracted in special clean laboratory facilities under highly stringent experimental conditions using standard protocols.

PCR and RT-PCR

To ensure the presence of the transgene, 50 ng of genomic DNA from each animal, isolated from blood samples were amplified using the following primers: phCMV_430F: 5'-GTCTCCACCCCATTGACGTC-3' (SEQ ID NO:156) and phCMV_646R: 5'-GGATCGGTCCCGGTGTCTTC-3' (SEQ ID NO:157) yielding a fragment of 217 bp using the following sample mix 1 μL 10×$MgCl_2$ free reaction buffer, 0.4 μL 50 mM $MgCl_2$, 10 pmol of each primer, 5 mM dNTP-mix, and 0.5 U Dynazyme Ext DNA polymerase. The reaction was performed in a total volume of 10 μL and accomplished as a touchdown PCR in a GeneAmp® PCR system 9700 (Applied Biosystems) under the following conditions: Initial denaturation at 95° C. for 3 min, denaturation at 95° C. for 30 sec, touchdown from 62° C. to 57° C. with a decrement of 0.5° C. for 20 sec, followed by 1 min of elongation at 72° C. pr cycle. Furthermore, 35 cycles of 30 sec denaturation at 95° C., 20 sec of annealing at 57° C., and 1 min of elongation at 72° C. was included together with a final elongation step at 72° C. for 7 min.

Southern Blot Analysis

Transgene integration was determined by Southern blot analysis of DNA from musculus longissimus dorsi from the affected sow. 10 μg of genomic DNA from the affected sow and from a wild type pig was digested with Bgl II and double digested with Bgl II and Bam HI, respectively, and separated on a 0.9% agarose gel, blotted to a nylon membrane and probed with [32P]-labelled collagen X NC1 fragment derived from PCR amplification using the following primers NC1_F: 5'-GCTCTAGAGGTCCCACCCACCCGAAGG-3' (SEQ ID NO:158) and NC1_R: 5'-TCTCTAGATCACATTGGAGCCACTACGAA-3' (SEQ ID NO:159).

Histopathology

From the right foreleg tissues from the growth plates (physis) and metaphyses of femur, ulna and radius were sampled together with the articular areas including the articular-epiphyseal cartilage complex of the shoulder-, elbow-, and carpal joints. From the two hind legs similar tissue samples were collected from the hip and knee joints, i.e. from the femoral and tibial bones. Also the osteo-chondral junction of three ribs was sampled for histology. All tissues were fixed in 10% neutral buffered formalin followed by decalcification in a solution containing 3.3% formaldehyde and 17% formic acid for 2 weeks. The tissues were processed through graded concentrations of alcohol and xylene, and embedded in paraffin wax blocks. Tissue sections of 4-5μ were stained by haematoxylin and eosin (HE), and in selected cases by Van Gieson for collagen and safranin o for cartilage matrix [78,79].

Results

Sperm Mediated Gene Transfer and Genetically Modified Pigs

Figure 34:
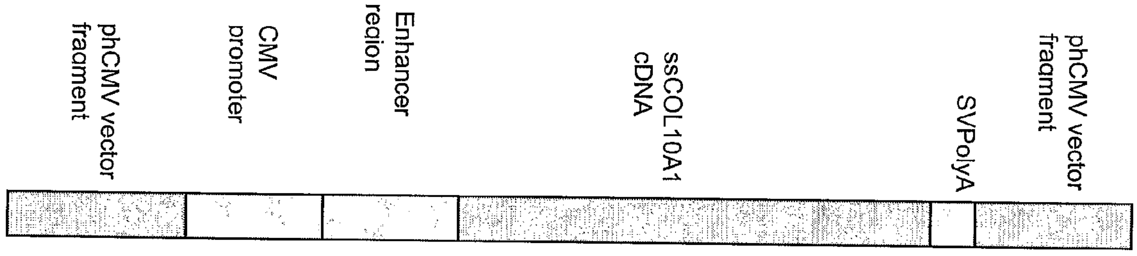
FIG. 34: COL10A1 linearised construct used to create transgenic pigs by means of SMGT. The fragment constitutes approximately 3600 bp and includes 5' and 3' prime phCMV vector fragment, a CMV promoter, an enhancer region, the porcine SOD1 cDNA, and the SVPolyA (simian virus 40 polyA).

In order to establish transgenic pigs which could shed light on the functional role of collagen X a COL10A1 cDNA wild type construct was generated. Interestingly, the porcine COL10A1 cDNA was isolated from trachea using primers generated from the previously known COL10A1 sequence [80]. The cDNA fragment was initially cloned into the pCR®2.1-TOPO vector and subsequently successfully removed to the phCMV1 expression vector facilitating constitutive expression qua the CMV promoter. In order to impede possible truncation of important elements following SMGT, the COL10A1 DNA fragment employed in the transgenic procedure, include additional nucleotides 5' and 3' prime to the CMV promoter and the polyA fragment which, constitutes a fragment of approximately 3600 bp in total, FIG. 34.

Figure 35:
FIG. 35: Examples of PCR analyses. PCR was performed on genomic DNA extracted from whole blood. Lane 1; PUC19 DNA Ladder, lanes 2-13 indicate the 12 piglets born, lanes 14-15; no DNA added, lane 16; negative control (wild type pig), lane 17; positive control.

Initially, eight Danish Landrace boars were used as sperm donors and the sperm fraction showing the highest motility after the initial washing procedure, introduced to remove seminal fluid, was chosen in the subsequent DNA incubation procedure. After ended gestation period 12 normal looking piglets were naturally born and PCR analysis, of DNA isolated from blood, amplifying a 217 bp DNA fragment, located in the 5'-prime phCMV fragment of the construct, showed that all 12 piglets harboured the transgene, see FIG. 35. However, due to economical reasons only 3 piglets were kept for phenotypical investigations.

Phenotypic Description

At the age of approximately 5½ month one of the three transgenic animals, a sow, developed clinical manifestations of lameness. The sow was oppressed in its movements rising from primarily difficulties with the forelegs, had a toddling gait, a curved back, which however could be a compensation for the abnormalities arising from the fore legs. The signs became slightly worse and at the age of approximately seven month the sow would only walk when forced to, and it would immediately bent down on the elbows and walk on these. However, for ethical reasons the sow was sacrificed at this point.

Southern Blot Analysis

Figure 36:
FIG. 36: Southern Blot analysis. Lane 1: Bgl II digested genomic DNA from the affected pig, lane 2: Bgl II digested genomic DNA from wt pig, lane 3: Bgl II and Bam HI digested genomic DNA from affected pig, lane 4 Bgl II and Bam HI digested genomic DNA from wt pig. Bgl II digestion. Bgl II only digested the DNA to a limited degree (lane 1 and 2), lane 3 and for show additional bands in the diseased sow, showing that the transgene is integrated into the genome.

Southern blot analysis, shown in FIG. 36, performed on tissue from musculus longissimus dorsi from the diseased sow and a normal wild type pig reveals additional bands in the affected pig, when digested with Bgl II and Bam HI in comparison to the control using the entire collagen NC1 domain as a radiolabelled probe. This therefore, led us to conclude that the transgene has become integrated into the genome of the affected pig. Unfortunately, Bgl II did only digest the genomic DNA to a limited degree, and hence no difference is seen regarding additional bands in the unidigestion using this enzyme alone (lane 1 and 2).

Expression Analysis

Figure 37:
FIG. 37: Analysis of COL10A1 expression in various porcine tissues. Lane 2-11 represents the diseased transgenic pig and lane 12-16 represent a wild type pig. Lane 1; DNA ladder, lane 2; musculus triceps brachii (left), lane 3; musculus triceps brachii (right), lane 4; ovary, lane 5; kidney, lane 6; skin, lane 7; liver, lane 8; lung, lane 9; musculus longissmus dorsi, lane 10; musculus semimembranosus (left), lane 11; heart, lane 12; liver, lane 13; spleen, lane 14: kidney, lane 15; lung, lane 16; heart, lane 17-18; -DNA, lane 19; positive control, lane 20; DNA ladder.

Expression of the COL10A1 construct was accomplished by RT-PCR using primers located in COL10A1 exon 2 and COL10A1 exon 3 on total RNA isolated musculus triceps brachii, ovary, kidney, skin, liver, lung, musculus longissmus dorsi, musculus semimembranosus, heart, and liver, spleen, kidney, lung, and heart from a wild type control. The RT-PCR analysis revealed expression of collage X in kidney, lung, and heat in the affected sow, although only very limited amounts of transcript are present in kidney, FIG. 37. However, since the PCR is only qualitative, the judgement of expression levels within the samples should be taken with precaution, although the same amount of total RNA has been used in the cDNA synthesis. Furthermore, no expression of COL10A1 is present in the wild type control tissues.

Histopathology

Figure 38:
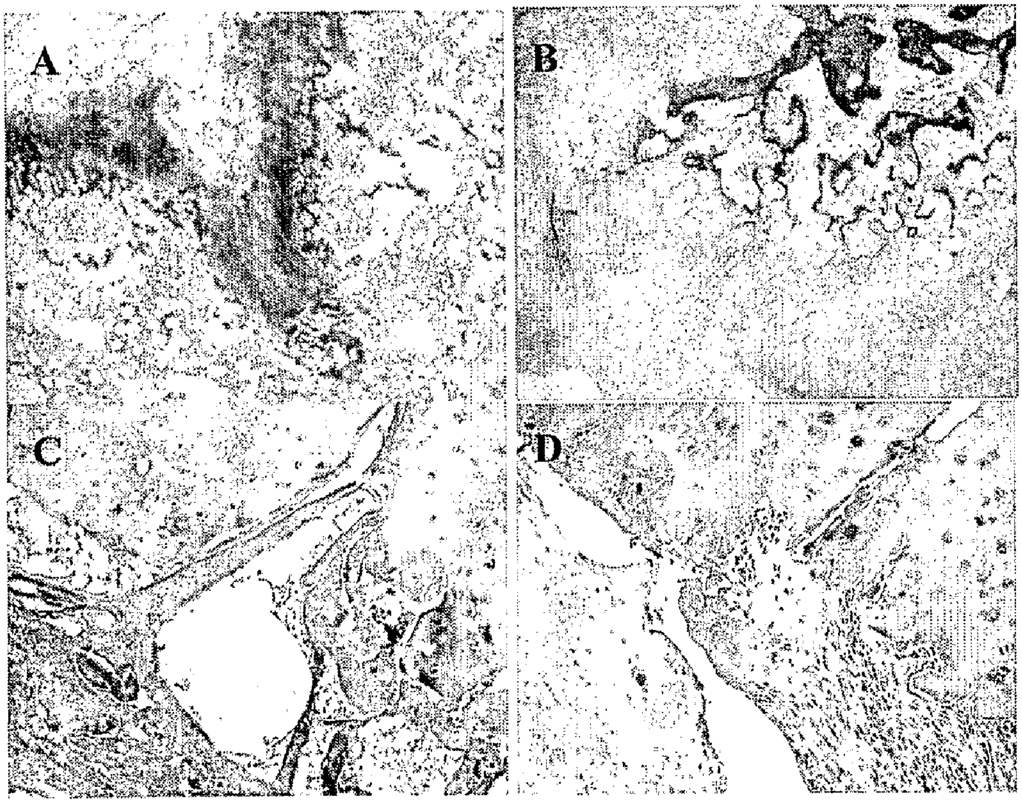
FIG. 38: Histopathological investigation of one of the affected forelegs. A) Distal humeral physis. An area of hypertropihic, non-ossified chondrocytes of the growth plate is retained within the metaphysic area. Safranin O, obj.×1. B) Distal humeral physis. At the margins of the growth plates non-ossified, hypertrophic chondrocytes are localized. Van Gieson, obj.×2. C) Articular-epiphysial junction from the elbow joint. Within the retained cartilage cavitations with contents of fibrin are present. HE, obj.×10. D) Articular-epiphysial junction from the elbow joint. Clefts and adjacent fibrosis is present within the chondroid tissue of the articular-epiphysial junction. HE, obj.×20.

The articular-epiphyseal area of the humeral trochlea constituting the proximal portion of the elbow joint, revealed severe alterations, see FIG. 38. The cartilage was retained with contents of hypertrophied chondrocytes. Within areas of retained cartilage formation of clefts were regularly seen, and in the depth irregular cavitations filled with fibrinous material were present along with eosinophilic streaks. Moreover, the distal growth plates of both ulna and radius were irregular with localized areas of retained cartilage. Lesions were not present within sections from the ribs, the articular-epiphyseal areas or the growth plates of the hind legs.

Thus in conclusion, the integration and expression of the COL10A1 transgene gave rise to a dyschondroplasia phenotype affecting especially the two fore limbs of a sow. The alterations present in the transgeneic sow, resembles osteochondrosis which is known to affect younger animals, and is characterised by similar lesions of the articular-epiphyseal cartilage complex [41] as observed in the forelegs of the present sow.

REFERENCES

1. Belsh J M: ALS diagnostic criteria of El Escorial Revisited: do they meet the needs of clinicians as well as researchers? *Amyotroph Lateral Scler Other Motor Neuron Disord* 2000, 1 Suppl 1: S57-S60.
2. Everett, C. M. and N. W. Wood, Trinucleotide repeats and neurodegenerative disease. Brain, 2004. 127(Pt 11): p. 2385-405.
3. Pearson, C. E., K. Nichol Edamura, and J. D. Cleary, Repeat instability: mechanisms of dynamic mutations. Nat Rev Genet, 2005. 6(10): p. 729-42.
4. Jin, P., et al., RNA-mediated neurodegeneration caused by the fragile X premutation rCGG repeats in *Drosophila*. Neuron, 2003. 39(5): p. 739-47.
5. Saveliev, A., et al., DNA triplet repeats mediate heterochromatin-protein-1-sensitive variegated gene silencing. Nature, 2003. 422(6934): p. 909-13.
6. Cho, D. H., et al., Antisense transcription and heterochromatin at the DM1 CTG repeats are constrained by CTCF. Mol Cell, 2005. 20(3): p. 483-9.
7. Galvao, R., et al., Triplet repeats, RNA secondary structure and toxic gain-of-function models for pathogenesis. Brain Res Bull, 2001. 56(3-4): p. 191-201.
8. Wells, R. D., Molecular basis of genetic instability of triplet repeats. J Biol Chem, 1996. 271(6): p. 2875-8.
9. Mirkin, S. M. and E. V. Smirnova, Positioned to expand. Nat Genet, 2002. 31(1): p. 5-6.
10. Cleary, J. D., et al., Evidence of cis-acting factors in replication-mediated trinucleotide repeat instability in primate cells. Nat Genet, 2002. 31(1): p. 37-46.
11. Nenguke, T., et al., Candidate DNA replication initiation regions at human trinucleotide repeat disease loci. Hum Mol Genet, 2003. 12(9): p. 1021-8.
12. Michlewski, G. and W. J. Krzyzosiak, Molecular architecture of CAG repeats in human disease related transcripts. J Mol Biol, 2004. 340(4): p. 665-79.
13. Andres, A. M., et al., Dynamics of CAG repeat loci revealed by the analysis of their variability. Hum Mutat, 2003. 21(1): p. 61-70.
14. Brinkmann, B., et al., Mutation rate in human microsatellites: influence of the structure and length of the tandem repeat. Am J Hum Genet, 1998. 62(6): p. 1408-15.
15. Mulvihill, D. J., et al., Effect of CAT or AGG interruptions and CpG methylation on nucleosome assembly upon trinucleotide repeats on spinocerebellar ataxia, type 1 and fragile X syndrome. J Biol Chem, 2005. 280(6): p. 4498-503.

16. Lin, Y., V. Dion, and J. H. Wilson, Transcription promotes contraction of CAG repeat tracts in human cells. Nat Struct Mol Biol, 2006. 13(2): p. 179-80.

17. Lavedan, C. N., L. Garrett, and R. L. Nussbaum, Trinucleotide repeats (CGG)22TGG(CGG)43TGG(CGG)21 from the fragile X gene remain stable in transgenic mice. Hum Genet, 1997. 100(3-4): p. 407-14.

18. Libby, R. T., et al., Genomic context drives SCA7 CAG repeat instability, while expressed SCA7 cDNAs are intergenerationally and somatically stable in transgenic mice. Hum Mol Genet, 2003. 12(1): p. 41-50.

19. Brook, J. D., et al., Molecular basis of myotonic dystrophy: expansion of a trinucleotide (CTG) repeat at the 3' end of a transcript encoding a protein kinase family member. Cell, 1992. 69(2): p. 385.

20. Harley, H. G., et al., Expansion of an unstable DNA region and phenotypic variation in myotonic dystrophy. Nature, 1992. 355(6360): p. 545-6.

21. Mahadevan, M., et al., Myotonic dystrophy mutation: an unstable CTG repeat in the 3' untranslated region of the gene. Science, 1992. 255(5049): p. 1253-5.

22. Fu, Y. H., et al., An unstable triplet repeat in a gene related to myotonic muscular dystrophy. Science, 1992. 255(5049): p. 1256-8.

23. Tsilfidis, C., et al., Correlation between CTG trinucleotide repeat length and frequency of severe congenital myotonic dystrophy. Nat Genet, 1992. 1(3): p. 192-5.

24. Fu, Y. H., et al., Variation of the CGG repeat at the fragile X site results in genetic instability: resolution of the Sherman paradox. Cell, 1991. 67(6): p. 1047-58.

25. Verkerk, A. J., et al., Identification of a gene (FMR-1) containing a CGG repeat coincident with a breakpoint cluster region exhibiting length variation in fragile X syndrome. Cell, 1991. 65(5): p. 905-14.

26. Knight, S. J., et al., Trinucleotide repeat amplification and hypermethylation of a CpG island in FRAXE mental retardation. Cell, 1993. 74(1): p. 127-34.

27. Holmes, S. E., et al., Expansion of a novel CAG trinucleotide repeat in the 5' region of PPP2R2B is associated with SCA12. Nat Genet, 1999. 23(4): p. 391-2.

28. Limprasert, P., et al., Comparative studies of the CAG repeats in the spinocerebellar ataxia type 1 (SCA1) gene. Am J Med Genet, 1997. 74(5): p. 488-93.

29. Choudhry, S., et al., CAG repeat instability at SCA2 locus: anchoring CAA interruptions and linked single nucleotide polymorphisms. Hum Mol Genet, 2001. 10(21): p. 2437-46.

30. Takiyama, Y., et al., The gene for Machado-Joseph disease maps to human chromosome 14q. Nat Genet, 1993. 4(3): p. 300-4.

31. Kawaguchi, Y., et al., CAG expansions in a novel gene for Machado-Joseph disease at chromosome 14q32.1. Nat Genet, 1994. 8(3): p. 221-8.

32. Limprasert, P., et al., Analysis of CAG repeat of the Machado-Joseph gene in human, chimpanzee and monkey populations: a variant nucleotide is associated with the number of CAG repeats. Hum Mol Genet, 1996. 5(2): p. 207-13.

33. Zhuchenko, o., et al., Autosomal dominant cerebellar ataxia (SCA6) associated with small polyglutamine expansions in the alpha 1A-voltage-dependent calcium channel. Nat Genet, 1997. 15(1): p. 62-9.

34. David, G., et al., Cloning of the SCA7 gene reveals a highly unstable CAG repeat expansion. Nat Genet, 1997. 17(1): p. 65-70.

35. Nakamura, K., et al., SCA17, a novel autosomal dominant cerebellar ataxia caused by an expanded polyglutamine in TATA-binding protein. Hum Mol Genet, 2001. 10(14): p. 1441-8.

36. Koide, R., et al., Unstable expansion of CAG repeat in hereditary dentatorubral-pallidoluysian atrophy (DRPLA). Nat Genet, 1994. 6(1): p. 9-13.

37. La Spada, A. R., et al., Meiotic stability and genotype-phenotype correlation of the trinucleotide repeat in X-linked spinal and bulbar muscular atrophy. Nat Genet, 1992. 2(4): p. 301-4.

38. Prockop D J, Kivirikko K I: Collagens: molecular biology, diseases, and potentials for therapy. Annu Rev Biochem 1995, 64: 403-434.

39. Kuivaniemi H, Tromp G, Prockop D J: Mutations in fibrillar collagens (types I, II, III, and XI), fibril-associated collagen (type IX), and network-forming collagen (type X) cause a spectrum of diseases of bone, cartilage, and blood vessels. Hum Mutat 1997, 9: 300-315.

40. Linsenmayer T F, Long F, Nurminskaya M, Chen Q, Schmid T M: Type X collagen and other up-regulated components of the avian hypertrophic cartilage program. Prog Nucleic Acid Res Mol Biol 1998, 60: 79-109.

41. Wardale R J, Duance V C: Characterisation of articular and growth plate cartilage collagens in porcine osteochondrosis. J Cell Sci 1994, 107 (Pt 1): 47-59.

42. Nielsen V H, Bendixen C, Arnbjerg J, Sorensen C M, Jensen H E, Shukri N M et al.: Abnormal growth plate function in pigs carrying a dominant mutation in type X collagen. Mamm Genome 2000, 11: 1087-1092.

43. Dharmavaram R M, Elberson M A, Peng M, Kirson L A, Kelley T E, Jimenez S A: Identification of a mutation in type X collagen in a family with Schmid metaphyseal chondrodysplasia. Hum Mol Genet 1994, 3: 507-509.

44. Lachman R S, Rimoin D L, Spranger J: Metaphyseal chondrodysplasia, Schmid type. Clinical and radiographic delineation with a review of the literature. Pediatr Radiol 1988, 18: 93-102.

45. Orrell R, de Belleroche J, Marklund S, Bowe F, Hallewell R: A novel SOD mutant and ALS. Nature 1995, 374: 504-505.

46. Orrell R W, Habgood J J, Malaspina A, Mitchell J, Greenwood J, Lane R J M et al.: Clinical characteristics of SOD1 gene mutations in UK families with ALS. Journal of the Neurological Sciences 1999, 169: 56-60.

47. Beauchamp C, Fridovich I: Superoxide dismutase: improved assays and an assay applicable to acrylamide gels. Anal Biochem 1971, 44: 276-287.

48. Pedersen P H, Oksbjerg N, Karlsson A H, Busk H, Bendixen E, Henckel P: A within litter comparison of muscle fibre characteristics and growth of halothane carrier and halothane free crossbred pigs. Livest Prod Sci 2001, 73: 15-24.

49. Manzini S, Vargiolu A, Stehle I M, Bacci M L, Cerrito M G, Giovannoni R et al.: Genetically modified pigs produced with a nonviral episomal vector. Proc Natl Acad Sci USA 2006, 103: 17672-17677.

50. Marklund S L: Extracellular superoxide dismutase in human tissues and human cell lines. J Clin Invest 1984, 74: 1398-1403.

51. Marklund S: Distribution of CuZn superoxide dismutase and Mn superoxide dismutase in human tissues and extracellular fluids. Acta physiol Scand Suppl 1980, 492: 19-23.

52. Pfaffl M W, Horgan G W, Dempfle L: Relative expression software tool (REST) for group-wise comparison and statistical analysis of relative expression results in real-time PCR. Nucleic Acids Res 2002, 30: e36.

53. Aldudo J, Bullido M J, Frank A, Valdivieso F: Missense mutation E318G of the presenilin-1 gene appears to be a nonpathogenic polymorphism. Ann Neurol 1998, 44: 985-986.

54. Colacicco A M, Panza F, Basile A M, Solfrizzi V, Capurso C, D'Introno A et al.: F175S change and a novel polymorphism in presenilin-1 gene in late-onset familial Alzheimer's disease. Eur Neurol 2002, 47: 209-213.

55. Raux G, Guyant-Marechal L, Martin C, Bou J, Penet C, Brice A et al.: Molecular diagnosis of autosomal dominant early onset Alzheimer's disease: an update. J Med Genet 2005, 42: 793-795.

56. Lleo A, Castelivi M, Blesa R, oliva R: Uncommon polymorphism in the presenilin genes in human familial Alzheimer's disease: not to be mistaken with a pathogenic mutation. Neurosci Lett 2002, 318: 166-168.

57. Wang J, Brunkan A L, Hecimovic S, Walker E, Goate A: Conserved "PAL" sequence in presenilins is essential for gamma-secretase activity, but not required for formation or stabilization of gamma-secretase complexes. Neurobiol Dis 2004, 15: 654-666.

58. Wolfe M S, Xia W, ostaszewski B L, Diehl T S, Kimberly W T, Selkoe D J: Two transmembrane aspartates in presenilin-1 required for presenilin endoproteolysis and gamma-secretase activity. Nature 1999, 398: 513-517.

59. Yerle M, Echard G, Robic A, Mairal A, Dubut-Fontana C, Riquet J et al.: A somatic cell hybrid panel for pig regional gene mapping characterized by molecular cytogenetics. Cytogenet Cell Genet 1996, 73: 194-202.

60. Lee M K, Slunt H H, Martin L J, Thinakaran G, Kim G, Gandy S E et al.: Expression of presenilin 1 and 2 (PS1 and PS2) in human and murine tissues. J Neurosci 1996, 16: 7513-7525.

61. Moreno-Flores M T, Medina M, Wandosell F: Expression of presenilin 1 in nervous system during rat development. J Comp Neurol 1999, 410: 556-570.

62. Wines-Samuelson M, Shen J: Presenilins in the developing, adult, and aging cerebral cortex. Neuroscientist 2005, 11: 441-451.

63. Donoviel D B, Hadjantonakis A K, Ikeda M, Zheng H, Hyslop P S, Bernstein A: Mice lacking both presenilin genes exhibit early embryonic patterning defects. Genes Dev 1999, 13: 2801-2810.

64. Steiner H, Duff K, Capell A, Romig H, Grim M G, Lincoln S et al.: A loss of function mutation of presenilin-2 interferes with amyloid beta-peptide production and notch signaling. J Biol Chem 1999, 274: 28669-28673.

65. Alba, M. M. and R. Guigo, Comparative analysis of amino acid repeats in rodents and humans. Genome Res, 2004. 14(4): p. 549-54.

66. Hancock, J. M., E. A. Worthey, and M. F. Santibanez-Koref, A role for selection in regulating the evolutionary emergence of disease-causing and other coding CAG repeats in humans and mice. Mol Biol Evol, 2001. 18(6): p. 1014-23.

67. Andres, A. M., et al., Comparative genetics of functional trinucleotide tandem repeats in humans and apes. J Mol Evol, 2004. 59(3): p. 329-39.

68. Yu, F., et al., Positive selection of a pre-expansion CAG repeat of the human SCA2 gene. PLoS Genet, 2005. 1(3): p. e41.

69. Miller, S. A., D. D. Dykes, and H. F. Polesky, A simple salting out procedure for extracting DNA from human nucleated cells. Nucleic Acids Res, 1988. 16(3): p. 1215.

70. Eichler, E. E., et al., Evolution of the cryptic FMR1 CGG repeat. Nat Genet, 1995. 11(3): p. 301-8.

71. Bowman, A. B., et al., Duplication of Atxn1l suppresses SCA1 neuropathology by decreasing incorporation of polyglutamine-expanded ataxin-1 into native complexes. Nat Genet, 2007. 39(3): p. 373-379.

72. orr, H. T., et al., Expansion of an unstable trinucleotide CAG repeat in spinocerebellar ataxia type 1. Nat Genet, 1993. 4(3): p. 221-6.

73. Pulst, S. M., et al., Moderate expansion of a normally biallelic trinucleotide repeat in spinocerebellar ataxia type 2. Nat Genet, 1996. 14(3): p. 269-76.

74. A novel gene containing a trinucleotide repeat that is expanded and unstable on Huntington's disease chromosomes. The Huntington's Disease Collaborative Research Group. Cell, 1993. 72(6): p. 971-83.

75. Matsuyama, N., et al., Identification and characterization of the miniature pig Huntington's disease gene homolog: evidence for conservation and polymorphism in the CAG triplet repeat. Genomics, 2000. 69(1): p. 72-85.

76. Sasano Y, Takahashi I, Mizoguchi I, Kagayama M, Takita H, Kuboki Y: Type X collagen is not localized in hypertrophic or calcified cartilage in the developing rat trachea. Anat Embryol (Berl) 1998, 197: 399-403.

77. Kusafuka K, Yamaguchi A, Kayano T, Takemura T: ossification of tracheal cartilage in aged humans: a histological and immunohistochemical analysis. J Bone Miner Metab 2001, 19: 168-174.

78. Bancroft J D, Stevens A: Theory and Practice of Histological Techniques., 4 edn. New York, USA: Churchill Livingstone; 1996.

79. Lune L G: Manual of Histologic Staining Methods of the Armed Forces Institute of Pathology., 3 edn. New York: McGraw Hill; 1968.

80. Madsen L B, Petersen A H, Nielsen V H, Nissen P H, Duno M, Krejci L et al.: Chromosome location, genomic organization of the porcine COL10A1 gene and model structure of the NC1 domain. Cytogenet Genome Res 2003, 102: 173-178.

The invention claimed is:

1. A transgenic pig model for a hereditary neurodegenerative autosomal dominant disease, comprising a transgenic pig whose genome comprises a DNA sequence encoding a protein involved in the development of a hereditary neurodeqenerative autosomal dominant disease, wherein the transgenic pig expresses the protein in nerve tissue and exhibits a reduction in the number of neurons in the nerve tissue and an accumulation of protein aggregates in the nerve tissue.

2. The pig model according to claim 1, wherein said hereditary neurodegenerative autosomal dominant disease is amyotrophic lateral sclerosis.

3. The pig model according to claim 1, wherein said hereditary neurodegenerative autosomal dominant disease is Alzheimer's Disease.

4. The pig model according to claim 1, wherein said hereditary neurodegenerative autosomal dominant disease is Parkinson's Disease.

5. The pig model according to claim 1, wherein said hereditary neurodegenerative autosomal dominant disease is a disease related to trinucleotide repeats.

6. The pig model according to claim 1, wherein said hereditary neurodegenerative autosomal dominant disease is Huntington's chorea.

7. The pig model according to claim 1, wherein said hereditary neurodegenerative autosomal dominant disease is dyschondroplasia.

8. The transgenic pig model according to claim 1 obtainable by a sperm mediated gene transfer method (SMGT) comprising the steps of:

i) providing semen from a male pig, ii) providing a DNA sequence encoding a protein involved in the development of a hereditary neurodeqenerative autosomal dominant disease, wherein the transgenic pig expresses the protein in nerve tissue and exhibits a reduction in the number of neurons in the nerve tissue and an accumulation of protein aggregates in the nerve tissue when the protein is expressed in said pig model, iii) contacting said semen and said genetic material, iv) fertilising an oocyte from a female pig with the semen and the genetic determinant, and v) incubating said fertilised oocyte under conditions allowing said fertilised oocyte to develop into said pig model.

9. A method for producing a transgenic pig model for a hereditary neurodegenerative autosomal dominant disease, comprising a transgenic pig whose genome comprises a DNA sequence encoding a protein involved in the development of a hereditary neurodeqenerative autosomal dominant disease, wherein the transgenic pig expresses the protein in nerve tissue and exhibits a reduction in the number of neurons in the nerve tissue and an accumulation of protein aggregates in the nerve tissue, said method comprising the steps of:

i) providing semen from a male pig, ii) providing a DNA sequence encoding a protein involved in the development of a hereditary neurodegenerative autosomal dominant disease, iii) contacting said semen and said DNA sequence, iv) fertilising an oocyte from a female pig with the semen and the genetic material, and v) incubating said fertilised oocyte under conditions allowing said fertilised oocyte to develop into said transgenic pig, wherein the transgenic pig expresses the protein in nerve tissue and exhibits a reduction in the number of neurons in the nerve tissue and an accumulation of protein aggregates in the nerve tissue.

10. The method of claim 9, wherein the step of contacting said semen and said genetic material occurs in a buffer composition comprising (a) glucose and (b) a citrate salt and/or a bicarbonate salt, optionally in combination with (c) a compound capable of chelating divalent metal ions, and further optionally in combination with (d) Bovine Serum Albumin (BSA), including any combination of (a) and (b) with (c) or (d).

11. A method for evaluating the response of a therapeutical treatment of a hereditary disease, said method comprising the steps of:

a. providing a transgenic pig model for a hereditary neurodegenerative autosomal dominant disease, comprising a transgenic pig whose genome comprises a DNA sequence encoding a protein involved in the development of a hereditary neurodeqenerative autosomal dominant disease, wherein the transgenic pig expresses the protein in nerve tissue and exhibits a reduction in the number of neurons in the nerve tissue and an accumulation of protein aggregates in the nerve tissue, b. treating said pig with at least one pharmaceutical composition exerting an effect on the reduction in the number of neurons in the nerve tissue or the accumulation of protein aggregates in the nerve tissue, and c. evaluating the effect observed.

12. The method of claim 11 comprising the further step of advising on medical treatment based on the afore-mentioned observed effects.

13. A transgenic pig sperm cell comprising a DNA sequence encoding a protein involved in the development of a hereditary neurodegenerative autosomal dominant disease wherein said protein is expressed in nerve tissue and exhibits a reduction in the number of neurons in the nerve tissue and an accumulation of protein aggregates in the nerve tissue when expressed in a pig host organism.

14. The pig sperm cell according to claim 13, wherein the DNA sequence is of mammalian origin, including human origin or porcine origin.

15. A method for producing a transgenic pig sperm cell comprising a DNA sequence encoding a protein involved in the development of a hereditary neurodegenerative autosomal dominant disease, wherein said protein is expressed in nerve tissue and exhibits a reduction in the number of neurons in the nerve tissue and an accumulation of protein aggregates in the nerve tissue when expressed in a pig host organism, said method comprising the steps of:

a. providing a pig sperm cell, b. providing a DNA sequence encoding a protein involved in the development of a hereditary neurodeqenerative autosomal dominant disease wherein said protein is expressed in nerve tissue and exhibits a reduction in the number of neurons in the nerve tissue and an accumulation of protein aggregates in the nerve tissue when expressed in a pig host organism, and c. contacting said pig sperm cell and said DNA sequence, wherein said contacting results in the uptake of the DNA sequence into the pig sperm cell.

16. A method for fertilising an oocyte by sperm-mediated gene transfer, said method comprising the steps of providing a pig sperm cell according to claim 13, and introducing said pig sperm cell into the oocyte to be fertilised, wherein said disease is a protein conformation disease.

17. A method for fertilising an oocyte by sperm-mediated gene transfer, said method comprising the step of providing a composition comprising a pig sperm cell in combination with a DNA sequence encoding a protein involved in the development of an hereditary neurodegenerative autosomal dominant disease wherein said protein is expressed in nerve tissue and exhibits a reduction in the number of neurons in the nerve tissue and an accumulation of protein aggregates in the nerve tissue when expressed in a pig host organism.

18. A transgenic embryo obtained by fertilising an oocyte with a pig sperm cell comprising a DNA sequence encoding a protein involved in the development of a hereditary neurodegenerative autosomal dominant disease wherein said protein is expressed in nerve tissue and exhibits a reduction in the number of neurons in the nerve tissue and an accumulation of protein aggregates in the nerve tissue when expressed in a pig host organism.

19. A transgenic embryo obtained by fertilising an oocyte with a composition comprising a DNA sequence encoding a protein involved in the development of a hereditary neurodegenerative autosomal dominant disease, wherein said protein is expressed in nerve tissue and exhibits a reduction in the number of neurons in the nerve tissue and an accumulation of protein aggregates in the nerve tissue when expressed in a pig host organism.

20. A method for the cultivation and development of a transgenic embryo obtained by fertilising an oocyte with a pig sperm cell comprising a DNA sequence encoding a protein involved in the development of a hereditary neurodegenerative autosomal dominant disease, said method comprising the step of cultivating said embryo under conditions allowing the embryo to develop into a pig offspring expressing said protein in nerve tissue and exhibiting a reduction in the number of neurons in the nerve tissue and an accumulation of protein aggregates in the nerve tissue.

21. A method for screening the efficacy of a pharmaceutical composition, said method comprising the steps of:

a. providing a transgenic pig model for a hereditary neurodegenerative autosomal dominant disease, comprising a transgenic pig whose genome comprises a DNA sequence encoding a protein involved in the development of a hereditary neurodegenerative autosomal dominant disease, wherein the transgenic pig expresses the protein in nerve tissue and exhibits a reduction in the number of neurons in the nerve tissue and an accumulation of protein aggregates in the nerve tissue, b. expressing in said pig model said DNA sequence involved in the development of a hereditary neurodegenerative autosomal dominant disease, c. administering to said pig the pharmaceutical composition, the efficacy of which is to be evaluated, and d. evaluating the effect, if any, of the pharmaceutical composition on the reduction in the number of neurons in the nerve tissue or the accumulation of protein aggregates in the nerve tissue exerted by the DNA sequence when expressed in the pig model.

22. The pig model according to claim 1, wherein said DNA sequence is expressed in a transient manner.

* * * * *